(12) United States Patent
Wang et al.

(10) Patent No.: US 6,482,597 B1
(45) Date of Patent: Nov. 19, 2002

(54) COMPOUNDS AND METHODS FOR THERAPY AND DIAGNOSIS OF LUNG CANCER

(75) Inventors: Tongtong Wang, Medina; Nancy A. Hosken; Michael D. Kalos, both of Seattle; Gary R. Fanger, Mill Creek; Liqun Fan, Bellevue, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/480,884

(22) Filed: Jan. 10, 2000

Related U.S. Application Data

(63) Continuation-in-part of application No. 09/476,496, filed on Dec. 30, 1999, which is a continuation-in-part of application No. 09/466,396, filed on Dec. 17, 1999, which is a continuation-in-part of application No. 09/285,479, filed as application No. PCT/US99/05798 on Mar. 17, 1999.

(51) Int. Cl.$^7$ .................... G01N 33/53; G01N 33/574; C07K 16/00; A61K 39/395
(52) U.S. Cl. .................... 435/7.1; 435/7.23; 530/387.1; 530/388.1; 424/130.1; 424/141.1; 424/155.1
(58) Field of Search .................... 530/350, 387.1, 530/388.1; 435/7.1, 7.2, 7.23, 810; 424/130.1, 141.1, 155.1

(56) References Cited

U.S. PATENT DOCUMENTS

| 5,705,159 A | 1/1998 | Irie et al. .................. 424/185.1 |
| 5,783,422 A | 7/1998 | Suminami et al. ......... 435/69.3 |

FOREIGN PATENT DOCUMENTS

| EP | 0695760 A1 | 2/1996 |
| WO | WO 91/18926 | 12/1991 |
| WO | WO 94/06929 | 3/1994 |
| WO | WO 95/21862 | 8/1995 |
| WO | WO96/02552 | 2/1996 |
| WO | WO 96/28473 | 9/1996 |
| WO | WO96/30389 | 10/1996 |
| WO | WO 97/07244 | 2/1997 |
| WO | WO 98/35985 | 8/1998 |
| WO | WO 98/46788 | 10/1998 |
| WO | WO 99/38973 | 8/1999 |
| WO | WO 99/47674 | 9/1999 |

OTHER PUBLICATIONS

Pillasch et. al.; Cloning of a gene highly overexpressed in cancer coding for a novel KH–domain containing protein, 1997, Oncogene 14: 2729–2733.*
GenBank Accession No. AF043977, Jun. 23, 1999.
GenBank Accession No. U85946, Jul. 30, 1999.
Geneseq Accession No. AAZ24653, Dec. 7, 1999.
Gruber et al., "Molecular cloning and transmembrane structure of hCLCA2 from human lung, trachea, and mammary gland," *Am. J. Physiol.* 276(Cell Physiol):C1261–C1270, 1999.
Guo et al., "Identification and characterization of homologues of the Exocyst component Sec 10p," *FEBS Letters* 404(2–3):135–139, 1997.
Brass et al., "Translation initiation factor eIF–4gamma is encoded by an amplified gene and induces an immune response in squamous cell lung carcinoma," *Human Molecular Genetics*, 6(1): 33–39, 1997.
Database EMBLest17 Accession No. AA340797:EST46165 Fetal kidney II Homo sapiens cDNA 3' end, Apr. 18, 1997.
Database EMBLest17 Accession No. W22264:Human retina cDNATsp–5091–cleaved sublibrary Homo sapiens cDNA not directional, May 9, 1996.
Finch et al., "Identification of a cloned sequence activated during multi–stage carcinogenesis in mouse skin," *Carcinogenesis*, 12(8):1519–1522, Aug. 1991.
Gerhold and Caskey, "It's the genes! EST access to human genome content," *BioEssays* 18(12):973–981, 1996.
Russell and Barton, "Structural features can be unconserved in proteins with similar folds," *J. Mol. Biol.* 244:332–350, 1994.
Wells and Peitsch, "The chemokine information source: identification and characterization of novel chemokines using the WorldWide Web and expressewd sequence tag databases," *Journal of Leukocyte Biology* 61:545–550, May 1997.
Baldi et al., "Differential expression of Rb2/p130 and p107 in normal human tissues and in primary lung cancer," *Clinical Cancer Research* 3(10):1691–1697, Oct. 1997.
Database EMBL Nucleotide and Protein Sequence, Accession No. AI468638, Mar. 17, 1999.
Davidson et al., "Lung tumors immunoreactive for parathyroid hormone related peptide: analysis of serum calcium levels and tumour type," *Journal of Pathology* 178:398–401, Jan. 1996.
Hara et al., "Characterization of cell phenotype by a novel cDNA library subtraction system: expression of CD8α in a mast cell–derived interleukin–4–dependent cell line," *Blood* 84(1):189–199, Jul. 1, 1994.
Henderson et al., "Identification of lung tumor antigens for cancer immunotherapy: immunological and molecular approaches," *Immunological Investigation* 29(2);87–91, May 2000.

(List continued on next page.)

*Primary Examiner*—Scott D. Priebe
*Assistant Examiner*—Shin-Lin Chen
(74) *Attorney, Agent, or Firm*—SEED Intellectual Property Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

6 Claims, No Drawings

OTHER PUBLICATIONS

Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27 Jan. 31, 1998.

Pastor et al., "Diagnostic value of SCC, CEA and CYFRA 21.1 in lung cancer: a Bayesian analysis," *Eur. Respir J.* 10(3):603–609, Mar. 1997.

Ramsay, G., "DNA chips: state–of–the art," *Nature Biotechnology* 16:40–44, Jan. 1998.

Rammensee et al., "MHC ligands and peptide motifs: first listing," *Immunogenetics* 41:178–228, 1995.

Ruppert et al., "Prominent role of secondary anchor residues in peptide binding to HLA–A2.1 molecules," *Cell* 74:929–937, Sep. 10, 1993.

Theobald et al., "Targeting p53 as a general tumor antigen," *Proc. Natl. Acad. Sci. USA* 92:11993–11997, Dec. 1995.

Visseren et al., "Identification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination of cDNA subtraction and microarray analysis," *Oncogene* 19(12):1519–1528, Mar. 16, 2000.

* cited by examiner

SEQUENCE LISTING

<160> NUMBER OF SEQ ID NOS: 330

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1

```
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt tttttttgggg gggaagcaat gggaanggta     240
naaattacaa atagaatcat ttgctgtaat ccttaaatgg caaacggtca ggccacgtga     300
aaaaaaaaaa aaaaa                                                      315
```

<210> SEQ ID NO 2
<211> LENGTH: 380
<212> TYPE: DNA
<213> ORGANISM: Homo sapien

<400> SEQUENCE: 2

```
atttaggctt aagattttgt ttacccttgt tactaaggag caaattagta ttaaagtata      60
atatatataa acaaatacaa aaagttttga gtggttcagc ttttttattt tttttaatgg     120
cataacttt aacaacactg ctctgtaatg ggttgaactg tggtactcag actgagataa     180
ctgaaatgag tggatgtata gtgttattgc ataattatcc cactatgaag caaagggact    240
ggataaattc ccagtctaga ttattagcct ttgttaacca tcaagcacct agaagaagaa    300
ttattggaaa ttttgtcctc tgtaactggc actttggggt gtgacttatc ttttgccttt    360
gtaaaaaaaa aaaaaaaaaa                                                380
```

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 3

```
ttgtaagtat acaattttag aaaggattaa atgttattga tcattttact gaatactgca     60
catcctcacc atacaccatc cactttccaa taacatttaa tcctttctaa aattgtaagt   120
atacaattgt actttctttg gattttcata acaaatatac catagactgt taatttatt    180
gaagtttcct taatggaatg agtcattttt gtcttgtgct tttgaggtta cctttgcttt    240
gacttccaac aatttgatca tatagtgttg agctgtggaa atctttaagt ttattctata   300
gcaataattt ctattnnnag annccnggnn naaaannann annaaa                  346
```

<210> SEQ ID NO 4
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 4

```
actagtctca ttactccaga attatgctct tgtacctgtg tggctgggtt tcttagtcgt     60
tggtttggtt tggttttttg aactggtatg tagggtggtt cacagttcta atgtaagcac   120
tctcttctcc aagttgtgct ttgtggggac aatcattctt tgaacattag agaggaaggc   180
agttcaagct gttgaaaaga ctattgctta tttttgtttt taaagaccta cttgacgtca   240
tgtggacagt gcacgtgcct tacgctacat cttgttttct aggaagaagg ggatgcnggg   300
aaggantggg tgcttttgtga tggataaaac gnctaaataa cacacccttta cattttgaaa  360
aaaacaaaac aa                                                       372
```

<210> SEQ ID NO 5
<211> LENGTH: 698
<212> TYPE: DNA
<213> ORGANISM: Homo sapien
<220> FEATURE:

<221> NAME/KEY: misc_feature
<222> LOCATION: (1)...(698)
<223> OTHER INFORMATION: n = A,T,C or G

<400> SEQUENCE: 5

| | | | | |
|---|---|---|---|---|
| actagtanga tagaaacact | gtgtcccgag | agtaaggaga | gaagctacta | ttgattagag | 60 |
| cctaacccag gttaactgca | agaagaggcg | ggatactttc | agcttccat | gtaactgtat | 120 |
| gcataaagcc aatgtagtcc | agtttctaag | atcatgttcc | aagctaactg | aatcccactt | 180 |
| caatacacac tcatgaactc | ctgatggaac | aataacaggc | ccaagcctgt | ggtatgatgt | 240 |
| gcacacttgc tagactcaga | aaaatacta | ctctcataaa | tgggtgggag | tattttgggt | 300 |
| gacaacctac tttgcttggc | tgagtgaagg | aatgatattc | atatnttcat | ttattccatg | 360 |
| gacatttagt tagtgctttt | tataccag | gcatgatgct | gagtgacact | cttgtgtata | 420 |
| tntccaaatn ttngtncngt | cgctgcacat | atctgaaatc | ctatattaag | antttcccaa | 480 |
| natgangtcc ctggttttc | cacgccactt | gatcngtcaa | ngatctcacc | tctgtntgtc | 540 |
| ctaaaaccnt ctnctnnang | gttagacngg | acctctcttc | tcccttcccg | aanaatnaag | 600 |
| tgtgngaaga nanccncncn | ccccctncn | tncnncctng | ccngctnnnc | cncntgtngg | 660 |
| gggngccgcc cccgcggggg | gacccccccn | ttttcccc | | | 698 |

<210> SEQ ID NO 6
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6

| | | | | |
|---|---|---|---|---|
| actagtcaaa aatgctaaaa | taatttggga | gaaaatattt | ttaagtagt | gttatagttt | 60 |
| catgtttatc ttttattatg | tnttgtgaag | ttgtgtcttt | tcactaatta | cctatactat | 120 |
| gccaatattt cctatatct | atccataaca | tttatactac | atttgtaaga | gaatatgcac | 180 |
| gtgaaactta acactttata | aggtaaaaat | gaggtttcca | agatttaata | atctgatcaa | 240 |
| gttcttgtta tttccaaata | gaatggactt | ggtctgttaa | ggggctaagg | gagaagaaga | 300 |
| agataaggtt aaaagttgtt | aatgaccaaa | cattctaaaa | gaaatgcaaa | aaaaaattta | 360 |
| ttttcaagcc ttcgaactat | ttaaggaaag | caaaatcatt | tcctanatgc | atatcatttg | 420 |
| tgagantttc tcantaatat | cctgaatcat | tcatttcagc | tnaggcttca | tgttgactcg | 480 |
| atatgtcatc tagggaaagt | ctatttcatg | gtccaaacct | gttgccatag | ttggtnaggc | 540 |
| tttcctttaa ntgtgaanta | ttnacangaa | attttctctt | tnanagttct | tnatagggtt | 600 |
| aggggtgtgg gaaaagcttc | taacaatctg | tagtgttncg | tgttatctgt | ncagaaccan | 660 |
| aatnacggat cgnangaagg | actgggtcta | tttacangaa | cgaatnatct | ngttnnntgt | 720 |
| gtnnncaact ccngggagcc | | | | | 740 |

<210> SEQ ID NO 7
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7

-continued

```
gctgggagc tcggcatggc ggtccccgct gcagccatgg ggccctcggc gttgggccag      60 agcggcccg gctcgatggc cccgtggtgc tcagtgagca gcggcccgtc gcgctacgtg     120
cttgggatgc aggagctgtt ccggggccac agcaagaccg cgagttcctg gcgcacagcg    180
ccaaggtgca ctcggtggcc tggagttgcg acgggcgtcg cctacctcgg ggtcttcgac    240
aagacgccac gtcttcttgc tgganaanga ccgttggtca aagaaaacaa ttatcgggga    300
catggggata gtgtggacca ctttgttggc atccaagtaa tcctgaccta tttgttacgg    360
cgtctggaga taaaaccatt cgcatctggg atgtgaggac tacaaaatgc attgccactg    420
tgaacactaa aggggagaac attaatatct gctggantcc tgatgggcan accattgctg    480
tagcnacaag gatgatgtgg tgactttatt gatgccaaga accccgttc caaagcaaaa     540 aaacanttcc aanttcgaag tcaccnaaat ctcctggaac aatgaacatn aatatnttct    600
tcctgacaat ggnccttggg tgtntcacat cctcagctnc cccaaaactg aancctgtnc    660 natccacccc                                                           670
```

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8

```
actagtatct aggaatgaac agtaaaagag gagcagttgg ctacttgatt acaacagagt     60
aaatgaagta ctggatttgg gaaaacctgg ttttattaga acatatggaa tgaaagccta    120
cacctagcat tgcctactta gccccctgaa ttaacagagc ccaattgaga caaacccctg    180
gcaacaggaa attcaaggga gaaaagtaa gcaacttggg ctaggatgag ctgactccct    240
tagagcaaag ganagacagc ccccattacc aaataccatt tttgcctggg gcttgtgcag    300
ctggcagtgt tcctgcccca gcatggcacc ttatngtttt gatagcaact tcgttgaatt    360
ttcaccaact tattacttga aattataata tagcctgtcc gtttgctgtn tccaggctgt    420
gatatatntt cctagtggtt tgactttnaa aataaatnag gtttantttt ctcccccnn     480 cnntnctncc nntcnctcnn cnntccccccc cnctcngtcc tccnnnnttn ggggggggccn  540 cccccncggn ggacccccct ttggtccctt agtggaggtt natggcccct ggnnttatcc    600
nggccntann tttccccgtn nnaaatgntt ccccctccca ntcccnccac ctcaanccgg    660
aagcctaagt ttntaccctg ggggtcccc                                      689
```

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9

```
gtccactctc ctttgagtgt actgtcttac tgtgcactct gttttcaac tttctagata      60 taaaaaatgc ttgttctata gtggagtaag agctcacaca cccaaggcag caagataact    120 gaaaaagcg aggcttttt gccaccttgg taaaggccag ttcactgcta tagaactgct     180
```

-continued

| | |
|---|---|
| ataagcctga agggaagtag ctatgagact ttccattttt cttagttctc ccaataggct | 240 |
| ccttcatgga aaaaggcttc ctgtaataat tttcacctaa tgaattagca gtgtgattat | 300 |
| ttctgaaata agagacaaat tgggccgcag agtcttcctg tgatttaaaa taaacaaccc | 360 |
| aaagttttgt ttggtcttca ccaaaggaca tactctaggg ggtatgttgt tgaagacatt | 420 |
| caaaaacatt agctgttctg tctttcaatt tcaagttatt tggagactg cctccatgtg | 480 |
| agttaattac tttgctctgg aactagcatt attgtcatta tcatcacatt ctgtcatcat | 540 |
| catctgaata atattgtgga tttcccccctc tgcttgcatc ttcttttgac tcctctggga | 600 |
| anaaatgtca aaaaaaaagg tcgatctact cngcaaggnc catctaatca ctgcgctgga | 660 |
| aggacccnct gccc | 674 |

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10

| | |
|---|---|
| actagtctgc tgatagaaag cactatacat cctattgttt ctttctttcc aaaatcagcc | 60 |
| ttctgtctgt aacaaaaatg tactttatag agatggagga aaggtctaa tactacatag | 120 |
| ccttaagtgt ttctgtcatt gttcaagtgt attttctgta acagaaacat atttggaatg | 180 |
| ttttctttt ccccttataa attgtaattc ctgaaatact gctgctttaa aaagtcccac | 240 |
| tgtcagatta tattatctaa caattgaata ttgtaaaatat acttgtctta cctctcaata | 300 |
| aaagggtact tttctattan nnagnngnnn gnnnnataaa anaaaa | 346 |

<210> SEQ ID NO 11
<211> LENGTH: 602
<212> TYPE: DNA
<213> ORGANISM: Homo sapien

<400> SEQUENCE: 11

| | |
|---|---|
| actagtaaaa agcagcattg ccaaataatc cctaattttc cactaaaaat ataatgaaat | 60 |
| gatgttaagc ttttttgaaaa gtttaggtta aacctactgt tgttagatta atgtatttgt | 120 |
| tgcttccctt tatctggaat gtggcattag cttttttatt ttaaccctct ttaattctta | 180 |
| ttcaattcca tgacttaagg ttggagagct aaacactggg attttttggat aacagactga | 240 |
| cagttttgca taattataat cggcattgta catagaaagg atatggctac cttttgttaa | 300 |
| atctgcactt tctaaatatc aaaaaaggga aatgaagtta taaatcaatt tttgtataat | 360 |
| ctgtttgaaa catgagtttt atttgcttaa tattagggct ttgcccccttt tctgtaagtc | 420 |
| tcttgggatc ctgtgtagaa ctgttctcat taaacaccaa acagttaagt ccattctctg | 480 |
| gtactagcta caaattcggt ttcatattct acttaacaat ttaaataaac tgaaatattt | 540 |
| ctagatggtc tacttctgtt catataaaaa caaaacttga tttccaaaaa aaaaaaaaaa | 600 |
| aa | 602 |

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12

| | | | | | |
|---|---|---|---|---|---|
| actagtcctg | tgaaagtaca | actgaaggca | gaaagtgtta | ggattttgca | tctaatgttc | 60 |
| attatcatgg | tattgatgga | cctaagaaaa | taaaaattag | actaagcccc | caaataagct | 120 |
| gcatgcattt | gtaacatgat | tagtagattt | gaatatatag | atgtagtatn | ttgggtatct | 180 |
| aggtgtttta | tcattatgta | aaggaattaa | agtaaaggac | tttgtagttg | tttttattaa | 240 |
| atatgcatat | agtagagtgc | aaaaatatag | caaaaatana | aactaaaggt | agaaaagcat | 300 |
| tttagatatg | ccttaatnta | nnaactgtgc | caggtggccc | tcggaataga | tgccaggcag | 360 |
| agaccagtgc | ctgggtggtg | cctcccttg | tctgccccc | tgaagaactt | ccctcacgtg | 420 |
| angtagtgcc | ctcgtaggtg | tcacgtggan | tantgggang | aggccgnncn | gtnanaagaa | 480 |
| ancanngtga | nagtttcncc | gtngangcng | aactgtccct | gngccnnnac | gctcccanaa | 540 |
| cntntccaat | ngacaatcga | gtttccnnnc | tccngnaacc | tngccgnnnn | cnngcccnnc | 600 |
| cantntgnta | accccgcgcc | cggatcgctc | tcnnntcgtt | ctcncncnaa | ngggntttcn | 660 |
| cnnccgccgt | cncnncccccg | cnncc | | | | 685 |

<210> SEQ ID NO 13
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13

| | | | | | |
|---|---|---|---|---|---|
| cactagtcac | tcattagcgt | tttcaatagg | gctcttaagt | ccagtagatt | acgggtagtc | 60 |
| agttgacgaa | gatctggttt | acaagaacta | attaaatgtt | tcattgcatt | tttgtaagaa | 120 |
| cagaataatt | ttataaaatg | tttgtagttt | ataattgccg | aaaataattt | aaagacactt | 180 |
| tttctctgtg | tgtgcaaatg | tgtgtttgtg | atccatttt | tttttttttt | taggacacct | 240 |
| gtttactagc | tagctttaca | atatgccaaa | aaaggatttc | tccctgaccc | catccgtggt | 300 |
| tcaccctctt | ttcccccat | gcttttttgcc | ctagtttata | acaaaggaat | gatgatgatt | 360 |
| taaaaagtag | ttctgtatct | tcagtatctt | ggtcttccag | aaccctctgg | ttgggaaggg | 420 |
| gatcattttt | tactggtcat | ttcccttttgg | agtgtactac | tttaacagat | ggaaagaact | 480 |
| cattggccat | ggaaacagcc | gangtgttgg | gagccagcag | tgcatggcac | cgtccggcat | 540 |
| ctggcntgat | tggtctggct | gccgtcattg | tcagcacagt | gccatgggac | atggggaana | 600 |
| ctgactgcac | ngccaatggt | tttcatgaag | aatacngcat | ncncngtgat | cacgtnancc | 660 |
| angacgctat | gggggncana | gggccanttg | cttc | | | 694 |

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14

| | | | | | |
|---|---|---|---|---|---|
| cagccgcctg | catctgtatc | cagcgccang | tcccgccagt | cccagctgcg | cgcgccccc | 60 |

-continued

```
agtcccgnac ccgttcggcc cangctnagt tagncctcac catnccggtc aaaggangca      120
ccaagtgcat caaatacctg cngtncggat ntaaattcat cttctggctt gccgggattg      180
ctgtccntgc cattggacta nggctccgat ncgactctca gaccanganc atcttcganc      240
naganactaa tnatnattnt tccagcttct acacaggagt ctatattctg atcggatccg      300
gcnccctcnt gatgctggtg ggcttcctga gctgctgcgg ggctgtgcaa gagtcccant      360
gcatgctggg actgttcttc ggcttcntct tggtgatatn cgccattgaa atacctgcgg      420
ccatctgggg atattccact ncgatnatgt gattaaggaa ntccacggag ttttacaagg      480
acacgtacaa cnacctgaaa accnnggatg anccccaccg ggaancnctg aangccatcc      540
actatgcgtt gaactgcaat ggtttggctg gggnccttga acaatttaat cncatacatc      600
tggccccann aaaggacntn ctcgannect tenccgtgna attcgttct gatnccatca       660 cagaagtctc gaacaatcc                                                   679
```

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 15

```
actagtggat aaaggccagg gatgctgctc aacctcctac catgtacagg gacgtctccc       60
cattacaact acccaatccg aagtgtcaac tgtgtcagga ctaanaaacc ctggttttga      120 ttaaaaagg gcctgaaaaa aggggagcca caaatctgtc tgcttcctca cnttantcnt      180
tggcaaatna gcattctgtc tcnttggctg cngcctcanc ncaaaaaanc ngaactcnat      240
cnggcccagg aatacatctc ncaatnaacn aaattganca aggcnntggg aaatgccnga      300
tgggattatc ntccgcttgt tganettcta agtttcnttc ccttcattcn accctgccag      360
ccnagttctg ttagaaaaat gccngaattc naacnccggt tttcntactc ngaatttaga     420
tctncanaaa cttcctggcc acnattcnaa ttnanggnca cgnacanatn ccttccatna     480
ancnaccccc acntttgana gccangacaa tgactgcntn aantgaaggc ntgaaggaan    540
aactttgaaa ggaaaaaaaa ctttgtttcc ggcccttcc aacncttctg tgttnancac     600
tgccttctng naaccctgga agcccngnga cagtgttaca tgttgttcta nnaaacngac     660
ncttnaatnt cnatcttccc nanaacgatt ncncc                                695
```

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16

```
cgccgaagca gcagcgcagg ttgtccccgt tcccctccc ccttcccttc tccggttgcc       60
ttcccgggcc ccttacactc cacagtcccg gtcccgccat gtcccagaaa caagaagaag      120
agaaccctgc ggaggagacc ggcgaggaga agcaggacac gcaggagaaa gaaggtattc      180
tgcctgagag agctgaagag gcaaagctaa aggccaaata cccaagccta ggacaaaagc      240
ctggaggctc cgacttcctc atgaagagac tccagaaagg gcaaaagtac tttgactcng     300
```

```
gagactacaa catggccaaa gccaacatga agaataagca gctgccaagt gcangaccag    360
acaagaacct ggtgactggt gatcacatcc ccaccccaca ggatctgccc agagaaagtc    420
ctcgctcgtc accagcaagc ttgcgggtgg ccaagttgaa tgatgctgcc ggggctctgc    480
canatctgag acgcttccct ccctgcccca cccgggtcct gtgctggctc ctgcccttcc    540
tgcttttgca gccangggtc aggaagtggc ncnggtngtg gctggaaagc aaaacccttt    600
cctgttggtg tcccacccat ggagccctg gggcgagccc angaacttga nccttttgt    660 tntcttncc                                                            669
```

<210> SEQ ID NO 17
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17

```
gcaagatatg gacaactaag tgagaaggta atnctctact gctctagntn ctccnggcnn    60
gacgcgctga ggagannnac gctggcccan ctgccggcca cacacgggga tcntggtnat   120
gcctgcccan gggancccca ncnctcggan cccatntcac accgnnccn tncgcccacn    180 ncctggctcn cncgcccng nccagctcnc gnccccctcc gccnnnctcn ttnncntctc    240 cncncctcc ncnacnacct cctacccncg gctccctccc cagccccccc ccgcaancct    300
ccacnacncc ntcnncncga ancnccctc gcnctcngcc ccngcccct gcccccgcc    360 cncnacnncg cgntcccccg cgcncgcngc ctcnccccct cccacnacag ncncacccgc   420
agncacgcnc tccgcccnct gacgcccnn cccgccgcgc tcaccttcat ggnccnacng   480
ccccgctcnc nccnctgcnc gccgncnngg cgccccgccc cnnccgngtn ccncncgnng   540 cccngcngn angcngtgcg cnncangncc gngccgnncn ncaccctccg nccnccgccc   600
cgcccgctgg gggctcccgc cncgcggntc antccccncc cntncgccca ctntccgntc   660
cnncnctcnc gctcngcgcn cgcccncccnc cccccc                            697
```

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

```
ctcgtgtgaa gggtgcagta cctaagccgg agcggggtag aggcgggccg gcaccccctt    60
ctgacctcca gtgccgccgg cctcaagatc agacatggcc cagaacttga acgacttggc   120
gggacggctg cccgccgggc cccggggcat gggcacggcc tgaagctgt tgctgggggc   180 cggcgccgtg gcctacggtg tgcgcgaatc tgtgttcacc gtggaaggcg ggcncagagc   240
catcttcttc aatcggatcg gtggagtgca caggacacta tcctgggccg anggccttca   300
cttcaggatc cttggttcca gtaccccanc atctatgaca ttcgggccag acctcgaaaa   360
aatctcctcc ctacaggctc caaagaccta cagatggtga atatctccct gcgagtgttg   420
tctcgaccaa tgctcangaa cttcctaaca tgttccancg cctaagggct ggactacnaa   480
```

| | |
|---|---|
| gaacgantgt tgccgtccat tgtcacgaag tgctcaagaa tttnggtggc caagttcaat | 540 |
| gncctcacnn ctgatcnccc agcggggcca agttanccct ggttgatccc cggggactg | 600 |
| acnnaaaagg gccaaggact tcccctcatc ctggataatg tggccntcac aaagctcaac | 660 |
| tttanccacc | 670 |

<210> SEQ ID NO 19
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 19

| | |
|---|---|
| actagtgcca acctcagctc ccaggccagt tctctgaatg tcgaggagtt ccaggatctc | 60 |
| tggcctcagt tgtccttggt tattgatggg ggacaaattg gggatggcca gagccccgag | 120 |
| tgtcgccttg gctcaactgt ggttgatttg tctgtgcccg gaaagtttgg catcattcgt | 180 |
| ccaggctgtg ccctggaaag tactacagcc atcctccaac agaagtacgg actgctcccc | 240 |
| tcacatgcgt cctacctgtg aaactctggg aagcaggaag gcccaagacc tggtgctgga | 300 |
| tactatgtgt ctgtccactg acgactgtca aggcctcatt tgcagaggcc accggagcta | 360 |
| gggcactagc ctgacttta aggcagtgtg tctttctgag cactgtagac caagcccttg | 420 |
| gagctgctgg tttagcctg cacctgggga aaggatgtat ttatttgtat tttcatatat | 480 |
| cagccaaaag ctgaatggaa aagttnagaa cattcctagg tggccttatt ctaataagtt | 540 |
| tcttctgtct gttttgtttt tcaattgaaa agttattaaa taacagattt agaatctagt | 600 |
| gagacc | 606 |

<210> SEQ ID NO 20
<211> LENGTH: 449
<212> TYPE: DNA
<213> ORGANISM: Homo sapien

<400> SEQUENCE: 20

| | |
|---|---|
| actagtaaac aacagcagca gaaacatcag tatcagcagc gtcgccagca ggagaatatg | 60 |
| cagcgccaga gccgaggaga accccgctc cctgaggagg acctgtccaa actcttcaaa | 120 |
| ccaccacagc cgcctgccag gatggactcg ctgctcattg caggccagat aaacacttac | 180 |
| tgccagaaca tcaaggagtt cactgcccaa aacttaggca agctcttcat ggcccaggct | 240 |
| cttcaagaat acaacaacta agaaaaggaa gtttccagaa aagaagttaa catgaactct | 300 |
| tgaagtcaca ccagggcaac tcttggaaga atatatttg catattgaaa agcacagagg | 360 |
| atttctttag tgtcattgcc gattttggct ataacagtgt ctttctagcc ataataaaat | 420 |
| aaaacaaaat cttgactgct tgctcaaaa | 449 |

<210> SEQ ID NO 21
<211> LENGTH: 409
<212> TYPE: DNA
<213> ORGANISM: Homo sapien

<400> SEQUENCE: 21

| | |
|---|---|
| tatcaatcaa ctggtgaata attaaacaat gtgtggtgtg atcatacaaa gggtaccact | 60 |
| caatgataaa aggaacaagc tgcctatatg tggaacaaca tggatgcatt tcagaaactt | 120 |
| tatgttgagt gaaagaacaa acacggagaa catactatgt ggttctcttt atgtaacatt | 180 |

```
acagaaataa aaacagaggc aaccaccttt gaggcagtat ggagtgagat agactggaaa      240
aaggaaggaa ggaaactcta cgctgatgga aatgtctgtg tcttcattgg gtggtagtta      300
tgtggggata tacatttgtc aaaatttatt gaactatata ctaaagaact ctgcatttta      360
ttgggatgta aataatacct caattaaaaa gacaaaaaaa aaaaaaaaa                  409
```

<210> SEQ ID NO 22
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 22

```
acaattttca ttatcttaag cacattgtac atttctacag aacctgtgat tattctcgca      60
tgataaggat ggtacttgca tatggtgaat tactactgtt gacagtttcc gcagaaatcc     120
tatttcagtg gaccaacatt gtggcatggc agcaaatgcc aacatttgt ggaatagcag      180 caaatctaca agagaccctg gttggttttt cgttttgttt tctttgtttt ttccccttc      240 tcctgaatca gcagggatgg aangagggta gggaagttat gaattactcc ttccagtagt     300
agctctgaag tgtcacattt aatatcagtt tttttttaaac atgattctag ttnaatgtag    360
aagagagaag aaagaggaag tgttcacttt tttaatacac tgatttagaa atttgatgtc     420
ttatatcagt agttctgagg tattgatagc ttgctttatt tctgccttta cgttgacagt    480
gttgaagcag ggtgaataac taggggcata tatattttt ttttttgtaa gctgtttcat     540 gatgtttct ttggaatttc cggataagtt caggaaaaca tctgcatgtt gttatctagt     600
ctgaagttcn tatccatctc attacaacaa aaacncccag aacggnttg                649
```

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 23

```
actagtgccg tactggctga atccctgca ggaccaggaa gagaaccagt tcagactttg      60
tactctcagt caccagctct ggaattagat aaattccttg aagatgtcag gaatgggatc    120
tatcctctga cagcctttgg gctgcctcgg ccccagcagc cacagcagga ggaggtgaca    180
tcacctgtcg tgccccctc tgtcaagact ccgacacctg aaccagctga ggtggagact     240
cgcaaggtgg tgctgatgca gtgcaacatt gagtcggtgg aggagggagt caaacaccac   300
ctgacacttc tgctgaagtt ggaggacaaa ctgaaccggc acctgagctg tgacctgatg    360
ccaaatgaga atatccccga gttggcggct gagctggtgc agctgggctt cattagtgag    420
gctgaccaga gccggttgac ttctctgcta aagagactt gaacaagttc aattttgcca    480
ggaacagtac cctcaactca gccgctgtca ccgtctcctc ttagagctca ctcgggccag    540
gccctgatct gcgctgtggc tgtcctggac gtgctgcacc ctctgtcctt cccccagtc    600 agtattacct gtgaagccct tccctccttt attattcagg anggctgggg gggctccttg   660 nttctaacc                                                            669
```

<210> SEQ ID NO 24
<211> LENGTH: 442
<212> TYPE: DNA
<213> ORGANISM: Homo sapien

<400> SEQUENCE: 24

| | | | | | |
|---|---|---|---|---|---|
| actagtacca | tcttgacaga | ggatacatgc | tcccaaaacg | tttgttacca | cacttaaaaa | 60 |
| tcactgccat | cattaagcat | cagtttcaaa | attatagcca | ttcatgattt | acttttcca | 120 |
| gatgactatc | attattctag | tcctttgaat | ttgtaagggg | aaaaaaaaca | aaaacaaaaa | 180 |
| cttacgatgc | acttttctcc | agcacatcag | atttcaaatt | gaaaattaaa | gacatgctat | 240 |
| ggtaatgcac | ttgctagtac | tacacacttt | ggtacaacaa | aaaacagagg | caagaaacaa | 300 |
| cggaaagaga | aaagccttcc | tttgttggcc | cttaaactga | gtcaagatct | gaaatgtaga | 360 |
| gatgatctct | gacgatacct | gtatgttctt | attgtgtaaa | taaaattgct | ggtatgaaat | 420 |
| gacctaaaaa | aaaaaaaga | aa | | | | 442 |

<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)
<223> OTHER INFORMATION: n = A,T,C or G

<400> SEQUENCE: 25

| | | | | | |
|---|---|---|---|---|---|
| tgcaagtacc | acacactgtt | tgaattttgc | acaaaaagtg | actgtaggat | caggtgatag | 60 |
| ccccggaatg | tacagtgtct | tggtgcacca | agatgccttc | taaaggctga | catacccttgg | 120 |
| accctaatgg | ggcagagagt | atagccctag | cccagtggtg | acatgaccac | tcccttctggg | 180 |
| aggcctgagg | tagagggggag | tggtatgtgt | tttctcagtg | gaagcagcac | atgagtgggt | 240 |
| gacaggatgt | tagataaagg | ctctagttag | ggtgtcattg | tcatttgaga | gactgacaca | 300 |
| ctcctagcag | ctggtaaagg | ggtgctggan | gccatggagg | anctctagaa | acattagcat | 360 |
| gggctgatct | gattacttcc | tggcatcccg | ctcacttta | tgggaagtct | tattagangg | 420 |
| atgggacagt | tttccatatc | cttgctgtgg | agctctggaa | cactctctaa | atttccctct | 480 |
| attaaaaatc | actgccctaa | ctacacttcc | tccttgaagg | aatagaaatg | gaactttctc | 540 |
| tgacatantt | cttggcatgg | ggagccagcc | acaaatgana | atctgaacgt | gtccaggttt | 600 |
| ctcctganac | tcatctacat | agaattggtt | aaaccctccc | ttggaataag | gaaaaa | 656 |

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

| | | | | | |
|---|---|---|---|---|---|
| actagttcag | actgccacgc | caaccccaga | aaatacccca | catgccagaa | aagtgaagtc | 60 |
| ctaggtgttt | ccatctatgt | ttcaatctgt | ccatctacca | ggcctcgcga | taaaaacaaa | 120 |
| acaaaaaaac | gctgccaggt | tttagaagca | gttctggtct | caaaaccatc | aggatcctgc | 180 |
| caccagggtt | cttttgaaat | agtaccacat | gtaaaaggga | atttggcttt | cacttcatct | 240 |
| aataactgaa | ttgtcaggct | ttgattgata | attgtagaaa | taagtagcct | tctgttgtgg | 300 |

```
gaataagtta taatcagtat tcatctcttt gtttttgtc actcttttct ctctaattgt    360
gtcatttgta ctgtttgaaa aatatttctt ctatnaaatt aaactaacct gccttaaaaa    420
aaaaaaaaaa aaaa                                                      434
```

```
<210> SEQ ID NO 27
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 27
```

```
actagtccaa cacagtcaga aacattgttt tgaatcctct gtaaaccaag gcattaatct     60
taataaacca ggatccattt aggtaccact tgatataaaa aggatatcca taatgaatat    120
tttatactgc atcctttaca ttagccacta aatacgttat tgcttgatga agacctttca    180
cagaatccta tggattgcag catttcactt ggctacttca tacccatgcc ttaaagaggg    240
gcagtttctc aaaagcagaa acatgccgcc agttctcaag ttttcctcct aactccattt    300
gaatgtaagg gcagctggcc cccaatgtgg ggaggtccga acattttctg aattcccatt    360
ttcttgttcg cggctaaatg acagtttctg tcattactta gattccgatc tttcccaaag    420
gtgttgattt acaaagaggc cagctaatag cagaaatcat gaccctgaaa gagagatgaa    480
attcaagctg tgagccaggc aggamctcag tatggcaaag gtcttgagaa tcngccattt    540
ggtacaaaaa aaattttaaa gcnttatgt tataccatgg aaccatagaa anggcaaggg    600
aattgttaag aanaatttta agtgtccaga cccanaanga aaaaaaaaaa aaaa          654
```

```
<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28
```

```
cgtgtgcaca tactgggagg atttccacag ctgcacggtc acagcccctta cggattgcca    60 ggaaggggcg aaagatatgt gggataaact gagaaaagaa nccaaaaacc tcaacatcca   120
aggcagctta ttcgaactct gcggcagcgg caacggggcg gcgggtccc tgctcccggc    180 gttcccggtg ctcctggtgt ctctctcggc agctttagcg acctgnctt ccttctgagc    240 gtggggccag ctcccccgc ggcgcccacc cacnctcact ccatgctccc ggaaatcgag    300
aggaagatca ttagttcttt ggggacgttn gtgattctct gtgatgctga aaacactca    360 tatagggaat gtgggaaatc ctganctctt tnttatntcg tntgatttct tgtgttttat    420
ttgccaaaat gttaccaatc agtgaccaac cnagcacagc caaaaatcgg acntcngctt    480
tagtccgtct tcacacacag aataagaaaa cggcaaaccc accccacttt tnantttnat    540
tattactaan tttttctgt tgggcaaaag aatctcagga acngccctgg ggccnccgta    600
ctanagttaa ccnagctagt tncatgaaaa atgatgggct ccnccctcaat gggaaagcca    660 agaaaaagnc                                                           670
```

```
<210> SEQ ID NO 29
```

<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29

| actagtcctc cacagcctgt gaatcccct agacctttca agcatagtga gcggagaaga | 60 |
| agatctcagc gtttagccac cttacccatg cctgatgatt ctgtagaaaa ggtttcttct | 120 |
| ccctctccag ccactgatgg gaaagtattc tccatcagtt ctcaaaatca gcaagaatct | 180 |
| tcagtaccag aggtgcctga tgttgcacat ttgccacttg agaagctggg accctgtctc | 240 |
| cctcttgact taagtcgtgg ttcagaagtt acagcaccgg tagcctcaga ttcctcttac | 300 |
| cgtaatgaat gtcccagggc agaaaaagag gatacncaga tgcttccaaa tccttcttcc | 360 |
| aaagcaatag ctgatgggaa gaggagctcc agcagcagca ggaatatcga aacagaaaa | 420 |
| aaaagtgaaa ttgggaagac aaaagctcaa cagcatttgg taaggagaaa aganaagatg | 480 |
| aggaaggaag agagaagaga gacnaagatc nctacggacc gnnncggaag aagaagaagn | 540 |
| aaaaaanaaa a | 551 |

<210> SEQ ID NO 30
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30

| actagttcta tctggaaaaa gcccggggttg gaagaagctg tggagagtgc gtgtgcaatg | 60 |
| cgagactcat ttcttggaag catccctggc aaaaatgcag ctgagtacaa ggttatcact | 120 |
| gtgatagaac ctggactgct ttttgagata atagagatgc tgcagtctga agagacttcc | 180 |
| agcacctctc agttgaatga attaatgatg gcttctgagt caactttact ggctcaggaa | 240 |
| ccacgagaga tgactgcaga tgtaatcgag cttaaaggga aattcctcat caacttagaa | 300 |
| ggtggtgata ttcgtgaaga gtcttcctat aaagtaattg tcatgccgac tacgaaagaa | 360 |
| aaatgccccc gttgttggaa gtatacagcg ggagtcttca gatacactgt gtcctcgatg | 420 |
| tgcagaagtt gtcagtggga aaatagtatt aacagctcac tcgagcaaga accctcctga | 480 |
| cagtactggg ctagaagttt ggatggatta tttacaatat aggaaagaaa gccaagaatt | 540 |
| aggtnatgag tggatgagta aatggtggan gatggggaat tcaaatcaga attatggaag | 600 |
| aagttnttcc tgttactata gaaaggaatt atgtttattt acatgcagaa aatatanatg | 660 |
| tgtggtgtgt accgtggatg gaan | 684 |

<210> SEQ ID NO 31
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31

| gcgcagaaaa ggaaccaata tttcagaaac aagcttaata ggaacagctg cctgtacatc | 60 |

```
aacatcttct cagaatgacc cagaagttat catcgtggga gctggcgtgc ttggctctgc    120
tttggcagct gtgctttcca gagatggaag aaaggtgaca gtcattgaga gagacttaaa    180
agagcctgac agaatagttg gagaattcct gcagccgggt ggttatcatg ttctcaaaga    240
ccttggtctt ggagatacag tggaaggtct tgatgcccag gttgtaaatg gttacatgat    300
tcatgatcag ggaaagcaaa tcagangttc agattcctta ccctctgtca gaaaacaatc    360
aagtgcagag tggaagagct ttccatcacg gaagattcat catgagtctc cggaaagcag    420
ctatggcaga gcccaatgca aagtttattg aaggtgttgt gttacagtta ttagaggaag    480
atgatgttgt gatgggagtt cagtacaagg ataaagagac tgggagatat caaggaactc    540
catgctccac tgactgttgt tgcagatggg cttttctcca anttcaggaa aagcctggtc    600
tcaataaagt ttctgtatca ctcatttggt tggcttctta tgaagaatgc nccc          654
```

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

```
actagtgaag aaaaagaaat tctgatacgg gacaaaaatg ctcttcaaaa catcattctt     60
tatcacctga caccaggagt tttcattgga aaaggatttg aacctggtgt tactaacatt    120
ttaaagacca cacaaggaag caaaatctttt ctgaaagaag taaatgatac acttctggtg    180
aatgaattga atcaaaaga atctgacatc atgacaacaa atggtgtaat tcatgttgta    240
gataaactcc tctatccagc agacacacct gttggaaatg atcaactgct ggaaatactt    300
aataaattaa tcaaatacat ccaaattaag tttgttcgtg gtagcacctt caaagaaatc    360
cccgtgactg tctatnagcc aattattaaa aaatacacca aaatcattga tgggagtgcc    420
tgtgggaaat aactgaaaaa gagaccgaga agaacgaatc attacaggtc ctgaaataaa    480
atacctagga tttctactgg aggtggagaa acagaagaac tctgaagaaa ttgttacaag    540
aagangtccc aaggtcacca aattcattga aggtggtgat ggtctttatt tgaagatgaa    600
gaaattaaaa gacgcttcag ggagacnccc catgaaggaa ttgccagcca caaaaaaatt    660
cagggattag aaa                                                       673
```

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33

```
actagttatt tactttcctc cgcttcagaa ggttttttcag actgagagcc taagcatact     60
ggatctgttg tttcttttgg gtctcacctc atcagtgtgc atagtggcag aaattataaa    120
gaaggttgaa aggagcaggg aaaagatcca gaagcatgtt agttcgacat catcatcttt    180
tcttgaagta tgatgcatat tgcattattt tatttgcaaa ctaggaattg cagtctgagg    240
atcatttaga agggcaagtt caagaggata tgaagatttg agaactttttt aactattcat    300
```

-continued

| | |
|---|---|
| tgactaaaaa tgaacattaa tgttnaagac ttaagacttt aacctgctgg cagtcccaaa | 360 |
| tgaaattatg caactttgat atcatattcc ttgatttaaa ttgggctttt gtgattgant | 420 |
| gaaactttat aaagcatatg gtcagttatt tnattaaaaa ggcaaaacct gaaccacctt | 480 |
| ctgcacttaa agaagtctaa cagtacaaat acctatctat cttagatgga tntatttntt | 540 |
| tntattttta aatattgtac tatttatggt nggtggggct tcttactaa tacacaaatn | 600 |
| aatttatcat ttcaanggca ttctatttgg gtttagaagt tgattccaag nantgcatat | 660 |
| ttcgctactg tnt | 673 |

<210> SEQ ID NO 34
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34

| | |
|---|---|
| actagtttat tcaagaaaag aacttactga ttcctctgtt cctaaagcaa gagtggcagg | 60 |
| tgatcagggc tggtgtagca tccggttcct ttagtgcagc taactgcatt tgtcactgat | 120 |
| gaccaaggag gaaatcacta agacatttga gaagcagtgg tatgaacgtt cttggacaag | 180 |
| ccacagttct gagccttaac cctgtagttt gcacacaaga acgagctcca cctccccttc | 240 |
| ttcaggagga atctgtgcgg atagattggc tggacttttc aatggttctg ggttgcaagt | 300 |
| gggcactgtt atggctgggt atggagcgga cagccccagg aatcagagcc tcagcccggc | 360 |
| tgcctggttg gaaggtacag gtgttcagca ccttcggaaa aagggcataa agtngtgggg | 420 |
| gacaattctc agtccaagaa gaatgcattg accattgctg gctatttgct tnccctagtan | 480 |
| gaattggatn cattttttgac cangatnntt ctnctatgct ttnttgcaat gaaatcaaat | 540 |
| cccgcattat ctacaagtgg tatgaagtcc tgcnnccccc agagaggctg ttcaggcnat | 600 |
| gtcttccaag gcagggtgg gttacaccat tttacctccc ctctccccc agattatgna | 660 |
| cncagaagga atttntttcc tccc | 684 |

<210> SEQ ID NO 35
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35

| | |
|---|---|
| actagtccaa cgcgttngcn aatattcccc tggtagccta cttccttacc cccgaatatt | 60 |
| ggtaagatcg agcaatggct tcaggacatg ggttctcttc tcctgtgatc attcaagtgc | 120 |
| tcactgcatg aagactggct tgtctcagtg tntcaacctc accagggctg tctcttggtc | 180 |
| cacacctcgc tccctgttag tgccgtatga cagcccccat canatgacct tggccaagtc | 240 |
| acggtttctc tgtggtcaat gttggtnggc tgattggtgg aaagtanggt ggaccaaagg | 300 |
| aagncncgtg agcagncanc nccagttctg caccagcagc gcctccgtcc tactngggtg | 360 |
| ttccngtttc tcctggccct gngtgggcta nggcctgatt cgggaanatg cctttgcang | 420 |
| gaaggganga taantgggat ctaccaattg attctggcaa aacnatntct aagattnttn | 480 |
| tgctttatgt ggganacana tctanctctc atttnntgct gnanatnaca ccctactcgt | 540 |

```
gntcgancnc gtcttcgatt ttcgganaca cnccantnaa tactggcgtt ctgttgttaa    600
aaaaaaaaaa aaaa                                                     614
```

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)
<223> OTHER INFORMATION: n = A,T,C or G

<400> SEQUENCE: 36

```
gtggctggcc cggttctccg cttctcccca tccctactt tcctccctcc ctccctttcc    60
ctccctcgtc gactgttgct tgctggtcgc agactccctg acccctccct caccctccc   120 taacctcggt gccaccggat tgccttctt ttcctgttgc ccagcccagc cctagtgtca   180 gggcggggc ctggagcagc ccgaggcact gcagcagaag ananaaaaga cacgacnaac   240
ctcagctcgc cagtccggtc gctngcttcc cgccgcatgg caatnagaca gacgccgctc   300
acctgctctg ggcacacgcg acccgtggtt gatttggcct tcagtggcat caccccttatg  360 ggtatttctt aatcagcgct tgcaaagatg gttaacctat gctacgccag ggagatacag   420
gagactggat tggaacattt ttggggtcta aaggtctgtt tggggtgcaa cactgaataa   480
ggatgccacc aaagcagcta cagcagctgc agatttcaca gcccaagtgt gggatgctgt   540
ctcagganat naattgataa cctggctcat aacacattgt caagaatgtg gatttcccca   600 ggatattat atttgtttac cggggganag gataactgtt tcncntattt taattgaaca   660
aactnaaaca aaanctaagg aaatcc                                       686
```

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37

```
gagacanacn naacgtcang agaanaaaag angcatggaa cacaanccag gcncgatggc    60
caccttccca ccagcancca gcgcccccca gcngccccca ngnccggang accangactc   120
cancctgnat caatctganc tctattcctg gcccatncct acctcggagg tggangccgn   180
aaaggtcgca cnnncagaga agctgctgcc ancaccancc gccccnnccc tgncgggctn   240
nataggaaac tggtgaccnn gctgcanaat tcatacagga gcacgcgang ggcacnnnct   300
cacactgagt tnnngatgan gcctnaccan ggacctnccc cagcnnattg annacnggac   360
tgcggaggaa ggaagacccc gnacnggatc ctggccggcn tgccaccccc ccaccccctag   420 gattatnccc cttgactgag tctctgaggg gctacccgaa cccgcctcca ttccctacca   480
natnntgctc natcgggact gacangctgg ggatnggagg ggctatcccc cancatcccc   540
tnanaccaac agcnacngan natngggggct cccngggtc gggncaacnc tcctncaccc   600
cggcgcnggc cttcggtgnt gtcctccntc aacnaattcc naaanggcgg gccccccngt   660
ggactcctcn ttgttccctc c                                            681
```

<210> SEQ ID NO 38

<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

```
canaaaaaaa aaaacatggc cgaaaccagn aagctgcgcg atggcgccac ggcccctctt      60
ctcccggcct gtgtccggaa ggtttccctc cgaggcgccc cggctcccgc aagcggagga     120
gagggcggga cntgccgggg ccggagctca naggccctgg ggccgctctg ctctcccgcc     180
atcgcaaggg cggcgctaac ctnaggcctc cccgcaaagg tccccnangc ggnggcggcg     240
gggggctgtg anaaccgcaa aaanaacgct gggcgcgcng cgaacccgtc caccccgcg      300
aaggananac ttccacagan gcagcgtttc cacagcccan agccactttt ctagggtgat     360
gcaccccagt aagttcctgn cggggaagct caccgctgtc aaaaaanctc ttcgctccac     420
cggcgcacna aggggangan ggcangangc tgccgcccgc acaggtcatc tgatcacgtc     480
gcccgcccta ntctgctttt gtgaatctcc actttgttca accccacccg ccgttctctc     540
ctccttgcgc cttcctctna ccttaanaac cagcttcctc tacccnatng tanttnctct     600
gcncnngtng aaattaattc ggtccnccgg aacctcttnc ctgtggcaac tgctnaaaga     660
aactgctgtt ctgnttactg cngtccc                                        687
```

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39

```
actagtctgg cctacaatag tgtgattcat gtaggacttc tttcatcaat tcaaacccc       60
tagaaaaacg tatacagatt atataagtag ggataagatt tctaacattt ctgggctctc    120
tgacccctgc gctagactgt ggaaagggag tattattata gtatacaaca ctgctgttgc    180
cttattagtt ataacatgat aggtgctgaa ttgtgattca caatttaaaa acactgtaat    240
ccaaactttt tttttaact gtagatcatg catgtgaatg ttaatgttaa tttgttcaan     300
gttgttatgg gtagaaaaaa ccacatgcct taaaatttta aaaagcaggg cccaaactta    360
ttagtttaaa attaggggta tgtttccagt ttgttattaa ntggttatag ctctgtttag    420
aanaaatcna ngaacangat ttngaaantt aagntgacat tatttnccag tgacttgtta    480
atttgaaatc anacacggca ccttccgttt tggtnctatt ggnntttgaa tccaancngg    540
ntccaaatct tnttggaaac ngtccnttta acttttttac nanatcttat ttttttattt    600
tggaatggcc ctatttaang ttaaaagggg ggggnnccac naccattcnt gaataaaact    660
naatatatat ccttggtccc ccaaaattta aggng                               695
```

<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40

| | | | | | |
|---|---|---|---|---|---|
| actagtagtc | agttgggagt | ggttgctata | ccttgacttc | atttatatga | atttccactt | 60 |
| tattaaataa | tagaaaagaa | atcccggtg | cttgcagtag | agttatagga | cattctatgc | 120 |
| ttacagaaaa | tatagccatg | attgaaatca | aatagtaaag | gctgttctgg | ctttttatct | 180 |
| tcttagctca | tcttaaataa | gtagtacact | tgggatgcag | tgcgtctgaa | gtgctaatca | 240 |
| gttgtaacaa | tagcacaaat | cgaacttagg | atgtgtttct | tctcttctgt | gtttcgattt | 300 |
| tgatcaattc | tttaattttg | ggaacctata | atacagtttt | cctattcttg | gagataaaaa | 360 |
| ttaaatggat | cactgatatt | taagtcattc | tgcttctcat | ctnaatattc | catattctgt | 420 |
| attagganaa | antacctccc | agcacagccc | cctctcaaac | cccacccaaa | accaagcatt | 480 |
| tggaatgagt | ctcctttatt | tccgaantgt | ggatggtata | acccatatcn | ctccaatttc | 540 |
| tgnttgggtt | gggtattaat | ttgaactgtg | catgaaaagn | ggnaatcttt | nctttgggtc | 600 |
| aaantttncc | ggttaatttg | nctngncaaa | tccaatttnc | tttaagggtg | tctttataaa | 660 |
| atttgctatt | cngg | | | | | 674 |

<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41

| | | | | | |
|---|---|---|---|---|---|
| gaaacatgca | agtaccacac | actgtttgaa | ttttgcacaa | aaagtgactg | tagggatcag | 60 |
| gtgatagccc | cggaatgtac | agtgtcttgg | tgcaccaaga | tgccttctaa | aggctgacat | 120 |
| accttgggac | cctaatgggg | cagagagtat | agccctagcc | cagtggtgac | atgaccactc | 180 |
| cctttgggag | gctgaagtta | aagggaatgg | tatgtgtttt | ctcatggaag | cagcacatga | 240 |
| atnggtnaca | ngatgttaaa | ntaaggntct | antttgggtg | tcttgtcatt | tgaaaaantg | 300 |
| acacactcct | ancanctggt | aaaggggtgc | tggaagccat | ggaagaactc | taaaaacatt | 360 |
| agcatgggct | gatctgatta | cttcctggca | tcccgctcac | ttttatggga | agtcttatta | 420 |
| naaggatggg | ananttttcc | atatccttgc | tgttggaact | ctggaacact | ctctaaattt | 480 |
| ccctctatta | aaaatcactg | nccttactac | acttcctcct | tganggaata | gaaatggacc | 540 |
| tttctctgac | ttagttcttg | gcatgggganc | cagcccaaat | taaaatctga | cttntccggt | 600 |
| ttctccngaa | ctcacctact | tgaattggta | aaacctcctt | tggaattagn | aaaaacc | 657 |

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42

| | | | | | |
|---|---|---|---|---|---|
| actagtgctg | aggaatgtaa | acaagtttgc | tgggccttgc | gagacttcac | caggttgttt | 60 |
| cgatagctca | cactcctgca | ctgtgcctgt | cacccaggaa | tgtctttttt | aattagaaga | 120 |
| caggaagaaa | acaaaaacca | gactgtgtcc | cacaatcaga | aacctccgtt | gtggcagang | 180 |

```
ggccttcacc gccaccaggg tgtcccgcca gacagggaga gactccagcc ttctgaggcc      240
atcctgaaga attcctgttt gggggttgtg aaggaaaatc acccggattt aaaaagatgc      300
tgttgcctgc ccgcgtngtn gggaagggac tggtttcctg gtgaatttct taaaagaaaa      360
atattttaag ttaagaaaaa aaaaaaaaa                                         389
```

<210> SEQ ID NO 43
<211> LENGTH: 279
<212> TYPE: DNA
<213> ORGANISM: Homo sapien

<400> SEQUENCE: 43

```
actagtgaca agctcctggt cttgagatgt cttctcgtta aggagatggg ccttttggag       60
gtaaaggata aaatgaatga gttctgtcat gattcactat tctagaactt gcatgacctt     120
tactgtgtta gctcttttgaa tgttcttgaa attttagact ttctttgtaa acaaataata    180
tgtccttatc attgtataaa agctgttatg tgcaacagtg tggagatcct tgtctgattt    240
aataaaatac ttaaacactg aaaaaaaaaa aaaaaaaa                             279
```

<210> SEQ ID NO 44
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 44

```
actagtagca tcttttctac aacgttaaaa ttgcagaagt agcttatcat taaaaaacaa       60
caacaacaac aataacaata atcctaagt gtaaatcagt tattctaccc cctaccaagg      120
atatcagcct gttttttccc ttttttctcc tgggaataat tgtgggcttc ttcccaaatt     180
tctacagcct ctttcctctt ctcatgcttg agcttccctg tttgcacgca tgcgttgtgc     240
aagantgggc tgtttngctt ggantncggt ccnagtggaa ncatgctttc ccttgttact    300
gttggaagaa actcaaacct tcnancccta ggtgttncca ttttgtcaag tcatcactgt    360 attttttgtac tggcattaac aaaaaaagaa atnaaatatt gttccattaa actttaataa    420
aactttaaaa gggaaaaaaa aaaaaaaa                                         449
```

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45

```
actagtgtgg gggaatcacg gacacttaaa gtcaatctgc gaaataattc ttttattaca       60
cactcactga agtttttgag tcccagagag ccattctatg tcaaacattc caagtactct     120
ttgagagccc agcattacat caacatgccc gtgcagttca aaccgaagtc cgcaggcaaa     180
tttgaagctt tgcttgtcat tcaaacagat gaaggcaaga gtattgctat tcgactaatt    240
ggtgaagctc ttggaaaaaa ttnactagaa tactttttgt gttaagttaa ttacataagt    300
tgtattttgt taactttatc tttctacact acaattatgc ttttgtatat atattttgta     360
tgatggatat ctataattgt agattttgtt tttacaagct aatactgaag actcgactga    420
```

```
aatattatgt atctagccca tagtattgta cttaactttt acagggtgaa aaaaaaattc    480
tgtgtttgca ttgattatga tattctgaat aaatatggga atatatttta atgtgggtaa    540
aaaaaaaaaa aaaaaggaa                                                 559

<210> SEQ ID NO 46
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 46
actagttcta gtaccatggc tgtcatagat gcaaccatta tattccattt agtttcttcc    60
tcaggttccc taacaattgt ttgaaactga atatatatgt ttatgtatgt gtgtgtgttc   120
actgtcatgt atatggtgta tatgggatgt gtgcagtttt cagttatata tatattcata   180
tatacatatg catatatatg tataatatac atatatacat gcatacactt gtataatata   240
catatatata cacatatatg cacacatatn atcactgagt tccaaagtga gtctttattt   300
ggggcaattg tattctctcc ctctgtctgc tcactgggcc tttgcaagac atagcaattg   360
cttgatttcc tttggataag agtcttatct tcggcactct tgactctagc cttaaccttta  420 gatttctatt ccagaatacc tctcatatct atcttaaaac ctaaganggg taagangtc    480 ataagattgt agtatgaaag antttgctta gttaaattat atctcaggaa actcattcat   540
ctacaaatta aattgtaaaa tgatggtttg ttgtatctga aaaatgtttt agaacaagaa   600
atgtaactgg gtacctgtta tatcaaagaa cctcnattta ttaagtctcc tcatagccan   660
atccttatat ngccctctct gacctganttt aatananact tgaataatga atagttaatt   720
taggnttggg c                                                        731

<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47
tgcgngccgg tttggccctt cttttgtanga cactttcatc cgccctgaaa tcttcccgat    60
cgttaataac tcctcaggtc cctgcctgca cagggttttt tcttantttg ttgcctaaca   120
gtacaccaaa tgtgacatcc tttcaccaat atngattnct tcataccaca tcntcnatgg   180
anacgactnc aacaattttt tgatnacccn aaanactggg ggctnnaana agtacantct   240
ggagcagcat ggacctgtcn gcnactaang gaacaanagt nntgaacatt tacacaacct   300
ttggtatgtc ttactgaaag anagaaacat gcttctnncc ctagaccacg aggncaaccg   360
caganattgc caatgccaag tccgagcggt tagatcaggt aatacattcc atggatgcat   420
tacatacntt gtccccgaaa nanaagatgc cctaanggct tcttcanact ggtccngaaa   480
acanctacac ctggtgcttg ganaacanac tctttggaag atcatctggc acaagttccc   540
cccagtgggt tttnccttgg cacctancttt accanatcna ttcggaancc attctttgcc   600
ntggcnttnt nttgggacca ntcttctcac aactgnaccc                         640
```

<210> SEQ ID NO 48
<211> LENGTH: 257
<212> TYPE: DNA
<213> ORGANISM: Homo sapien

<400> SEQUENCE: 48

| | | | | | |
|---|---|---|---|---|---|
| actagtatat | gaaaatgtaa | atatcacttg | tgtactcaaa | caaaagttgg | tcttaagctt | 60 |
| ccaccttgag | cagccttgga | aacctaacct | gcctctttta | gcataatcac | attttctaaa | 120 |
| tgattttctt | tgttcctgaa | aaagtgattt | gtattagttt | tacatttgtt | ttttggaaga | 180 |
| ttatatttgt | atatgtatca | tcataaaata | tttaaataaa | agtatctttt | agagtgaaaa | 240 |
| aaaaaaaaaa | aaaaaaa | | | | | 257 |

<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49

| | | | | | |
|---|---|---|---|---|---|
| actagttcag | atgagtggct | gctgaagggg | cccccttgtc | attttcatta | taacccaatt | 60 |
| tccacttatt | tgaactctta | agtcataaat | gtataatgac | ttatgaatta | gcacagttaa | 120 |
| gttgacacta | gaaactgccc | atttctgtat | tacactatca | aataggaaac | attggaaaga | 180 |
| tggggaaaaa | aatcttattt | taaaatggct | tagaaagttt | tcagattact | ttgaaaattc | 240 |
| taaacttctt | tctgtttcca | aaacttgaaa | atatgtagat | ggactcatgc | attaagactg | 300 |
| ttttcaaagc | tttcctcaca | tttttaaagt | gtgattttcc | ttttaatata | catatttatt | 360 |
| ttctttaaag | cagctatatc | ccaacccatg | actttggaga | tataccctatn | aaaccaatat | 420 |
| aacagcangg | ttattgaagc | agctttctca | aatgttgctt | cagatgtgca | agttgcaaat | 480 |
| tttattgtat | ttgtanaata | caattttttgt | tttaaactgt | atttcaatct | atttctccaa | 540 |
| gatgcttttc | atatagagtg | aaatatccca | ngataactgc | ttctgtgtcg | tcgcatttga | 600 |
| cgcataactg | cacaaatgaa | cagtgtatac | ctcttggttg | tgcattnacc | cc | 652 |

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50

| | | | | | |
|---|---|---|---|---|---|
| ttgcgctttg | atttttttag | ggcttgtgcc | ctgtttcact | tatagggtct | agaatgcttg | 60 |
| tgttgagtaa | aaaggagatg | cccaatattc | aaagctgcta | aatgttctct | ttgccataaa | 120 |
| gactccgtgt | aactgtgtga | acacttggga | ttttttctcct | ctgtcccgag | gtcgtcgtct | 180 |
| gctttctttt | ttgggttctt | tctagaagat | tgagaaatgc | atatgacagg | ctgagancac | 240 |
| ctccccaaac | acacaagctc | tcagccacan | gcagcttctc | cacagcccca | gcttcgcaca | 300 |
| ggctcctgga | nggctgcctg | ggggaggcag | acatgggagt | gccaaggtgg | ccagatggtt | 360 |
| ccaggactac | aatgtcttta | tttttaactg | tttgccactg | ctgccctcac | ccctgcccgg | 420 |
| ctctggagta | ccgtctgccc | canacaagtg | ggantgaaat | gggggtgggg | gggaacactg | 480 |

| | |
|---|---|
| attcccantt agggggtgcc taactgaaca gtagggatan aaggtgtgaa cctgngaant | 540 |
| gcttttataa attatnttcc ttgttanatt tattttttaa tttaatctct gttnaactgc | 600 |
| ccngggaaaa gggaaaaaa aaaaaaaaat tctntttaaa cacatgaaca | 650 |

<210> SEQ ID NO 51
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 51

| | |
|---|---|
| tggcgtgcaa ccagggtagc tgaagtttgg gtctgggact ggagattggc cattaggcct | 60 |
| cctganattc cagctcccctt ccaccaagcc cagtcttgct acgtggcaca gggcaaacct | 120 |
| gactcccttt gggcctcagt ttcccctccc cttcatgana tgaaaagaat actacttttt | 180 |
| cttgttggtc taacnttgct ggacncaaag tgtngtcatt attgttgtat tgggtgatgt | 240 |
| gtncaaaact gcagaagctc actgcctatg agaggaanta agagagatag tggatganag | 300 |
| ggacanaagg agtcattatt tggtatagat ccacccntcc caacctttct ctcctcagtc | 360 |
| cctgcncctc atgtntctgg tntggtgagt cctttgtgcc accanccatc atgctttgca | 420 |
| ttgctgccat cctgggaagg gggtgnatcg tctcacaact tgttgtcatc gtttganatg | 480 |
| catgctttct tnatnaaaca aanaaannaa tgtttgacag ngtttaaaat aaaaaanaaa | 540 |
| caaaa | 545 |

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52

| | |
|---|---|
| actagtagaa gaactttgcc gcttttgtgc ctctcacagg cgcctaaagt cattgccatg | 60 |
| ggaggaagac gatttggggg gggagggggg ggggcangg tccgtggggc tttccctant | 120 |
| ntatctccat ntccantgnn cnntgtcgcc tcttccctcg tcncattnga anttantccc | 180 |
| tggncccnn ncctctccn ncctncncct ccccccctccg ncctccnn cttttntan | 240 |
| ncttcccccat ctccntcccc cctnanngtc ccaacnccgn cagcaatnnc ncacttnctc | 300 |
| nctccncncc tccnnccgtt cttctntctct cnacntntnc ncnnntnccn tgccnntnaa | 360 |
| annctctccc cnctgcaanc gattctctcc ctccncnnan ctntccactc cntncttctc | 420 |
| ncncgctcct nttcntcnnc ccacctctcn ccttcgnccc cantacnctc nccnccttn | 480 |
| cgnntcnttn nnntcctcnn accncccncc tcccttcncc cctcttctcc ccggtntntc | 540 |
| tctctcccnc nncncnncct cnnccccntcc nngcgnccnt ttccgccccn cnccnccntt | 600 |
| ccttcntcnc cantccatcn cntntnccat nctncctncc nctcacnccc gctncccccn | 660 |
| ntctctttca cacngtcc | 678 |

<210> SEQ ID NO 53
<211> LENGTH: 502
<212> TYPE: DNA

```
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53
tgaagatcct ggtgtcgcca tgggccgccg ccccgcccgt tgttaccggt attgtaagaa      60
caagccgtac ccaaagtctc gcttctgccg aggtgtccct gatgccaaaa ttcgcatttt     120
tgacctgggg cggaaaaang caaaantgga tgagtctccg ctttgtggcc acatggtgtc     180
agatcaatat gagcagctgt cctctgaagc cctgnangct gcccgaattt gtgccaataa     240
gtacatggta aaaagtngtg gcnaagatgc ttccatatcc gggtgcggnt ccacccttc     300 cacgtcatcc gcatcaacaa gatgttgtcc tgtgctgggg ctgacaggct cccaacaggc     360
atgcgaagtg cctttggaaa acccanggca ctgtggccag ggttcacatt gggccaattn     420
atcatgttca tccgcaccaa ctgcagaaca angaacntgt naattnaagc cctgcccagg     480
gncaanttca aatttcccgg cc                                              502

<210> SEQ ID NO 54
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 54
actagtccaa gaaaaatatg cttaatgtat attacaaagg ctttgtatat gttaacctgt      60
tttaatgcca aaagtttgct tgtccacaa tttccttaag acctcttcag aaagggattt     120
gtttgcctta atgaatactg ttgggaaaaa acacagtata atgagtgaaa agggcagaag     180
caagaaattt ctacatctta gcgactccaa gaagaatgag tatccacatt tagatggcac     240
attatgagga ctttaatctt tccttaaaca caataatgtt ttcttttttc ttttattcac     300
atgatttcta agtatatttt tcatgcagga cagttttttca accttgatgt acagtgactg     360
tgttaaattt ttctttcagt ggcaacctct ataatcttta aaatatggtg agcatcttgt     420 ctgtttttgaa ngggatatga cnatnaatct atcagatggg aaatcctgtt tccaagttag     480
aaaaaaaaaa aaaa                                                        494

<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55
actagtaaaa agcagcattg ccaaataatc cctaattttc cactaaaaat ataatgaaat      60
gatgttaagc tttttgaaaa gtttaggtta aacctactgt tgttagatta atgtatttgt     120
tgcttcccct tatctggaat gtggcattag cttttttatt ttaaccctct ttaattctta     180
ttcaattcca tgacttaagg ttggagagct aaacactggg attttttggat aacagactga     240 cagttttgca taattataat cggcattgta catagaaagg atatggctac cttttgttaa     300
atctgcactt tctaaatatc aaaaaaggga aatgaagtat aaatcaattt ttgtataatc     360
```

```
tgtttgaaac atganttta tttgcttaat attanggctt tgcccttttc tgttagtctc    420
ttgggatcct gtgtaaaact gttctcatta acaccaaac agttaagtcc attctctggt    480
actagctaca aattccgttt catattctac ntaacaattt aaattaactg aaatatttct   540
anatggtcta cttctgtcnt ataaaaacna aacttgantt nccaaaaaaa aaaaaaaaa    600 aaaaaa                                                              606

<210> SEQ ID NO 56
<211> LENGTH: 183
<212> TYPE: DNA
<213> ORGANISM: Homo sapien

<400> SEQUENCE: 56
actagtatat ttaaacttac aggcttattt gtaatgtaaa ccaccatttt aatgtactgt    60
aattaacatg gttataatac gtacaatcct tccctcatcc catcacacaa cttttttgt   120 gtgtgataaa ctgattttgg tttgcaataa aaccttgaaa ataaaaaaaa aaaaaaaaa   180 aaa                                                                 183

<210> SEQ ID NO 57
<211> LENGTH: 622
<212> TYPE: DNA
<213> ORGANISM: Homo sapien
<220> FEATURE:
<221> NAME/KEY: misc_feature
<222> LOCATION: (1)...(622)
<223> OTHER INFORMATION: n = A,T,C or G

<400> SEQUENCE: 57
actagtcact actgtcttct ccttgtagct aatcaatcaa tattcttccc ttgcctgtgg    60
gcagtggaga gtgctgctgg gtgtacgctg caccctgccca ctgagttggg gaaagaggat   120
aatcagtgag cactgttctg ctcagagctc ctgatctacc ccaccccta ggatccagga   180 ctgggtcaaa gctgcatgaa accaggcct ggcagcaacc tgggaatggc tggaggtggg    240
agagaacctg acttctcttt ccctctccct cctccaacat tactggaact ctatcctgtt   300
agggatcttc tgagcttgtt tccctgctgg gtgggacaga agacaaagga gaagggangg   360
tctacaanaa gcagcccttc tttgtcctct ggggttaatg agcttgacct ananttcatg   420
gaganaccan aagcctctga tttttaattt ccntnaaatg tttgaagtnt atatntacat   480
atatatattt ctttnaatnt ttgagtcttt gatatgtctt aaaatccant ccctctgccn   540
gaaacctgaa ttaaaaccat gaanaaaaat gtttnccta aagatgttan taattaattg    600
aaacttgaaa aaaaaaaaaa aa                                            622

<210> SEQ ID NO 58
<211> LENGTH: 433
<212> TYPE: DNA
<213> ORGANISM: Homo sapien

<400> SEQUENCE: 58
gaacaaattc tgattggtta tgtaccgtca aaagacttga agaaatttca tgattttgca    60
gtgtggaagc gttgaaaatt gaaagttact gcttttccac ttgctcatat agtaaaggga   120
tcctttcagc tgccagtgtt gaataatgta tcatccagag tgatgttatc tgtgacagtc   180
accagcttta agctgaacca ttttatgaat accaaataaa tagacctctt gtactgaaaa   240
catatttgtg actttaatcg tgctgcttgg atagaaatat ttttactggt tcttctgaat   300
```

```
tgacagtaaa cctgtccatt atgaatggcc tactgttcta ttatttgttt tgacttgaat      360
ttatccacca aagacttcat tgtgtatca tcaataaagt tgtatgtttc aactgaaaaa      420
aaaaaaaaaa aaa                                                        433
```

<210> SEQ ID NO 59
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 59

```
actagttatt atctgactt cnggttataa tcattctaat gagtgtgaag tagcctctgg       60
tgtcatttgg atttgcattt ctctgatgag tgatgctatc aagcaccttt gctggtgctg     120
ttggccatat gtgtatgttc cctggagaag tgtctgtgct gagccttggc ccacttttta    180
attaggcgtn tgtcttttta ttactgagtt gtaaganttc tttatatatt ctggattcta    240
gacccttatc agatacatgg tttgcaaata ttttctccca ttctgtgggt tgtgttttca    300
ctttatcgat aatgtcctta gacatataat aaatttgtat tttaaaagtg acttgatttg    360
ggctgtgcaa ggtgggctca cgcttgtaat cccagcactt tgggagactg aggtgggtgg    420
atcatatgan gangctagga gttcgaggtc agcctggcca gcatagcgaa aacttgtctc    480
tacnaaaaat acaaaaatta gtcaggcatg gtggtgcacg tctgtaatac cagcttctca    540
ggangctgan gcacaaggat cacttgaacc ccagaangaa gangttgcag tganctgaag    600
atcatgccag gcaacaaaa atgagaactt gtttaaaaaa aaaaaaaa                  649
```

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60

```
actagttcag gccttccagt tcactgacaa acatggggaa gtgtgcccag ctggctggaa      60
acctggcagt gataccatca agcctgatgt ccaaaagagc aaagaatatt tctccaagca    120
gaagtgagcg ctgggctgtt ttagtgccag gctgcggtgg gcagccatga aacaaaacc     180 tcttctgtat ttttttttc cattagtana acacaagact cngattcagc cgaattgtgg    240
tgtcttacaa ggcagggctt tcctacaggg ggtgganaaa acagcctttc ttcctttggt    300
aggaatggcc tgagttggcg ttgtgggcag gctactggtt tgtatgatgt attagtagag    360
caacccatta atcttttgta gtttgtatna aacttganct gagaccttaa acaaaaaaaa    420
aaa                                                                   423
```

<210> SEQ ID NO 61
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61

```
cgggactgga atgtaaagtg aagttcggag ctctgagcac gggctcttcc cgccgggtcc      60
tccctcccca gacccagag ggagaggccc accccgccca gccccgcccc agccctgct      120 caggtctgag tatgctggg agtcgggggc cacaggcctc tagctgtgct gctcaagaag      180
actggatcag ggtanctaca agtgccgggc ccttgccttt gggattctac cctgttccta      240
atttggtgtt ggggtgcggg gtccctggcc ccctttttcca cactncctcc ctccngacag      300
caacctccct tggggcaatt gggcctggnt ctccncccgn tgttgcnacc ctttgttggt      360 ttaaggncttt taaaaatgtt annttttccc ntgccngggt aaaaaagga aaaactnaa       420 aaa                                                                  423

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62
gctggagagg ggtacggact ttcttggagt tgtcccaggt tggaatgaga ctgaactcaa      60
gaagagaccc taagagactg gggaatggtt cctgccttca ggaaagtgaa agacgcttag     120
gctgtcaaca cttaaaggaa gtccccttga agcccagagt ggacagacta gacccattga     180
tggggccact ggccatggtc cgtggacaag acattccngt gggccatggc acaccggggg     240
ggatcaaaat gtgtacttgt ggggtctcgc cccttgccaa aaccaaacca ntcccactcc     300
tgtcnttgga ctttcttccc attccctcct ccccaaatgc acttccctc ctccctctgc     360 ccctcctgtg ttttttggaat tctgtttccc tcaaaattgt taattttta nttttngacc     420 atgaacttat gtttgggtc nangttcccc ttnccaatgc atactaatat attaatggtt      480
attttatttt gaaatatttt ttaatgaact tggaaaaaat tnntgaatt tccttncttc      540 cntttnttt ggggggggtg ggggntggg ttaaaattttt tttggaancc cnatnggaaa      600
ttnttacttg gggcccccct naaaaantn anttccaatt cttnnatgc ccctnttccn       660 ctaaaaaaaa ananannaaa aan                                             683

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63
actagtcata aagggtgtgc gcgtcttcga cgtggcggtc ttggcgccac tgctgcgaga      60
cccggccctg gacctcaagg tcatccactt ggtgcgtgat cccgcgcgg tggcgagttc     120 acggatccgc tcgcgccacg gcctcatccg tgagagccta caggtggtgc gcagccgaga     180
ccgcgagctc accgcatgcc cttcttggag gccgcgggcc acaagcttgg cgcccanaaa     240
gaaggcgtng ggggcccgca aantaccacg ctctgggcgc tatggaangt cctcttgcaa     300
taatattggt tnaaaanctg canaanagcc cctgcanccc cctgaactgg gntgcagggc     360
cncttacctn gtttggntgc ggttacaaag aacctgtttn ggaaaaccct nccnaaaacc     420
```

```
ttccgggaaa attntncaaa tttttnttgg ggaattnttg ggtaaacccc ccnaaaatgg      480
gaaacntttt tgccctnnaa antaaaccat tnggttccgg gggccccccc ncaaaaccct      540 tttttnttt tttntgcccc cantnncccc ccggggcccc tttttttngg ggaaaanccc      600
cccccctncc nanantttta aaagggnggg anaattttn nttnccccc gggnccccn       660 ggngntaaaa nggtttcncc ccccgaggg gngggnnnc ctcnnaaacc cntntcnnna      720 ccncttttn n                                                         731

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64
actagttgtg caaaccacga ctgaagaaag acgaaaagtg ggaaataact tgcaacgtct      60
gttagagatg gttgctacac atgttgggtc tgtagagaaa catcttgagg agcagattgc     120
taaagttgat agagaatatg aagaatgcat gtcagaagat ctctcggaaa atattaaaga     180
gattagagat aagtatgaga agaaagctac tctaattaag tcttctgaag aatgaagatn     240
aaatgttgat catgtatata tatccatagt gaataaaatt gtctcagtaa agttgtaaaa     300
aaaaaaaaaa aaa                                                      313

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65
actagttccc tggcaggcaa gggcttccaa ctgaggcagt gcatgtgtgg cagagagagg      60
caggaagctg gcagtggcag cttctgtgtc tagggagggg tgtggctccc tccttccctg     120
tctgggaggt tggagggaag aatctaggcc ttagcttgcc ctcctgccac ccttcccctt     180
gtagatactg ccttaacact ccctcctctc tcagctgtgg ctgccaccca agccaggttt     240
ctccgtgctc actaatttat ttccaggaaa ggtgtgtgga agacatgagc cgtgtataat     300
atttgtttta acattttcat tgcaagtatt gaccatcatc cttggttgtg tatcgttgta     360
acacaaatta atgatattaa aaagcatcca aacaaagccn annnnnaana nnannngaaa     420

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
<223> OTHER INFORMATION: n = A,T,C or G

<400> SEQUENCE: 66 actagttttcc tatgatcatt aaactcattc tcagggttaa gaaaggaatg taaatttctg      60
cctcaatttg tacttcatca ataagttttt gaagagtgca gatttttagt caggtcttaa     120
aaataaactc acaaatctgg atgcatttct aaattctgca aatgtttcct ggggtgactt     180
```

```
aacaaggaat aatcccacaa tatacctagc tacctaatac atggagctgg ggctcaaccc    240
actgttttta aggatttgcg cttacttgtg gctgaggaaa aataagtagt tccgagggaa    300
gtagttttta aatgtgagct tatagatngg aaacagaata tcaacttaat tatggaaatt    360
gttagaaacc tgttctcttg ttatctgaat cttgattgca attactattg tactggatag    420
actccagccc attgcaaagt ctcagatatc ttanctgtgt agttgaattc cttggaaatt    480 cttttttaaga aaaattgga gtttnaaaga aataaacccc tttgttaaat gaagcttggc    540
tttttggtga aaaanaatca tcccgcaggg cttattgttt aaaaanggaa ttttaagcct    600
ccctggaaaa anttgttaat taaatgggga aaatgntggg naaaaattat ccgttagggt    660
ttaaagggaa aactta                                                    676

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67
caccattaaa gctgcttacc aagaacttcc ccagcatttt gacttccttg tttgatagct     60
gaattgtgag caggtgatag aagagccttt ctagttgaac atacagataa tttgctgaat    120
acattccatt taatgaaggg gttacatctg ttacgaagct actaagaagg agcaagagca    180 tagggggaaaa aaatctgatc agaacgcatc aaactcacat gtgcccctc tactacaaac    240 agattgtagt gctgtggtgg tttattccgt tgtgcagaac ttgcaagctg agtcactaaa    300
cccaaagaga ggaaattata ggttagttaa acattgtaat cccaggaact aagtttaatt    360 cactttgaa gtgttttgtt tttatttttt ggtttgtctg atttactttg ggggaaaang    420
ctaaaaaaaa aggatatca atctctaatt cagtgcccac taaagttgt ccctaaaaag    480 tctttactgg aanttatggg acttttttaag ctccaggtnt tttggtcctc caaattaacc    540
ttgcatgggc cccttaaaat tgttgaanggg cattcctgcc tctaagtttg gggaaaattc    600
ccccnttttn aaaatttgga                                                620

<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68
actagtagct ggtacataat cactgaggag ctatttctta acatgctttt atagaccatg     60
ctaatgctag accagtattt aagggctaat ctcacacctc cttagctgta agagtctggc    120
ttagaacaga cctctctgtg caataacttg tggccactgg aaatccctgg gccggcatt    180 gtattggggt tgcaatgact cccaagggcc aaaagagtta aaggcacgac tgggatttct    240
tctgagactg tggtgaaact ccttccaagg ctgagggggt cagtangtgc tctggaggg    300 actcggcacc actttgatat tcaacaagcc acttgaagcc caattataaa attgttattt    360
tacagctgat ggaactcaat ttgaaccttc aaaactttgt tagtttatcc tattatattg    420
```

| | |
|---|---|
| ttaaacctaa ttacatttgt ctagcattgg atttggttcc tgtngcatat gttttttcn | 480 |
| cctatgtgct cccctccccc nnatcttaat ttaaaccnca attttgcnat tcnccnnnnn | 540 |
| nannnannna a | 551 |

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69

| | |
|---|---|
| cagaaatgga aagcagagtt ttcatttctg tttataaacg tctccaaaca aaaatggaaa | 60 |
| gcagagtttt cattaaatcc tttacctttt tttttttctt ggtaatcccc tcaaataaca | 120 |
| gtatgtggga tattgaatgt taaagggata ttttttttcta ttatttttat aattgtacaa | 180 |
| aattaagcaa atgttaaaag ttttatatgc tttattaatg ttttcaaaag gtatnataca | 240 |
| tgtgatacat tttttaagct tcagttgctt gtcttctggt actttctgtt atgggctttt | 300 |
| ggggagccan aaaccaatct acnatctctt tttgtttgcc aggacatgca ataaaattta | 360 |
| aaaaataaat aaaaactatt nagaaattga aaaaaa | 396 |

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70

| | |
|---|---|
| actagtgcaa aagcaaatat aaacatcgaa aaggcgttcc tcacgttagc tgaagatatc | 60 |
| cttcgaaaga cccctgtaaa agagcccaac agtgaaaatg tagatatcag cagtggagga | 120 |
| ggcgtgacag gctggaagag caaatgctgc tgagcattct cctgttccat cagttgccat | 180 |
| ccactacccc gttttctctt cttgctgcaa aataaaccac tctgtccatt tttaactcta | 240 |
| aacagatatt tttgtttctc atcttaacta tccaagccac ctatttatt tgttctttca | 300 |
| tctgtgactg cttgctgact ttatcataat tttcttcaaa caaaaaatg tatagaaaaa | 360 |
| tcatgtctgt gacttcattt ttaaatgnta cttgctcagc tcaactgcat ttcagttgtt | 420 |
| ttatagtcca gttcttatca acattnaaac ctatngcaat catttcaaat ctattctgca | 480 |
| aattgtataa gaataaaagt tagaatttaa caattaaaaa aaaaaaaaa aaaaaa | 536 |

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)
<223> OTHER INFORMATION: n = A,T,C or G

<400> SEQUENCE: 71

| | |
|---|---|
| gacaaagcgt taggagaaga anagaggcag ggaanactnc ccaggcacga tggccncctt | 60 |
| cccaccagca accagcgccc cccaccagcc cccaggcccg gacgacgaag actccatcct | 120 |
| ggattaatct nacctctntc gcctgnccca ttcctacctc ggaggtggag gccggaaagg | 180 |

-continued

```
tcncaccaag aganaanctg ctgccaacac caaccgcccc agccctggcg ggcacganag    240
gaaactggtg accaatctgc agaattctna gaggaanaag cnaggggccc cgcgctnaga    300
cagagctgga tatgangcca gaccatggac nctacncccn ncaatncana cgggactgcg    360
gaagatggan gacccncgac nngatcaggc cngctnncca nccccccacc cctatgaatt    420
attcccgctg aangaatctc tganngcgtt ccannaaagc gcctccccnc cnaacgnaan    480
tncaacatng ggattananng ctgggaactg naaggggcaa ancctnnaat atccccagaa    540
acaanctctc ccnaanaaac tggggcncct catnggtggn accaactatt aactaaaccg    600
cacgccaagn aantataaaa gggggccccc tccncggnng acccccttt  gtcccttaat    660 ganggttatc cnccttgcgt accatggtnc ccnnttctgt ntgnatgttt ccnctcccct    720
ccncctatnt cnagccgaac tcnnatttnc ccgggggtgc natcnantng tncnccttn     780 ttngttgncc cngcccttc cgncggaacn cgtttccccg ttantaacgg cacccggggn     840
aagggtgntt ggcccctcc ctccc                                         865
```

<210> SEQ ID NO 72
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 72

```
cctggacttg tcttggttcc agaacctgac gacccggcga cggcgacgtc tcttttgact     60
aaaagacagt gtccagtgct ccngcctagg agtctacggg gaccgcctcc cgcgccgcca    120
ccatgcccaa cttctctggc aactggaaaa tcatccgatc ggaaaacttc gangaattgc    180
tcnaantgct gggggtgaat gtgatgctna ngaanattgc tgtggctgca gcgtccaagc    240
cagcagtgga gatcnaacag gagggagaca ctttctacat caaaacctcc accaccgtgc    300
gcaccacaaa gattaacttc nnngttgggg aggantttga ggancaaact gtggatngga    360
ngcctgtnaa aacctggtga aatgggagaa tganaataaa atggtctgtg ancanaaact    420
cctgaaagga gaaggccccc anaactcctg gaccngaaaa actgacccnc cnatngggga    480
actgatnctt gaaccctgaa cgggcgggat ganccttttt tnttgccncc naangggttc    540
tttccntttc cccaaaaaaa                                                560
```

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73

```
ctggggancc ggcggtnngc nccatntcnn gncgcgaagg tggcaataaa aanccnctga     60
aaccgcncaa naaacatgcc naagatatgg acgaggaaga tngngctttc nngnacaanc    120
gnanngagga acanaacaaa ctcnangagc tctcaagcta atgccgcggg aagggggccc    180
ttggccacnn gtggaattaa gaaatctggc aaanngtann tgttccttgt gcctnangag    240
ataagngacc cttatttca tctgtatta aacctctctn ttccctgnca taacttcttt     300
```

```
tnccacgtan agntggaant anttgttgtc ttggactgtt gtncatttta gannaaactt    360
ttgttcaaaa aaaaaataa                                                 379
```

```
<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 74
actagttcag actgccacgc caaccccaga aaatacccca catgccagaa aagtgaagtc     60
ctaggtgttt ccatctatgt ttcaatctgt ccatctacca ggcctcgcga taaaaacaaa    120
acaaaaaaac gctgccaggt tttanaagca gttctggtct caaaaccatc aggatcctgc    180
caccagggtt cttttgaaat agtaccacat gtaaaaggga atttggcttt cacttcatct    240
aatcactgaa ttgtcaggct ttgattgata attgtagaaa taagtagcct tctgttgtgg    300
gaataagtta taatcagtat tcatctcttt gttttttgtc actcttttct ctctnattgt    360
gtcatttgta ctgtttgaaa aatatttctt ctataaaatt aaactaacct gccttaaaaa    420
aaaaaaaaaa aaaaaaa                                                   437
```

```
<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75
ctccgtcgcc gccaagatga tgtgcggggc gccctccgcc acgcagccgg ccaccgccga     60
gacccagcac atcgccgacc aggtgaggtc ccagcttgaa gagaaagaaa caagaagtt    120 ccctgtgttt aaggccgtgt cattcaagag ccaggtggtc gcggggacaa actacttcat    180
caaggtgcac gtcggcgacg aggacttcgt cacctgcga gtgttccaat ctctccctca    240
tgaaaacaag cccttgacct tatctaacta ccagaccaac aaagccaagc atgatgagct    300
gacctatttc tgatcctgac tttggacaag gcccttcagc cagaagactg acaaagtcat    360
cctccgtcta ccagagcgtg cacttgtgat cctaaaataa gcttcatctc cgggctgtgc    420
ccttggggtg aaggggcan gatctgcact gcttttgcat ttctcttcct aaatttcatt    480
gtgttgattc tttccttcca ataggtgatc ttnattactt tcagaatatt ttccaaatna    540
gatatatttt naaaatcctt aaaaaaaaaa aaaaaaaa                            579
```

```
<210> SEQ ID NO 76
<211> LENGTH: 666
<212> TYPE: DNA
<213> ORGANISM: Homo sapien
<220> FEATURE:
<221> NAME/KEY: misc_feature
<222> LOCATION: (1)...(666)
<223> OTHER INFORMATION: n = A,T,C or G

<400> SEQUENCE: 76
gtttatccta tctctccaac cagattgtca gctccttgag ggcaagagcc acagtatatt     60
tccctgtttc ttccacagtg cctaataata ctgtggaact aggttttaat aatttttaa    120
```

```
ttgatgttgt tatgggcagg atggcaacca gaccattgtc tcagagcagg tgctggctct    180
ttcctggcta ctccatgttg gctagcctct ggtaacctct tacttattat cttcaggaca    240
ctcactacag ggaccaggga tgatgcaaca tccttgtctt tttatgacag gatgtttgct    300
cagcttctcc aacaataaaa agcacgtggt aaaacacttg cggatattct ggactgtttt    360
taaaaaatat acagtttacc gaaaatcata ttatcttaca atgaaaagga ntttatagat    420
cagccagtga acaacctttt cccaccatac aaaaattcct tttcccgaan gaaaanggct    480
ttctcaataa ncctcacttt cttaanatct tacaagatag ccccganatc ttatcgaaac    540
tcattttagg caaatatgan ttttattgtn cgttacttgt ttcaaaattt ggtattgtga    600
atatcaatta ccaccccat ctcccatgaa anaaanggga aanggtgaan ttcntaancg     660
cttaaa                                                                666

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77
ctgcagcccg ggggatccac taatctacca nggttatttg gcagctaatt ctanatttgg     60
atcattgccc aaagttgcac ttgctggtct cttgggatttg ggccttggaa aggtatcata   120
catanganta tgccanaata aattccattt ttttgaaaat canctccntg gggctggttt    180
tggtccacag cataacangc actgcctcct tacctgtgag gaatgcaaaa taaagcatgg    240
attaagtgag aagggagact ctcagccttc agcttcctaa attctgtgtc tgtgactttc    300 gaagttttt aaacctctga atttgtacac atttaaaatt tcaagtgtac tttaaaataa    360
aatacttcta atgggaacaa aaaaaaaaaa aaaaaa                              396

<210> SEQ ID NO 78
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 78
gcatcctagc cgccgactca cacaaggcag gtgggtgagg aaatccagag ttgccatgga     60
gaaaattcca gtgtcagcat tcttgctcct tgtggccctc tcctacactc tggccagaga   120
taccacagtc aaacctggag ccaaaaagga cacaaaggac tctcgaccca aactgcccca   180
gaccctctcc agaggttggg gtgaccaact catctggact cagacatatg aagaagctct   240
atataaatcc aagacaagca acaaacccttt gatgattatt catcacttgg atgagtgccc   300
acacagtcna gctttaaaga aagtgtttgc tgaaaataaa gaaatccaga aattggcaga   360
gcagtttgtc ctcctcaatc tggtttatga acaactgac aaacacctttt ctcctgatgg    420 ccagtatgtc ccaggattat gtttgttgac ccatctctga cagttgaagc cgatatcctg   480
ggaagatatt cnaccgtct ctatgcttac aaactgcaga tacgctctgt tgcttgacac    540
atgaaaaagc tctcaagttg ctnaaaatga attgtaagaa aaaaaatctc cagccttctg   600
```

| | |
|---|---|
| tctgtcggct tgaaaattga aaccagaaaa atgtgaaaaa tggctattgt ggaacanatn | 660 |
| gacacctgat taggttttgg ttatgttcac cactatttt aanaaaanan nttttaaaat | 720 |
| ttggttcaat tntcttttn aaacaatntg tttctacntt gnganctgat ttctaaaaaa | 780 |
| aataatnttt ggc | 793 |

<210> SEQ ID NO 79
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

| | |
|---|---|
| actagtatgg ggtgggaggc cccacccttc tccctaggc gctgttcttg ctccaaaggg | 60 |
| ctccgtggag agggactggc agagctgang ccacctgggg ctggggatcc cactcttctt | 120 |
| gcagctgttg agcgcaccta accactggtc atgcccccac ccctgctctc cgcacccgct | 180 |
| tcctcccgac cccangacca ggctacttct cccctcctct tgcctccctc ctgcccctgc | 240 |
| tgcctctgat cgtangaatt gangantgtc ccgccttgtg gctganaatg gacagtggca | 300 |
| ggggctggaa atgggtgtgt gtgtgtgtgt gtgtgtgtgt gtgtgtgtgt gcnccccccc | 360 |
| tgcaagaccg agattgaggg aaancatgtc tgctgggtgt gaccatgttt cctctccata | 420 |
| aantncccct gtgacnctca naaaaaaaaa aaaaaa | 456 |

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

| | |
|---|---|
| ctttgtacct ctagaaaaga taggtattgt gtcatgaaac ttgagtttaa attttatata | 60 |
| taaaactaaa agtaatgctc actttagcaa cacatactaa aattggaacc atactgagaa | 120 |
| gaatagcatg acctccgtgc aaacaggaca agcaaatttg tgatgtgttg attaaaaaga | 180 |
| aataaataaa tgtgtatatg tgtaacttgt atgtttatgt ggaatacaga ttgggaaata | 240 |
| aaatgtattt cttactgtga aaaaaaaaaa aaaaaaaaa aana | 284 |

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

| | |
|---|---|
| gccaccaaca ttccaagcta ccctgggtac ctttgtgcag tagaagctag tgagcatgtg | 60 |
| agcaagcggt gtgcacacgg agactcatcg ttataattta ctatctgcca agagtagaaa | 120 |
| gaaaggctgg ggatatttgg gttggcttgg ttttgatttt ttgcttgttt gtttgttttg | 180 |
| tactaaaaca gtattatctt ttgaatatcg tagggacata agtatataca tgttatccaa | 240 |
| tcaagatggc tagaatggtg cctttctgag tgtctaaaac ttgacacccc tggtaaatct | 300 |

```
ttcaacacac ttccactgcc tgcgtaatga agttttgatt cattttaac cactggaatt      360 tttcaatgcc gtcattttca gttagatnat tttgcacttt gagattaaaa tgccatgtct      420
atttgattag tcttattttt ttattttac aggcttatca gtctcactgt tggctgtcat      480
tgtgacaaag tcaaataaac ccccnaggac aacacacagt atgggatcac atattgtttg      540
acattaagct ttggccaaaa aatgttgcat gtgttttacc tcgacttgct aaatcaatan      600
canaaaggct ggctnataat gttggtggtg aaataattaa tnantaacca aaaaaaaan      660 aaaaaaaaa a                                                             671
```

<210> SEQ ID NO 82
<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82

```
ctgcagatgt ttcttgaatg ctttgtcaaa ttaanaaagt taaagtgcaa taatgtttga       60
agacaataag tggtggtgta tcttgtttct aataagataa actttttttgt ctttgcttta      120 tcttattagg gagttgtatg tcagtgtata aaacatactg tgtggtataa caggcttaat      180
aaattcttta aaggaaaaa aaaaaaaaaa aaaaaaa                                 217
```

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83

```
cgcgagtggg agcaccagga tctcgggctc ggaacgagac tgcacggatt gtttttaagaa      60 aatggcagac aaaccagaca tgggggaaat cgccagcttc gatnaggcca agctgaanaa      120
aacggagacg caggagaaga acaccctgcc gaccaaagag accattgagc angagaagcg      180
gagtgaaatt tcctaagatc ctggaggatt tcctaccccc gtcctcttcg agacccagt       240 cgtgatgtgg aggaagagcc acctgcaaga tggacacgag ccacaagctg cactgtgaac      300
ctgggcactc cgcgccgatg ccaccggcct gtgggtctct gaagggaccc cccccaatcg      360
gactgccaaa ttctccggtt tgccccggga tattatacaa nattatttgt atgaataatg      420
annataaaac acacctcgtg gcancaaana aaaaaaaaa                              460
```

<210> SEQ ID NO 84
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 84

```
tggtggatct tggctctgtg gagctgctgg gacgggatct aaaagactat tctggaagct       60
gtggtccaan gcatttgct ggcttaacgg gtcccggaac aaaggacacc agctctctaa       120
```

-continued

| aattgaagtt tacccganat aacaatcttt tgggcagaga tgcctatttt aacaaacncc | 180 |
| gtccctgcgc aacaacnaac aatctctggg aaataccggc catgaacntg ctgtctcaat | 240 |
| cnancatctc tctagctgac cgatcatatc gtcccagatt actacanatc ataataattg | 300 |
| atttcctgta naaaaaaaaa aaa | 323 |

<210> SEQ ID NO 85
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85

| aaactgggta ctcaacactg agcagatctg ttctttgagc taaaaaccat gtgctgtacc | 60 |
| aanagtttgc tcctggctgc tttgatgtca gtgctgctac tccacctctg cggcgaatca | 120 |
| gaagcaagca actttgactg ctgtcttgga tacacagacc gtattcttca tcctaaattt | 180 |
| attgtgggct tcacacggca gctggccaat gaaggctgtg acatcaatgc tatcatcttt | 240 |
| cacacaaaga aaaagttgtc tgtgtgcgca aatccaaaac agacttgggt gaaatatatt | 300 |
| gtgcgtctcc tcagtaaaaa agtcaagaac atgtaaaaac tgtggttttt ctggaatgga | 360 |
| attggacata gcccaagaac agaaagaact tgctggggtt ggaggtttca cttgcacatc | 420 |
| atgganggtt tagtgcttat cttatttgtg cctcctggac ttgtccaatt natgaagtta | 480 |
| atcatattgc atcatanttt gctttgttta acatcacatt naaattaaac tgtatttttat | 540 |
| gttatttata gctntaggtt ttctgtgttt aactttttat acnaantttc ctaaactatt | 600 |
| ttggtntant gcaanttaaa aattatattt gggggggggaa taaatattgg antttctgca | 660 |
| gccacaagct tttttttaaaa aaccantaca nccnngttaa atggtnggtc ccnaatggtt | 720 |
| tttgcttttn antagaaaat ttnttagaac natttgaaaa aaaaaaaaa a | 771 |

<210> SEQ ID NO 86
<211> LENGTH: 628
<212> TYPE: DNA
<213> ORGANISM: Homo sapien
<220> FEATURE:
<221> NAME/KEY: misc_feature
<222> LOCATION: (1)...(628)
<223> OTHER INFORMATION: n = A,T,C or G

<400> SEQUENCE: 86

| actagtttgc tttacattt tgaaaagtat tattttttgtc caagtgctta tcaactaaac | 60 |
| cttgtgttag gtaagaatgg aatttattaa gtgaatcagt gtgacccttc ttgtcataag | 120 |
| attatcttaa agctgaagcc aaaatatgct tcaaaagaaa angactttat tgttcattgt | 180 |
| agttcataca ttcaaagcat ctgaactgta gtttctatag caagccaatt acatccataa | 240 |
| gtggagaang aaatagatta atgtcnaagt atgattggtg gagggagcaa ggttgaagat | 300 |
| aatctggggt tgaaattttc tagttttcat tctgtacatt tttagttnga catcagattt | 360 |
| gaaatattaa tgtttacctt tcaatgtgtg gtatcagctg gactcantaa cacccctttc | 420 |
| ttccctnggg gatggggaat ggattattgg aaaatggaaa gaaaaaagta cttaaagcct | 480 |
| tcctttcnca gttctggct cctacccctac tgatttancc agaataagaa aacatttttat | 540 |
| catcntctgc tttattccca ttaatnaant tttgatgaat aaatctgctt ttatgcnnac | 600 |
| ccaaggaatt nagtggnttc ntcnttgt | 628 |

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87

```
tttttattt tttttagaga gtagttcagc ttttatttat aaatttattg cctgttttat      60
tataacaaca ttatactgtt tatggtttaa tacatatggt tcaaaatgta taatacatca     120
agtagtacag ttttaaaatt ttatgcttaa aacaagtttt gtgtaaaaaa tgcagataca     180
ttttacatgg caaatcaatt tttaagtcat cctaaaaatt gatttttttt tgaaatttaa     240
aaacacattt aatttcaatt tctctcttat ataaccttta ttactatagc atggtttcca     300
ctacagttta acaatgcagc aaaattccca tttcacggta aattgggttt taagcggcaa     360
ggttaaaatg ctttgaggat cctnaatacc ctttgaactt caaatgaagg ttatggttgt     420
naatttaacc ctcatgccat aagcagaagc acaagtttag ctgcattttg ctctaaactg     480
taaaancgag cccccgttg aaaaagcaaa agggaccc                              518
```

<210> SEQ ID NO 88
<211> LENGTH: 1844
<212> TYPE: DNA
<213> ORGANISM: Homo sapien

<400> SEQUENCE: 88

```
gagacagtga atcctagtat caaaggattt ttggcctcag aaaagttgt tgattatttt       60
tattttattt tattttttcga gactccgtct caaaaaaaaa aaaaaaaaaa agaatcacaa    120
ggtatttgct aaagcatttt gagctgcttg gaaaaaggga agtagttgca gtagagtttc    180
ttccatcttc ttggtgctgg gaagccatat atgtgtcttt tactcaagct aaggggtata    240
agcttatgtg ttgaatttgc tacatctata tttcacatat tctcacaata agagaatttt    300
gaaatagaaa tatcatagaa catttaagaa agtttagtat aaataatatt ttgtgtgttt    360
taatcccttt gaagggatct atccaaagaa atatttttac actgagctcc ttcctacacg    420
tctcagtaac agatcctgtg ttagtctttg aaaatagctc attttttaaa tgtcagtgag    480
tagatgtagc atacatatga tgtataatga cgtgtattat gttaacaatg tctgcagatt    540
ttgtaggaat acaaaacatg gcctttttta taagcaaaac gggccaatga ctagaataac    600
acatagggca atctgtgaat atgtattata agcagcattc cagaaaagta gttggtgaaa    660
taattttcaa gtcaaaaagg gatatggaaa gggaattatg agtaacctct attttttaag    720
ccttgctttt aaattaaacg ctacagccat ttaagccttg aggataataa agcttgagag    780
taataatgtt aggttagcaa aggtttagat gtatcacttc atgcatgcta ccatgatagt    840
aatgcagctc ttcgagtcat ttctggtcat tcaagatatt cacccttttg cccatagaaa    900
gcaccctacc tcacctgctt actgacattg tcttagctga tcacaagatc attatcagcc    960
tccattattc cttactgtat ataaaataca gagttttata ttttcctttc ttcgttttc    1020
accatattca aaacctaaat ttgttttgc agatggaatg caaagtaatc aagtgttcgt    1080
gctttcacct agaagggtgt ggtcctgaag gaaagaggtc cctaaatatc ccccacctg    1140
ggtgctcctc cttccctggt accctgacta ccagaagtca ggtgctagag cagctggaga    1200
```

```
agtgcagcag cctgtgcttc cacagatggg ggtgctgctg caacaaggct ttcaatgtgc    1260
ccatcttagg gggagaagct agatcctgtg cagcagcctg gtaagtcctg aggaggttcc    1320
attgctcttc ctgctgctgt cctttgcttc tcaacggggc tcgctctaca gtctagagca    1380
catgcagcta acttgtgcct ctgcttatgc atgagggtta aattaacaac cataaccttc    1440
atttgaagtt caaggtgtta ttcaggatcc tcaaagcatt ttaaccttgc cgcttaaaac    1500
ccaatttacc gtgaaatggg aattttgctg cattgttaaa ctgtagtgga aaccatgcta    1560
tagtaataaa ggttatataa gagagaaatt gaaattaaat gtgttttttaa atttcaaaaa   1620 aaaatcaatc tttaggatga cttaaaaatt gatttgccat gtaaaatgta tctgcatttt    1680
ttacacaaaa cttgttttaa gcataaaatt ttaaaactgt actacttgat gtattataca    1740
ttttgaacca tatgtattaa accataaaca gtataatgtt gttataataa aacaggcaat    1800
aaatttataa ataaaagctg aaaaaaaaaa aaaaaaaaa aaaa                      1844
```

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89

```
ttttttttt ttttttagt caatccacat ttattgatca cttattatgt accaggcact       60
gggataaaga tgactgttag tcactcacag taaggaagaa aactagcaaa taagacgatt    120
acaatatgat gtagaaaatg ctaagccaga gatatagaaa ggtcctattg ggtccttctg    180
tcaccttgtc tttccacatc cctacccttc acaggccttc cctccagctt cctgcccccg    240
ctccccactg cagatcccct gggattttgc ctagagctaa acgagganat gggcccctg     300 gccctggcat gacttgaacc caaccacaga ctgggaaagg gagcctttcg anagtggatc    360
actttgatna gaaaacacat agggaattga agagaaantc cccaaatggc cacccgtgct    420
ggtgctcaag aaaagtttgc agaatggata aatgaaggat caagggaatt aatanatgaa    480
taattgaatg gtggctcaat aagaatgact ncnttgaatg acc                      523
```

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90

```
ccagtgtggt ggaatgcaaa gattaccccg gaagctttcg agaagctggg attccctgca     60
gcaaaggaaa tagccaatat gtgtcgtttc tatgaaatga agccagaccg agatgtcaat    120
ctcacccacc aactaaatcc caaagtcaaa agcttcagcc agtttatctc agagaaccag    180 gggagcettc aagggcatgt agaaaatcag ctgttcagat aggcctctgc accacacagc    240
ctctttcctc tctgatcctt ttcctcttta cggcacaaca ttcatgtttg acagaacatg    300
ctggaatgca attgtttgca acaccgaagg atttcctgcg gtcgcctctt cagtaggaag    360
cactgcattg gtgataggac acggtaattt gattcacatt taacttgcta gttagtgata    420 agggggtggta cacctgtttg gtaaaatgag aagcctcgga aacttgggag cttctctcct   480
```

```
accactaatg gggagggcag attattactg ggatttctcc tggggtgaat taatttcaag    540
ccctaattgc tgaaattccc ctnggcaggc tccagttttc tcaactgcat tgcaaaattc    600
cccc                                                                 604
```

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

```
ttttttttt ttttttttta tgattattat ttttttttatt gatctttaca tcctcagtgt     60
tggcagagtt tctgatgctt aataaacatt tgttctgatc agataagtgg aaaaaattgt    120
catttcctta ttcaagccat gcttttctgt gatattctga tcctagttga acatacagaa    180
ataaatgtct aaaacagcac ctcgattctc gtctataaca ggactaagtt cactgtgatc    240
ttaaataagc ttggctaaaa tgggacatga gtggaggtag tcacacttca gcgaagaaag    300
agaatctcct gtataatctc accaggagat tcaacgaatt ccaccacact ggactagtgg    360
atcccccggg ctgcaggaat tcgatatcaa gcttatcgat accgtcgacc tcgagggggg    420
gcccggtacc caattcgccc tatagtgagt cgtattacgc gcgctcactg gccgtcgttt    480
tacaacgtcg tgactgggaa accctggcg ttacccaact taatcgcctt gcagcacatc    540
cccctttcgc cagctggcgt aatagcgaan agcccgcacc gatcgccctt ncaacagttg    600
cgcagcctga atggcgaatg ggacgcgccc tgtagcggcg cattaaagcg ggcngggtg     660 tggnggntcc cccacgtgac cgntacactt ggcagcgcct tacgccggtc nttcgctttc    720
ttcccttcct ttctcgcacc gttcgccggg tttccccgnn agctnttaat cggggggnctc   780 cctttanggg tncnaattaa nggnttacng gaccttngan cccaaaaact ttgattaggg    840
ggaaggtccc cgaagggg                                                  858
```

<210> SEQ ID NO 92
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92

```
gttgaatctc ctggtgagat tatacaggag attctctttc ttcgctgaag tgtgactacc     60
tccactcatg tccatttta gccaagctta tttaagatca cagtgaactt agtcctgtta    120
tagacgagaa tcgaggtgct gttttagaca tttatttctg tatgttcaac taggatcaga    180
atatcacaga aaagcatggc ttgaataagg aaatgacaat tttttccact tatctgatca    240
gaacaaatgt ttattaagca tcagaaactc tgccaacact gaggatgtaa agatcaataa    300
aaaaaataat aatcatnann naaanannan nngaagggcg gccgccaccg cggtggagct    360
ccagcttttg ttccctttag tgagggttaa ttgcgcgctt ggcgttaatc atggtcatag    420
ctgtttcctg tgtgaaattg ttatccggct cacaattccn cncaacatac gagccggaa     480 gcntnangtg taaaagcctg ggggtgccta attgagtgag ctnactcaca ttaattgngt    540
```
tgcgctccac ttgcccgctt ttccantccg ggaaacctgt tcgnc                        585

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93
cggcagtgtt gctgtctgcg tgtccacctt ggaatctggc tgaactggct gggaggacca      60
agactgcggc tggggtgggc anggaaggga accgggggct gctgtgaagg atcttggaac     120
ttccctgtac ccaccttccc cttgcttcat gtttgtanag gaaccttgtg ccggccaagc     180
ccagtttcct tgtgtgatac actaatgtat ttgctttttt tgggaaatan anaaaaatca     240
attaaattgc tantgtttct ttgaannnnn nnnnnnnnn nnnnnngggg ggggncgccc       300
ccncggngga aacncccct tttgttccct taattgaaa ggttaattng cncncntggc       360
gttaanccnt gggccaaanc tngttnccg tgntgaaatt gttatcccc tcccaaattc       420 ccccccnncc ttccaaaccc ggaaanccth annntgttna ancccggggg gttgcctaan     480
ngnaattnaa ccnaaccccc ntttaaatng nntttgcncn ccacnngccc cncttcccca     540
nttcggggaa aaccctntcc gtgccca                                         567

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94
actagtcaaa aatgctaaaa taatttggga gaaaatattt tttaagtagt gttatagttt      60
catgtttatc ttttattatg ttttgtgaag ttgtgtcttt tcactaatta cctatactat     120
gccaatattt cctatatct atccataaca tttatactac atttgtaana naatatgcac     180
gtgaaactta acactttata aggtaaaaat gaggtttcca anatttaata atctgatcaa     240
gttcttgtta tttccaaata gaatggactt ggtctgttaa gggctaagga gaagaggaag     300
ataaggttaa aagttgttaa tgaccaaaca ttctaaaaga aatgcaaaaa aaaagtttat     360
tttcaagcct tcgaactatt taaggaaagc aaaatcattt cctaaatgca tatcatttgt     420
gagaatttct cattaatatc ctgaatcatt catttcacta aggctcatgt tnactccgat     480
atgtctctaa gaaagtacta tttcatggtc caaacctggt tgccatantt gggtaaaggc     540
tttcccttaa gtgtgaaant atttaaaatg aaatttttcct cttttttaaaa attctttana   600 agggttaagg gtgttgggga                                                 620

<210> SEQ ID NO 95
<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

-continued

```
ctcgaccttc tctgcacagc ggatgaaccc tgagcagctg aagaccagaa aagccactat     60
nactttntgc ttaattcang agcttacang attcttcaaa gagtgngtcc agcatccttt    120
gaaacatgag ttcttaccag cagaagcaga cctttacccc accacctcag cttcaacagc    180
agcaggtgaa acaacccatc cagcctccac ctnaggaaat atttgttccc acaaccaagg    240
agccatgcca ctcaaaggtt ccacaacctg naaacacaaa nattccagag ccaggctgta    300
ccaaggtccc tgagccaggg ctgtaccaan gtccctgagc caggttgtac caangtccct    360
gagccaggat gtaccaaggt ccctgancca ggttgtccca ggtccctgag ccaggctaca    420
ccaagggcct gngccaggca gcatcaangt ccctgaccaa ggcttatcaa               470
```

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

```
tttttttttt tttttttttt ggaattaaaa gcaatttaat gagggcagag caggaaacat     60
gcatttcttt tcattcgaat cttcagatga accctgagca gccgaagacc agaaaagcca    120
tgaagacttt ctgcttaatt cagggcttaa caggattctt cagagtgtgt gtgaacaaaa    180
gctttatagt acgtattttt aggatacaaa taagagagag actatggctt ggggtgagaa    240
tgtactgatt acaaggtcta cagacaatta agacacagaa acagatggga agagggtgnc    300
cagcatctgg nggttggctt ctcaagggct tgtctgtgca ccaaattact tctgcttggn    360
cttctgctga gctgggcctg gagtgaccgt tgaaggacat ggctctggta cctttgtgta    420
gcctgncaca ggaactttgg tgtatccttg ctcaggaact ttgatggcac ctggctcagg    480
aaacttgatg aagccttggt caagggacct tgatgcttgc tggctcaggg accttggngn    540 anccctgggct canggacctt tgncncaacc ttggcttcaa gggaccctg gnacatcctg    600 gcnnagggac ccttgggncc aaccctgggc ttnagggacc ctttggntnc nanccttggc    660
```

<210> SEQ ID NO 97
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97

```
gggaccatac anagtattcc tctcttcaca ccaggaccag ccactgttgc agcatgagtt     60
cccagcagca gaagcagccc tgcatccac cccctcagct tcagcagcag caggtgaaac    120
agccttgcca gcctccacct caggaaccat gcatccccaa aaccaaggag ccctgccacc    180
ccaaggtgcc tgagccctgc accccaaag tgcctgagcc ctgccagccc aaggttccag    240
agccatgcca ccccaaggtg cctgagccct gcccttcaat agtcactcca gcaccagccc    300
agcagaanac caagcagaag taatgtggtc cacagccatg cccttgagga gccggccacc    360
agatgctgaa tccctatcc cattctgtgt atgagtccca tttgccttgc aattagcatt    420
ctgtctcccc caaaaaaaaa a                                             441
```

<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98

```
gtattcctct cttcacacca ggaccagcca ctgttgcagc atgagttccc agcagcagaa      60
gcagccctgc atcccacccc ctcagcttca gcagcagcag gtgaaacagc cttgccagcc     120
tccacctcag gaaccatgca tccccaaaac caaggagccc tgccacccca aggtgcctga     180
gccctgccac cccaaagtgc ctgagccctg ccagcccaag gttccagagc catgccaccc     240
caaggtgcct gagccctgcc cttcaatagt cactccagca ccagcccagc agaanaccaa     300
gcagaagtaa tgtggtccac agccatgccc ttgaggagcc ggccaccana tgctgaatcc     360
cctatcccat tctgtgtatg agtcccattt gccttgcaat tagcattctg tctccccaa      420
aaaagaatgt gctatgaagc tttctttcct acacactctg agtctctgaa tgaagctgaa     480
ggtcttaant acaganctag ttttcagctg ctcagaattc tctgaagaaa agatttaaga     540
tgaaaggcaa atgattcagc tccttattac cccattaaat tcnctttcaa ttccaaaaaa     600
```

<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99

```
actagtgact gagttcctgg caaagaaatt tgacctggac cagttgataa ctcatgtttt      60
accatttaaa aaaatcagtg aaggatttga gctgctcaat tcaggacaaa gcattcgaac     120
ggtcctgacg ttttgagatc caaagtggca ggaggtctgt gttgtcatgg tgaactggag     180
tttctcttgt gagagttccc tcatctgaaa tcatgtatct gtctcacaaa tacaagcata     240
agtagaagat tgttgaaga catagaaccc ttataaagaa ttattaacct ttataaacat      300
ttaaagtctt gtgagcacct gggaattagt ataataacaa tgttnatatt tttgatttac     360
attttgtaag gctataattg tatcttttaa gaaaacatac cttggatttc tatgttgaaa     420
tggagatttt taagagtttt aaccagctgc tgcagatata ttactcaaaa cagatatagc     480
gtataaagat atagtaaatg catctcctag agtaatattc acttaacaca ttggaaacta     540
ttattttta gatttgaata tnaatgttat tttttaaaca cttgttatga gttacttggg     600
attacatttt gaaatcagtt cattccatga tgcanattac tgggattaga ttaagaaga     660
cggaaaa                                                              667
```

<210> SEQ ID NO 100
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

```
gttttgtttg taagatgatc acagtcatgt tacactgatc taaaggacat atatataacc    60
ctttaaaaaa aaaatcactg cctcattctt atttcaagat gaatttctat acagactaga   120 tgttttctg aagatcaatt agacattttg aaaatgattt aaagtgtttt ccttaatgtt    180
ctctgaaaac aagtttcttt tgtagtttta accaaaaaag tgccttttt gtcactggat    240 tctcctagca ttcatgattt ttttttcata caatgaaatt aaaattgcta aaatcatgga   300
ctggctttct ggttggattt caggtaagat gtgtttaagg ccagagcttt tctcagtatt   360
tgattttttt ccccaatatt tgatttttta aaaatataca catnggtgct gcatttatat   420
ctgctggttt aaaattctgt catatttcac ttctagcctt ttagttatgg caaatcatat   480
tttactttta cttaaagcat ttggtnattt ggantatctg gttctannct aaaaaaanta   540
attctatnaa ttgaantttt ggtactcnnc catatttgga tcc                     583
```

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101

```
gtggagacgt acaaagagca gccgctcaag acacctggga agaaaagaa aggcaagccc     60 gggaaacgca aggagcagga aaagaaaaaa cggcgaactc gctctgcctg gttagactct   120
ggagtgactg ggagtgggct agaaggggac cacctgtctg acacctccac aacgtcgctg   180
gagctcgatt cacggaggca ttgaaatttt cagcaganac cttccaagga catattgcag   240
gattctgtaa tagtgaacat atggaaagta ttagaaatat ttattgtctg taaatactgt   300
aaatgcattg gaataaaact gtctccccca ttgctctatg aaactgcaca ttggtcattg   360
tgaatatttt ttttttgcc aaggctaatc caattattat tatcacattt accataattt    420
attttgtcca ttgatgtatt tatttgtaa atgtatcttg gtgctgctga atttctatat    480
tttttgtaca taatgcnttt anatatacct atcaagtttg ttgataaatg acncaatgaa   540
gtgncncnan ttggnggttg aatttaatga atgcctaatt ttattatccc aa           592
```

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102

```
cgtcctaagc acttagacta catcagggaa gaacacagac cacatccctg tcctcatgcg     60
gcttatgttt tctggaagaa agtggagacc nagtccttgg ctttagggct ccccggctgg   120
gggctgtgca ntccggtcag ggcgggaagg gaaatgcacc gctgcatgtg aacttacagc   180
ccaggcggat gccccttccc ttagcactac ctggcctcct gcatccctc gcctcatgtt    240 cctcccacct tcaaanaatg aanaacccca tgggcccagc ccttgccct ggggaaccaa    300 ggcagccttc caaaactcag gggctgaagc anactattag gcaggggct gactttgggt    360 gacactgccc attccctctc agggcagctc angtcaccn ggnctcttga acccagcctg    420
```

```
ttcctttgaa aaagggcaaa actgaaaagg gctttttccta naaaaagaaa aaccagggaa      480
ctttgccagg gcttcnntnt taccaaaacn ncttctcnng gatttttaat tccccattng      540
gcctccactt accngggcn atgccccaaa attaanaatt tcccatc                     587
```

<210> SEQ ID NO 103
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 103

```
anaggactgg ccctacntgc tctctctcgt cctacctatc aatgcccaac atggcagaac       60
ctgcanccct tggncactgc anatggaaac ctctcagtgt cttgacatca ccctacccnt      120
gcggtgggtc tccaccacaa ccactttgac tctgtggtcc ctgnanggtg gnttctcctg      180
actggcagga tggaccttan ccacatatc cctctgttcc ctctgctnag anaaagaatt       240
cccttaacat gatataatcc acccatgcaa ntngctactg gcccagctac catttaccat      300
ttgcctacag aatttcattc agtctacact ttggcattct ctctggcgat agagtgtggc      360
tgggctgacc gcaaaaggtg ccttacacac tggcccccac cctcaaccgt tgacncatca     420
gangcttgcc tcctccttct gattnncccc catgttggat atcagggtgc tcnagggatt      480
ggaaaagaaa caaaac                                                      496
```

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104

```
gcacctgctc tcaatccnnc tctcaccatg atcctccgcc tgcanaaact cctctgccaa       60
ctatggangt ggttttcnggg gtggctcttg ccaactggga agaagccgtg gtgtctctac     120
ctgttcaact cngtttgtgt ctgggggatc aactngggc tatggaagcg gctnaactgt      180
tgttttggtg gaagggctgg taattggctt tgggaagtng cttatngaag ttggcctngg     240
gaagttgcta ttgaaagtng ccntggaagt ngntttggtg ggggttttg ctggtggcct     300 ttgttnaatt tgggtgcttt gtnaatggcg gccccctcnc ctgggcaatg aaaaaaatca     360
ccnatgcngn aaacctcnac nnaacagcct gggcttccct cacctcgaaa aaagttgctc     420 ccccccaaa aaaggncaan ccctcaann tggaangttg aaaaaatcct cgaatgggga       480
ncccnaaaac aaaaanccc ccntttcccn gnaangggg aatacncc cccccactta        540 cnaaacccct tntaaaaac ccccgggaa aaaaa                                  575
```

<210> SEQ ID NO 105
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105

```
cactagtagg atagaaacac tgtgtcccga gagtaaggag agaagctact attgattaga    60
gcctaaccca ggttaactgc aagaagaggc gggatacttt cagcttttcca tgtaactgta   120 tgcataaagc caatgtagtc cagtttctaa gatcatgttc caagctaact gaatcccact   180
tcaatacaca ctcatgaact cctgatgaa caataacagg cccaagcctg tggtatgatg    240
tgcacacttg ctagactcan aaaaaatact actctcataa atgggtggga gtattttggt   300
gacaacctac tttgcttggc tgagtgaagg aatgatattc atatattcat ttattccatg   360
gacatttagt tagtgctttt tatataccag gcatgatgct gagtgacact cttgtgtata   420
tttccaaatt tttgtacagt cgctgcacat atttgaaatc atatattaag acttccaaaa   480
aatgaagtcc ctggtttttc atggcaactt gatcagtaaa ggattcncct ctgtttggta   540
cttaaaacat ctactatatn gttnanatga aattcctttt cccncctcc cgaaaaaana    600 aagtggtggg gaaaaaaaa                                                619

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106
cattggtnct ttcatttgct ntggaagtgt nnatctctaa cagtggacaa agttcccngt    60
gccttaaact ctgtnacact tttgggaant gaaaanttng tantatgata ggttattctg   120
angtanagat gttctggata ccattanatn tgccccngt gtcagaggct catattgtgt    180
tatgtaaatg gtatntcatt cgctactatn antcaattg aaatanggtc tttgggttat    240
gaatantnng cagcncanct nanangctgt ctgtngtatt cattgtggtc atagcacctc   300
acancattgt aacctcnatc nagtgagaca nactagnaan ttcctagtga tggctcanga   360
ttccaaatgg nctcatntcn aatgtttaaa agttanttaa gtgtaagaaa tacagactgg   420
atgttccacc aactagtacc tgtaatgacn ggcctgtccc aacacatctc ccttttccat   480
gactgtggta ncccgcatcg gaaaaa                                        506

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107
gttgagtctg tactaaacag taagatatct caatgaacca taaattcaac tttgtaaaaa    60
tcttttgaag catagataat attgtttggt aaatgtttct tttgtttggt aaatgtttct   120
tttaaagacc ctcctattct ataaaactct gcatgtagag gcttgtttac ctttctctct   180
ctaaggttta caataggagt ggtgatttga aaaatataaa attatgagat tggttttcct   240
gtggcataaa ttgcatcact gtatcatttt cttttttaac cggtaagant ttcagtttgt   300
tggaaagtaa ctgtganaac ccagtttccc gtccatctcc cttagggact acccatagaa   360
catgaaaagg tccccacnga agcaagaaga taagtctttc atggctgctg gttgcttaaa   420
```

```
ccactttaaa accaaaaaat tccccttgga aa                                    452

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108
atcttcttcc cttaattagt tnttatttat ntattaaatt ttattgcatg tcctggcaaa       60
caaaaagaga ttgtagattg gcttctggct ccccaaaagc ccataacaga aagtaccaca      120
agaccncaac tgaagcttaa aaatctatc acatgtataa tacctttnga agaacattaa       180
tanagcatat aaaactttta acatntgctt aatgttgtnc aattataaaa ntaatngaaa      240
aaaatgtccc tttaacatnc aatatcccac atagtgttat ttnaggggat taccnngnaa      300
naaaaaaagg gtagaaggga tttaatgaaa actctgctnn ccatttctgt ttanaaacgt      360
ctccagaaca aaaacttntc aantctttca gctaaccgca tttgagctna ggccactcaa      420
aaactccatt agncccactt tctaanggtc tctanagctt actaancctt ttgacccctt      480
accctggnta ctcctgccct ca                                               502

<210> SEQ ID NO 109
<211> LENGTH: 1308
<212> TYPE: DNA
<213> ORGANISM: Homo sapien

<400> SEQUENCE: 109
acccgaggtc tcgctaaaat catcatggat tcacttggcg ccgtcagcac tcgacttggg       60
tttgatcttt tcaaagagct gaagaaaaca aatgatggca acatcttctt ttcccctgtg      120
ggcatcttga ctgcaattgg catggtcctc ctggggaccc gaggagccac cgcttcccag      180
ttggaggagg tgtttcactc tgaaaaagag acgaagagct caagaataaa ggctgaagaa      240
aagaggtga ttgagaacac agaagcagta catcaacaat tccaaaagtt tttgactgaa       300
ataagcaaac tcactaatga ttatgaactg aacataacca acaggctgtt tggagaaaaa      360
acatacctct tccttcaaaa atacttagat tatgttgaaa aatattatca tgcatctctg      420
gaacctgttg attttgtaaa tgcagccgat gaaagtcgaa agaagattaa ttcctggggtt     480
gaaagcaaaa caaatgaaaa aatcaaggac ttgttcccag atggctctat tagtagctct      540
accaagctgt gctggtgaa catggttttat tttaaagggc aatgggacag ggagtttaag      600
aaagaaaata ctaaggaaga gaaattttgg atgaataaga gcacaagtaa atctgtacag      660
atgatgacac agagccattc ctttagcttc actttcctgg aggacttgca ggccaaaatt      720
ctagggattc catataaaaa caacgaccta agcatgtttg tgcttctgcc caacgacatc      780
gatggcctgg agaagataat agataaaata agtcctgaga aattggtaga gtggactagt      840
ccagggcata tggaagaaag aaaggtgaat ctgcacttgc cccggtttga ggtggaggac      900
agttacgatc tagaggcggt cctggctgcc atggggatgg cgatgccttc agtgagcac       960
aaagccgact actcgggaat gtcgtcaggc tccggttgt acgcccagaa gttcctgcac     1020
agttcctttg tggcagtaac tgaggaaggc accgaggctg cagctgccac tgcataggc     1080
tttactgtca catccgcccc aggtcatgaa aatgttcact gcaatcatcc cttcctgttc    1140
ttcatcaggc acaatgaatc caacagcatc ctcttcttcg gcagattttc ttctccttaa    1200
```

```
gatgatcgtt gccatggcat tgctgctttt agcaaaaaac aactaccagt gttactcata   1260
tgattatgaa aatcgtccat tcttttaaat ggtggctcac ttgcattt              1308
```

<210> SEQ ID NO 110
<211> LENGTH: 391
<212> TYPE: PRT
<213> ORGANISM: Homo sapien

<400> SEQUENCE: 110

| | | | | | | | | | | | | | | |
|---|---|---|---|---|---|---|---|---|---|---|---|---|---|---|
| Met | Asp | Ser | Leu | Gly | Ala | Val | Ser | Thr | Arg | Leu | Gly | Phe | Asp | Leu | Phe |
| 1 | | | | 5 | | | | | 10 | | | | | 15 | |
| Lys | Glu | Leu | Lys | Lys | Thr | Asn | Asp | Gly | Asn | Ile | Phe | Phe | Ser | Pro | Val |
| | | | 20 | | | | | 25 | | | | | 30 | | |
| Gly | Ile | Leu | Thr | Ala | Ile | Gly | Met | Val | Leu | Leu | Gly | Thr | Arg | Gly | Ala |
| | | | | 35 | | | | | 40 | | | | | 45 | |
| Thr | Ala | Ser | Gln | Leu | Glu | Glu | Val | Phe | His | Ser | Glu | Lys | Glu | Thr | Lys |
| | | 50 | | | | | 55 | | | | | 60 | | | |
| Ser | Ser | Arg | Ile | Lys | Ala | Glu | Glu | Lys | Glu | Val | Ile | Glu | Asn | Thr | Glu |
| 65 | | | | | 70 | | | | | 75 | | | | | 80 |
| Ala | Val | His | Gln | Gln | Phe | Gln | Lys | Phe | Leu | Thr | Glu | Ile | Ser | Lys | Leu |
| | | | | 85 | | | | | 90 | | | | | 95 | |
| Thr | Asn | Asp | Tyr | Glu | Leu | Asn | Ile | Thr | Asn | Arg | Leu | Phe | Gly | Glu | Lys |
| | | | | 100 | | | | | 105 | | | | | 110 | |
| Thr | Tyr | Leu | Phe | Leu | Gln | Lys | Tyr | Leu | Asp | Tyr | Val | Glu | Lys | Tyr | Tyr |
| | | | 115 | | | | | 120 | | | | | 125 | | |
| His | Ala | Ser | Leu | Glu | Pro | Val | Asp | Phe | Val | Asn | Ala | Ala | Asp | Glu | Ser |
| | 130 | | | | | 135 | | | | | 140 | | | | |
| Arg | Lys | Lys | Ile | Asn | Ser | Trp | Val | Glu | Ser | Lys | Thr | Asn | Glu | Lys | Ile |
| 145 | | | | | 150 | | | | | 155 | | | | | 160 |
| Lys | Asp | Leu | Phe | Pro | Asp | Gly | Ser | Ile | Ser | Ser | Thr | Lys | Leu | Val |
| | | | | 165 | | | | | 170 | | | | | 175 | |
| Leu | Val | Asn | Met | Val | Tyr | Phe | Lys | Gly | Gln | Trp | Asp | Arg | Glu | Phe | Lys |
| | | | 180 | | | | | 185 | | | | | 190 | | |
| Lys | Glu | Asn | Thr | Lys | Glu | Glu | Lys | Phe | Trp | Met | Asn | Lys | Ser | Thr | Ser |
| | | | 195 | | | | | 200 | | | | | 205 | | |
| Lys | Ser | Val | Gln | Met | Met | Thr | Gln | Ser | His | Ser | Phe | Ser | Phe | Thr | Phe |
| | 210 | | | | | 215 | | | | | 220 | | | | |
| Leu | Glu | Asp | Leu | Gln | Ala | Lys | Ile | Leu | Gly | Ile | Pro | Tyr | Lys | Asn | Asn |
| 225 | | | | | 230 | | | | | 235 | | | | | 240 |
| Asp | Leu | Ser | Met | Phe | Val | Leu | Leu | Pro | Asn | Asp | Ile | Asp | Gly | Leu | Glu |
| | | | | 245 | | | | | 250 | | | | | 255 | |
| Lys | Ile | Ile | Asp | Lys | Ile | Ser | Pro | Glu | Lys | Leu | Val | Glu | Trp | Thr | Ser |
| | | | 260 | | | | | 265 | | | | | 270 | | |
| Pro | Gly | His | Met | Glu | Glu | Arg | Lys | Val | Asn | Leu | His | Leu | Pro | Arg | Phe |
| | | 275 | | | | | 280 | | | | | 285 | | | |
| Glu | Val | Glu | Asp | Ser | Tyr | Asp | Leu | Glu | Ala | Val | Leu | Ala | Ala | Met | Gly |
| | 290 | | | | | 295 | | | | | 300 | | | | |
| Met | Gly | Asp | Ala | Phe | Ser | Glu | His | Lys | Ala | Asp | Tyr | Ser | Gly | Met | Ser |
| 305 | | | | | 310 | | | | | 315 | | | | | 320 |
| Ser | Gly | Ser | Gly | Leu | Tyr | Ala | Gln | Lys | Phe | Leu | His | Ser | Ser | Phe | Val |
| | | | | 325 | | | | | 330 | | | | | 335 | |
| Ala | Val | Thr | Glu | Glu | Gly | Thr | Glu | Ala | Ala | Ala | Ala | Thr | Gly | Ile | Gly |
| | | | 340 | | | | | 345 | | | | | 350 | | |

```
Phe Thr Val Thr Ser Ala Pro Gly His Glu Asn Val His Cys Asn His
            355                 360                 365

Pro Phe Leu Phe Phe Ile Arg His Asn Glu Ser Asn Ser Ile Leu Phe
        370                 375                 380

Phe Gly Arg Phe Ser Ser Pro
385                 390
```

<210> SEQ ID NO 111
<211> LENGTH: 1419
<212> TYPE: DNA
<213> ORGANISM: Homo sapien

<400> SEQUENCE: 111

```
ggagaactat aaattaagga tcccagctac ttaattgact tatgcttcct agttcgttgc     60
ccagccacca ccgtctctcc aaaaacccga ggtctcgcta aaatcatcat ggattcactt    120
ggcgccgtca gcactcgact tgggtttgat cttttcaaag agctgaagaa aacaaatgat    180
ggcaacatct tcttttcccc tgtgggcatc ttgactgcaa ttggcatggt cctcctgggg    240
acccgaggag ccaccgcttc ccagttggag gaggtgtttc actctgaaaa agagacgaag    300
agctcaagaa taaaggctga agaaaaagag gtggtaagaa taaaggctga aggaaaagag    360
attgagaaca cagaagcagt acatcaacaa ttccaaaagt ttttgactga ataagcaaa     420
ctcactaatg attatgaact gaacataacc aacaggctgt ttggagaaaa acataccctc    480
ttccttcaaa atacttaga ttatgttgaa aaatattatc atgcatctct ggaacctgtt     540
gattttgtaa atgcagccga tgaaagtcga agaagatta attcctgggt tgaaagcaaa     600
acaaatgaaa aaatcaagga cttgttccca gatggctcta ttagtagctc taccaagctg    660
gtgctggtga acatggttta ttttaagggg caatgggaca gggagtttaa gaaagaaaat    720
actaaggaag agaaattttg gatgaataag agcacaagta atctgtaca gatgatgaca     780
cagagccatt cctttagctt cactttcctg gaggacttgc aggccaaaat tctagggatt    840
ccatataaaa acaacgacct aagcatgttt gtgcttctgc ccaacgacat cgatggcctg    900
gagaagataa tagataaaat aagtcctgag aaattggtag agtggactag tccagggcat    960
atggaagaaa gaaggtgaa tctgcacttg ccccggtttg aggtggagga cagttacgat   1020
ctagaggcgg tcctggctgc catggggatg ggcgatgcct tcagtgagca caaagccgac   1080
tactcgggaa tgtcgtcagg ctccggggttg tacgcccaga agttcctgca cagttccttt   1140
gtggcagtaa ctgaggaagg caccgaggct gcagctgcca ctggcatagg ctttactgtc   1200
acatccgccc caggtcatga aaatgttcac tgcaatcatc ccttcctgtt cttcatcagg   1260
cacaatgaat ccaacagcat cctcttcttc ggcagatttt cttctcctta agatgatcgt   1320
tgccatggca ttgctgcttt tagcaaaaaa caactaccag tgttactcat atgattatga   1380
aaatcgtcca ttctttttaaa tggtggctca cttgcattt                         1419
```

<210> SEQ ID NO 112
<211> LENGTH: 400
<212> TYPE: PRT
<213> ORGANISM: Homo sapien

<400> SEQUENCE: 112

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
            20                  25                  30
```

```
Gly Ile Leu Thr Ala Ile Gly Met Val Leu Gly Thr Arg Gly Ala
            35                  40                  45

Thr Ala Ser Gln Leu Glu Glu Val Phe His Ser Glu Lys Glu Thr Lys
 50                  55                  60

Ser Ser Arg Ile Lys Ala Glu Glu Lys Glu Val Val Arg Ile Lys Ala
 65                  70                  75                  80

Glu Gly Lys Glu Ile Glu Asn Thr Glu Ala Val His Gln Gln Phe Gln
                     85                  90                  95

Lys Phe Leu Thr Glu Ile Ser Lys Leu Thr Asn Asp Tyr Glu Leu Asn
                100                 105                 110

Ile Thr Asn Arg Leu Phe Gly Glu Lys Thr Tyr Leu Phe Leu Gln Lys
            115                 120                 125

Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Ser Thr Lys Leu Val Leu Val Asn Met Val Tyr Phe
            180                 185                 190

Lys Gly Gln Trp Asp Arg Glu Phe Lys Lys Glu Asn Thr Lys Glu Glu
        195                 200                 205

Lys Phe Trp Met Asn Lys Ser Thr Ser Lys Ser Val Gln Met Met Thr
    210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                245                 250                 255

Leu Pro Asn Asp Ile Asp Gly Leu Glu Lys Ile Ile Asp Lys Ile Ser
            260                 265                 270

Pro Glu Lys Leu Val Glu Trp Thr Ser Pro Gly His Met Glu Glu Arg
        275                 280                 285

Lys Val Asn Leu His Leu Pro Arg Phe Glu Val Glu Asp Ser Tyr Asp
    290                 295                 300

Leu Glu Ala Val Leu Ala Ala Met Gly Met Gly Asp Ala Phe Ser Glu
305                 310                 315                 320

His Lys Ala Asp Tyr Ser Gly Met Ser Ser Gly Ser Gly Leu Tyr Ala
                325                 330                 335

Gln Lys Phe Leu His Ser Ser Phe Val Ala Val Thr Glu Glu Gly Thr
            340                 345                 350

Glu Ala Ala Ala Ala Thr Gly Ile Gly Phe Thr Val Thr Ser Ala Pro
        355                 360                 365

Gly His Glu Asn Val His Cys Asn His Pro Phe Leu Phe Phe Ile Arg
    370                 375                 380

His Asn Glu Ser Asn Ser Ile Leu Phe Phe Gly Arg Phe Ser Ser Pro
385                 390                 395                 400

<210> SEQ ID NO 113
<211> LENGTH: 957
<212> TYPE: DNA
<213> ORGANISM: Homo sapien

<400> SEQUENCE: 113
ctcgaccttc tctgcacagc ggatgaaccc tgagcagctg aagaccagaa aagccactat      60
```

-continued

```
gactttctgc ttaattcagg agcttacagg attcttcaaa gagtgtgtcc agcatccttt      120
gaaacatgag ttcttaccag cagaagcaga cctttacccc accacctcag cttcaacagc      180
agcaggtgaa acaacccagc cagcctccac ctcaggaaat atttgttccc acaaccaagg      240
agccatgcca ctcaaaggtt ccacaacctg gaaacacaaa gattccagag ccaggctgta      300
ccaaggtccc tgagccaggc tgtaccaagg tccctgagcc aggttgtacc aaggtccctg      360
agccaggatg taccaaggtc cctgagccag gttgtaccaa ggtccctgag ccaggctaca      420
ccaaggtccc tgagccaggc agcatcaagg tccctgacca aggcttcatc aagtttcctg      480
agccaggtgc catcaaagtt cctgagcaag gatacaccaa agttcctgtg ccaggctaca      540
caaaggtacc agagccatgt ccttcaacgg tcactccagg cccagctcag cagaagacca      600
agcagaagta atttggtgca cagacaagcc cttgagaagc caaccaccag atgctggaca      660
ccctcttccc atctgtttct gtgtcttaat tgtctgtaga ccttgtaatc agtacattct      720 cacccccaagc catagtctct ctcttatttg tatcctaaaa atacggtact ataaagcttt      780
tgttcacaca cactctgaag aatcctgtaa gccccctgaat taagcagaaa gtcttcatgg      840
cttttctggt cttcggctgc tcagggttca tctgaagatt cgaatgaaaa gaaatgcatg      900
tttcctgctc tgccctcatt aaattgcttt taattccaaa aaaaaaaaaa aaaaaaa       957
```

<210> SEQ ID NO 114
<211> LENGTH: 161
<212> TYPE: PRT
<213> ORGANISM: Homo sapien

<400> SEQUENCE: 114

```
Met Ser Ser Tyr Gln Gln Lys Gln Thr Phe Thr Pro Pro Gln Leu
 1               5                   10                  15

Gln Gln Gln Gln Val Lys Gln Pro Ser Gln Pro Pro Gln Glu Ile
                20                  25                  30

Phe Val Pro Thr Thr Lys Glu Pro Cys His Ser Lys Val Pro Gln Pro
                35                  40                  45

Gly Asn Thr Lys Ile Pro Glu Pro Gly Cys Thr Lys Val Pro Glu Pro
        50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
                100                 105                 110

Gly Phe Ile Lys Phe Pro Glu Pro Gly Ala Ile Lys Val Pro Glu Gln
                115                 120                 125

Gly Tyr Thr Lys Val Pro Val Pro Gly Tyr Thr Lys Val Pro Glu Pro
                130                 135                 140

Cys Pro Ser Thr Val Thr Pro Gly Pro Ala Gln Gln Lys Thr Lys Gln
145                 150                 155                 160

Lys
```

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115

```
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgccccngt gtcagaggct catattgtgt      180
tatgtaaatg gtatntcatt cgctactatn antcaattng aaatanggtc tttgggttat    240
gaatantnng cagcncanct nanangctgt ctgtngtatt cattgtggtc atagcacctc    300
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg gaaaaa                                         506
```

<210> SEQ ID NO 116
<211> LENGTH: 3079
<212> TYPE: DNA
<213> ORGANISM: Homo sapien

<400> SEQUENCE: 116

```
ggatccccgg gtttcctaaa ccccccacag agtcctgccc aggccaaaga gcaaggaaaa      60
ggtcaaaggg cagaaaaaat gctgagttag gaggagctat ggaaggataa acctggcctt    120
aaagaggtca aagtggttta taggggggcgc tgagggcttc ccacattctc tggcctaaac    180
cttgcaggca gatctgccca gtgggctctg ggatagctgt gccttcccta acaaaaaaat    240
tgtgcacaaa aggatgaaac tctatttttcc ctctagcaca taaccaagaa tataaggcta    300
cagattgcct ttcccagagg gaaaaccctg cagcaacctg ctgcctggaa aagtgtaaga    360
gcagatcact ggggaatcgt ttgccccccg ctgatggaca gcttcccaa gctccaaggg    420
caggtgctca gcatgtaccg tactgggatg gttgtcaata ctcctggtcc tgtaagagtc    480
ccaggacact gccatgccaa tgcccccctca gttcctggca tcctttttgg gctgctcaca    540
gcccagcct ctatggtgaa gacatacttg ctagcagcgt caccaacttg ttgccaagag    600
atcagtgctc gaaggcaagg ttatttctaa ctgagcagag cctgccagga agaaagcgtt    660
tgcaccccac accactgtgc aggtgtgacc ggtgagctca cagctgcccc ccaggcatgc    720
ccagcccact taatcatcac agctcgacag ctctctcgcc cagcccagtt ctggaaggga    780
taaaagggg catcaccgtt cctgggtaac agagccacct tctgcgtcct gctgagctct    840
gttctctcca gcacctccca acccactagt gcctggttct cttgctccac caggaacaag    900
ccaccatgtc tcgccagtca agtgtgtctt ccggagcggg gggcagtcgt agcttcagca    960
ccgcctctgc catcaccccg tctgtctccc gcaccagctt cacctccgtg tcccggtccg   1020
gggtggcgg tggtggtggc ttcggcaggg tcagccttgc gggtgcttgt ggagtgggtg   1080
gctatggcag ccggagcctc tacaacctgg ggggctccaa gaggatatcc atcagcacta   1140
gtggtggcag cttcaggaac cggtttggtg ctggtgctgg aggcggctat ggctttggag   1200
gtggtgccgg tagtggattt ggtttcggcg gtggagctgg tggtggcttt gggctcggtg   1260
gcggagctgc ctttggaggt ggcttcgtg gccctggctt tcctgtctgc cctcctggag   1320
gtatccaaga ggtcactgtc aaccagagtc tcctgactcc cctcaacctg caaatcgacc   1380
ccagcatcca gagggtgagg accgaggagc gcgagcagat caagaccctc aacaataagt   1440
ttgcctcctt catcgacaag gtgcggttcc tggagcagca gaacaaggtt ctggaaacaa   1500
```

-continued

```
agtggaccct gctgcaggag cagggcacca agactgtgag gcagaacctg gagccgttgt    1560
tcgagcagta catcaacaac ctcaggaggc agctggacag catcgtgggg gaacggggcc    1620
gcctggactc agagctgaga aacatgcagg acctggtgga agacttcaag aacaagtatg    1680
aggatgaaat caacaagcgt accactgctg agaatgagtt tgtgatgctg aagaaggatg    1740
tagatgctgc ctacatgaac aaggtggagc tggaggccaa ggttgatgca ctgatggatg    1800
agattaactt catgaagatg ttctttgatg cggagctgtc ccagatgcag acgcatgtct    1860
ctgacacctc agtggtcctc tccatggaca acaaccgcaa cctggacctg gatagcatca    1920
tcgctgaggt caaggcccag tatgaggaga ttgccaaccg cagccggaca gaagccgagt    1980
cctggtatca gaccaagtat gaggagctgc agcagacagc tggccggcat ggcgatgacc    2040
tccgcaacac caagcatgag atctctgaga tgaaccggat gatccagagg ctgagagccg    2100
agattgacaa tgtcaagaaa cagtgcgcca atctgcagaa cgccattgcg gatgccgagc    2160
agcgtgggga gctggccctc aaggatgcca ggaacaagct ggccgagctg gaggaggccc    2220
tgcagaaggc caagcaggac atggcccggc tgctgcgtga gtaccaggag ctcatgaaca    2280
ccaagctggc cctggacgtg gagatcgcca cttaccgcaa gctgctggag ggcgaggaat    2340
gcagactcag tggagaagga gttggaccag tcaacatctc tgttgtcaca agcagtgttt    2400
cctctggata tggcagtggc agtggctatg gcggtggcct cggtggaggt cttggcggcg    2460
gcctcggtgg aggtcttgcc ggaggtagca gtggaagcta ctactccagc agcagtgggg    2520
gtgtcggcct agtggtgggg ctcagtgtgg ggggctctgg cttcagtgca agcagtagcc    2580
gagggctggg ggtgggcttt ggcagtggcg ggggtagcag ctccagcgtc aaatttgtct    2640
ccaccacctc ctcctcccgg aagagcttca agagctaaga acctgctgca agtcactgcc    2700
ttccaagtgc agcaacccag cccatggaga ttgcctcttc taggcagttg ctcaagccat    2760
gttttatcct tttctggaga gtagtctaga ccaagccaat tgcagaacca cattctttgg    2820
ttcccaggag agccccattc ccagcccctg gtctcccgtg ccgcagttct atattctgct    2880
tcaaatcagc cttcaggttt cccacagcat ggccctgct gacacgagaa cccaaagttt     2940
tcccaaatct aaatcatcaa aacagaatcc ccaccccaat cccaaatttt gttttggttc    3000
taactacctc cagaatgtgt tcaataaaat gttttataat ataagctggt gtgcagaatt    3060
gttttttttt tctacccaa                                                 3079
```

<210> SEQ ID NO 117
<211> LENGTH: 6921
<212> TYPE: DNA
<213> ORGANISM: Homo sapien

<400> SEQUENCE: 117

```
aattctgac tgtccactca aaacttctat tccgatcaaa gctatctgtg actacagaca       60 attgagata accatttaca aagacgatga atgtgttttg gcgaataact ctcatcgtgc      120 aaatggaag gtcattagtc ctactgggaa tgaggctatg gtcccatctg tgtgcttcac      180 gttcctcca ccaaacaaag aagcggtgga ccttgccaac agaattgagc aacagtatca      240 aatgtcctg actctttggc atgagtctca cataaacatg aagagtgtag tatcctggca      300 tatctcatc aatgaaattg atagaattcg agctagcaat gtggcttcaa taaagacaat      360 ctacctggt gaacatcagc aagttctaag taatctacaa tctcgttttg aagattttct      420 gaagatagc caggaatccc aagtcttttc aggctcagat ataacacaac tggaaaagga      480 gttaatgta tgtaagcagt attatcaaga acttcttaaa tctgcagaaa gagaggagca      540
```

```
gaggaatca gtttataatc tctacatctc tgaagttcga aacattagac ttcggttaga      600 aactgtgaa gatcggctga ttagacagat tcgaactccc ctggaaagag atgatttgca      660 gaaagtgtg ttcagaatca cagaacagga gaaactaaag aaagagctgg aacgacttaa      720 gatgatttg ggaacaatca caaataagtg tgaggagttt tcagtcaag cagcagcctc       780 tcatcagtc cctaccctac gatcagagct taatgtggtc cttcagaaca tgaaccaagt      840 tattctatg tcttccactt acatagataa gttgaaaact gttaacttgg tgttaaaaaa      900 actcaagct gcagaagccc tcgtaaaact ctatgaaact aaactgtgtg aagaagaagc      960 gttatagct gacaagaata atattgagaa tctaataagt actttaaagc aatggagatc     1020 gaagtagat gaaaagagac aggtattcca tgccttagag gatgagttgc agaaagctaa     1080 gccatcagt gatgaaatgt ttaaaacgta taagaacgg gaccttgatt ttgactggca      1140 aaagaaaaa gcagatcaat tagttgaaag gtggcaaaat gttcatgtgc agattgacaa     1200 aggttacgg gacttagagg gcattggcaa atcactgaag tactacagag acacttacca     1260 cctttagat gattggatcc agcaggttga aactactcag agaaagattc aggaaaatca     1320 cctgaaaat agtaaaaccc tagccacaca gttgaatcaa cagaagatgc tggtgtccga     1380 atagaaatg aaacagagca aaatggacga gtgtcaaaaa tatgcagaac agtactcagc     1440 acagtgaag gactatgaat tacaaacaat gacctaccgg gccatggtag attcacaaca     1500 aaatctcca gtgaacgcc gaagaatgca gagttcagca gatctcatta ttcaagagtt      1560 atggaccta aggactcgat atactgccct ggtcactctc atgacacaat atattaaatt     1620 gctggtgat tcattgaaga ggctggaaga ggaggagatt aaaaggtgta aggagacttc     1680 gaacatggg gcatattcag atctgcttca gcgtcagaag gcaacagtgc ttgagaatag     1740 aaacttaca ggaaagataa gtgagttgga aagaatggta gctgaactaa agaaacaaaa     1800 tcccgagta gaggaagaac ttccgaaggt cagggaggct gcagaaaatg aattgagaaa     1860 cagcagaga aatgtagaag atatctctct gcagaagata agggctgaaa gtgaagccaa     1920 cagtaccgc agggaacttg aaaccattgt gagagagaag gaagccgctg aaagagaact     1980 gagcgggtg aggcagctca ccatagaggc cgaggctaaa agagctgccg tggaagagaa     2040 ctcctgaat tttcgcaatc agttggagga aaacaccttt accagacgaa cactggaaga     2100 catcttaaa agaaagatt taagtctcaa tgatttggag caacaaaaaa ataaattaat      2160 gaagaatta agaagaaga gagacaatga ggaagaactc ttgaagctga taaagcagat     2220 gaaaaagac cttgcatttc agaaacaggt agcagagaaa cagttgaaag aaaagcagaa     2280 attgaattg gaagcaagaa gaaaaataac tgaaattcag tatacatgta gagaaaatgc     2340 ttgccagtg tgtccgatca cacaggctac atcatgcagg gcagtaacgg gtctccagca     2400 gaacatgac aagcagaaag cagaagaact caaacagcag gtagatgaac taacagctgc     2460 aatagaaag gctgaacaag acatgagaga gctgacatat gaacttaatg ccctccagct     2520 gaaaaaacg tcatctgagg aaaaggctcg tttgctaaaa gataaactag atgaaacaaa     2580 aatacactc agatgcctta agttggagct ggaaaggaag gatcaggcgg agaaagggta     2640 tctcaacaa ctcagagagc ttggtaggca attgaatcaa accacaggta aagctgaaga     2700 gccatgcaa gaagctagtg atctcaagaa aataaagcgc aattatcagt tagaattaga     2760 tctcttaat catgaaaaag ggaaactaca aagagaagta gacagaatca caaggcaca     2820 gctgtagct gagaagaata ttcagcattt aaattcacaa attcattctt ttcgagatga     2880
```

```
aaagaatta gaaagactac aaatctgcca gagaaaatca gatcatctaa aagaacaatt   2940 gagaaaagc catgagcagt tgcttcaaaa tatcaaagct gaaaagaaaa ataatgataa   3000 atccaaagg ctcaatgaag aattggagaa aagtaatgag tgtgcagaga tgctaaaaca   3060 aaagtagag gagcttacta ggcagaataa tgaaaccaaa ttaatgatgc agagaattca   3120 gcagaatca gagaatatag ttttagagaa acaaactatc cagcaaagat gtgaagcact   3180 aaaattcag gcagatggtt ttaaagatca gctacgcagc acaaatgaac acttgcataa   3240 cagacaaaa acagagcagg attttcaaag aaaaattaaa tgcctagaag aagacctggc   3300 aaaagtcaa aatttggtaa gtgaatttaa gcaaaagtgt gaccaacaga acattatcat   3360 cagaatacc aagaaagaag ttagaaatct gaatgcggaa ctgaatgctt ccaaagaaga   3420 aagcgacgc ggggagcaga aagttcagct acaacaagct caggtgcaag agttaaataa   3480 aggttgaaa aaagtacaag acgaattaca cttaaagacc atagaggagc agatgaccca   3540 agaaagatg gttctgtttc aggaagaatc tggtaaattc aaacaatcag cagaggagtt   3600 cggaagaag atggaaaaat taatggagtc caaagtcatc actgaaaatg atatttcagg   3660 attaggctt gactttgtgt ctcttcaaca agaaaactct agagcccaag aaaatgctaa   3720 ctttgtgaa acaaacatta aagaacttga aagacagctt caacagtatc gtgaacaaat   3780 cagcaaggg cagcacatgg aagcaaatca ttaccaaaaa tgtcagaaac ttgaggatga   3840 ctgatagcc cagaagcgtg aggttgaaaa cctgaagcaa aaaatggacc aacagatcaa   3900 gagcatgaa catcaattag ttttgctcca gtgtgaaatt caaaaaaaga gcacagccaa   3960 gactgtacc ttcaaaccag attttgagat gacagtgaag gagtgccagc actctggaga   4020 ctgtcctct agaaacactg gacaccttca cccaacaccc agatcccctc tgttgagatg   4080 actcaagaa ccacagccat tggaagagaa gtggcagcat cgggttgttg aacagatacc   4140 aaagaagtc caattccagc caccaggggc tccactcgag aaagagaaaa gccagcagtg   4200 tactctgag tacttttctc agacaagcac cgagttacag ataactttg atgagacaaa   4260 cccattaca agactgtctg aaattgagaa gataagagac caagccctga acaattctag   4320 ccacctgtt aggtatcaag ataacgcatg tgaaatggaa ctggtgaagg ttttgacacc   4380 ttagagata gctaagaaca agcagtatga tatgcataca gaagtcacaa cattaaaaca   4440 gaaaagaac ccagttccca gtgctgaaga atggatgctt gaagggtgca gagcatctgg   4500 ggactcaag aaagggggatt tccttaagaa gggcttagaa ccagagacct tccagaactt   4560 gatggtgat catgcatgtt cagtcaggga tgatgaattt aaattccaag ggcttaggca   4620 actgtgact gccaggcagt tggtggaagc taagcttctg gacatgagaa caattgagca   4680 ctgcgactc ggtcttaaga ctgttgaaga agttcagaaa actcttaaca agtttctgac   4740 aaagccacc tcaattgcag ggctttacct agaatctaca aagaaaaga tttcatttgc   4800 tcagcggcc gagagaatca taatagacaa aatggtggct ttggcatttt tagaagctca   4860 gctgcaaca ggttttataa ttgatcccat ttcaggtcag acatattctg ttgaagatgc   4920 gttcttaaa ggagttgttg acccgaatt cagaattagg cttcttgagg cagagaaggc   4980 gctgtggga tattcttatt cttctaagac attgtcagtg tttcaagcta tggaaaatag   5040 atgcttgac agacaaaaag gtaaacatat cttggaagcc cagattgcca gtgggggtgt   5100 attgaccct gtgagaggca ttcgtgttcc tccagaaatt gctctgcagc aggggttgtt   5160 aataatgcc atcttacagt ttttacatga gccatccagc aacacaagag ttttccctaa   5220 cccaataac aagcaagctc tgtattactc agaattactg cgaatgtgtg tatttgatgt   5280
```

-continued

```
gagtcccaa tgctttctgt ttccatttgg ggagaggaac atttccaatc tcaatgtcaa    5340 aaaacacat agaatttctg tagtagatac taaaacagga tcagaattga ccgtgtatga    5400 gctttccag agaaacctga ttgagaaaag tatatatctt gaactttcag ggcagcaata    5460 cagtggaag gaagctatgt tttttgaatc ctatgggcat tcttctcata tgctgactga    5520 actaaaaca ggattacact tcaatattaa tgaggctata gagcagggaa caattgacaa    5580 gccttggtc aaaaagtatc aggaaggcct catcacactt acagaacttg ctgattcttt    5640 ctgagccgg ttagtcccca agaaagattt gcacagtcct gttgcagggt attggctgac    5700 gctagtggg gaaaggatct ctgtactaaa agcctcccgt agaaatttgg ttgatcggat    5760 actgccctc cgatgccttg aagcccaagt cagtacaggg ggcataattg atcctcttac    5820 ggcaaaaag taccgggtgg ccgaagcttt gcatagaggc ctggttgatg aggggtttgc    5880 cagcagctg cgacagtgtg aattagtaat cacagggatt ggccatccca tcactaacaa    5940 atgatgtca gtggtggaag ctgtgaatgc aaatattata ataaggaaa tgggaatccg    6000 tgtttggaa tttcagtact tgacaggagg gttgatagag ccacaggttc actctcggtt    6060 tcaatagaa gaggctctcc aagtaggtat tatagatgtc ctcattgcca caaaactcaa    6120 gatcaaaag tcatatgtca gaaatataat atgccctcag acaaaaagaa agttgacata    6180 aaagaagcc ttagaaaaag ctgattttga tttccacaca ggacttaaac tgttagaagt    6240 tctgagccc ctgatgacag gaatttctag cctctactat tcttcctaat gggacatgtt    6300 aaataactg tgcaagggt gatgcaggct ggttcatgcc acttttttcag agtatgatga    6360 atcggctac atatgcagtc tgtgaattat gtaacatact ctatttcttg agggctgcaa    6420 ttgctaagt gctcaaaata gagtaagttt taaattgaaa attacataag atttaatgcc    6480 ttcaaatgg tttcatttag ccttgagaat ggttttttga aacttggcca cactaaaatg    6540 tttttttt tttacgtaga atgtgggata aacttgatga actccaagtt cacagtgtca    6600 ttcttcaga actccccttc attgaatagt gatcatttat taaatgataa attgcactcg    6660 tgaaagagc acgtcatgaa gcaccatgga atcaaagaga aagatataaa ttcgttccca    6720 agccttcaa gctgcagtgt tttagattgc ttcaaaaaat gaaaaagttt tgccttttc    6780 atatagtga ccttctttgc atattaaaat gtttaccaca atgtcccatt tctagttaag    6840 cttcgcact tgaaagctaa cattatgaat attatgtgtt ggaggagggg aaggattttc    6900 tcattctgt gtattttccg g                                             6921
```

<210> SEQ ID NO 118
<211> LENGTH: 946
<212> TYPE: DNA
<213> ORGANISM: Homo sapien

<400> SEQUENCE: 118

```
cttctgactg ggctcaggct gacaggtaga gctcaccatg gcttcttgtg tccttgtccc     60
ctccccatca cagctgtggt gcagtccacc gtctccagtg gctatggcgg tgccagtggt    120
gtcggcagtg gcttaggcct gggtggagga agcagctact cctatggcag tggtcttggc    180
gttggaggtg gcttcagttc cagcagtggc agagccattg ggggtggcct cagctctgtt    240
ggaggcggca gttccaccat caagtacacc accacctcct cctccagcag gaagagctat    300
aagcactaaa gtgcgtctgc tagctctcgg tcccacagtc ctcaggcccc tctctggctg    360
cagagccctc tcctcaggtt gcctgtcctc tcctggcctc cagtctcccc tgctgtccca    420
```

-continued

| | |
|---|---|
| ggtagagctg gggatgaatg cttagtgccc tcacttcttc tctctctctc tataccatct | 480 |
| gagcacccat tgctcaccat cagatcaacc tctgatttta catcatgatg taatcaccac | 540 |
| tggagcttca ctgttactaa attattaatt tcttgcctcc agtgttctat ctctgaggct | 600 |
| gagcattata agaaaatgac ctctgctcct tttcattgca gaaaattgcc aggggcttat | 660 |
| ttcagaacaa cttccactta ctttccactg gctctcaaac tctctaactt ataagtgttg | 720 |
| tgaaccccca cccaggcagt atccatgaaa gcacaagtga ctagtcctat gatgtacaaa | 780 |
| gcctgtatct ctgtgatgat ttctgtgctc ttcactgttt gcaattgcta ataaagcag | 840 |
| atttataata catatattct tttactttgc cttgctttgg ggccaaagtt ttgggcttaa | 900 |
| acttttttat ctgataagtg aatagttgtt tttaaaagat aatcta | 946 |

<210> SEQ ID NO 119
<211> LENGTH: 8948
<212> TYPE: DNA
<213> ORGANISM: Homo sapien

<400> SEQUENCE: 119

| | |
|---|---|
| caacagccc ctgctccttg ggccctcca tgccatgccg taatctctcc cacccgacca | 60 |
| caccaacac ccagctccga cgcagctcct ctgcgccctt gccgccctcc gagccacagc | 120 |
| ttcctcccg ctcctgcccc cggccgtcg ccgtctccgc gctcgcagcg gcctcgggag | 180 |
| gcccaggta gcgagcagcg acctcgcgag ccttccgcac tcccgcccgg ttccccggcc | 240 |
| tccgcctat ccttggcccc ctccgctttc tccgcgccgg cccgcctcgc ttatgcctcg | 300 |
| cgctgagcc gctctcccga ttgcccgccg acatgagctg caacggaggc tcccacccgc | 360 |
| gatcaacac tctgggccgc atgatccgcg ccgagtctgg cccggacctg cgctacgagg | 420 |
| gaccagcgg cggcgggggc accagcagga tgtactattc tcggcgcggc gtgatcaccg | 480 |
| ccagaactc ggacggctac tgtcaaaccg gcacgatgtc caggcaccag aaccagaaca | 540 |
| catccagga gctgctgcag aactgctccg actgcttgat gcgagcagag ctcatcgtgc | 600 |
| gcctgaatt gaagtatgga gatggaatac aactgactcg gagtcgagaa ttggatgagt | 660 |
| ttttgccca ggccaatgac caaatggaaa tcctcgacag cttgatcaga gagatgcggc | 720 |
| gatgggcca gccctgtgat gcttaccaga aaaggcttct tcagctccaa gagcaaatgc | 780 |
| agccctttta taaagccatc agtgtccctc gagtccgcag ggccagctcc aagggtggtg | 840 |
| aggctacac ttgtcagagt ggctctggct gggatgagtt caccaaacat gtcaccagtg | 900 |
| atgtttggg gtggatgagg cagcaaaggg cggagatgga catggtggcc tggggtgtgg | 960 |
| cctggcctc agtggagcag cacattaaca gccaccgggg catccacaac tccatcggcg | 1020 |
| ctatcgctg gcagctggac aaaatcaaag ccgacctgcg cgagaaatct gcgatctacc | 1080 |
| gttggagga ggagtatgaa aacctgctga aagcgtcctt tgagaggatg gatcacctgc | 1140 |
| acagctgca gaacatcatt caggccacgt ccagggagat catgtggatc aatgactgcg | 1200 |
| ggaggagga gctgctgtac gactggagcg acaagaacac caacatcgct cagaaacagg | 1260 |
| ggccttctc catacgcatg agtcaactgg aagttaaaga aaaagagctc aataagctga | 1320 |
| acaagaaag tgaccaactt gtcctcaatc agcatccagc ttcagacaaa attgaggcct | 1380 |
| tatggacac tctgcagacg cagtggagtt ggattcttca gatcaccaag tgcattgatg | 1440 |
| tcatctgaa agaaaatgct gcctactttc agtttttttga agaggcgcag tctactgaag | 1500 |
| atacctgaa ggggctccag gactccatca ggaagaagta ccccctgcgac aagaacatgc | 1560 |
| cctgcagca cctgctggaa cagatcaagg agctggagaa agaacgagag aaaatccttg | 1620 |

```
atacaagcg tcaggtgcag aacttggtaa acaagtctaa gaagattgta cagctgaagc    1680 tcgtaaccc agactacaga agcaataaac ccattattct cagagctctc tgtgactaca    1740 acaagatca gaaaatcgtg cataagggggg atgagtgtat cctgaaggac aacaacgagc   1800 cagcaagtg gtacgtgacg ggcccgggag gcgttgacat gcttgttccc tctgtgggc    1860 gatcatccc tcctccgaac ccactggccg tggacctctc ttgcaagatt gagcagtact    1920 cgaagccat cttggctctg tggaaccagc tctacatcaa catgaagagc ctggtgtcct    1980 gcactactg catgattgac atagagaaga tcagggccat gacaatcgcc aagctgaaaa    2040 aatgcggca ggaagattac atgaagacga tagccgacct tgagttacat taccaagagt    2100 catcagaaa tagccaaggc tcagagatgt ttggagatga tgacaagcgg aaaatacagt    2160 tcagttcac cgatgcccag aagcattacc agaccctggt cattcagctc cctggctatc    2220 ccagcacca gacagtgacc acaactgaaa tcactcatca tggaacctgc caagatgtca    2280 ccataataa agtaattgaa accaacagag aaaatgacaa gcaagaaaca tggatgctga    2340 ggagctgca gaagattcgc aggcagatag agcactgcga gggcaggatg actctcaaaa    2400 cctccctct agcagaccag gggtcttctc accacatcac agtgaaaatt aacgagctta    2460 gagtgtgca gaatgattca caagcaattg ctgaggttct caaccagctt aaagatatgc    2520 tgccaactt cagaggttct gaaaagtact gctatttaca gaatgaagta tttggactat    2580 tcagaaact ggaaaatatc aatggtgtta cagatggcta cttaaatagc ttatgcacag    2640 aagggcact gctccaggct attctccaaa cagaagacat gttaaaggtt tatgaagcca    2700 gctcactga ggaggaaact gtctgcctgg acctggataa agtggaagct taccgctgtg    2760 actgaagaa aataaaaaat gacttgaact tgaagaagtc gttgttggcc actatgaaga    2820 agaactaca gaaagcccag cagatccact ctcagacttc acagcagtat ccactttatg    2880 tctggactt gggcaagttc ggtgaaaaag tcacacagct gacagaccgc tggcaaagga    2940 agataaaca gatcgacttt agattatggg acctggagaa acaaatcaag caattgagga    3000 ttatcgtga taactatcag gctttctgca agtggctcta tgatcgtaaa cgccgccagg    3060 ttccttaga atccatgaaa tttggagatt ccaacacagt catgcggttt ttgaatgagc    3120 gaagaactt gcacagtgaa atatctggca aacgagacaa atcagaggaa gtacaaaaaa    3180 tgctgaact ttgcgccaat tcaattaagg attatgagct ccagctggcc tcatacacct    3240 aggactgga aactctgcta acatacccta tcaagaggac catgattcag tccccttctg    3300 ggtgattct gcaagaggct gcagatgttc atgctcggta cattgaacta cttacaagat    3360 tggagacta ttacaggttc ttaagtgaga tgctgaagag tttggaagat ctgaagctga    3420 aaataccaa gatcgaagtt ttggaagagg agctcagact ggcccgagat gccaactcgg    3480 aaactgtaa taagaacaaa ttcctggatc agaacctgca gaaataccag gcagagtgtt    3540 ccagttcaa agcgaagctt gcgagcctgg aggagctgaa gagacaggct gagctggatg    3600 gaagtcggc taagcaaaat ctagacaagt gctacggcca aataaaagaa ctcaatgaga    3660 gatcacccg actgacttat gagattgaag atgaaagag aagaagaaaa tctgtggaag    3720 cagatttga ccaacagaag aatgactatg accaactgca gaaagcaagg caatgtgaaa    3780 ggagaacct tggttggcag aaattagagt ctgagaaagc catcaaggag aaggagtacg    3840 gattgaaag gttgagggtt ctactgcagg aagaaggcac ccggaagaga gaatatgaaa    3900 tgagctggc aaaggtaaga aaccactata atgaggagat gagtaattta aggaacaagt    3960
```

```
tgaaacaga gattaacatt acgaagacca ccatcaagga gatatccatg caaaagagg    4020 tgattccaa aaatcttaga aaccagcttg atagactttc aagggaaaat cgagatctga    4080 ggatgaaat tgtcaggctc aatgacagca tcttgcaggc cactgagcag cgaaggcgag    4140 tgaagaaaa cgcccttcag caaaaggcct gtggctctga gataatgcag aagaagcagc    4200 tctggagat agaactgaag caggtcatgc agcagcgctc tgaggacaat gcccggcaca    4260 gcagtccct ggaggaggct gccaagacca ttcaggacaa aaataaggag atcgagagac    4320 caaagctga gtttcaggag gaggccaagc gccgctggga atatgaaaat gaactgagta    4380 ggtaagaaa caattatgat gaggagatca ttagcttaaa aaatcagttt gagaccgaga    4440 caacatcac caagaccacc atccaccagc tcaccatgca aaggaagag gataccagtg    4500 ctaccgggc tcagatagac aatctcaccc gagaaaacag gagcttatct gaagaaataa    4560 gaggctgaa gaacactcta acccagacca cagagaatct caggagggtg aagaagaca     4620 ccaacagca aaggccact ggctctgagg tgtctcagag gaaacagcag ctggaggttg      4680 gctgagaca agtcactcag atgcgaacag aggagagcgt aagatataag caatctcttg    4740 tgatgctgc caaaaccatc caggataaaa acaaggagat agaaaggtta aaacaactga    4800 cgacaaaga aacaaatgac cggaaatgcc tggaagatga aaacgcgaga ttacaagggg    4860 ccagtatga cctgcagaaa gcaaacagta gtgcgacgga gacaataaac aaactgaagg    4920 tcaggagca agaactgaca cgcctgagga tcgactatga aagggtttcc caggagagga    4980 tgtgaagga ccaggatatc acgcggttcc agaactctct gaaagagctg cagctgcaga    5040 gcagaaggt ggaagaggag ctgaatcggc tgaagaggac cgcgtcagaa gactcctgca   5100 gaggaagaa gctggaggaa gagctggaag gcatgaggag gtcgctgaag gagcaagcca    5160 caaaatcac caacctgacc cagcagctgg agcaggcatc cattgttaag aagaggagtg    5220
ggatgaccct ccggcagcag agggacgtgc tggatggcca cctgagggaa aagcagagga    5280 ccaggaaga gctgaggagg ctctcttctg aggtcgaggc cctgaggcgg cagttactcc    5340 ggaacagga aagtgtcaaa caagctcact tgaggaatga gcatttccag aaggcgatag    5400 agataaaag cagaagctta aatgaaagca aaatagaaat tgagaggctg cagtctctca    5460
agagaaacct gaccaaggag cacttgatgt tagaagaaga actgcggaac ctgaggctgg    5520 gtacgatga cctgaggaga ggacgaagcg aagcggacag tgataaaaat gcaaccatct   5580 ggaactaag gagccagctg cagatcagca caaaccggac cctggaactg caggggctga    5640 taatgattt acagagagag agggaaaatt tgagacagga aattgagaaa ttccaaaagc   5700 ggctttaga ggcatctaat aggattcagg aatcaaagaa tcagtgtact caggtggtac    5760 ggaaagaga gagccttctg gtgaaaatca aagtcctgga gcaagacaag gcaaggctgc    5820 gaggctgga ggatgagctg aatcgtgcaa aatcaactct agaggcagaa accagggtga    5880 acagcgcct ggagtgtgag aaacagcaaa ttcagaatga cctgaatcag tggaagactc    5940 atattcccg caaggaggag gctattagga agatagaatc ggaaagagaa aagagtgaga    6000 agagaagaa cagtcttagg agtgagatcg aaagactcca agcagagatc aagagaattg    6060 agagaggtg caggcgtaag ctggaggatt ctaccaggga gacacagtca cagttagaaa    6120 agaacgctc ccgatatcag agggagattg ataaactcag acagcgccca tatgggtccc    6180 tcgagagac ccagactgag tgtgagtgga ccgttgcac ctccaagctg gtgtttgatg     6240 gctgaggaa gaaggtgaca gcaatgcagc tctatgagtg tcagctgatc gacaaaacaa    6300 cttggacaa actattgaag gggaagaagt cagtggaaga agttgcttct gaaatccagc    6360
```

-continued

```
attccttcg gggtgcagga tctatcgctg gagcatctgc ttctcctaag gaaaaatact      6420 tttggtaga ggccaagaga aagaaattaa tcagcccaga atccacagtc atgcttctgg      6480 ggcccaggc agctacaggt ggtataattg atccccatcg gaatgagaag ctgactgtcg      6540 cagtgccat agctcgggac ctcattgact tcgatgaccg tcagcagata tatgcagcag      6600 aaaagctat cactggtttt gatgatccat tttcaggcaa gacagtatct gtttcagaag      6660 catcaagaa aaatttgatt gatagagaaa ccggaatgcg cctgctggaa gcccagattg      6720
ttcagggggg tgtagtagac cctgtgaaca gtgtcttttt gccaaaagat gtcgccttgg      6780
ccggggggct gattgataga gatttgtatc gatccctgaa tgatccccga gatagtcaga      6840 aaactttgt ggatccagtc accaaaaaga aggtcagtta cgtgcagctg aaggaacggt      6900 cagaatcga accacatact ggtctgctct tgctttcagt acagaagaga agcatgtcct      6960 ccaaggaat cagacaacct gtgaccgtca ctgagctagt agattctggt atattgagac      7020 gtccactgt caatgaactg gaatctggtc agatttctta tgacgaggtt ggtgagagaa      7080 taaggactt cctccagggt tcaagctgca tagcaggcat atacaatgag accacaaaac      7140 gaagcttgg catttatgag gccatgaaaa ttggcttagt ccgacctggt actgctctgg      7200 gttgctgga agcccaagca gctactggct ttatagtgga tcctgttagc aacttgaggt      7260 accagtgga ggaagcctac aagagaggtc tggtgggcat tgagttcaaa gagaagctcc      7320 gtctgcaga acgagctgtc actgggtata atgatcctga acaggaaac atcatctctt      7380 gttccaagc catgaataag gaactcatcg aaaagggcca cggtattcgc ttattagaag      7440 acagatcgc aaccgggggg atcattgacc caaggagag ccatcgttta ccagttgaca      7500 agcatataa gagggctat ttcaatgagg aactcagtga gattctctca gatccaagtg      7560 tgataccaa aggattttttt gaccccaaca ctgaagaaaa tcttacctat ctgcaactaa      7620 agaaagatg cattaaggat gaggaaacag ggctctgtct tctgcctctg aaagaaaaga      7680 gaaacaggt gcagacatca caaagaata cctcaggaa gcgtagagtg gtcatagttg      7740 cccagaaac caataaagaa atgtctgttc aggaggccta caagaagggc ctaattgatt      7800
tgaaaccctt caaagaactg tgtgagcagg aatgtgaatg ggaagaaata accatcacgg      7860 atcagatgg ctccaccagg gtggtcctgg tagatagaaa gacaggcagt cagtatgata      7920 tcaagatgc tattgacaag ggccttgttg acaggaagtt ctttgatcag taccgatccg      7980 cagcctcag cctcactcaa tttgctgaca tgatctcctt gaaaaatggt gtcggcacca      8040 cagcagcat gggcagtggt gtcagcgatg atgttttttag cagctcccga catgaatcag      8100 aagtaagat ttccaccata tccagcgtca ggaatttaac cataaggagc agctcttttt      8160 agacaccct ggaagaatcg agccccattg cagccatctt tgacacagaa aacctggaga      8220 aatctccat tacagaaggt atagagcggg gcatcgttga cagcatcacg ggtcagaggc      8280 tctggaggc tcaggcctgc acaggtggca tcatccaccc aaccacgggc cagaagctgt      8340 acttcagga cgcagtctcc cagggtgtga ttgaccaaga catggccacc agcgtgaagc      8400 tgctcagaa agccttcata ggcttcgagg gtgtgaaggg aaagaagaag atgtcagcag      8460 agaggcagt gaaagaaaaa tggctcccgt atgaggctgg ccagcgcttc ctggagttcc      8520 gtacctcac gggaggtctt gttgacccgg aagtgcatgg gaggataagc accgaagaag      8580 catccggaa ggggttcata gatggccgcg ccgcacagag gctgcaagac accagcagct      8640 tgccaaaat cctgacctgc cccaaaacca aattaaaaat atcctataag gatgccataa      8700
```

```
tcgctccat ggtagaagat atcactgggc tgcgccttct ggaagccgcc tccgtgtcgt    8760 caagggctt acccagccct tacaacatgt cttcggctcc ggggtcccgc tccggctccc    8820 ctcgggatc tcgctccgga tctcgctccg ggtcccgcag tgggtcccgg agaggaagct    8880 tgacgccac agggaattct tcctactctt attcctactc atttagcagt agttctattg    8940
gcactag                                                            8948
```

<210> SEQ ID NO 120
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 120

```
cgtcctaagc acttagacta catcagggaa gaacacagac cacatccctg tcctcatgcg     60
gcttatgttt tctggaagaa agtggagacc nagtccttgg ctttagggct ccccggctgg    120
gggctgtgca ntccggtcag ggcgggaagg gaaatgcacc gctgcatgtg aacttacagc    180
ccaggcggat gccccttccc ttagcactac ctggcctcct gcatcccctc gcctcatgtt    240
cctcccacct tcaaanaatg aanaacccca tgggcccagc cccttgccct ggggaaccaa    300
ggcagccttc caaaactcag gggctgaagc anactattag ggcaggggct gactttgggt    360
gacactgccc attccctctc agggcagctc angtcacccn ggnctcttga acccagcctg    420
ttcctttgaa aaagggcaaa actgaaaagg gcttttccta naaaaagaaa aaccagggaa    480
ctttgccagg gcttcnntnt taccaaaacn ncttctcnng gattttttaat tccccattng    540 gcctccactt accngggggcn atgccccaaa attaanaatt tcccatc                 587
```

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 121

```
cactagtagg atagaaacac tgtgtcccga gagtaaggag agaagctact attgattaga     60
gcctaaccca ggttaactgc aagaagaggc gggatacttt cagctttcca tgtaactgta    120
tgcataaagc caatgtagtc cagtttctaa gatcatgttc caagctaact gaatcccact    180
tcaatacaca ctcatgaact cctgatggaa caataacagg cccaagcctg tggtatgatg    240
tgcacacttg ctagactcan aaaaaatact actctcataa atgggtggga gtattttggt    300
gacaacctac tttgcttggc tgagtgaagg aatgatattc atatattcat ttattccatg    360
gacatttagt tagtgctttt tatataccag gcatgatgct gagtgacact cttgtgtata    420
tttccaaatt tttgtacagt cgctgcacat atttgaaatc atatattaag acttccaaaa    480
aatgaagtcc ctggtttttc atggcaactt gatcagtaaa ggattcncct ctgtttggta    540
cttaaaacat ctactatatn gttnanatga aattccttttt cccnccctcc cgaaaaaana    600
aagtggtggg gaaaaaaaa                                                 619
```

<210> SEQ ID NO 122
<211> LENGTH: 1475

```
<212> TYPE: DNA
<213> ORGANISM: Homo sapien

<400> SEQUENCE: 122
tccacctgtc cccgcagcgc cggctcgcgc cctcctgccg cagccaccga gccgccgtct      60
agcgccccga cctcgccacc atgagagccc tgctggcgcg cctgcttctc tgcgtcctgg     120
tcgtgagcga ctccaaaggc agcaatgaac ttcatcaagt tccatcgaac tgtgactgtc     180
taaatggagg aacatgtgtg tccaacaagt acttctccaa cattcactgg tgcaactgcc     240
caaagaaatt cggagggcag cactgtgaaa tagataagtc aaaaacctgc tatgagggga     300
atggtcactt ttaccgagga aaggccagca ctgacaccat gggccggccc tgcctgccct     360
ggaactctgc cactgtcctt cagcaaacgt accatgccca cagatctgat gctcttcagc     420
tgggcctggg gaaacataat tactgcagga acccagacaa ccggaggcga ccctggtgct     480
atgtgcaggt gggcctaaag ccgcttgtcc aagagtgcat ggtgcatgac tgcgcagatg     540
gaaaaaagcc ctcctctcct ccagaagaat aaaatttca gtgtggccaa agactctga      600 ggccccgctt taagattatt gggggagaat tcaccaccat cgagaaccag ccctggtttg     660
cggccatcta caggaggcac cgggggggct ctgtcaccta cgtgtgtgga ggcagcctca     720
tcagcccttg ctgggtgatc agcgccacac actgcttcat tgattaccca agaaggagg     780 actacatcgt ctacctgggt cgctcaaggc ttaactccaa cacgcaaggg gagatgaagt     840
ttgaggtgga aaacctcatc ctacacaagg actacagcgc tgacacgctt gctcaccaca     900
acgacattgc cttgctgaag atccgttcca aggagggcag gtgtgcgcag ccatcccgga     960
ctatacagac catctgcctg ccctcgatgt ataacgatcc ccagtttggc acaagctgtg    1020
agatcactgg cttttggaaaa gagaattcta ccgactatct ctatccggag cagctgaaga    1080
tgactgttgt gaagctgatt cccaccggga gtgtcagca gccccactac tacggctctg    1140
aagtcaccac caaaatgctg tgtgctgctg acccacagtg gaaaacagat tcctgccagg    1200
gagactcagg gggaccccct gtctgttccc tccaaggccg catgactttg actggaattg    1260
tgagctgggg ccgtggatgt gccctgaagg acaagccagg cgtctacacg agagtctcac    1320
acttcttacc ctggatccgc agtcacacca aggaagagaa tggcctggcc ctctgagggt    1380
ccccagggag gaaacgggca ccacccgctt tcttgctggt tgtcattttt gcagtagagt    1440
catctccatc agctgtaaga agagactggg aagat                               1475

<210> SEQ ID NO 123
<211> LENGTH: 2294
<212> TYPE: DNA
<213> ORGANISM: Homo sapien

<400> SEQUENCE: 123
cagcgccggc tcgcgccctc ctgccgcagc caccgagccg ccgtctagcg ccccgacctc      60
gccaccatga gagccctgct ggcgcgcctg cttctctgcg tcctggtcgt gagcgactcc     120
aaaggcagca atgaacttca tcaagttcca tcgaactgta ctgtctaaa tggaggaaca     180 tgtgtgtcca acaagtactt ctccaacatt cactggtgca actgcccaaa gaaattcgga     240
gggcagcact gtgaaataga taagtcaaaa acctgctatg aggggaatgg tcacttttac     300
cgaggaaagg ccagcactga caccatgggc cggcctgcc tgcctggaa ctctgccact     360 gtccttcagc aaacgtacca tgcccacaga tctgatgctc ttcagctggg cctggggaaa     420
cataattact gcaggaaccc agacaaccgg aggcgaccct ggtgctatgt gcaggtgggc     480
```

```
ctaaagccgc ttgtccaaga gtgcatggtg catgactgcg cagatggaaa aaagccctcc      540
tctcctccag aagaattaaa atttcagtgt ggccaaaaga ctctgaggcc ccgctttaag      600
attattgggg gagaattcac caccatcgag aaccagccct ggtttgcggc catctacagg      660
aggcaccggg ggggctctgt cacctacgtg tgtggaggca gcctcatcag cccttgctgg      720
gtgatcagcg ccacacactg cttcattgat tacccaaaga aggaggacta catcgtctac      780
ctgggtcgct caaggcttaa ctccaacacg caaggggaga tgaagtttga ggtggaaaac      840
ctaatcctac acaaggacta cagcgctgac acgcttgctc accacaacga cattgccttg      900
ctgaagatcc gttccaagga gggcaggtgt gcgcagccat cccggactat acagaccatc      960
tgcctgccct cgatgtataa cgatccccag tttggcacaa gctgtgagat cactggcttt     1020
ggaaaagaga attctaccga ctatctctat ccggagcagc tgaaaatgac tgttgtgaag     1080
ctgatttccc accgggagtg tcagcagccc cactactacg gctctgaagt caccaccaaa     1140
atgctgtgtg ctgctgaccc acagtggaaa acagattcct gccagggaga ctcaggggga     1200
cccctcgtct gttccctcca aggccgcatg actttgactg gaattgtgag ctggggccgt     1260
ggatgtgccc tgaaggacaa gccaggcgtc tacacgagag tctcacactt cttaccctgg     1320
atccgcagtc acaccaagga agagaatggc ctggccctct gagggtcccc agggaggaaa     1380
cgggcaccac ccgctttctt gctggttgct attttgcagt agagtcatct ccatcagctg     1440
taagaagagc tgggaatata ggctctgcac agatggattt gcctgtgcca ccaccagggc     1500
gaacgacaat agctttaccc tcaggcatag gcctgggtgc tggctgccca gacccctctg     1560
gccaggatgg aggggtggtc ctgactcaac atgttactga ccagcaactt gtcttttct      1620 ggactgaagc ctgcaggagt taaaaagggc aagggcatct ctgtgcatgg gctcgaaggg     1680
agagccagct cccccgaccg gtgggcattt gtgaggccca tggttgagaa atgaataatt     1740
tcccaattag gaagtgtaag cagctgaggt ctcttgaggg agcttagcca atgtgggagc     1800
agcggtttgg ggagcagaga cactaacgac ttcagggcag ggctctgata ttccatgaat     1860
gtatcaggaa atatatatgt gtgtgtatgt ttgcacactt gtgtgtgggc tgtgagtgta     1920
agtgtgagta agagctggtg tctgattgtt aagtctaaat atttccttaa actgtgtgga     1980
ctgtgatgcc acacagagtg gtcttctctg agaggttata ggtcactcct ggggcctctt     2040
gggtccccca cgtgacagtg cctgggaatg tattattctg cagcatgacc tgtgaccagc     2100
actgtctcag tttcactttc acatagatgt ccctttcttg gccagttatc ccttcctttt     2160
agcctagttc atccaatcct cactgggtgg ggtgaggacc actcctgtac actgaatatt     2220
tatatttcac tattttattt tatattttg taatttaaa taaagtgat caataaaatg       2280 tgattttct gatg                                                       2294
```

<210> SEQ ID NO 124
<211> LENGTH: 956
<212> TYPE: DNA
<213> ORGANISM: Homo sapien

<400> SEQUENCE: 124

```
gatgagttcc gcaccaagtt tgagacagac caggccctgc gcctgagtgt ggaggccgac       60
atcaatggcc tgcgcagggt gctggatgag ctgacccctgg ccagagccga cctggagatg     120
cagattgaga acctcaagga ggagctggcc tacctgaaga gaaccacgga ggaggagatg      180
aacgccctgc gaggccaggt gggtggtgag atcaatgtgg agatggacgc tgccccaggc      240
gtggacctga gccgcatcct caacgagatg cgtgaccagt atgagaagat ggcagagaag       300
```

```
aaccgcaagg atgccgagga ttggttcttc agcaagacag aggaactgaa ccgcgaggtg      360
gccaccaaca gtgagctggt gcagagtggc aagagtgaga tctcggagct ccggcgcacc      420
atgcaggcct tggagataga gctgcagtcc cagctcagca tgaaagcatc cctggagggc      480
aacctggcgg agacagagaa ccgctactgc gtgcagctgt cccagatcca ggggctgatt      540
ggcagcgtgg aggagcagct ggcccagctt cgctgcgaga tggagcagca gaaccaggaa      600
tacaaaatcc tgctggatgt gaagacgcgg ctggagcagg agattgccac ctaccgccgc      660
ctgctggagg gagaggatgc ccacctgact cagtacaaga agaaccggt gaccacccgt       720 caggtgcgta ccattgtgga agaggtccag gatggcaagg tcatctcctc ccgcgagcag      780
gtccaccaga ccacccgctg aggactcagc taccccggcc ggccacccag gaggcaggga      840
cgcagccgcc ccatctgccc cacagtctcc ggcctctcca gcctcagccc cctgcttcag      900
tcccttcccc atgcttcctt gcctgatgac aataaaagct tgttgactca gctatg          956

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125
aaattatata tagtgnttca gctcccattg tggtgttcat agtcttctag gaacagataa       60
acttaagtat tcaattcact cttggcattt tttctttaat ataggctttt tagcctattt      120
ttggaaaact gctttcttc tgagaacctt attctgaatg tcatcaactt taccaaacct       180
tctaagtcca gagctaactt agtactgttt aagttactat tgactgaatt ttcttcattt      240
tctgtttagc cagtgttacc aaggtaagct ggggaatgaa gtataccaac ttctttcaga      300
gcattttagg acattatggc agctttagaa ggctgtcttg tttctagcca agggagagcc      360
agcgcaggtt ttggatacta gagaaagtca tttgcttgta ctattgccat tttagaaagc      420
tctgatgtga attcaaattt tacctctgtt acttaaagcc aacaatttta aggcagtagt      480
tttact                                                                  486

<210> SEQ ID NO 126
<211> LENGTH: 3552
<212> TYPE: DNA
<213> ORGANISM: Homo sapien

<400> SEQUENCE: 126
cggcaggcag gtctcgtctc ggcaccctcc cggcgcccgc gttctcctgg ccctgcccgg       60
catcccgatg gccgccgctg ggccccggcg ctccgtgcgc ggagccgtct gcctgcatct      120
gctgctgacc ctcgtgatct tcagtcgtgc tggtgaagcc tgcaaaaagg tgatacttaa      180
tgtaccttct aaactagagg cagacaaaat aattggcaga gttaatttgg aagagtgctt      240
caggtctgca gacctcatcc ggtcaagtga tcctgatttc agagttctaa atgatgggtc      300
agtgtacaca gccagggctg ttgcgctgtc tgataagaaa agatcattta ccatatggct      360
ttctgacaaa aggaaacaga cacagaaaga ggttactgtg ctgctagaac atcagaagaa      420
ggtatcgaag acaagacaca ctagagaaac tgttctcagg cgtgccaaga ggagatgggc      480
acctattcct tgctctatgc aagagaattc cttgggccct ttcccattgt ttcttcaaca      540
```

-continued

```
agttgaatct gatgcagcac agaactatac tgtcttctac tcaataagtg gacgtggagt    600
tgataaagaa cctttaaatt tgttttatat agaaagagac actggaaatc tattttgcac    660
tcggcctgtg gatcgtgaag aatatgatgt ttttgatttg attgcttatg cgtcaactgc    720
agatggatat tcagcagatc tgcccctccc actacccatc agggtagagg atgaaaatga    780
caaccaccct gttttcacag aagcaattta aattttgaa gttttggaaa gtagtagacc     840
tggtactaca gtgggggtgg tttgtgccac agacagagat gaaccggaca caatgcatac    900
gcgcctgaaa tacagcattt tgcagcagac accaaggtca cctgggctct tttctgtgca    960
tcccagcaca ggcgtaatca ccacagtctc tcattatttg gacagagagg ttgtagacaa   1020
gtactcattg ataatgaaag tacaagacat ggatggccag tttttttggat tgataggcac   1080
atcaacttgt atcataacag taacagattc aaatgataat gcacccactt tcagacaaaa   1140
tgcttatgaa gcatttgtag aggaaaatgc attcaatgtg gaaatcttac gaataccttat   1200
agaagataag gatttaatta acactgccaa ttggagagtc aattttacca ttttaagggg   1260
aaatgaaaat ggacatttca aaatcagcac agacaaagaa actaatgaag gtgttctttc   1320
tgttgtaaag ccactgaatt atgaagaaaa ccgtcaagtg aacctggaaa ttggagtaaa   1380
caatgaagcg ccatttgcta gagatattcc cagagtgaca gccttgaaca gagccttggt   1440
tacagttcat gtgagggatc tggatgaggg gcctgaatgc actcctgcag cccaatatgt   1500
gcggattaaa gaaaacttag cagtgggggtc aaagatcaac ggctataagg catatgaccc   1560
cgaaaataga aatggcaatg gtttaaggta caaaaaattg catgatccta aaggttggat   1620
caccattgat gaaatttcag ggtcaatcat aacttccaaa atcctggata gggaggttga   1680
aactcccaaa aatgagttgt ataatattac agtcctggca atagacaaag atgatagatc   1740
atgtactgga acacttgctg tgaacattga agatgtaaat gataatccac cagaaatact   1800
tcaagaatat gtagtcattt gcaaaccaaa aatgggggtat accgacattt tagctgttga   1860
tcctgatgaa cctgtccatg gagctccatt ttatttcagt ttgcccaata cttctccaga   1920
aatcagtaga ctgtggagcc tcaccaaagt taatgataca gctgcccgtc tttcatatca   1980
gaaaaatgct ggatttcaag aatataccat tcctattact gtaaaagaca gggccggcca   2040
agctgcaaca aaattattga gagttaatct gtgtgaatgt actcatccaa ctcagtgtcg   2100
tgcgacttca aggagtacag gagtaatact tggaaaatgg gcaatccttg caatattact   2160
gggtatagca ctgctctttt ctgtattgct aactttagta tgtggagttt ttggtgcaac   2220
taagggaaaa cgttttcctg aagatttagc acagcaaaac ttaattatat caaacacaga   2280
agcacctgga gacgatagag tgtgctctgc caatggattt atgacccaaa ctaccaacaa   2340
ctctagccaa ggtttttgtg gtactatggg atcaggaatg aaaaatggag gcaggaaac    2400
cattgaaatg atgaaaggag gaaaccagac cttggaatcc tgccgggggg ctgggcatca   2460
tcatacccctg gactcctgca ggggaggaca cacggaggtg gacaactgca gatacactta   2520
ctcggagtgg cacagtttta tcaacccccg tctcggtgaa aaattgcatc gatgtaatca   2580
gaatgaagac cgcatgccat cccaagatta tgtcctcact tataactatg agggaagagg   2640
atctccagct ggttctgtgg gctgctgcag tgaaaagcag gaagaagatg gccttgactt   2700
tttaaataat ttggaaccca aatttattac attagcagaa gcatgcacaa agagataatg   2760
tcacagtgct acaattaggt ctttgtcaga cattctggag gtttccaaaa ataatattgt   2820
aaagttcaat ttcaacatgt atgtatatga tgatttttttt ctcaatttttg aattatgcta   2880
ctcaccaatt tatatttttta aagcaagttg ttgcttatct tttccaaaaa gtgaaaaatg   2940
```

-continued

```
ttaaaacaga caactggtaa atctcaaact ccagcactgg aattaaggtc tctaaagcat     3000
ctgctctttt tttttttac agatatttta gtaataaata tgctggataa atattagtcc      3060
aacaatagct aagttatgct aatatcacat tattatgtat tcactttaag tgatagttta    3120
aaaaataaac aagaaatatt gagtatcact atgtgaagaa agttttggaa agaaaacaat    3180
gaagactgaa ttaaattaaa aatgttgcag ctcataaaga attggactca cccctactgc    3240
actaccaaat tcatttgact ttggaggcaa aatgtgttga agtgccctat gaagtagcaa    3300
ttttctatag gaatatagtt ggaaataaat gtgtgtgtgt atattattat taatcaatgc    3360
aatatttaaa tgaaatgaga acaaagagga aaatggtaaa aacttgaaat gaggctgggg    3420
tatagtttgt cctacaatag aaaaaagaga gagcttccta ggcctgggct cttaaatgct    3480
gcattataac tgagtctatg aggaaatagt tcctgtccaa tttgtgtaat ttgttttaaaa   3540 ttgtaaataa at                                                         3552

<210> SEQ ID NO 127
<211> LENGTH: 754
<212> TYPE: DNA
<213> ORGANISM: Homo sapien

<400> SEQUENCE: 127 ttttttttt tgtcattgt tcattgattt taatgagaaa gctaagagag gaaataagta       60
gcctttcaaa ggtcacacag aagtaagtga cagatccagg attcatatcc aagcattctg    120
gctctagtgt ccatgcttct caaccattat gacccaatat tcaaccaaat caatactgaa    180
ggacacgtga aatgtatccg gtattttact attacaaaca aaatccaat gaacattctt     240 gaagacatac acaaaaataa tggttacaat agaagttact ggaattgaaa ttttggttca    300
acctatatta aaatgtaagg cttttgatat agctaataga ttttttgaaat gatcagtctt   360 aacgtttgta ggggagcaca ctcctgcatg gggaaaagat tcactgtgaa gcacagagca    420
cctttatggt tggatcatct tgtcattaaa gttcaggcgt tatctatcct gtaagtggca    480
gaatcaagac tgcaatatcg cctgcttttc ttttaactc atgttttccc ttgactacac     540
tggtcctcaa agtaaaaccc ctgtgtcagt gtactattca tggaatactc tgcaattata    600
accaccttct aatactttta atacccaatc aaaatttatt atacatatgt atcatagata    660
ctcatctgta aagctgtgct tcaaaatagt gatctcttcc caacattaca atatatatta    720
atgatgtcga acctgcccgg gcggccgctc gaag                                 754

<210> SEQ ID NO 128
<211> LENGTH: 374
<212> TYPE: DNA
<213> ORGANISM: Homo sapien

<400> SEQUENCE: 128
aggttttgat taaaaggca aatgatttta ttgttcgata atcttttaaa aaaataagag      60
gaaggagtaa aattaaagat gaaagatgat ttttatttcc ttgtgacctc tatatcccc     120 ttcccctgcc cttggtaagt aactcttgat ggagaaagga ttaaagactc ttatttaacc    180
aaaaaacaga gccagctaat catttccaaa ggttagtatc tccctgctga cctcttcttt    240
ggtttaattg aataaaacta tatgttcata tatgtattaa aacaactcag aataacatct    300
tttcttcctt agttaaggca ttataagggc tatactatca tccataataa ccaaggcaat    360
aacttaaaaa gctg                                                      374
```

<210> SEQ ID NO 129
<211> LENGTH: 546
<212> TYPE: DNA
<213> ORGANISM: Homo sapien

<400> SEQUENCE: 129

```
agtgtgatgg atatctgcag aattcgggct aagcgtggtc gcggcccgag gtctggaact      60
tcccagcacy tgaaaaggag cctcctgagc tgactcggct aaagccccac tttcgctcct     120
cctcatttct gcctactgat ttccttggag cattcatctg aatattaccg tttgctgtgt     180
aacctggtac atacatagca tgactccctg aatagagtg ggctggggtg cttatgctgg      240
gagagtgatt gacatgcact ttcaagctat atctaccatt tgcagcaaag gagaaaaaat     300
acctcgagta aattccatca ttttttataa catcagcacc tgctccatca tcaaggagtc     360
tcagcgtaac aggatctcca gtctctggct caactgtggc agtgacagtg cattaagaa      420
tgggataaaa tccctgtttc acattggcat aaatcatcac aggatgagga aaatggaggc     480
tgtctctttc cacaaaggct tccacagtgg ctgggggcac agacctgccc gggcggccgc     540
tcgaaa                                                                  546
```

<210> SEQ ID NO 130
<211> LENGTH: 5156
<212> TYPE: DNA
<213> ORGANISM: Homo sapien

<400> SEQUENCE: 130

```
ccaaccgag gcgccgggca gcgaccctg cagcggagac agagactgag cggcccggca       60
cgccatgcc tgcgctctgg ctgggctgct gcctctgctt gtcgctcctc ctgcccgcag     120
ccgggccac ctccaggagg gaagtctgtg attgcaatgg gaagtccagg cagtgtatct     180
tgatcggga acttcacaga caaactggta atggattccg ctgcctcaac tgcaatgaca     240
cactgatgg cattcactgc gagaagtgca agaatggctt ttaccggcac agagaaaggg     300
ccgctgttt gccctgcaat tgtaactcca aaggttctct tagtgctcga tgtgacaact     360
cggacggtg cagctgtaaa ccaggtgtga caggagccag atgcgaccga tgtctgccag     420
cttccacat gctcacggat gcggggtgca cccaagacca gagactgcta gactccaagt     480
tgactgtga cccagctggc atcgcagggc cctgtgacgc gggccgctgt gtctgcaagc     540
agctgtcac tggagaacgc tgtgataggt gtcgatcagg ttactataat ctggatgggg     600
gaacccctga gggctgtacc cagtgtttct gctatgggca ttcagccagc tgccgcagct     660
tgcagaata cagtgtccat aagatcacct ctacctttca tcaagatgtt gatggctgga     720
ggctgtcca acgaaatggg tctcctgcaa agctccaatg gtcacagcgc catcaagatg     780
gtttagctc agcccaacga ctagaccctg tctattttgt ggctcctgcc aaatttcttg     840
gaatcaaca ggtgagctat ggtcaaagcc tgtcctttga ctaccgtgtg gacagaggag     900
cagacaccc atctgcccat gatgtgattc tggaaggtgc tggtctacgg atcacagctc     960
cttgatgcc acttggcaag acactgcctt gtgggctcac caagacttac acattcaggt    1020
aaatgagca tccaagcaat aattggagcc cccagctgag ttactttgag tatcgaaggt    1080
actgcggaa tctcacagcc ctccgcatcc gagctacata tggagaatac agtactgggt    1140
cattgacaa tgtgaccctg atttcagccc gccctgtctc tggagcccca gcaccctggg    1200
tgaacagtg tatatgtcct gttgggtaca aggggcaatt ctgccaggat tgtgcttctg    1260
ctacaagag agattcagcg agactggggc ttttggcac ctgtattcct tgtaactgtc    1320
```

```
aggggagg ggcctgtgat ccagacacag gagattgtta ttcagggat gagaatcctg    1380 cattgagtg tgctgactgc ccaattggtt tctacaacga tccgcacgac ccccgcagct    1440 caagccatg tccctgtcat aacggttca gctgctcagt gatgccgga acggaggagg    1500 ggtgtgcaa taactgccct cccggggtca ccggtgcccg ctgtgagctc tgtgctgatg    1560 ctactttgg ggaccccttt ggtgaacatg gcccagtgag gccttgtcag ccctgtcaat    1620 caacaacaa tgtggacccc agtgcctctg ggaattgtga ccggctgaca ggcaggtgtt    1680 gaagtgtat ccacaacaca gccggcatct actgcgacca gtgcaaagca ggctacttcg    1740 ggacccatt ggctcccaac ccagcagaca agtgtcgagc ttgcaactgt aaccccatgg    1800 ctcagagcc tgtaggatgt cgaagtgatg gcacctgtgt ttgcaagcca ggatttggtg    1860 ccccaactg tgagcatgga gcattcagct gtccagcttg ctataatcaa gtgaagattc    1920 gatggatca gtttatgcag cagcttcaga gaatggaggc cctgatttca aaggctcagg    1980 tggtgatgg agtagtacct gatacagagc tggaaggcag gatgcagcag gctgagcagg    2040 ccttcagga cattctgaga gatgcccaga tttcagaagg tgctagcaga tcccttggtc    2100 ccagttggc caaggtgagg agccaagaga acagctacca gagccgcctg gatgacctca    2160 gatgactgt ggaaagagtt cgggctctgg gaagtcagta ccagaaccga gttcgggata    2220 tcacaggct catcactcag atgcagctga gcctggcaga aagtgaagct tccttgggaa    2280 cactaacat tcctgcctca gaccactacg tggggccaaa tggcttttaaa agtctggctc    2340 ggaggccac aagattagca gaaagccacg ttgagtcagc cagtaacatg gagcaactga    2400 aagggaaac tgaggactat tccaaacaag ccctctcact ggtgcgcaag gccctgcatg    2460 aggagtcgg aagcggaagc ggtagcccgg acggtgctgt ggtgcaaggg cttgtggaaa    2520 attggagaa aaccaagtcc ctggcccagc agttgacaag ggaggccact caagcggaaa    2580 tgaagcaga taggtcttat cagcacagtc tccgcctcct ggattcagtg tctcggcttc    2640 gggagtcag tgatcagtcc tttcaggtgg aagaagcaaa gaggatcaaa caaaaagcgg    2700 ttcactctc aagcctggta accaggcata tggatgagtt caagcgtaca cagaagaatc    2760 gggaaactg gaaagaagaa gcacagcagc tcttacgaaa tggaaaaagt gggagagaga    2820 atcagatca gctgctttcc cgtgccaatc ttgctaaaag cagagcacaa gaagcactga    2880 tatgggcaa tgccactttt tatgaagttg agagcatcct taaaaacctc agagagtttg    2940 cctgcaggt ggacaacaga aaagcagaag ctgaagaagc catgaagaga ctctcctaca    3000 cagccgaaa ggttttcagat gccagtgaca agacccagca agcagaaaga gccctgggga    3060 cgctgctgc tgatgcacag agggcaaaga atggggccgg ggaggccctg gaaatctcca    3120 tgagattga acaggagatt gggagtctga acttggaagc caatgtgaca gcagatggag    3180 cttggccat ggaaaaggga ctggcctctc tgaagagtga gatgagggaa gtggaaggag    3240 gctggaaag gaaggagctg gagtttgaca cgaatatgga tgcagtacag atggtgatta    3300 agaagccca gaaggttgat accagagcca gaacgctgg ggttacaatc aagacacac    3360 caacacatt agacggcctc ctgcatctga tggaccagcc tctcagtgta gatgaagagg    3420 gctggtctt actggagcag aagctttccc gagccaagac ccagatcaac agccaactgc    3480 gcccatgat gtcagagctg aagagaggg cacgtcagca gaggggccac ctccatttgc    3540 ggagacaag catagatggg attctggctg atgtgaagaa cttggagaac attagggaca    3600 cctgccccc aggctgctac aatacccagg ctcttgagca acagtgaagc tgccataaat    3660
```

-continued

| | |
|---|---|
| tttctcaac tgaggttctt gggatacaga tctcagggct cgggagccat gtcatgtgag | 3720 |
| gggtgggat ggggacattt gaacatgttt aatgggtatg ctcaggtcaa ctgacctgac | 3780 |
| ccattcctg atcccatggc caggtggttg tcttattgca ccatactcct tgcttcctga | 3840 |
| gctgggcaa tgaggcagat agcactgggt gtgagaatga tcaaggatct ggaccccaaa | 3900 |
| aatagactg gatggaaaga caaactgcac aggcagatgt ttgcctcata atagtcgtaa | 3960 |
| tggagtcct ggaatttgga caagtgctgt tgggatatag tcaacttatt ctttgagtaa | 4020 |
| gtgactaaa ggaaaaaact ttgactttgc ccaggcatga aattcttcct aatgtcagaa | 4080 |
| agagtgcaa cccagtcaca ctgtggccag taaaatacta ttgcctcata ttgtcctctg | 4140 |
| aagcttctt gctgatcaga gttcctccta cttacaaccc agggtgtgaa catgttctcc | 4200 |
| ttttcaagc tggaagaagt gagcagtgtt ggagtgagga cctgtaaggc aggcccattc | 4260 |
| gagctatgg tgcttgctgg tgcctgccac cttcaagttc tggacctggg catgacatcc | 4320 |
| ttcttttaa tgatgccatg gcaacttaga gattgcattt ttattaaagc atttcctacc | 4380 |
| gcaaagcaa atgttgggaa agtatttact ttttcggttt caaagtgata gaaagtgtg | 4440 |
| cttgggcat tgaaagaggt aaaattctct agatttatta gtcctaattc aatcctactt | 4500 |
| tagaacacc aaaaatgatg cgcatcaatg tattttatct tattttctca atctcctctc | 4560 |
| ctttcctcc acccataata agagaatgtt cctactcaca cttcagctgg gtcacatcca | 4620 |
| ccctccatt catccttcca tccatctttc catccattac ctccatccat ccttccaaca | 4680 |
| atatttatt gagtacctac tgtgtgccag gggctggtgg acagtggtg acatagtctc | 4740 |
| gccctcata gagttgattg tctagtgagg aagacaagca tttttaaaaa ataaatttaa | 4800 |
| cttacaaac tttgtttgtc acaagtggtg tttattgcaa taccgcttg gtttgcaacc | 4860 |
| ctttgctca acagaacata tgttgcaaga ccctcccatg ggggcacttg agttttggca | 4920 |
| ggctgacag agctctgggt tgtgcacatt tctttgcatt ccagctgtca ctctgtgcct | 4980 |
| tctacaact gattgcaaca gactgttgag ttatgataac accagtggga attgctggag | 5040 |
| aaccagagg cacttccacc ttggctggga agactatggt gctgccttgc ttctgtattt | 5100 |
| cttggatttt tcctgaaagt gtttttaaat aaagaacaat tgttagaaaa aaaaaa | 5156 |

<210> SEQ ID NO 131
<211> LENGTH: 671
<212> TYPE: DNA
<213> ORGANISM: Homo sapien

<400> SEQUENCE: 131

| | |
|---|---|
| aggtctggag ggcccacagc cggatgtggg acaccgggaa aaagtggtca tagcacacat | 60 |
| ttttgcatcc cggttgcagt gtgttgcaga cgaagtcctc ttgctcgtca ccccacactt | 120 |
| cctgggcagc caycacgagg atcatgactc ggaaaataaa gatgactgtg atccacacct | 180 |
| tcccgatgct ggtggagtgt tgttgacac ccccgatgaa agtgtgcagc gtcccccaat | 240 |
| ccattgcgct ggtttatccc tgagtcctgt ttccaacgac tgccagtgtt tcagacccaa | 300 |
| agaatgaggg caagatccct ctgcgagggt ttcagacctc cttctcctac cccactggag | 360 |
| tgcctagaag ccaatgggtg cacagtgatg atacgaatgt caatctttgc tcggtcagtg | 420 |
| aggatgtcgc ctggaatatt caaattgaat tacagatgca tgaagagggc gtacaagtta | 480 |
| gaattttct ttcgccatac agaaattgtt tagccagatc ttctgtactt cttttccttc | 540 |
| cctgacccctt cctgctcccc aggaagggag gtcagccccg tttgcaaaac acaggatgcc | 600 |
| cgtgacaccg gagacaggtc ttcttcaccg acaggaagtg ccttctggtg cctgcacgtt | 660 |

```
ttaactgcta t                                                              671
```

<210> SEQ ID NO 132
<211> LENGTH: 590
<212> TYPE: DNA
<213> ORGANISM: Homo sapien

<400> SEQUENCE: 132

```
ctgaatggaa aagcttatgg ctctgtgatg atattagtga ccagcggaga tgataagctt          60
cttggcaatt gcttacccac tgtgctcagc agtggttcaa caattcactc cattgccctg         120
ggttcatctg cagccccaaa tctggaggaa ttatcacgtc ttacaggagg tttaaagttc         180
tttgttccag atatatcaaa ctccaatagc atgattgatg ctttcagtag aatttcctct         240
ggaactggag acattttcca gcaacatatt cagcttgaaa gtacaggtga aaatgtcaaa         300
cctcaccatc aattgaaaaa cacagtgact gtggataata ctgtgggcaa cgacactatg         360
tttctagtta cgtggcaggc cagtggtcct cctgagatta tattatttga tcctgatgga         420
cgaaaatact acacaaataa ttttatcacc aatctaactt ttcggacagc tagtctttgg         480
attccaggaa cagctaagcc tgggcactgg acttacaccc tgaacaatac ccatcattct         540
ctgcaagccc tgaaagtgac agtgacctct cgcgcctcca actcagacct                    590
```

<210> SEQ ID NO 133
<211> LENGTH: 581
<212> TYPE: DNA
<213> ORGANISM: Homo sapien

<400> SEQUENCE: 133

```
aggtcctgtc cgggggcact gagaactccc tctggaattc ttgggggtg ttggggagag           60
actgtgggcc tggagataaa acttgtctcc tctaccacca ccctgtaccc tagcctgcac         120
ctgtcctcat ctctgcaaag ttcagcttcc ttccccaggt ctctgtgcac tctgtcttgg         180
atgctctggg gagctcatgg gtggaggagt ctccaccaga gggaggctca ggggactggt         240
tgggccaggg atgaatattt gagggataaa aattgtgtaa gagccaaaga attggtagta         300
gggggagaac agagaggagc tgggctatgg gaaatgattt gaataatgga gctgggaata         360
tggctggata tctggtacta aaaaagggtc tttaagaacc tacttcctaa tctcttcccc         420
aatccaaacc atagctgtct gtccagtgct ctcttcctgc ctccagctct gccccaggct         480
cctcctagac tctgtccctg ggctagggca ggggaggagg gagagcaggg ttggggaga         540
ggctgaggag agtgtgacat gtggggagag gaccagacct c                            581
```

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)
<223> OTHER INFORMATION: n = A,T,C or G

<400> SEQUENCE: 134

```
cctgggacca aagtgctgcc cagagctgag ggtcctggag ccacatgaga aggcttctcc          60
ctgtgtacct gtgcagcaca gggtagggtg agtccactca gctgtctagg agaggaccca         120
ggagcagcag agacncgcca agcctttact catacccatat tctgatcctt ttccagcaaa         180
ttgtggctac taatttgccc cctgaagatc aagatggctc tggggatgac tctgacaact         240
```

-continued

```
tctccggctc aggtgcaggt gaggttgtca tgggggcccc ccccacccaa gacggcaaca    300
ggtcatgcct gggggcagtg gtcaggcagt ctcctgtgtt tactgagcat gtactgagtg    360
caccctgcct gccctgtctc cacccagctg gctccaaagg gcaatgctga ggagaggaat    420
ggggtcgtga gctgctgtta aggagagctc atgcttggag gtgaggtgaa ggctgtgagc    480
tccagaaggc cccagggcgc nctgctgcac gcaggctcat attcactagg aatagcttta    540
ctcactaaga aacctctgga accccttca gaaggttatt tgactcctga gcctctattt    600
tctcatctgc aaaatgggaa taataccttg acctgataag cttgtggagc tgtaaggcag    660
cacagagcca gctggggtgt agctcttcca tccaagctcc cttccttact tcccctttcc    720
tgtggggact gggggagaga agtccctgag ctggaggtgg tcagggaagc ttcacagagg    780
aggtggctct tgagtggacc tcaggaagag gggtgagaga gctaaggaag gaggctgagg    840
tcatccctgg ggaagtgacc tagcggaggc ctgagagctg caaggtagga tatctgttgt    900
tggaagtgtc tgttgttgga agtgggggcc ttttttcag ggagggtggg gccagagaag    960
tgtgtgccct gggataagta ggataaccac agtagttatg ccctaaggg atgcccaccc   1020
caccctgtg gtcacagaaa agctttccca ggtggcctag gcacctgtct cgtggctcca   1080
gagacaggct gcacctgaca cacacaatgg aaggacagct ctccttgtcc attttccaag   1140
gagcttagcc tcagctgcct tgtccaggta ctagcctccc tcatagcctg agcttggcca   1200
gcccaggtgc tctggagcct cccccgaccc acccaacaca ctctgcttct ggtcctcccc   1260
accccccacc tccccaacac actctgcttc tggtcctgca ggtgctttgc aagatatcac   1320
cttgtcacag cagaccccct ccacttggaa ggacacgcag ctcctgacgg ctattcccac   1380
gtctccagaa cccaccggcc tggaggctac agctgcctcc acctccaccc tgccggctgg   1440
agagggcccc aaggagggag aggctgtagt cctgccagaa gtggagcctg cctcaccgc    1500
ccgggagcag gaggccaccc cccgacccag ggagaccaca cagctcccga ccactcatca   1560
ggcctcaacg accacagcca ccacggccca ggagcccgcc acctcccacc cccacaggga   1620
catgcagcct ggccaccatg agacctcaac ccctgcagga cccagccaag ctgaccttca   1680
cactccccac acagaggatg gaggtccttc tgccaccgag agggctgctg aggatggagc   1740
ctccagtcag ctcccagcag cagagggctc tggggagcag gtgagtggcc tctgcattcc   1800
ttgggaaatt gagtgggttg gtcctaatgc ctggcacttg gcaggcccta cacctgtgcc   1860
ctgcgcgatc tcgtattcct caccaggaag acagggcaca ggggccgcct tcccctaccc   1920
ccagggcctc gcagagcagg acagactaac tatgagatca gagcagaagc accttaaag    1980
atcacccaag agagggctcc caaactcaca atccaaactt gcagccctcg tcgaagagtg   2040
aacgttatac cagtcatttt atttatagct tcgtggattt acgcttacac taaatagtct   2100
gctattcata caaaatgtgt gctttgtatc acttttttg atatccatgc catggtccag    2160
ccagggtccg gagttgatgt ggcaagaagg cctggctttc gggccctgtg cgatcctggt   2220
ttgggtgcat ctgagtgggt ggtggcaaag atcaggagg caggagctgc ttctgggtct    2280
gtagtggagc tggttgctgc tgctggcggt gacctggcca acccaatctg cccctgccct   2340
cccacaggac ttcacctttg aaacctcggg ggagaatacg gctgtagtgg ccgtggagcc   2400
tgaccgccgg aaccagtccc cagtggatca gggggccacg ggggcctcac agggcctcct   2460
ggacaggaaa gaggtgctgg gaggtgagtt ttcttcagg ggggtagttt ggggtgaatt   2520
gctgctgtgg ggtcagggtg gggctgacca cagccaaggc cactgctttg ggagggtctg   2580
cacgagagcc caaggagccg ctgagctgag ctggccccgt ctacctgccc tagggggtcat   2640
```

```
tgccggaggc ctcgtggggc tcatctttgc tgtgtgcctg gtgggtttca tgctgtaccg    2700
catgaagaag aaggacgaag gcagctactc cttggaggag ccgaaacaag ccaacggcgg    2760
ggcctaccag aagcccacca acaggagga attctatgcc tgacgcggga gccatgcgcc    2820
ccctccgccc tgccactcac taggccccca cttgcctctt ccttgaagaa ctgcaggccc    2880
tggcctcccc tgccaccagg ccacctcccc agcattccag cccctctggt cgctcctgcc    2940
cacggagtcg tgggtgtgct ggagctcca ctctgcttct ctgacttctg cctggagact    3000
tagggcacca ggggtttctc gcataggacc tttccaccac agccagcacc tggcatcgca    3060
ccattctgac tcggtttctc caaactgaag cagcctctcc ccaggtccag ctctggaggg    3120 gaggggatc cgactgcttt ggacctaaat ggcctcatgt ggctggaaga tcctgcgggt    3180
ggggcttggg gctcacacac ctgtagcact tactggtagg accaagcatc ttggggggt    3240 ggccgctgag tggcagggga caggagtcac tttgtttcgt ggggaggtct aatctagata    3300
tcgacttgtt tttgcacatg tttcctctag ttctttgttc atagcccagt agaccttgtt    3360
acttctgagg taagttaagt aagttgattc ggtatccccc catcttgctt ccctaatcta    3420
tggtcgggag acagcatcag ggttaagaag actttttttt tttttttaa actaggagaa    3480 ccaaatctgg aagccaaaat gtaggcttag tttgtgtgtt gtctcttgag tttgtcgctc    3540
atgtgtgcaa cagggtatgg actatctgtc tggtggcccc gttctggtgg tctgttggca    3600
ggctggccag tccaggctgc cgtggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggactg tagggagggc ggcaggggcc    3780
tggagatcct cctgcaggct cacgcccgtc ctcctgtggc gccgtctcca ggggctgctt    3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt cttttgcttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
attctggttc cagggtccct ctgtgtattt gctttttttgt tttggctgaa attctcctgg    4260
aggtcggtag gttcagccaa ggtttataa ggctgatgtc aatttctgtg ttgccaagct    4320
ccaagcccat cttctaaatg gcaaaggaag gtggatggcc ccagcacagc ttgacctgag    4380
gctgtggtca cagcggaggt gtggagccga ggcctacccc ncagacacct tggacatcct    4440
cctcccaccc ggctgcagag gccagannnc agcccagggt cctgcactta cttgcttatt    4500
tgacaacgtt tcagcgactc cgttggccac tccgagagtg ggccagtctg tggatcagag    4560
atgcaccacc aagccaaggg aacctgtgtc cggtattcga tactgcgact ttctgcctgg    4620
agtgtatgac tgcacatgac tcgggggtgg ggaaagggg cggctgacca tgctcatctg    4680
ctggtccgtg gacggtncc caagccagag gtgggttcat tgtgtaacg acaataaacg    4740 gtacttgtca tttcgggcaa cggctgctgt ggtggtggtt gagtctcttc ttggcct       4797
```

<210> SEQ ID NO 135
<211> LENGTH: 2856
<212> TYPE: DNA
<213> ORGANISM: Homo sapien

```
<400> SEQUENCE: 135
tagtcgcggg tccccgagtg agcacgccag ggagcaggag accaaacgac ggggtcgga      60 gtcagagtcg cagtgggagt ccccggaccg gagcacgagc ctgagcggga gagcgccgct    120
cgcacgcccg tcgccacccg cgtacccggc gcagccagag ccaccagcgc agcgctgcca    180
tggagcccag cagcaagaag ctgacgggtc gcctcatgct ggctgtggga ggagcagtgc    240
ttggctccct gcagtttggc tacaacactg gagtcatcaa tgcccccag aaggtgatcg     300 aggagttcta caaccagaca tgggtccacc gctatgggga gagcatcctg cccaccacgc    360
tcaccacgct ctggtccctc tcagtggcca tcttttctgt tgggggcatg attggctcct    420
tctctgtggg cctttttcgtt aaccgctttg gccggcggaa ttcaatgctg atgatgaacc   480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc cccgcttcct gctcatcaac cgcaacgagg    840
agaaccgggc caagagtgtg ctaaagaagc tgcgcggac agctgacgtg acccatgacc    900
tgcaggagat gaaggaagag agtcggcaga tgatgcggga aagaaggtc accatcctgg    960 agctgttccg ctcccccgcc taccgccagc ccatcctcat cgctgtggtg ctgcagctgt   1020
cccagcagct gtctggcatc aacgctgtct ctattactc cacgagcatc ttcgagaagg   1080 cggggtgca gcagcctgtg tatgccacca ttggctccgg tatcgtcaac acggccttca    1140
ctgtcgtgtc gctgtttgtg gtggagcgag caggccggcg gaccctgcac ctcataggcc    1200
tcgctggcat ggcggttgt gccatactca tgaccatcgc gctagcactg ctggagcagc    1260
taccctggat gtcctatctg agcatcgtgg ccatctttgg ctttgtggcc ttctttgaag    1320
tgggtcctgg ccccatccca tggttcatcg tggctgaact cttcagccag gtccacgtc    1380 cagctgccat tgccgttgca ggcttctcca actggacctc aaatttcatt gtgggcatgt    1440
gcttccagta tgtggagcaa ctgtgtggtc cctacgtctt catcatcttc actgtgctcc    1500
tggttctgtt cttcatcttc acctacttca agttcctga gactaaaggc cggaccttcg    1560
atgagatcgc ttccggcttc cggcagggg gagccagcca aagtgataag acacccgagg    1620
agctgttcca tcccctgggg gctgattccc aagtgtgagt cgccccagat caccagcccg    1680
gcctgctccc agcagcccta aggatctctc aggagcacag gcagctggat gagacttcca    1740
aacctgacag atgtcagccg agccgggcct ggggctcctt tctccagcca gcaatgatgt    1800
ccagaagaat attcaggact taacggctcc aggattttaa caaaagcaag actgttgctc    1860
aaatctattc agacaagcaa caggtttttat aatttttttta ttactgattt tgttattttt   1920
atatcagcct gagtctcctg tgcccacatc ccaggcttca ccctgaatgg ttccatgcct    1980
gagggtggag actaagccct gtcgagacac ttgccttctt cacccagcta atctgtaggg    2040
ctggacctat gtcctaagga cacactaatc gaactatgaa ctacaaagct tctatcccag    2100
gaggtggcta tggccacccg ttctgctggc ctggatctcc ccactctagg ggtcaggctc    2160
cattaggatt tgcccctcc catctcttcc tacccaacca ctcaaattaa tctttctttta    2220 cctgagacca gttgggagca ctggagtgca gggaggagag gggaagggcc agtctgggct   2280
gccgggttct agtctccttt gcactgaggg ccacactatt accatgagaa gagggcctgt    2340
```

```
gggagcctgc aaactcactg ctcaagaaga catggagact cctgccctgt tgtgtataga    2400
tgcaagatat ttatatatat ttttggttgt caatattaaa tacagacact aagttatagt    2460
atatctggac aagccaactt gtaaatacac cacctcactc ctgttactta cctaaacaga    2520
tataaatggc tggtttttag aaacatggtt ttgaaatgct tgtggattga ggtaggagg     2580 tttggatggg agtgagacag aagtaagtgg ggttgcaacc actgcaacgg cttagacttc    2640
gactcaggat ccagtccctt acacgtacct ctcatcagtg tcctcttgct caaaaatctg    2700
tttgatccct gttacccaga gaatatatac attcttatc ttgacattca aggcatttct     2760
atcacatatt tgatagttgg tgttcaaaaa aacactagtt ttgtgccagc cgtgatgctc    2820
aggcttgaaa tcgcattatt ttgaatgtga agggaa                              2856
```

<210> SEQ ID NO 136
<211> LENGTH: 356
<212> TYPE: DNA
<213> ORGANISM: Homo sapien

<400> SEQUENCE: 136

```
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356
```

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137

```
gcaggtggag aagacatttt attgttcctg ggtctctgg aggcccattg gtggggctgg       60
gtcactggct gcccccggaa cagggcgctg ctccatggct ctgcttgtgg tagtctgtgg    120
ctatgtctcc cagcaaggac agaaactcag aaaaatcaat cttcttatcc tcattcttgt    180
cctttttctc aaagacatcg gcgaggtaat ttgtgccctt tttacctcgg cccgcgacca    240
cgctaaggcc aaanttccag acanayggcc gggccggtnc nataggggan cccaacttgg    300
ggacccaaac tctggcgcgg aaacacangg gcataagctt gnttcctgtg gggaaa        356
```

<210> SEQ ID NO 138
<211> LENGTH: 353
<212> TYPE: DNA
<213> ORGANISM: Homo sapien

<400> SEQUENCE: 138

```
aggtccagtc ctccacttgg cctgatgaga gtggggagtg gcaagggacg tttctcctgc     60
aatagacact tagatttctc tcttgtggga agaaaccacc tgtccatcca ctgactcttc    120
tacattgatg tggaaattgc tgctgctacc accacctcct gaagaggctt ccctgatgcc    180
aatgccagcc atcttggcat cctggccctc gagcaggctg cggtaagtag cgatctcctg    240
```

```
ctccagccgt gtctttatgt caagcagcat cttgtactcc tggttctgag cctccatctc    300
gcatcggagc tcactcagac ctcgsccgsg mssmcgctam gccgaattcc agc            353
```

<210> SEQ ID NO 139
<211> LENGTH: 371
<212> TYPE: DNA
<213> ORGANISM: Homo sapien

<400> SEQUENCE: 139

```
agcgtggtcg cggccgaggt ccatccgaag caagattgca gatggcagtg tgaagagaga     60
agacatattc tacacttcaa gctttggtg caattcccat cgaccagagt tggtccgacc    120
agccttggaa aggtcactga aaaatcttca attggattat gttgacctct accttattca   180
ttttccagtg tctgtaaagc caggtgagga agtgatccca aaagatgaaa atggaaaaat   240
actatttgac acagtggatc tctgtgccac gtgggaggcc gtggagaagt gtaaagatgc   300
aggattggac ctgcccgggc ggccgctcga aagccgaatt ccagcacact ggcggccgtt   360
actagtggat c                                                         371
```

<210> SEQ ID NO 140
<211> LENGTH: 370
<212> TYPE: DNA
<213> ORGANISM: Homo sapien

<400> SEQUENCE: 140

```
tagcgtggtc gcggccgagg tccatctccc tttgggaact aggggctgc tggtgggaaa      60 tgggagccag ggcagatgtt gcattccttt gtgtccctgt aaatgtggga ctacaagaag   120
aggagctgcc tgagtggtac tttctcttcc tggtaatcct ctggcccagc ctcatggcag   180
aatagaggta tttttaggct attttttgtaa tatggcttct ggtcaaaatc cctgtgtagc   240
tgaattccca agccctgcat tgtacagccc cccactcccc tcaccaccta ataaaggaat   300
agttaacact caaaaaaaaa aaaaaacctg cccgggcggc cgctcgaaag ccgaattcca   360
gcacactggc                                                           370
```

<210> SEQ ID NO 141
<211> LENGTH: 371
<212> TYPE: DNA
<213> ORGANISM: Homo sapien

<400> SEQUENCE: 141

```
tagcgtggtc gcggccgagg tcctctgtgc tgcctgtcac agcccgatgg taccagcgca     60
gggtgtaggc agtgcaggag ccctcatcca gtggcaggga acaggggtca tcactatccc   120
aaggagcttc agggtcctgg tactcctcca cagaatactc ggagtattca gagtactcat   180
catcctcagg gggtacccgc tcttcctcct ctgcatgaga gacgcggagc acaggcacag   240
catggagctg ggagccggca gtgtctgcag cataactagg gaggggtcgt gatccagatg   300
cgatgaactg gccctggcag gcacagtgct gactcatctc ttggcgacct gcccgggcgg   360
ccgctcgaag c                                                         371
```

<210> SEQ ID NO 142
<211> LENGTH: 343
<212> TYPE: DNA
<213> ORGANISM: Homo sapien

<400> SEQUENCE: 142

```
gcgttttgag gccaatggtg taaaaggaaa tatcttcaca taaaaactag atggaagcat     60
```

```
tgtcagaaac ctctttgtga tgtttgcttt caactcacag agttgaacat tccttttcat    120
agagcagttt tgaaacactc ttttgtagaa tttgcaagcg gatgattgga tcgctatgag    180
gtcttcattg gaaacgggat acctttacat aaaaactaga cagtagcatt ctcagaaatt    240
tctttgggat gtgggcattc aacccacaga ggagaacttc atttgataga gcagttttga    300 aacaccctt ttgtagaatc tacaggtgga catttagagt gct                       343

<210> SEQ ID NO 143
<211> LENGTH: 354
<212> TYPE: DNA
<213> ORGANISM: Homo sapien

<400> SEQUENCE: 143
aggtctgatg gcagaaaaac tcagactgtc tgcaacttta cagatggtgc attggttcag     60
catcaggagt gggatgggaa ggaaagcaca ataacaagaa aattgaaaga tgggaaatta    120
gtggtggagt gtgtcatgaa caatgtcacc tgtactcgga tctatgaaaa agtagaataa    180
aaattccatc atcactttgg acaggagtta ttaagagaa tgaccaagct cagttcaatg    240
agcaaatctc catactgttt ctttcttttt tttttcatta ctgtgttcaa ttatctttat    300
cataaacatt ttacatgcag ctatttcaaa gtgtgttgga ttaattagga tcat          354

<210> SEQ ID NO 144
<211> LENGTH: 353
<212> TYPE: DNA
<213> ORGANISM: Homo sapien

<400> SEQUENCE: 144
ggtcaaggac ctgggggacc cccaggtcca gcagccacat gattctgcag cagacaggga     60
cctagagcac atctggatct cagccccacc cctggcaacc tgcctgccta gagaactccc    120
aagatgacag actaagtagg attctgccat ttagaataat tctggtatcc tgggcgttgc    180
gttaagttgc ttaactttca ttctgtctta cgatagtctt cagaggtggg aacagatgaa    240
gaaaccatgc cccagagaag gttaagtgac ttcctcttta tggagccagt gttccaacct    300
aggtttgcct gataccagac ctgtggcccc acctcccatg caggtctctg tgg           353

<210> SEQ ID NO 145
<211> LENGTH: 371
<212> TYPE: DNA
<213> ORGANISM: Homo sapien

<400> SEQUENCE: 145
caggtctgtc ataaactggt ctggagtttc tgacgactcc ttgttcacca aatgcaccat     60
ttcctgagac ttgctggcct ctccgttgag tccacttggc tttctgtcct ccacagctcc    120
attgccactg ttgatcacta gcttttctt ctgcccacac cttcttcgac tgttgactgc    180
aatgcaaact gcaagaatca aagccaaggc caagagggat gccaagatga tcagccattc    240
tggaatttgg ggtgtcctta taggaccaga ggttgtgttt gctccacctt cttgactccc    300
atgtgagacc tcggccgcga ccacgctaag ccgaattcca gcacactggc ggcccgttac    360
tagtggatcc g                                                          371

<210> SEQ ID NO 146
<211> LENGTH: 355
<212> TYPE: DNA
<213> ORGANISM: Homo sapien
```

<400> SEQUENCE: 146

```
ggtcctccgt cctcttccca gaggtgtcgg ggcttggccc cagcctccat cttcgtctct       60
caggatggcg agtagcagcg gctccaaggc tgaattcatt gtcggaggga aatataaact      120
ggtacggaag atcgggtctg gctccttcgg ggacatctat ttggcgatca acatcaccaa      180
cggcgaggaa gtggcagtga agctagaatc tcagaaggcc aggcatcccc agttgctgta      240
cgagagcaag ctctataaga ttcttcaagg tggggttggc atcccccaca tacggtggta      300
tggtcaggaa aaagactaca atgtactagt catggatctt ctgggaccta gcctc          355
```

<210> SEQ ID NO 147
<211> LENGTH: 355
<212> TYPE: DNA
<213> ORGANISM: Homo sapien

<400> SEQUENCE: 147

```
ggtctgttac aaaatgaaga cagacaacac aacatttact ctgtggagat atcctactca       60
tactatgcac gtgctgtgat tttgaacata actcgtccca aaaacttgtc acgatcatcc      120
tgacttttta ggttggctga tccatcaatc ttgcactcaa ctgttacttc tttcccagtg      180
ttgttaggag caaagctgac ctgaacagca accaatggct gtagataccc aacatgcagt      240
tttttcccat aatatgggaa atattttaag tctatcattc cattatgagg ataaactgct      300
acatttggta tatcttcatt ctttgaaaca caatctatcc ttggcactcc ttcag          355
```

<210> SEQ ID NO 148
<211> LENGTH: 369
<212> TYPE: DNA
<213> ORGANISM: Homo sapien

<400> SEQUENCE: 148

```
aggtctctct ccccctctcc ctctcctgcc agccaagtga agacatgctt acttcccctt       60
caccttcctt catgatgtgg gaagagtgct gcaacccagc cctagccaac accgcatgag      120
agggagtgtg ccgagggctt ctgagaaggt ttctctcaca tctagaaaga agcgcttaag      180
atgtggcagc ccctcttctt caagtggctc ttgtcctgtt gccctgggag ttctcaaatt      240
gctgcagcag cctccatcca gcctgaggat gacatcaata cacagaggaa gaagagtcag      300
gaaaagatga gagaagttac agactctcct gggcgacccc gagagcttac cattcctcag      360
acttcttca                                                              369
```

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 149

```
actagtcaaa aatgctaaaa taatttggga gaaaatattt tttaagtagt gttatagttt       60
catgtttatc tttttattatg tttttgtgaag ttgtgtcttt tcactaatta cctatactat   120
gccaatattt ccttatatct atccataaca tttatactac atttgtaana naatatgcac    180
gtgaaactta acactttata aggtaaaaat gaggtttcca anatttaata atctgatcaa    240
gttcttgtta tttccaaata gaatggactt ggtctgttaa gggctaagga gaagaggaag   300
ataaggttaa aagttgttaa tgaccaaaca ttctaaaaga aatgcaaaaa aaaagtttat   360
```

```
tttcaagcct tcgaactatt taaggaaagc aaaatcattt cctaaatgca tatcatttgt      420
gagaatttct cattaatatc ctgaatcatt catttcacta aggctcatgt tnactccgat      480
atgtctctaa gaaagtacta tttcatggtc caaacctggt tgccatantt gggtaaaggc      540
tttcccttaa gtgtgaaant atttaaaatg aaatttccct ctttttaaaa attctttana      600
agggttaagg gtgttgggga                                                  620

<210> SEQ ID NO 150
<211> LENGTH: 371
<212> TYPE: DNA
<213> ORGANISM: Homo sapien

<400> SEQUENCE: 150
ggtccgatca aaacctgcta cctccccaag actttactag tgccgataaa ctttctcaaa       60
gagcaaccag tatcacttcc ctgtttataa aacctctaac catctctttg ttctttgaac      120
atgctgaaaa ccacctggtc tgcatgtatg cccgaatttg yaattctttt ctctcaaatg      180
aaaatttaat tttagggatt catttctata ttttcacata tgtagtatta ttatttcctt      240
atatgtgtaa ggtgaaattt atggtatttg agtgtgcaag aaaatatatt tttaaagctt      300 tcattttttcc cccagtgaat gatttagaat tttttatgta aatatacaga atgttttttc      360
ttacttttat a                                                          371

<210> SEQ ID NO 151
<211> LENGTH: 4655
<212> TYPE: DNA
<213> ORGANISM: Homo sapien

<400> SEQUENCE: 151
gggacttgag ttctgttatc ttcttaagta gattcatatt gtaagggtct cggggtgggg       60
gggttggcaa atcctggag ccagaagaaa ggacagcagc attgatcaat cttacagcta      120
acatgttgta cctggaaaac aatgcccaga ctcaatttag tgagccacag tacacgaacc      180
tggggctcct gaacagcatg gaccagcaga ttcagaacgg ctcctcgtcc accagtccct      240
ataacacaga ccacgcgcag aacagcgtca cggcgccctc gccctacgca cagcccagct      300
ccaccttcga tgctctctct ccatcacccg ccatcccctc aacaccgac tacccaggcc      360 cgcacagttt cgacgtgtcc ttccagcagt cgagcaccgc caagtcggcc acctggacgt      420
attccactga actgaagaaa ctctactgcc aaattgcaaa gacatgcccc atccagatca      480
aggtgatgac cccacctcct cagggagctg ttatccgcgc catgcctgtc tacaaaaaag      540
ctgagcacgt cacggaggtg gtgaagcggt gccccaacca tgagctgagc cgtgaattca      600
acgagggaca gattgcccct yctagtcatt tgattcgagt agagggaac agccatgccc      660 agtatgtaga gatccccatc acaggaagac agagtgtgct ggtaccttat gagccacccc      720
aggttggcac tgaattcacg acagtcttgt acaatttcat gtgtaacagc agttgtgttg      780
gagggatgaa ccgccgtcca atttaatca ttgttactct ggaaaccaga gatgggcaag      840
tcctgggccg acgctgcttt gaggcccgga tctgtgcttg cccaggaaga gacaggaagg      900
cggatgaaga tagcatcaga aagcagcaag tttcggacag tacaaagaac ggtgatggta      960
cgaagcgccc gtttcgtcag aacacacatg gtatccagat gacatccatc aagaaacgaa     1020
gatccccaga tgatgaactg gtatacttac cagtgagggg ccgtgagact tatgaaatgc     1080
tggtgaagat caaagagtcc ctggaactca tgcagtacct tcttcagcac acaattgaaa     1140
```

-continued

```
cgtacaggca acagcaacag cagcagcacc agcacttact tcagaaacag acctcaatac   1200
agtctccatc ttcatatggt aacagctccc cacctctgaa caaaatgaac agcatgaaca   1260
agctgccttc tgtgagccag cttatcaacc ctcagcagcg caacgccctc actcctacaa   1320
ccattcctga tggcatggga gccaacattc ccatgatggg cacccacatg ccaatggctg   1380
gagacatgaa tggactcagc cccacccagg cactccctcc cccactctcc atgccatcca   1440
cctcccactg cacaccccca cctccgtatc ccacagattg cagcattgtc agtttcttag   1500
cgaggttggg ctgttcatca tgtctggact atttcacgac ccaggggctg accaccatct   1560
atcagattga gcattactcc atggatgatc tggcaagtct gaaaatccct gagcaatttc   1620
gacatgcgat ctggaagggc atcctggacc accggcagct ccacgaattc tcctcccctt   1680
ctcatctcct gcggacccca agcagtgcct ctacagtcag tgtgggctcc agtgagaccc   1740 gggtgagcg tgttattgat gctgtgcgat tcaccctccg ccagaccatc tctttcccac   1800
cccgagatga gtggaatgac ttcaactttg acatggatgc tcgccgcaat aagcaacagc   1860
gcatcaaaga ggaggggggag tgagcctcac catgtgagct cttcctatcc ctctcctaac   1920
tgccagcccc ctaaaagcac tcctgcttaa tcttcaaagc cttctcccta gctcctcccc   1980
ttcctcttgt ctgatttctt aggggaagga gaagtaagag gcttacttct taccctaacc   2040
atctgacctg gcatctaatt ctgattctgg ctttaagcct tcaaaactat agcttgcaga   2100
actgtagctt gccatggcta gtagaagtg agcaaaaaag agttgggtgt ctccttaagc   2160
tgcagagatt tctcattgac ttttataaag catgttcacc cttatagtct aagactatat   2220
atataaatgt ataaatatac agtatagatt tttgggtggg gggcattgag tattgtttaa   2280
aatgtaattt aaatgaaaga aaattgagtt gcacttattg accatttttt aatttacttg   2340
ttttggatgg cttgtctata ctccttccct taaggggtat catgtatggt gataggtatc   2400
tagagcttaa tgctacatgt gagtgacgat gatgtacaga ttctttcagt tctttggatt   2460
ctaaatacat gccacatcaa acctttgagt agatccattt ccattgctta ttatgtaggt   2520
aagactgtag atatgtattc ttttctcagt gttggtatat tttatattac tgacatttct   2580
tctagtgatg atggttcacg ttggggtgat ttaatccagt tataagaaga agttcatgtc   2640
caaacgtcct ctttagtttt tggttgggaa tgaggaaaat tcttaaaagg cccatagcag   2700
ccagttcaaa acacccgac gtcatgtatt tgagcatatc agtaaccccc ttaaatttaa   2760
taccagatac cttatcttac aatattgatt gggaaaacat ttgctgccat tacagaggta   2820
ttaaaactaa atttcactac tagattgact aactcaaata cacatttgct actgttgtaa   2880
gaattctgat tgatttgatt gggatgaatg ccatctatct agttctaaca gtgaagtttt   2940
actgtctatt aatattcagg gtaaatagga atcattcaga aatgttgagt ctgtactaaa   3000
cagtaagata tctcaatgaa ccataaattc aactttgtaa aaatctttg aagcatagat   3060 aatattgttt ggtaaatgtt tcttttgttt ggtaaatgtt tcytttaaag accctcctat   3120
tctataaaac tctgcatgta gaggcttgtt tacctttctc tctctaaggt ttacaatagg   3180
agtggtgatt tgaaaaatat aaaattatga gattggtttt cctgtggcat aaattgcatc   3240
actgtatcat tttctttttt aaccggtaag agtttcagtt tgttggaaag taactgtgag   3300
aacccagttt cccgtccatc tcccttaggg actacccata gacatgaaag gtccccacag   3360
agcaagagat aagtctttca tggctgctgt tgcttaaacc acttaaacga agagttccct   3420
tgaaactttg ggaaaacatg ttaatgacaa tattccagat ctttcagaaa tataacacat   3480
ttttttgcat gcatgcaaat gagctctgaa atcttcccat gcattctggt caagggctgt   3540
```

-continued

```
cattgcacat aagcttccat tttaatttta aagtgcaaaa gggccagcgt ggctctaaaa    3600
ggtaatgtgt ggattgcctc tgaaaagtgt gtatatattt tgtgtgaaat tgcatacttt    3660
gtattttgat tatttttttt ttcttcttgg gatagtggga tttccagaac cacacttgaa    3720
accttttttt atcgttttg tattttcatg aaaataccat ttagtaagaa taccacatca    3780
aataagaaat aatgctacaa ttttaagagg ggagggaagg gaaagttttt tttttatta    3840
tttttttaaa attttgtatg ttaaagagaa tgagtccttg atttcaaagt tttgttgtac    3900
ttaaatggta ataagcactg taaacttctg caacaagcat gcagctttgc aaacccatta    3960
aggggaagaa tgaaagctgt tccttggtcc tagtaagaag acaaactgct tcccttactt    4020
tgctgagggt ttgaataaac ctaggacttc cgagctatgt cagtactatt caggtaacac    4080
tagggccttg gaaatccctg tactgtgtct catggatttg gcactagcca aagcgaggca    4140
cccttactg gcttacctcc tcatggcagc ctactctcct tgagtgtatg agtagccagg    4200
gtaaggggta aaggatagt aagcatagaa accactagaa agtgggctta atggagttct    4260
tgtggcctca gctcaatgca gttagctgaa gaattgaaaa gttttttgttt ggagacgttt    4320
ataaacagaa atggaaagca gagttttcat taaatccttt tacctttttt ttttcttggt    4380
aatcccctaa aataacagta tgtgggatat tgaatgttaa agggatattt ttttctatta    4440
tttttataat tgtacaaaat taagcaaatg ttaaaagttt tatatgcttt attaatgttt    4500
tcaaaaggta ttatacatgt gatacatttt ttaagcttca gttgcttgtc ttctggtact    4560
ttctgttatg ggcttttggg gagccagaag ccaatctaca atctctttt gtttgccagg    4620
acatgcaata aaatttaaaa aataaataaa aacta                               4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Ser Ser His Leu Ile Arg Val Glu Gly Asn
                165                 170                 175
```

```
Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
            195                 200                 205

Leu Tyr Asn Phe Met Cys Asn Ser Ser Cys Val Gly Met Asn Arg
            210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
            245                 250                 255

Asp Arg Lys Ala Asp Glu Asp Ser Ile Arg Lys Gln Val Ser Asp
            260                 265                 270

Ser Thr Lys Asn Gly Asp Gly Thr Lys Arg Pro Phe Arg Gln Asn Thr
            275                 280                 285

His Gly Ile Gln Met Thr Ser Ile Lys Lys Arg Arg Ser Pro Asp Asp
            290                 295                 300

Glu Leu Val Tyr Leu Pro Val Arg Gly Arg Glu Thr Tyr Glu Met Leu
305                 310                 315                 320

Val Lys Ile Lys Glu Ser Leu Glu Leu Met Gln Tyr Leu Leu Gln His
            325                 330                 335

Thr Ile Glu Thr Tyr Arg Gln Gln Gln Gln Gln His Gln His Leu
            340                 345                 350

Leu Gln Lys Gln Thr Ser Ile Gln Ser Pro Ser Ser Tyr Gly Asn Ser
            355                 360                 365

Ser Pro Pro Leu Asn Lys Met Asn Ser Met Asn Lys Leu Pro Ser Val
            370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
            405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
            435                 440                 445

Tyr Pro Thr Asp Cys Ser Ile Val Ser Phe Leu Ala Arg Leu Gly Cys
            450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
            485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
            515                 520                 525

Ala Ser Thr Val Ser Val Gly Ser Ser Glu Thr Arg Gly Glu Arg Val
            530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
            565                 570                 575

Lys Gln Gln Arg Ile Lys Glu Glu Gly Glu
            580                 585
```

-continued

```
<210> SEQ ID NO 153
<211> LENGTH: 2007
<212> TYPE: DNA
<213> ORGANISM: Homo sapien

<400> SEQUENCE: 153
gaattcgtcg ctgctccagg gaaagttctg ttactccact gactctctct tttcctgata      60
acatggccag caagaaagta attacagtgt ttggagcaac aggagctcaa ggtggctctg     120
tggccagggc aattttggag agcaaaaaat ttgcagtgag agcagtgacc agggatgtga     180
cttgaccaaa tgccctggag ctccagcgcc ttggagctga ggtggtcaaa ggtgacctga     240
atgataaagc atcggtggac agtgccttaa aaggtgtcta tggggccttc ttggtgacca     300
acttctggga ccctctcaac caagataagg aagtgtgtcg ggggaagctg gtggcagact     360
ccgccaagca cctgggtctg aagcacgtgg tgtacagcgg cctggagaac gtcaagcgac     420
tgacggatgg caagctggag gtgccgcact ttgacagcaa gggcgaggtg gaggagtact     480
tctggtccat tggcatcccc atgaccagtg tccgcgtggc ggcctacttt gaaaactttc     540
tcgcggcgtg gcggcccgtg aaagcctctg atggagatta ctacaccttg gctgtaccga     600
tgggagatgt accaatggat ggtatctctg ttgctgatat tggagcagcc gtctctagca     660 ttttttaattc tccagaggaa ttttttaggca aggccgtggg gctcagtgca gaagcactaa     720
caatacagca atatgctgat gttttgtcca aggctttggg gaaagaagtc cgagatgcaa     780
agattacccc ggaagctttc gagaagctgg gattccctgc agcaaaggaa atagccaata     840
tgtgtcgttt ctatgaaatg aagccagacc gagatgtcaa tctcacccac caactaaatc     900
ccaaagtcaa aagcttcagc cagtttatct cagagaacca gggagccttc aagggcatgt     960
agaaaatcag ctgttcagat aggcctctgc accacacagc ctctttcctc tctgatcctt    1020 ttcctctttta cggcacaaca ttcatgttga cagaacatgc tggaatgcaa ttgtttgcaa    1080
caccgaagga tttcctgcgg tcgcctcttc agtaggaagc actgcattgg tgataggaca    1140
cggtaatttg attcacattt aacttgctag ttagtgataa gggtggtaca actgtttggt    1200
aaaatgagaa gcctcggaac ttggagcttc tctcctacca ctaatgggag ggcagattat    1260
actgggattt ctcctgggtg agtaatttca agccctaatg ctgaaattcc cctaggcagc    1320
tccagttttc tcaactgcat tgcaaaattc ccagtgaact tttaagtact tttaacttaa    1380
aaaaatgaac atctttgtag agaattttct ggggaacatg gtgttcaatg aacaagcaca    1440
agcattggaa atgctaaaat tcagttttgc ctcaagattg gaagtttatt ttctgactca    1500
ttcatgaagt catctattga gccaccattc aattattcat ctattaattc cttgatcctt    1560
catttatcca ttctgcaaac ttttcttgag caccagcacg ggtggccatt tgtggacttc    1620
tcttcattcc tatgtgtttt cttatcaaag tgatccactc tcgaaaggct cctttccagt    1680
ctgtggttgg gttcaagtca tgccagggcc agggggccca tctcctcgtt tagctctagg    1740
caaaatccag gggatctgca gtggggagcg gggcaggaa gctggaggga aggcctgtga    1800
agggtaggga tgtggaaaga caaggtgaca gaaggaccca ataggacctt tctatatctc    1860
tggcttagca ttttctacat catattgtaa tcgtcttatt tgctagtttt cttccttact    1920
gtgagtgact aacagtcatc tttatcccag tgcctggtac ataataagtg atcaataaat    1980
gttgattgac taaaaaaaaa aaaaaaa                                         2007

<210> SEQ ID NO 154
<211> LENGTH: 2148
```

<212> TYPE: DNA
<213> ORGANISM: Homo sapien

<400> SEQUENCE: 154

| | |
|---|---:|
| gaattcgtcg ctgctccagg gaaagttctg ttactccact gactctctct tttcctgata | 60 |
| acatggccag caagaaagta attacagtgt ttggagcaac aggagctcaa ggtggctctg | 120 |
| tggccagggc aattttggag agcaaaaaat ttgcagtgag agcagtgacc agggatgtga | 180 |
| cttgaccaaa tgccctggag ctccagcgcc ttggagctga ggtggtcaaa ggtgacctga | 240 |
| atgataaagc atcggtggac agtgccttaa aaggggaagc tggtggcaga ctccgccaag | 300 |
| cacctgggtc tgaagcacgt ggtgtacagc ggcctggaga acgtcaagcg actgacggat | 360 |
| ggcaagctgg aggtgccgca ctttgacagc aagggcgagg tggaggagta cttctggtcc | 420 |
| attggcatcc ccatgaccag tgtccgcgtg gcggcctact ttgaaaactt tctcgcggcg | 480 |
| tggcggcccg tgaaagcctc tgatggagat tactacacct ggctgtacc gatgggagat | 540 |
| gtaccaatgg atggtatctc tgttgctgat attggagcag ccgtctctag cattttaat | 600 |
| tctccagagg aatttttagg caaggccgtg ggctcagtg cagaagcact aacaatacag | 660 |
| caatatgctg atgttttgtc caaggctttg gggaagaag tccgagatgc aaagactatc | 720 |
| tgtgctatag atgaccagaa aacagtggaa gaaggttca tggaagacgt gggcttgagt | 780 |
| tggtccttga gggaacatga ccatgtatag acagaggagg catcaagaag gctggcctgg | 840 |
| ctaattctgg aataaacacg acaaaccaga ggcagtacgg gaaggaggca aattctggct | 900 |
| ctgcctctat ccttgattac cccggaagct ttcgagaagc tgggattccc tgcagcaaag | 960 |
| gaaatagcca atatgtgtcg tttctatgaa atgaagccag accagatgt caatctcacc | 1020 |
| caccaactaa atcccaaagt caaaagcttc agccatttta tctcagagaa ccagggagcc | 1080 |
| ttcaagggca tgtagaaaat cagctgttca gataggcctc tgcaccacac agcctctttc | 1140 |
| ctctctgatc cttttcctct ttacggcaca acattcatgt tgacagaaca tgctggaatg | 1200 |
| caattgtttg caacaccgaa ggatttcctg cggtcgcctc ttcagtagga agcactgcat | 1260 |
| tggtgatagg acacggtaat ttgattcaca tttaacttgc tagttagtga taagggtggt | 1320 |
| acaactgttt ggtaaaatga gaagcctcgg aacttggagc ttctctccta ccactaatgg | 1380 |
| gagggcagat tatactggga tttctcctgg gtgagtaatt tcaagcccta atgctgaaat | 1440 |
| tcccctaggc agctccagtt ttctcaactg cattgcaaaa ttcccagtga acttttaagt | 1500 |
| acttttaact taaaaaaatg aacatctttg tagagaattt tctggggaac atggtgttca | 1560 |
| atgaacaagc acaagcattg gaaatgctaa aattcagttt tgcctcaaga ttggaagttt | 1620 |
| attttctgac tcattcatga agtcatctat tgagccacca ttcaattatt catctattaa | 1680 |
| ttccttgatc cttcatttat ccattctgca aacttttctt gagcaccagc acgggtggcc | 1740 |
| atttgtggac ttctcttcat tcctatgtgt tttcttatca aagtgatcca ctctcgaaag | 1800 |
| gctccttttcc agtctgtggt tgggttcaag tcatgccagg ccaggggggc ccatctcctc | 1860 |
| gtttagctct aggcaaaatc caggggatct gcagtgggga gcggggcag gaagctggag | 1920 |
| ggaaggcctg tgaagggtag ggatgtggaa agacaaggtg acagaaggac ccaataggac | 1980 |
| cttttctatat ctctggctta gcattttcta catcatattg taatcgtctt atttgctagt | 2040 |
| tttcttcctt actgtgagtg actaacagtc atctttatcc cagtgcctgg tacataataa | 2100 |
| gtgatcaata aatgttgatt gactaaatga aaaaaaaaa aaaaaaaa | 2148 |

<210> SEQ ID NO 155

<211> LENGTH: 153
<212> TYPE: PRT
<213> ORGANISM: Homo sapien

<400> SEQUENCE: 155

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
        50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150
```

<210> SEQ ID NO 156
<211> LENGTH: 128
<212> TYPE: PRT
<213> ORGANISM: Homo sapien

<400> SEQUENCE: 156

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
        50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Thr Ile
                85                  90                  95

Cys Ala Ile Asp Asp Gln Lys Thr Val Glu Glu Gly Phe Met Glu Asp
            100                 105                 110

Val Gly Leu Ser Trp Ser Leu Arg Glu His Asp His Val Ala Gly Ala
        115                 120                 125
```

<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157

```
ctgcagcccg ggggatccac tagtccagtg tggtggaatt cattggtctt tacaagactt      60
ggatacatta cagcagacat ggaaatataa ttttaaaaaa tttctctcca acctccttca     120
aattcagtca ccactgttat attaccttct ccaggaaccc tccagtgggg aaggctgcga     180
tattagattt ccttgtatgc aaagttttg ttgaaagctg tgctcagagg agtgagagg      240
agaggaagga gaaaactgca tcataacttt acagaattga atctagagtc ttccccgaaa     300
agcccagaaa cttctctgcn gnatctggct tgtccatctg gtctaaggtg gctgcttctt     360
ccccagccat cgagtcagtt tgtgcccatg aataatacac gacctgctat ttcccatgac     420
tgct                                                                  424
```

<210> SEQ ID NO 158
<211> LENGTH: 2099
<212> TYPE: DNA
<213> ORGANISM: Homo sapien

<400> SEQUENCE: 158

```
ccgcggttaa aaggcgcagc aggtgggagc cggggccttc acccgaaacc cgacgagagc      60
ccgacagccg gcggcgcccg agcccgacct gcctgcccag ccggagcgaa gggcgccgcc     120
ccgcgcagag cccgcgccag ggccgccggc cgcagagcag ttaaaacgtg caggcaccag     180
aaggcacttc ctgtcggtga agaagacctg tctccggtgt cacggcatcc ctgtgttttg     240
caaacggggc tgacctccct tcctggggag caggaagggt cagggaagga aaagaagtac     300
agaagatctg gctaaacaat ttctgtatgg cgaaagaaaa attctaactt gtacgccctc     360
ttcatgcatc tttaattcaa tttgaatatt ccaggcgaca tcctcactga ccgagcaaag     420
attgacattc gtatcatcac tgtgcaccat ggcttctag gcactccagt ggggtaggag     480
aaggaggtct gaaaccctcg cagagggatc ttgccctcat tctttgggtc tgaaacactg     540
gcagtcgttg gaaacaggac tcagggataa accagcgcaa tggattgggg gacgctgcac     600
actttcatcg ggggtgtcaa caaacactcc accagcatcg ggaaggtgtg gatcacagtc     660
atctttattt tccgagtcat gatcctcgtg gtggctgccc aggaagtgtg gggtgacgag     720
caagaggact tcgtctgcaa cacactgcaa ccgggatgca aaaatgtgtg ctatgaccac     780
ttttttcccgg tgtcccacat ccggctgtgg gccctccagc tgatcttcgt ctccacccca     840
gcgctgctgg tggccatgca tgtggcctac tacaggcacg aaaccactcg caagttcagg     900
cgaggagaga agaggaatga tttcaaagac atagaggaca ttaaaaagca gaaggttcgg    960
atagaggggt cgctgtggtg gacgtacacc agcagcatct ttttccgaat catctttgaa    1020
gcagccttta tgtatgtgtt ttacttcctt tacaatggga ccacctgcc ctgggtgttg    1080
aaatgtggga ttgaccccctg ccccaacctt gttgactgct ttatttctag gccaacagag    1140
aagaccgtgt ttaccatttt tatgatttct gcgtctgtga tttgcatgct gcttaacgtg    1200
gcagagttgt gctacctgct gctgaaagtg tgttttagga gatcaaagag agcacagacg    1260
caaaaaaatc accccaatca tgccctaaag gagagtaagc agaatgaaat gaatgagctg    1320
atttcagata gtggtcaaaa tgcaatcaca ggttcccaag ctaaacattt caaggtaaaa    1380
tgtagctgcg tcataaggag acttctgtct tctccagaag gcaataccaa cctgaaagtt    1440
ccttctgtag cctgaagagt ttgtaaatga ctttcataat aaatagacac ttgagttaac    1500
ttttttgtagg atacttgctc cattcataca caacgtaatc aaatatgtgg tccatctctg    1560
aaaacaagag actgcttgac aaaggagcat tgcagtcact ttgacaggtt cctttaagt    1620
```

-continued

```
ggactctctg acaaagtggg tactttctga aaatttatat aactgttgtt gataaggaac    1680
atttatccag gaattgatac gtttattagg aaaagatatt tttataggct tggatgtttt    1740
tagttctgac tttgaattta tataaagtat ttttataatg actggtcttc cttacctgga    1800
aaaacatgcg atgttagttt tagaattaca ccacaagtat ctaaatttgg aacttacaaa    1860
gggtctatct tgtaaatatt gttttgcatt gtctgttggc aaatttgtga actgtcatga    1920
tacgcttaag gtggaaagtg ttcattgcac aatatatttt tactgctttc tgaatgtaga    1980
cggaacagtg tggaagcaga aggctttttt aactcatccg tttgccaatc attgcaaaca    2040
actgaaatgt ggatgtgatt gcctcaataa agctcgtccc cattgcttaa aaaaaaaaa     2099
```

<210> SEQ ID NO 159
<211> LENGTH: 291
<212> TYPE: PRT
<213> ORGANISM: Homo sapien

<400> SEQUENCE: 159

```
Met Asp Trp Gly Thr Leu His Thr Phe Ile Gly Gly Val Asn Lys His
 1               5                  10                  15

Ser Thr Ser Ile Gly Lys Val Trp Ile Thr Val Ile Phe Ile Phe Arg
            20                  25                  30

Val Met Ile Leu Val Val Ala Ala Gln Glu Val Trp Gly Asp Glu Gln
        35                  40                  45

Glu Asp Phe Val Cys Asn Thr Leu Gln Pro Gly Cys Lys Asn Val Cys
    50                  55                  60

Tyr Asp His Phe Phe Pro Val Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205

Glu Leu Cys Tyr Leu Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Ser Gln Ala Lys His Phe Lys Val Lys Cys Ser Cys Val Ile
            260                 265                 270

Arg Arg Leu Leu Ser Ser Pro Glu Gly Asn Thr Asn Leu Lys Val Pro
        275                 280                 285

Ser Val Ala
```

290

<210> SEQ ID NO 160
<211> LENGTH: 3951
<212> TYPE: DNA
<213> ORGANISM: Homo sapien

<400> SEQUENCE: 160

| | | | | | |
|---|---|---|---|---|---|
| tctgcatcca | tattgaaaac | ctgacacaat | gtatgcagca | ggctcagtgt | gagtgaactg | 60 |
| gaggcttctc | tacaacatga | cccaaaggag | cattgcaggt | cctatttgca | acctgaagtt | 120 |
| tgtgactctc | ctggttgcct | taagttcaga | actcccattc | ctgggagctg | gagtacagct | 180 |
| tcaagacaat | gggtataatg | gattgctcat | tgcaattaat | cctcaggtac | ctgagaatca | 240 |
| gaacctcatc | tcaaacatta | aggaaatgat | aactgaagct | tcattttacc | tatttaatgc | 300 |
| taccaagaga | agagtatttt | tcagaaatat | aaagatttta | atacctgcca | catggaaagc | 360 |
| taataataac | agcaaaataa | aacaagaatc | atatgaaaag | gcaaatgtca | tagtgactga | 420 |
| ctggtatggg | gcacatggag | atgatccata | caccctacaa | tacagagggt | gtggaaaaga | 480 |
| gggaaaatac | attcatttca | cacctaattt | cctactgaat | gataacttaa | cagctggcta | 540 |
| cggatcacga | ggccgagtgt | tgtccatga | atgggcccac | ctccgttggg | gtgtgttcga | 600 |
| tgagtataac | aatgacaaac | ctttctacat | aaatgggcaa | atcaaatta | aagtgacaag | 660 |
| gtgttcatct | gacatcacag | gcattttgt | gtgtgaaaaa | ggtccttgcc | cccaagaaaa | 720 |
| ctgtattatt | agtaagcttt | ttaaagaagg | atgcaccttt | atctacaata | gcacccaaaa | 780 |
| tgcaactgca | tcaataatgt | tcatgcaaag | tttatcttct | gtggttgaat | tttgtaatgc | 840 |
| aagtacccac | aaccaagaag | caccaaacct | acagaaccag | atgtgcagcc | tcagaagtgc | 900 |
| atgggatgta | atcacagact | ctgctgactt | tcaccacagc | tttcccatga | acgggactga | 960 |
| gcttccacct | cctcccacat | tctcgcttgt | agaggctggt | gacaaagtgg | tctgtttagt | 1020 |
| gctggatgtg | tccagcaaga | tggcagaggc | tgacagactc | cttcaactac | aacaagccgc | 1080 |
| agaatttat | ttgatgcaga | ttgttgaaat | tcataccttc | gtgggcattg | ccagtttcga | 1140 |
| cagcaaagga | gagatcagag | cccagctaca | ccaaattaac | agcaatgatg | atcgaaagtt | 1200 |
| gctggtttca | tatctgccca | ccactgtatc | agctaaaaca | gacatcagca | tttgttcagg | 1260 |
| gcttaagaaa | ggatttgagg | tggttgaaaa | actgaatgga | aaagcttatg | ctctgtgat | 1320 |
| gatattagtg | accagcggag | atgataagct | tcttggcaat | tgcttaccca | ctgtgctcag | 1380 |
| cagtggttca | acaattcact | ccattgccct | gggttcatct | gcagccccaa | atctggagga | 1440 |
| attatcacgt | cttacaggag | gtttaaagtt | ctttgttcca | gatatatcaa | actccaatag | 1500 |
| catgattgat | gctttcagta | gaatttcctc | tggaactgga | gacattttcc | agcaacatat | 1560 |
| tcagcttgaa | agtacaggtg | aaaatgtcaa | acctcaccat | caattgaaaa | acacagtgac | 1620 |
| tgtggataat | actgtgggca | acgacactat | gtttctagtt | acgtggcagg | ccagtggtcc | 1680 |
| tcctgagatt | atattatttg | atcctgatgg | acgaaaatac | tacacaaata | atttttatcac | 1740 |
| caatctaact | tttcggacag | ctagtctttg | gattccagga | acagctaagc | ctgggcactg | 1800 |
| gacttacacc | ctgaacaata | cccatcattc | tctgcaagcc | ctgaaagtga | cagtgacctc | 1860 |
| tcgcgcctcc | aactcagctg | tgccccagc | cactgtggaa | gcctttgtgg | aaagagacag | 1920 |
| cctccatttt | cctcatcctg | tgatgattta | tgccaatgtg | aaacaggat | tttatcccat | 1980 |
| tcttaatgcc | actgtcactg | ccacagttga | gccagagact | ggagatcctg | ttacgctgag | 2040 |
| actccttgat | gatggagcag | gtgctgatgt | tataaaaaat | gatggaattt | actcgaggta | 2100 |

```
tttttctcc tttgctgcaa atggtagata tagcttgaaa gtgcatgtca atcactctcc   2160
cagcataagc accccagccc actctattcc agggagtcat gctatgtatg taccaggtta   2220
cacagcaaac ggtaatattc agatgaatgc tccaaggaaa tcagtaggca gaaatgagga   2280
ggagcgaaag tggggcttta gccgagtcag ctcaggaggc tccttttcag tgctgggagt   2340
tccagctggc ccccaccctg atgtgtttcc accatgcaaa attattgacc tggaagctgt   2400
aaaagtagaa gaggaattga ccctatcttg gacagcacct ggagaagact ttgatcaggg   2460
ccaggctaca agctatgaaa taagaatgag taaaagtcta cagaatatcc aagatgactt   2520
taacaatgct attttagtaa atacatcaaa gcgaaatcct cagcaagctg catcaggga   2580
gatatttacg ttctcacccc aaatttccac gaatggacct gaacatcagc caatggaga   2640
aacacatgaa agccacagaa tttatgttgc aatacgagca atggatagga actccttaca   2700
gtctgctgta tctaacattg cccaggcgcc tctgtttatt ccccccaatt ctgatcctgt   2760
acctgccaga gattatctta tattgaaagg agttttaaca gcaatgggtt tgataggaat   2820
catttgcctt attatagttg tgacacatca tactttaagc aggaaaaaga gagcagacaa   2880
gaaagagaat ggaacaaaat tattataaat aaatatccaa agtgtcttcc ttcttagata   2940
taagacccat ggccttcgac tacaaaaaca tactaacaaa gtcaaattaa catcaaaact   3000
gtattaaaat gcattgagtt tttgtacaat acagataaga ttttttacatg gtagatcaac   3060
aaattctttt tggggtaga ttagaaaacc cttacacttt ggctatgaac aaataataaa   3120
aattattctt taaagtaatg tctttaaagg caaagggaag ggtaaagtcg gaccagtgtc   3180
aaggaaagtt tgttttattg aggtggaaaa atagccccaa gcagagaaaa ggagggtagg   3240
tctgcattat aactgtctgt gtgaagcaat catttagtta ctttgattaa ttttctttt   3300
ctccttatct gtgcagaaca ggttgcttgt ttacaactga agatcatgct atatttcata   3360
tatgaagccc ctaatgcaaa gctctttacc tcttgctatt ttgttatata tattacagat   3420
gaaatctcac tgctaatgct cagagatctt ttttcactgt aagaggtaac ctttaacaat   3480
atgggtatta cctttgtctc ttcataccgg ttttatgaca aaggtctatt gaatttattt   3540
gtttgtaagt ttctactccc atcaaagcag cttttttaagt tattgccttg gttattatgg   3600
atgatagtta tagcccttat aatgccttaa ctaaggaaga aaagatgtta ttctgagttt   3660
gttttaatac atatatgaac atatagtttt attcaattaa accaaagaag aggtcagcag   3720
ggagatacta acctttggaa atgattagct ggctctgttt tttggttaaa taagagtctt   3780
taatcctttc tccatcaaga gttacttacc aagggcaggg gaaggggat atagaggtcc   3840
caaggaaata aaaatcatct ttcatcttta attttactcc ttcctcttat ttttttaaaa   3900
gattatcgaa caataaaatc atttgccttt ttaattaaaa acataaaaaa a   3951
```

<210> SEQ ID NO 161
<211> LENGTH: 943
<212> TYPE: PRT
<213> ORGANISM: Homo sapien

<400> SEQUENCE: 161

Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

-continued

```
Pro Gln Val Pro Glu Asn Gln Asn Leu Ile Ser Asn Ile Lys Glu Met
 50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
                115                 120                 125

Tyr Arg Gly Cys Gly Lys Glu Gly Lys Tyr Ile His Phe Thr Pro Asn
        130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
450                 455                 460
```

```
Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
            485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
            515                 520                 525

Thr Trp Gln Ala Ser Gly Pro Pro Glu Ile Ile Leu Phe Asp Pro Asp
530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
            565                 570                 575

Tyr Thr Leu Asn Asn Thr His His Ser Leu Gln Ala Leu Lys Val Thr
            580                 585                 590

Val Thr Ser Arg Ala Ser Asn Ser Ala Val Pro Pro Ala Thr Val Glu
            595                 600                 605

Ala Phe Val Glu Arg Asp Ser Leu His Phe Pro His Pro Val Met Ile
610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
            645                 650                 655

Leu Asp Asp Gly Ala Gly Ala Asp Val Ile Lys Asn Asp Gly Ile Tyr
            660                 665                 670

Ser Arg Tyr Phe Phe Ser Phe Ala Ala Asn Gly Arg Tyr Ser Leu Lys
            675                 680                 685

Val His Val Asn His Ser Pro Ser Ile Ser Thr Pro Ala His Ser Ile
            690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
            725                 730                 735

Arg Lys Trp Gly Phe Ser Arg Val Ser Ser Gly Ser Phe Ser Val
            740                 745                 750

Leu Gly Val Pro Ala Gly Pro His Pro Asp Val Phe Pro Pro Cys Lys
            755                 760                 765

Ile Ile Asp Leu Glu Ala Val Lys Val Glu Glu Leu Thr Leu Ser
            770                 775                 780

Trp Thr Ala Pro Gly Glu Asp Phe Asp Gln Gly Gln Ala Thr Ser Tyr
785                 790                 795                 800

Glu Ile Arg Met Ser Lys Ser Leu Gln Asn Ile Gln Asp Asp Phe Asn
            805                 810                 815

Asn Ala Ile Leu Val Asn Thr Ser Lys Arg Asn Pro Gln Gln Ala Gly
            820                 825                 830

Ile Arg Glu Ile Phe Thr Phe Ser Pro Gln Ile Ser Thr Asn Gly Pro
            835                 840                 845

Glu His Gln Pro Asn Gly Glu Thr His Glu Ser His Arg Ile Tyr Val
            850                 855                 860

Ala Ile Arg Ala Met Asp Arg Asn Ser Leu Gln Ser Ala Val Ser Asn
865                 870                 875                 880

Ile Ala Gln Ala Pro Leu Phe Ile Pro Pro Asn Ser Asp Pro Val Pro
```

|   |   |   | 885 |   |   |   | 890 |   |   |   | 895 |   |
|---|---|---|---|---|---|---|---|---|---|---|---|---|
| Ala | Arg | Asp | Tyr | Leu | Ile | Leu | Lys | Gly | Val | Leu | Thr | Ala | Met | Gly | Leu |
|   |   |   | 900 |   |   |   | 905 |   |   |   | 910 |   |

| Ile | Gly | Ile | Ile | Cys | Leu | Ile | Ile | Val | Val | Thr | His | His | Thr | Leu | Ser |
|   |   |   | 915 |   |   |   | 920 |   |   |   | 925 |   |

| Arg | Lys | Lys | Arg | Ala | Asp | Lys | Lys | Glu | Asn | Gly | Thr | Lys | Leu | Leu |
|   |   |   | 930 |   |   |   | 935 |   |   |   | 940 |   |

<210> SEQ ID NO 162
<211> LENGTH: 498
<212> TYPE: DNA
<213> ORGANISM: Homo sapien

<400> SEQUENCE: 162

```
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180
gaccaccccc tgccaggact ccctgccaac aggaactgga ccaggtcctg gagcggatct     240
ccaccatgcg ccttccggat gagcggggcc ctctggagca cctctactcc ctgcacatcc     300
caactgtga caagcatggc ctgtacaacc tcaaacagtg gcaagatgtc tctgaacggg     360
cagcgtgggg agtgctggtg tgtgaacccc aacaccggga agctgatcca gggagccccc     420
accatccggg gggaccccga gtgtcatctc ttctacaatg agcagcagga ggctcgcggg     480
gtgcacaccc cagcggat                                                  498
```

<210> SEQ ID NO 163
<211> LENGTH: 1128
<212> TYPE: DNA
<213> ORGANISM: Homo sapien

<400> SEQUENCE: 163

```
gccacctggc cctcctgatc gacgacacac gcacttgaaa cttgttctca gggtgtgtgg      60
aatcaacttt ccggaagcaa ccagcccacc agaggaggtc ccgagcgcga gcggagacga    120
tgcagcggag actggttcag cagtggagcg tcgcggtgtt cctgctgagc tacgcggtgc    180
cctcctgcgg gcgctcggtg gagggtctca gccgccgcct caaaagagct gtgtctgaac    240
atcagctcct ccatgacaag gggaagtcca tccaagattt acggcgacga ttcttccttc    300
accatctgat cgcagaaatc cacacagctg aaatcagagc tacctcggag gtgtcccta    360
actccaagcc ctctcccaac acaaagaacc accccgtccg atttgggtct gatgatgagg    420
gcagatacct aactcaggaa actaacaagg tggagacgta caaagagcag ccgctcaaga    480
cacctgggaa gaaaagaaa ggcaagcccg ggaaacgcaa ggagcaggaa aagaaaaaac    540
ggcgaactcg ctctgcctgg ttagactctg gagtgactgg gagtgggcta aaggggacc    600
acctgtctga cacctccaca acgtcgctgg agctcgattc acggaggcat gaaattttc    660
agcagagacc ttccaaggac atattgcagg attctgtaat agtgaacata tggaaagtat    720
tagaaatatt tattgtctgt aaatactgta aatgcattgg aataaaactg tctccccat    780
tgctctatga aactgcacat tggtcattgt gaatatttt tttttttgcca aggctaatcc    840
aattattatt atcacatttta ccataattta ttttgtccat tgatgtattt attttgtaaa    900
tgtatcttgg tgctgctgaa tttctatatt ttttgtaaca taatgcactt tagatataca    960
tatcaagtat gttgataaat gacacaatga agtgtctcta ttttgtggtt gattttaatg    1020
```

-continued aatgcctaaa tataattatc caaattgatt ttcctttgtg catgtaaaaa taacagtatt   1080
ttaaatttgt aaagaatgtc taataaaata taatctaatt acatcatg   1128

<210> SEQ ID NO 164
<211> LENGTH: 1310
<212> TYPE: DNA
<213> ORGANISM: Homo sapien

<400> SEQUENCE: 164
gggcctggtt cgcaaagaag ctgacttcag aggggggaaac tttcttcttt taggaggcgg    60
ttagccctgt tccacgaacc caggagaact gctggccaga ttaattagac attgctatgg   120
gagacgtgta aacacactac ttatcattga tgcatatata aaaccatttt attttcgcta   180
ttatttcaga ggaagcgcct ctgatttgtt tcttttttcc cttttttgctc tttctggctg   240 tgtggtttgg agaaagcaca gttggagtag ccggttgcta aataagtccc gagcgcgagc   300
ggagacgatg cagcggagac tggttcagca gtggagcgtc gcggtgttcc tgctgagcta   360
cgcggtgccc tcctgcgggc gctcggtgga gggtctcagc cgccgcctca aaagagctgt   420
gtctgaacat cagctcctcc atgacaaggg gaagtccatc caagatttac ggcgacgatt   480
cttccttcac catctgatcg cagaaatcca cacagctgaa atcagagcta cctcggaggt   540
gtcccctaac tccaagccct ctcccaacac aaagaaccac cccgtccgat ttgggtctga   600
tgatgagggc agatacctaa ctcaggaaac taacaaggtg gagacgtaca agagcagcc   660 gctcaagaca cctgggaaga aaagaaagg caagcccggg aaacgcaagg agcaggaaaa   720
gaaaaaacgg cgaactcgct ctgcctggtt agactctgga gtgactggga gtgggctaga   780
aggggaccac ctgtctgaca cctccacaac gtcgctggga ctcgattcac ggaggcattg   840
aaattttcag cagagacctt ccaaggacat attgcaggat tctgtaatag tgaacatatg   900
gaaagtatta gaaatattta ttgtctgtaa atactgtaaa tgcattggaa taaaactgtc   960
tcccccattg ctctatgaaa ctgcacattg gtcattgtga atatttttt ttttgccaag   1020 gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
ttttaatgaa tgcctaaata taattatcca aattgatttt cctttgtgcc cgtaaaaata   1260
acagtatttt aaatttgtaa agaatgtcta ataaaatata atctaattac   1310

<210> SEQ ID NO 165
<211> LENGTH: 177
<212> TYPE: PRT
<213> ORGANISM: Homo sapien

<400> SEQUENCE: 165

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
            85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
            115                 120                 125

Lys Pro Gly Lys Arg Lys Glu Gln Glu Lys Lys Lys Arg Arg Thr Arg
130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
            165                 170                 175

His

<210> SEQ ID NO 166
<211> LENGTH: 177
<212> TYPE: PRT
<213> ORGANISM: Homo sapien

<400> SEQUENCE: 166

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
            35                  40                  45

Lys Ser Ile Gln Asp Leu Arg Arg Arg Phe Phe Leu His His Leu Ile
        50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
            85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
            115                 120                 125

Lys Pro Gly Lys Arg Lys Glu Gln Glu Lys Lys Lys Arg Arg Thr Arg
130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
            165                 170                 175

His

<210> SEQ ID NO 167
<211> LENGTH: 3362
<212> TYPE: DNA
<213> ORGANISM: Homo sapien

<400> SEQUENCE: 167
cacaatgtat gcagcaggct cagtgtgagt gaactggagg cttctctaca acatgaccca    60
aaggagcatt gcaggtccta tttgcaacct gaagtttgtg actctcctgg ttgccttaag   120
ttcagaactc ccattcctgg gagctggagt acagcttcaa gacaatgggt ataatggatt   180
gctcattgca attaatcctc aggtacctga gaatcagaac ctcatctcaa acattaagga   240

-continued

```
aatgataact gaagcttcat tttacctatt taatgctacc aagagaagag tattttcag      300 aaatataaag attttaatac ctgccacatg gaaagctaat aataacagca aaataaaaca     360
agaatcatat gaaaaggcaa atgtcatagt gactgactgg tatggggcac atggagatga    420
tccatacacc ctacaataca gagggtgtgg aaagaggga aatacattc atttcacacc      480 taatttccta ctgaatgata acttaacagc tggctacgga tcacgaggcc gagtgtttgt    540
ccatgaatgg gcccacctcc gttggggtgt gttcgatgag tataacaatg acaaaccttt    600
ctacataaat gggcaaaatc aaattaaagt gacaaggtgt tcatctgaca tcacaggcat    660
ttttgtgtgt gaaaaaggtc cttgccccca agaaaactgt attattagta agcttttaa     720 agaaggatgc acctttatct acaatagcac ccaaaatgca actgcatcaa taatgttcat    780
gcaaagttta tcttctgtgg ttgaattttg taatgcaagt acccacaacc aagaagcacc    840
aaacctacag aaccagatgt gcagcctcag aagtgcatgg gatgtaatca cagactctgc    900
tgactttcac cacagctttc ccatgaacgg gactgagctt ccacctcctc ccacattctc    960
gcttgtagag gctggtgaca agtggtctg tttagtgctg gatgtgtcca gcaagatggc    1020
agaggctgac agactccttc aactacaaca agccgcagaa tttatttga tgcagattgt    1080 tgaaattcat accttcgtgg gcattgccag tttcgacagc aaaggagaga tcagagccca    1140
gctacaccaa attaacagca atgatgatcg aaagttgctg gtttcatatc tgcccaccac    1200
tgtatcagct aaaacagaca tcagcatttg ttcagggctt aagaaaggat ttgaggtggt    1260
tgaaaaactg aatggaaaag cttatggctc tgtgatgata ttagtgacca gcggagatga    1320
taagcttctt ggcaattgct tacccactgt gctcagcagt ggttcaacaa ttcactccat    1380
tgccctgggt tcatctgcag ccccaaatct ggaggaatta tcacgtctta caggaggttt    1440
aaagttcttt gttccagata tatcaaactc caatagcatg attgatgctt tcagtagaat    1500
ttcctctgga actggagaca ttttccagca acatattcag cttgaaagta caggtgaaaa    1560
tgtcaaacct caccatcaat tgaaaaacac agtgactgtg gataatactg tgggcaacga    1620
cactatgttt ctagttacgt ggcaggccag tggtcctcct gagattatat tatttgatcc    1680
tgatggacga aaatactaca caaataattt tatcaccaat ctaacttttc ggacagctag    1740
tctttggatt ccaggaacag ctaagcctgg gcactggact tacaccctga tgtgtttcca    1800
ccatgcaaaa ttattgacct ggaagctgta aaagtagaag aggaattgac cctatcttgg    1860
acagcacctg gagaagactt tgatcagggc aggctacaa gctatgaaat aagaatgagt     1920
aaaagtctac agaatatcca agatgacttt aacaatgcta ttttagtaaa tacatcaaag    1980
cgaaatcctc agcaagctgg catcagggag atatttacgt tctcacccca aatttccacg    2040
aatggacctg aacatcagcc aaatggagaa acacatgaaa gccacagaat ttatgttgca    2100
atacgagcaa tggataggaa ctccttacag tctgctgtat ctaacattgc ccaggcgcct    2160
ctgtttattc ccccccaattc tgatcctgta cctgccagag attatcttat attgaaagga    2220
gttttaacag caatgggttt gataggaatc atttgcctta ttatagttgt gacacatcat    2280
actttaagca ggaaaaagag agcagacaag aaagagaatg gaacaaaatt attataaata    2340
aatatccaaa gtgtcttcct tcttagatat aagacccatg gccttcgact acaaaaacat    2400
actaacaaag tcaaattaac atcaaaactg tattaaaatg cattgagttt ttgtacaata    2460
cagataagat ttttacatgg tagatcaaca aattcttttt gggggtagat tagaaaaccc    2520
ttacactttg gctatgaaca ataataaaa attattcttt aaagtaatgt ctttaaaggc     2580
aaagggaagg gtaaagtcgg accagtgtca aggaaagttt gttttattga ggtggaaaaa    2640
```

-continued

```
tagccccaag cagagaaaag gagggtaggt ctgcattata actgtctgtg tgaagcaatc    2700
atttagttac tttgattaat ttttcttttc tccttatctg tgcagaacag gttgcttgtt    2760
tacaactgaa gatcatgcta tatttcatat atgaagcccc taatgcaaag ctctttacct    2820
cttgctattt tgttatatat attacagatg aaatctcact gctaatgctc agagatcttt    2880
tttcactgta agaggtaacc tttaacaata tgggtattac ctttgtctct tcataccggt    2940
tttatgacaa aggtctattg aatttatttg tttgtaagtt tctactccca tcaaagcagc    3000
tttctaagtt attgccttgg ttattatgga tgatagttat agcccttata atgccttaac    3060
taaggaagaa aagatgttat tctgagtttg ttttaataca tatatgaaca tatagtttta    3120
ttcaattaaa ccaaagaaga ggtcagcagg gagatactaa cctttggaaa tgattagctg    3180
gctctgtttt tggttaaat aagagtcttt aatcctttct ccatcaagag ttacttacca    3240
agggcagggg aaggggggata tagaggtcac aaggaaataa aaatcatctt tcatctttaa    3300
ttttactcct tcctcttatt tttttaaaag attatcgaac aataaaatca tttgcctttt    3360
tt                                                                   3362

<210> SEQ ID NO 168
<211> LENGTH: 2784
<212> TYPE: DNA
<213> ORGANISM: Homo sapien

<400> SEQUENCE: 168
tctgcatcca tattgaaaac ctgacacaat gtatgcagca ggctcagtgt gagtgaactg      60
gaggcttctc tacaacatga cccaaaggag cattgcaggt cctatttgca acctgaagtt     120
tgtgactctc ctggttgcct taagttcaga actcccattc ctgggagctg agtacagct      180 tcaagacaat gggtataatg gattgctcat tgcaattaat cctcaggtac ctgagaatca     240
gaacctcatc tcaaacatta aggaaatgat aactgaagct tcattttacc tatttaatgc     300
taccaagaga agagtatttt tcagaaatat aaagatttta ataccctgcca catggaaagc     360 taataataac agcaaaataa aacaagaatc atatgaaaag gcaaatgtca tagtgactga     420
ctggtatggg gcacatggag atgatccata caccctacaa tacagagggt gtggaaaaga     480
gggaaaatac attcatttca cacctaattt cctactgaat gataacttaa cagctggcta     540
cggatcacga ggccgagtgt ttgtccatga atgggcccac ctccgttggg gtgtgttcga     600
tgagtataac aatgacaaac ctttctacat aaatgggcaa atcaaatta agtgacaag      660 gtgttcatct gacatcacag gcatttttgt gtgtgaaaaa ggtccttgcc cccaagaaaa    720
ctgtattatt agtaagcttt ttaaagaagg atgcaccttt atctacaata gcacccaaaa    780
tgcaactgca tcaataatgt tcatgcaaag tttatcttct gtggttgaat tttgtaatgc    840
aagtacccac aaccaagaag caccaaacct acagaaccag atgtgcagcc tcagaagtgc     900
atgggatgta atcacagact ctgctgactt tcaccacagc tttcccatga acgggactga    960
gcttccacct cctcccacat tctcgcttgt agaggctggt gacaaagtgg tctgtttagt   1020
gctggatgtg tccagcaaga tggcagaggc tgacagactc cttcaactac aacaagccgc    1080
agaattttat ttgatgcaga ttgttgaaat tcataccttc gtgggcattg ccagtttcga    1140
cagcaaagga gagatcagag cccagctaca ccaaattaac agcaatgatg atcgaaagtt    1200
gctggtttca tatctgccca ccactgtatc agctaaaaca gacatcagca tttgttcagg    1260
gcttaagaaa ggatttgagg tggttgaaaa actgaatgga aaagcttatg ctctctgtgat    1320
```

-continued

```
gatattagtg accagcggag atgataagct tcttggcaat tgcttaccca ctgtgctcag   1380
cagtggttca acaattcact ccattgccct gggttcatct gcagcccaa atctggagga    1440
attatcacgt cttacaggag gtttaaagtt ctttgttcca gatatatcaa actccaatag   1500
catgattgat gctttcagta gaatttcctc tggaactgga gacattttcc agcaacatat   1560
tcagcttgaa agtacaggtg aaaatgtcaa acctcaccat caattgaaaa acacagtgac   1620
tgtggataat actgtgggca acgacactat gtttctagtt acgtggcagg ccagtggtcc   1680
tcctgagatt atattatttg atcctgatgg acgaaaatac tacacaaata attttatcac   1740
caatctaact tttcggacag ctagtctttg gattccagga acagctaagc ctgggcactg   1800
gacttacacc ctgaacaata cccatcattc tctgcaagcc ctgaaagtga cagtgacctc   1860
tcgcgcctcc aactcagctg tgcccccagc cactgtggaa gcctttgtgg aaagagacag   1920
cctccatttt cctcatcctg tgatgattta tgccaatgtg aaacagggat tttatcccat   1980
tcttaatgcc actgtcactg ccacagttga gccagagact ggagatcctg ttacgctgag   2040
actccttgat gatggagcag gtgctgatgt tataaaaaat gatggaattt actcgaggta   2100
tttttttctcc tttgctgcaa atggtagata tagcttgaaa gtgcatgtca atcactctcc   2160
cagcataagc accccagccc actctattcc agggagtcat gctatgtatg taccaggtta   2220
cacagcaaac ggtaatattc agatgaatgc tccaaggaaa tcagtaggca gaaatgagga   2280
ggagcgaaag tggggctta gccgagtcag ctcaggaggc tccttttcag tgctgggagt    2340
tccagctggc ccccaccctg atgtgtttcc accatgcaaa attattgacc tggaagctgt   2400
aaatagaaga ggaattgacc ctatcttgga cagcacctgg agaagacttt gatcagggcc   2460
aggctacaag ctatgaaata agaatgagta aagtctaca gaatatccaa gatgacttta    2520
acaatgctat tttagtaaat acatcaaagc gaaatcctca gcaagctggc atcagggaga   2580
tatttacgtt ctcaccccaa atttccacga atggacctga acatcagcca aatggagaaa   2640
cacatgaaag ccacagaatt tatgttgcaa tacgagcaat ggataggaac tccttacagt   2700
ctgctgtatc taacattgcc caggcgcctc tgtttattcc ccccaattct gatcctgtac   2760
ctgccagaga ttatcttata ttga                                         2784
```

<210> SEQ ID NO 169
<211> LENGTH: 592
<212> TYPE: PRT
<213> ORGANISM: Homo sapien

<400> SEQUENCE: 169

```
Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110
```

-continued

```
Val Thr Asp Trp Tyr Gly Ala His Gly Asp Pro Tyr Thr Leu Gln
    115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
```

```
                530             535             540
Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Met Cys Phe His His Ala Lys Leu Leu Thr Trp Lys Leu
                580                 585                 590

<210> SEQ ID NO 170
<211> LENGTH: 791
<212> TYPE: PRT
<213> ORGANISM: Homo sapien

<400> SEQUENCE: 170

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
                20                  25                  30

Val Gln Leu Gln Asp Asn Gly Tyr Asn Gly Leu Leu Ile Ala Ile Asn
            35                  40                  45

Pro Gln Val Pro Glu Asn Gln Asn Leu Ile Ser Asn Ile Lys Glu Met
50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
290                 295                 300

Val Glu Ala Gly Asp Lys Val Val Cys Leu Val Leu Asp Val Ser Ser
305                 310                 315                 320
```

```
Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
                355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
                435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
                500                 505                 510

Thr Val Thr Val Asp Asn Thr Val Gly Asn Asp Thr Met Phe Leu Val
                515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
    595                 600                 605

Ala Phe Val Glu Arg Asp Ser Leu His Phe Pro His Pro Val Met Ile
610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
                660                 665                 670

Ser Arg Tyr Phe Phe Ser Phe Ala Ala Asn Gly Arg Tyr Ser Leu Lys
                675                 680                 685

Val His Val Asn His Ser Pro Ser Ile Ser Thr Pro Ala His Ser Ile
    690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
```

| | | | | | | | | | | | |
|---|---|---|---|---|---|---|---|---|---|---|---|
| | | 740 | | | | 745 | | | | 750 | |
| Leu | Gly | Val | Pro | Ala | Gly | Pro | His | Pro | Asp | Val | Phe | Pro | Pro | Cys | Lys |
| | | | 755 | | | | | 760 | | | | | 765 | | |
| Ile | Ile | Asp | Leu | Glu | Ala | Val | Asn | Arg | Arg | Gly | Ile | Asp | Pro | Ile | Leu |
| | | 770 | | | | | 775 | | | | | 780 | | | |
| Asp | Ser | Thr | Trp | Arg | Arg | Leu | | | | | | | | | |
| 785 | | | | | 790 | | | | | | | | | | |

<210> SEQ ID NO 171
<211> LENGTH: 1491
<212> TYPE: DNA
<213> ORGANISM: Homo sapien

<400> SEQUENCE: 171

```
cctcctgcca gccaagtgaa gacatgctta cttcccctto accttccttc atgatgtggg     60
aagagtgctg caacccagcc ctagccaacg ccgcatgaga gggagtgtgc cgagggcttc    120
tgagaaggtt tctctcacat ctagaaagaa gcgcttaaga tgtggcagcc cctcttcttc    180
aagtggctct tgtcctgttg ccctgggagt tctcaaattg ctgcagcagc ctccacccag    240
cctgaggatg acatcaatac acagaggaag aagagtcagg aaaagatgag agaagttaca    300
gactctcctg gcgaccccg agagcttacc attcctcaga cttcttcaca tggtgctaac    360
agatttgttc ctaaaagtaa agctctagag gccgtcaaat tggcaataga agccgggttc    420
caccatattg attctgcaca tgtttacaat aatgaggagc aggttggact ggccatccga    480
agcaagattg cagatggcag tgtgaagaga aagacatat tctacacttc aaagctttgg    540
agcaattccc atcgaccaga gttggtccga ccagccttgg aaaggtcact gaaaaatctt    600
caattggact atgttgacct ctatcttatt cattttccag tgtctgtaaa gccaggtgag    660
gaagtgatcc caaagatga aaatggaaaa atactatttg acacagtgga tctctgtgcc    720
acatgggagg ccatggagaa gtgtaaagat gcaggattgg ccaagtccat cggggtgtcc    780
aacttcaacc acaggctgct ggagatgatc ctcaacaagc cagggctcaa gtacaagcct    840
gtctgcaacc aggtggaatg tcatccttac ttcaaccaga gaaaactgct ggatttctgc    900
aagtcaaaag acattgttct ggttgcctat agtgctctgg gatcccatcg agaagaacca    960
tgggtggacc cgaactcccc ggtgctcttg gaggacccag tcctttgtgc cttggcaaaa   1020
aagcacaagc gaaccccagc cctgattgcc ctgcgctacc agctgcagcg tggggttgtg   1080
gtcctggcca agagctacaa tgagcagcgc atcagacaga acgtgcaggt gtttgaattc   1140
cagttgactt cagaggagat gaaagccata gatggcctaa acagaaatgt gcgatatttg   1200
acccttgata ttttttgctgg cccccctaat tatccatttt ctgatgaata ttaacatgga   1260
gggcattgca tgaggtctgc cagaaggccc tgcgtgtgga tggtgacaca gaggatggct   1320
ctatgctggt gactggacac atcgcctctg gttaaatctc tcctgcttgg cgacttcagt   1380
aagctacagc taagcccatc ggccggaaaa gaaagacaat aattttgttt ttcattttga   1440
aaaaattaaa tgctctctcc taagagattct tcacctaaaa aaaaaaaaa a            1491
```

<210> SEQ ID NO 172
<211> LENGTH: 364
<212> TYPE: PRT
<213> ORGANISM: Homo sapien

<400> SEQUENCE: 172

| | | | | | | | | | | | | | |
|---|---|---|---|---|---|---|---|---|---|---|---|---|---|
| Met | Trp | Gln | Pro | Leu | Phe | Phe | Lys | Trp | Leu | Leu | Ser | Cys | Cys | Pro | Gly |
| 1 | | | | 5 | | | | | 10 | | | | | 15 | |

```
Ser Ser Gln Ile Ala Ala Ala Ser Thr Gln Pro Glu Asp Asp Ile
         20                  25                  30
Asn Thr Gln Arg Lys Lys Ser Gln Glu Lys Met Arg Glu Val Thr Asp
         35                  40                  45
Ser Pro Gly Arg Pro Arg Glu Leu Thr Ile Pro Gln Thr Ser Ser His
 50                  55                  60
Gly Ala Asn Arg Phe Val Pro Lys Ser Lys Ala Leu Glu Ala Val Lys
 65                  70                  75                  80
Leu Ala Ile Glu Ala Gly Phe His His Ile Asp Ser Ala His Val Tyr
                 85                  90                  95
Asn Asn Glu Glu Gln Val Gly Leu Ala Ile Arg Ser Lys Ile Ala Asp
                100                 105                 110
Gly Ser Val Lys Arg Glu Asp Ile Phe Tyr Thr Ser Lys Leu Trp Ser
            115                 120                 125
Asn Ser His Arg Pro Glu Leu Val Arg Pro Ala Leu Glu Arg Ser Leu
        130                 135                 140
Lys Asn Leu Gln Leu Asp Tyr Val Asp Leu Tyr Leu Ile His Phe Pro
145                 150                 155                 160
Val Ser Val Lys Pro Gly Glu Glu Val Ile Pro Lys Asp Glu Asn Gly
                165                 170                 175
Lys Ile Leu Phe Asp Thr Val Asp Leu Cys Ala Thr Trp Glu Ala Met
                180                 185                 190
Glu Lys Cys Lys Asp Ala Gly Leu Ala Lys Ser Ile Gly Val Ser Asn
            195                 200                 205
Phe Asn His Arg Leu Leu Glu Met Ile Leu Asn Lys Pro Gly Leu Lys
        210                 215                 220
Tyr Lys Pro Val Cys Asn Gln Val Glu Cys His Pro Tyr Phe Asn Gln
225                 230                 235                 240
Arg Lys Leu Leu Asp Phe Cys Lys Ser Lys Asp Ile Val Leu Val Ala
                245                 250                 255
Tyr Ser Ala Leu Gly Ser His Arg Glu Glu Pro Trp Val Asp Pro Asn
                260                 265                 270
Ser Pro Val Leu Leu Glu Asp Pro Val Leu Cys Ala Leu Ala Lys Lys
            275                 280                 285
His Lys Arg Thr Pro Ala Leu Ile Ala Leu Arg Tyr Gln Leu Gln Arg
        290                 295                 300
Gly Val Val Val Leu Ala Lys Ser Tyr Asn Glu Gln Arg Ile Arg Gln
305                 310                 315                 320
Asn Val Gln Val Phe Glu Phe Gln Leu Thr Ser Glu Glu Met Lys Ala
                325                 330                 335
Ile Asp Gly Leu Asn Arg Asn Val Arg Tyr Leu Thr Leu Asp Ile Phe
                340                 345                 350
Ala Gly Pro Pro Asn Tyr Pro Phe Ser Asp Glu Tyr
            355                 360

<210> SEQ ID NO 173
<211> LENGTH: 1988
<212> TYPE: DNA
<213> ORGANISM: Homo sapiens

<400> SEQUENCE: 173
cgggagccgc ctccccgcgg cctcttcgct tttgtggcgg cgcccgcgct cgcaggccac    60
tctctgctgt cgcccgtccc gcgcgctcct ccgacccgct ccgctccgct ccgctcggcc   120
```

```
ccgcgccgcc cgtcaacatg atccgctgcg gcctggcctg cgagcgctgc cgctggatcc      180
tgcccctgct cctactcagc gccatcgcct tcgacatcat cgcgctggcc ggccgcggct      240
ggttgcagtc tagcgaccac ggccagacgt cctcgctgtg gtggaaatgc tcccaagagg      300
gcggcggcag cgggtcctac gaggagggct gtcagagcct catggagtac gcgtggggta      360
gagcagcggc tgccatgctc ttctgtggct tcatcatcct ggtgatctgt ttcatcctct      420
ccttcttcgc cctctgtgga ccccagatgc ttgtcttcct gagagtgatt ggaggtctcc      480
ttgccttggc tgctgtgttc cagatcatct ccctggtaat ttaccccgtg aagtacaccc      540
agaccttcac ccttcatgcc aaccctgctg tcacttacat ctataactgg gcctacggct      600
tgggtgggc agccacgatt atcctgatcg gctgtgcctt cttcttctgc tgcctcccca      660
actacgaaga tgaccttctg ggcaatgcca agcccaggta cttctacaca tctgcctaac      720
ttgggaatga atgtgggaga aaatcgctgc tgctgagatg gactccagaa gaagaaactg      780
tttctccagg cgactttgaa cccattttt ggcagtgttc atattattaa actagtcaaa      840
aatgctaaaa taatttggga gaaaatattt tttaagtagt gttatagttt catgtttatc      900
ttttattatg ttttgtgaag ttgtgtcttt tcactaatta cctatactat gccaatattt      960
ccttatatct atccataaca tttatactac atttgtaaga gaatatgcac gtgaaactta     1020
acactttata aggtaaaaat gaggtttcca agatttaata atctgatcaa gttcttgtta     1080
tttccaaata gaatggactt ggtctgttaa gggctaagga gaagaggaag ataaggttaa     1140
aagttgttaa tgaccaaaca ttctaaaaga aatgcaaaaa aaagtttat tttcaagcct      1200
tcgaactatt taaggaaagc aaaatcattt cctaaatgca tatcatttgt gagaatttct     1260
cattaatatc ctgaatcatt catttcagct aaggcttcat gttgactcga tatgtcatct     1320
aggaaagtac tatttcatgg tccaaacctg ttgccatagt tggtaaggct ttcctttaag     1380
tgtgaaatat ttagatgaaa ttttctcttt taaagttctt tatagggtta gggtgtggga     1440
aaatgctata ttaataaatc tgtagtgttt tgtgtttata tgttcagaac cagagtagac     1500
tggattgaaa gatggactgg gtctaattta tcatgactga tagatctggt taagttgtgt     1560
agtaaagcat taggagggtc attcytgtca caaagtgcc actaaaacag cctcaggaga      1620
ataaatgact tgcttttcta aatctcaggt ttatctgggc tctatcatat agacaggctt     1680
ctgatagttt gcarctgtaa gcagaaacct acatatagtt aaaatcctgg tctttcttgg     1740
taaacagatt ttaaatgtct gatataaaac atgccacagg agaattcggg gatttgagtt     1800
tctctgaata gcatatatat gatgcatcgg ataggtcatt atgatttttt accatttcga     1860
cttacataat gaaaaccaat tcattttaaa tatcagatta ttattttgta agttgtggaa     1920
aaagctaatt gtagttttca ttatgaagtt ttcccaataa accaggtatt ctaaaaaaaa     1980
aaaaaaaa                                                              1988
```

<210> SEQ ID NO 174
<211> LENGTH: 238
<212> TYPE: PRT
<213> ORGANISM: Homo sapiens

<400> SEQUENCE: 174

Gly Ala Ala Ser Pro Arg Pro Leu Arg Phe Cys Gly Gly Ala Arg Ala
               5                  10                  15

Arg Arg Pro Leu Ser Ala Val Ala Arg Pro Ala Arg Ser Ser Asp Pro
           20                  25                  30

Leu Arg Ser Ala Pro Leu Gly Pro Ala Pro Pro Val Asn Met Ile Arg

```
                  35                  40                  45
Cys Gly Leu Ala Cys Glu Arg Cys Arg Trp Ile Leu Pro Leu Leu
             50                  55                  60
Leu Ser Ala Ile Ala Phe Asp Ile Ile Ala Leu Ala Gly Arg Gly Trp
 65                  70                  75                  80
Leu Gln Ser Ser Asp His Gly Gln Thr Ser Ser Leu Trp Trp Lys Cys
                 85                  90                  95
Ser Gln Glu Gly Gly Gly Ser Gly Ser Tyr Glu Glu Gly Cys Gln Ser
                100                 105                 110
Leu Met Glu Tyr Ala Trp Gly Arg Ala Ala Ala Ala Met Leu Phe Cys
                115                 120                 125
Gly Phe Ile Ile Leu Val Ile Cys Phe Ile Leu Ser Phe Phe Ala Leu
            130                 135                 140
Cys Gly Pro Gln Met Leu Val Phe Leu Arg Val Ile Gly Gly Leu Leu
145                 150                 155                 160
Ala Leu Ala Ala Val Phe Gln Ile Ile Ser Leu Val Ile Tyr Pro Val
                165                 170                 175
Lys Tyr Thr Gln Thr Phe Thr Leu His Ala Asn Pro Ala Val Thr Tyr
            180                 185                 190
Ile Tyr Asn Trp Ala Tyr Gly Phe Gly Trp Ala Ala Thr Ile Ile Leu
            195                 200                 205
Ile Gly Cys Ala Phe Phe Cys Cys Leu Pro Asn Tyr Glu Asp Asp
            210                 215                 220
Leu Leu Gly Asn Ala Lys Pro Arg Tyr Phe Tyr Thr Ser Ala
225                 230                 235

<210> SEQ ID NO 175
<211> LENGTH: 4181
<212> TYPE: DNA
<213> ORGANISM: Homo sapiens
<220> FEATURE:
<221> NAME/KEY: misc_feature
<222> LOCATION: (1)...(4181)
<223> OTHER INFORMATION: n=A,T,C or G

<400> SEQUENCE: 175
ggtggatgcg tttgggttgt agctaggctt tttcttttct ttctctttta aaacacatct     60
agacaaggaa aaacaagcc tcggatctga ttttcactc ctcgttcttg tgcttggttc    120
ttactgtgtt tgtgtatttt aaaggcgaga agacgagggg aacaaaacca gctggatcca    180
tccatcaccg tgggtggttt taattttttcg ttttttctcg ttatttttt ttaaacaacc    240
actcttcaca atgaacaaac tgtatatcgg aaacctcagc gagaacgccg cccctcgga    300
cctagaaagt atcttcaagg acgccaagat cccggtgtcg ggaccttcc tggtgaagac    360
tggctacgcg ttcgtggact gcccggacga gagctgggcc ctcaaggcca tcgaggcgct    420
ttcaggtaaa atagaactgc acgggaaacc catagaagtt gagcactcgg tcccaaaaag    480
gcaaaggatt cggaaacttc agatacgaaa tatcccgcct catttacagt gggaggtgct    540
ggatagttta ctagtccagt atggagtggt ggagagctgt gagcaagtga acactgactc    600
ggaaactgca gttgtaaatg taacctattc cagtaaggac caagctagac aagcactaga    660
caaactgaat ggatttcagt tagagaattt caccttgaaa gtagcctata tccctgatga    720
aatggccgcc cagcaaaacc ccttgcagca gccccgaggt cgccggggc ttggcagag    780
gggctcctca aggcagggt ctccaggatc cgtatccaag cagaaaccat gtgatttgcc    840
tctgcgcctg ctggttccca cccaatttgt tggagccatc ataggaaaag aaggtgccac    900
```

```
cattcggaac atcaccaaac agacccagtc taaaatcgat gtccaccgta agaaaatgc      960
gggggctgct gagaagtcga ttactatcct ctctactcct gaaggcacct ctgcggcttg   1020
taagtctatt ctggagatta tgcataagga agctcaagat ataaaattca cagaagagat   1080
cccttgaag attttagctc ataataactt tgttggacgt cttattggta agaaggaag     1140
aaatcttaaa aaaattgagc aagacacaga cactaaaatc acgatatctc cattgcagga   1200
attgacgctg tataatccag aacgcactat tacagttaaa ggcaatgttg agacatgtgc   1260
caaagctgag gaggagatca tgaagaaaat cagggagtct tatgaaaatg atattgcttc   1320
tatgaatctt caagcacatt taattcctgg attaaatctg aacgccttgg gtctgttccc   1380
acccacttca gggatgccac ctcccacctc agggccccct tcagccatga ctcctcccta   1440
cccgcagttt gagcaatcag aaacggagac tgttcatcag tttatcccag ctctatcagt   1500
cggtgccatc atcggcaagc agggccagca catcaagcag ctttctcgct tgctggagc    1560
ttcaattaag attgctccag cggaagcacc agatgctaaa gtgaggatgg tgattatcac   1620
tggaccacca gaggctcagt tcaaggctca gggaagaatt tatggaaaaa ttaaagaaga   1680
aaactttgtt agtcctaaag aagaggtgaa acttgaagct catatcagag tgccatcctt   1740
tgctgctggc agagttattg gaaaggagg caaaacggtg aatgaacttc agaatttgtc    1800
aagtgcagaa gttgttgtcc ctcgtgacca gacacctgat gagaatgacc aagtggttgt   1860
caaaataact ggtcacttct atgcttgcca ggttgcccag agaaaaattc aggaaattct   1920
gactcaggta aagcagcacc aacaacagaa ggctctgcaa agtggaccac ctcagtcaag   1980
acggaagtaa aggctcagga aacagcccac cacagaggca gatgccaaac caagacaga    2040
ttgcttaacc aacagatggg cgctgacccc ctatccagaa tcacatgcac aagttttac    2100
ctagccagtt gtttctgagg accaggcaac ttttgaactc ctgtctctgt gagaatgtat   2160
actttatgct ctctgaaatg tatgacaccc agctttaaaa caaacaaaca aacaaacaaa   2220
aaaagggtgg gggagggagg gaaagagaag agctctgcac ttcccttgt tgtagtctca   2280
cagtataaca gatattctaa ttcttcttaa tattccccca taatgccaga aattggctta   2340
atgatgcttt cactaaaattc atcaaatagg ttgctcctaa atccaattgt taaaattgga   2400
tcagaataat tatcacagga acttaaatgt taagccatta gcatagaaaa actgttctca   2460
gtttttatttt tacctaacac taacatgagt aacctaaggg aagtgctgaa tggtgttggc   2520
agggtatta aacgtgcatt tttactcaac tacctcaggt attcagtaat acaatgaaaa    2580
gcaaattgt tccttttttt tgaaaatttt atatacttta taatgataga agtccaaccg    2640
tttttaaaa ataaaattta aatttaaca gcaatcagct aacaggcaaa ttaagatttt     2700
tacttctggc tggtgacagt aaagctggaa aattaatttc agggtttttt gaggcttttg   2760
acacagttat tagttaaatc aaatgttcaa aaatacggag cagtgcctag tatctggaga   2820
gcagcactac catttattct ttcatttata gttgggaaag ttttttgacgg tactaacaaa   2880
gtggtcgcag gagattttgg aacggctggt ttaaatggct tcaggagact tcagtttttt   2940
gtttagctac atgattgaat gcataataaa tgctttgtgc ttctgactat caatacctaa   3000
agaaagtgca tcagtgaaga gatgcaagac tttcaactga ctggcaaaaa gcaagcttta   3060
gcttgtctta taggatgctt agtttgccac tacacttcag accaatggga cagtcataga   3120
tggtgtgaca gtgtttaaac gcaacaaaag gctacatttc catggggcca gcactgtcat   3180
gagcctcact aagctatttt gaagattttt aagcactgat aaattaaaaa aaaaaaaaaa   3240
```

-continued

```
aaattagact ccaccttaag tagtaaagta taacaggatt tctgtatact gtgcaatcag    3300
ttctttgaaa aaaagtcaa agatagaga atacaagaaa agttttnggg atataatttg    3360
aatgactgtg aaaacatatg acctttgata acgaactcat ttgctcactc cttgacagca    3420
aagcccagta cgtacaattg tgttgggtgt gggtggtctc caaggccacg ctgctctctg    3480
aattgatttt ttgagttttg gnttgnaaga tgatcacagn catgttacac tgatcttnaa    3540
ggacatatnt tataaccctt taaaaaaaaa atcccctgcc tcattcttat ttcgagatga    3600
atttcgatac agactagatg tctttctgaa gatcaattag acattntgaa aatgatttaa    3660
agtgttttcc ttaatgttct ctgaaaacaa gtttcttttg tagttttaac caaaaaagtg    3720 cccttttttgt cactggtttc tcctagcatt catgattttt ttttcacaca atgaattaaa    3780
attgctaaaa tcatggactg gctttctggt tggatttcag gtaagatgtg tttaaggcca    3840
gagcttttct cagtatttga ttttttttccc caatatttga tttttttaaaa atatacacat    3900 aggagctgca tttaaaaacct gctggtttaa attctgtcan atttcacttc tagccttttta    3960 gtatggcnaa tcanaattta cttttactta agcatttgta atttggagta tctggtacta    4020
gctaagaaat aattcnataa ttgagttttg tactcnccaa anatgggtca ttcctcatgn    4080
ataatgtncc cccaatgcag cttcattttc caganaccctt gacgcaggat aaatttttc    4140 atcatttagg tccccaaaaa aaaaaaaaaa aaaaaaaaaa a                          4181
```

<210> SEQ ID NO 176
<211> LENGTH: 579
<212> TYPE: PRT
<213> ORGANISM: Homo sapiens

<400> SEQUENCE: 176

```
Met Asn Lys Leu Tyr Ile Gly Asn Leu Ser Glu Asn Ala Ala Pro Ser
                5                  10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205
```

```
Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
                260                 265                 270

Phe Thr Glu Glu Ile Pro Leu Lys Ile Leu Ala His Asn Asn Phe Val
            275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
                340                 345                 350

Asn Asp Ile Ala Ser Met Asn Leu Gln Ala His Leu Ile Pro Gly Leu
            355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
    435                 440                 445

Ala Lys Val Arg Met Val Ile Ile Thr Gly Pro Pro Glu Ala Gln Phe
450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Pro Arg Asp Gln Thr
    515                 520                 525

Pro Asp Glu Asn Asp Gln Val Val Lys Ile Thr Gly His Phe Tyr
530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys

<210> SEQ ID NO 177
<211> LENGTH: 401
<212> TYPE: DNA
<213> ORGANISM: Homo sapiens

<400> SEQUENCE: 177
```

-continued

| | | |
|---|---|---|
| atgcccgta aatgtcttca gtgttcttca gggtagttgg gatctcaaaa gatttggttc | 60 | |
| agatccaaac aaatacacat tctgtgtttt agctcagtgt tttctaaaaa agaaactgc | 120 | |
| cacacagcaa aaaattgttt actttgttgg acaaaccaaa tcagttctca aaaaatgacc | 180 | |
| ggtgcttata aaaagttata aatatcgagt agctctaaaa caaaccacct gaccaagagg | 240 | |
| gaagtgagct tgtgcttagt atttacattg gatgccagtt ttgtaatcac tgacttatgt | 300 | |
| gcaaactggt gcagaaattc tataaactct ttgctgtttt tgatacctgc tttttgtttc | 360 | |
| attttgtttt gttttgtaaa aatgataaaa cttcagaaaa t | 401 | |

<210> SEQ ID NO 178
<211> LENGTH: 561
<212> TYPE: DNA
<213> ORGANISM: Homo sapiens

<400> SEQUENCE: 178

| | | |
|---|---|---|
| acgcctttca agggtgtacg caaagcactc attgataccc ttttggatgg ctatgaaaca | 60 | |
| gcccgctatg ggacagggt ctttggccag aatgagtacc tacgctatca ggaggccctg | 120 | |
| agtgagctgg ccactgcggt taaagcacga attgggagct ctcagcgaca tcaccagtca | 180 | |
| gcagccaaag acctaactca gtcccctgag gtctccccaa caaccatcca ggtgacatac | 240 | |
| ctcccctcca gtcagaagag taaacgtgcc aagcacttcc ttgaattgaa gagctttaag | 300 | |
| gataactata acacattgga gagtactctg tgacggagct gaaggactct tgccgtagat | 360 | |
| taagccagtc agttgcaatg tgcaagacag gctgcttgcc gggccgccct cggaacatct | 420 | |
| ggcccagcag gcccagactg tatccatcca agttcccgtt gtatccagag ttcttagagc | 480 | |
| ttgtgtctaa agggtaattc cccaaccctt ccttatgagc attttagaa cattggctaa | 540 | |
| gactattttc ccccagtagc g | 561 | |

<210> SEQ ID NO 179
<211> LENGTH: 521
<212> TYPE: DNA
<213> ORGANISM: Homo sapiens

<400> SEQUENCE: 179

| | | |
|---|---|---|
| cccaacgcgt ttgcaaatat tcccctggta gcctacttcc ttaccccga atattggtaa | 60 | |
| gatcgagcaa tggcttcagg acatgggttc tcttctcctg tgatcattca agtgctcact | 120 | |
| gcatgaagac tggcttgtct cagtgtttca acctcaccag ggctgtctct tggtccacac | 180 | |
| ctcgctccct gttagtgccg tatgacagcc cccatcaaat gaccttggcc aagtcacggt | 240 | |
| ttctctgtgg tcaaggttgg ttggctgatt ggtggaaagt agggtggacc aaaggaggcc | 300 | |
| acgtgagcag tcagcaccag ttctgcacca gcagcgcctc cgtcctagtg ggtgttcctg | 360 | |
| tttctcctgg ccctgggtgg gctagggcct gattcgggaa gatgcctttg cagggagggg | 420 | |
| aggataagtg ggatctacca attgattctg gcaaaacaat ttctaagatt tttttgcttt | 480 | |
| atgtgggaaa cagatctaaa tctcatttta tgctgtattt t | 521 | |

<210> SEQ ID NO 180
<211> LENGTH: 417
<212> TYPE: DNA
<213> ORGANISM: Homo sapiens

<400> SEQUENCE: 180

| | | |
|---|---|---|
| ggtggaattc gccgaagatg gcggaggtgc aggtcctggt gcttgatggt cgaggccatc | 60 | |
| tcctgggccg cctggcggcc atcgtggcta acaggtact gctgggccgg aagtggtgg | 120 | |

```
tcgtacgctg tgaaggcatc aacatttctg gcaatttcta cagaaacaag ttgaagtacc    180
tggctttcct ccgcaagcgg atgaacacca acccttcccg aggcccctac cacttccggg    240
cccccagccg catcttctgg cggaccgtgc gaggtatgct gccccacaaa accaagcgag    300
gccaggccgc tctggaccgt ctcaaggtgt ttgacggcat cccaccgccc tacgacaaga    360
aaaagcggat ggtggttcct gctgccctca aggtcgtgcg tctgaagcct acaagaa       417
```

<210> SEQ ID NO 181
<211> LENGTH: 283
<212> TYPE: DNA
<213> ORGANISM: Homo sapiens
<220> FEATURE:
<221> NAME/KEY: misc_feature
<222> LOCATION: (1)...(283)
<223> OTHER INFORMATION: n=A,T,C or G

<400> SEQUENCE: 181

```
gatttcttct aaataggatg taaaacttct ttcanattac tcttcctcag tcctgcctgc     60
caagaactca agtgtaactg tgataaaata acctttccca ggtatattgg caggtatgtg    120
tgtaatctca gaatacacag gtgacataga tatgatatga caactggtaa tggtggattc    180
atttacattg tttacacttc tatgaccagg ccttaaggga aggtcagttt tttaaaaaac    240
caagtagtgt cttcctacct atctccagat acatgtcaaa aaa                      283
```

<210> SEQ ID NO 182
<211> LENGTH: 401
<212> TYPE: DNA
<213> ORGANISM: Homo sapiens

<400> SEQUENCE: 182

```
atattcttgc tgcttatgca gctgacattg ttgccctccc taaagcaacc aagtagcctt     60
tatttcccac agtgaaagaa aacgctggcc tatcagttac attacaaaag gcagatttca    120
agaggattga gtaagtagtt ggatggcttt cataaaaaca agaattcaag aagaggattc    180
atgctttaag aaacatttgt tatacattcc tcacaaatta tacctgggat aaaaactatg    240
tagcaggcag tgtgttttcc ttccatgtct ctctgcacta cctgcagtgt gtcctctgag    300
gctgcaagtc tgtcctatct gaattcccag cagaagcact aagaagctcc accctatcac    360
ctagcagata aaactatggg gaaaacttaa atctgtgcat a                        401
```

<210> SEQ ID NO 183
<211> LENGTH: 366
<212> TYPE: DNA
<213> ORGANISM: Homo sapiens
<220> FEATURE:
<221> NAME/KEY: misc_feature
<222> LOCATION: (1)...(366)
<223> OTHER INFORMATION: n=A,T,C or G

<400> SEQUENCE: 183

```
accgtgtcca gtttttaga accttgtta gccagaccga ggtgtcctgg tcaccgtttc       60
accatcatgc tttgatgttc ccctgtcttt ctctcttctg ctctcaagag caaaggttaa    120
tttaaggaca aagatgaagt cactgtaaac taatctgtca ttgtttttac cttccttttc    180
tttttcagtg cagaaattaa aagtaagtat aaagcaccgt gattgggagt gttttgcgt    240
gtgtcggaat cactggtaaa tgttggctga gaacaatccc tcccttgca cttgtgaaaa    300
cactttgagc gctttaagag attanccgtga gaaataatta aatatctttt ctcttcaaaa   360
```

```
aaaaaa                                                                  366

<210> SEQ ID NO 184
<211> LENGTH: 370
<212> TYPE: DNA
<213> ORGANISM: Homo sapiens

<400> SEQUENCE: 184
tcttacttca aagaaaaat  aaacataaaa aataagttgc tggttcctaa caggaaaaat        60
tttaataatt gtactgagag aaactgctta cgtacacatt gcagatcaaa tatttggagt       120
taaaatgtta gtctacatag atgggtgatt gtaactttat tgccattaaa agatttcaaa       180
ttgcattcat gcttctgtgt acacataatg aaaaatgggc aaataatgaa gatctctcct       240
tcagtctgct ctgtttaatt ctgctgtctg ctcttctcta atgctgcgtc cctaattgta       300
cacagtttag tgatatctag gagtataaag ttgtcgccca tcaataaaaa tcacaaagtt       360
ggtttaaaaa                                                              370

<210> SEQ ID NO 185
<211> LENGTH: 107
<212> TYPE: DNA
<213> ORGANISM: Homo sapiens

<400> SEQUENCE: 185
ctcatattat tttccttttg agaaattgga aactctttct gttgctatta tattaataaa        60
gttggtgttt attttctggt agtcaccttc cccatttaaa aaaaaa                     107

<210> SEQ ID NO 186
<211> LENGTH: 309
<212> TYPE: DNA
<213> ORGANISM: Homo sapiens

<400> SEQUENCE: 186
gaaaggatgg ctctggttgc cacagagctg ggacttcatg ttcttctaga gagggccaca        60
agagggccac agggtggcc  gggagttgtc agctgatgcc tgctgagagg caggaattgt       120
gccagtgagt gacagtcatg agggagtgtc tcttcttggg gaggaaagaa ggtagagcct       180
ttctgtctga atgaaaggcc aaggctacag tacaggcccc cgcccagcc  agggtgttaa       240 tgcccacgta gtggaggcct ctggcagatc ctgcattcca aggtcactgg actgtacgtt       300
tttatggtt                                                              309

<210> SEQ ID NO 187
<211> LENGTH: 477
<212> TYPE: DNA
<213> ORGANISM: Homo sapiens

<400> SEQUENCE: 187
ttcagtccta gcaagaagcg agaattctga gatcctccag aaagtcgagc agcacccacc        60
tccaacctcg ggccagtgtc ttcaggcttt actgggacc  tgcgagctgg cctaatgtgg       120
tggcctgcaa gccaggccat ccctgggcgc cacagacgag ctccgagcca ggtcaggctt       180
cggaggccac aagctcagcc tcaggcccag gcactgattg tggcagaggg gccactaccc       240
aaggtctagc taggcccaag acctagttac ccagacagtg agaagcccct ggaaggcaga       300
aaagttggga gcatggcaga cagggaaggg aaacattttc agggaaaaga catgtatcac       360
atgtcttcag aagcaagtca ggtttcatgt aaccgagtgt cctcttgcgt gtccaaaagt       420
agcccagggc tgtagcacag gcttcacagt gattttgtgt tcagccgtga gtcacac        477
```

<210> SEQ ID NO 188
<211> LENGTH: 220
<212> TYPE: DNA
<213> ORGANISM: Homo sapiens

<400> SEQUENCE: 188

| | | | | | |
|---|---|---|---|---|---|
| taaatatggt | agatattaat | attcctctta | gatgaccagt | gattccaatt | gtcccaagtt | 60 |
| ttaaataagt | accctgtgag | tatgagataa | attagtgaca | atcagaacaa | gtttcagtat | 120 |
| cagatgttca | agaggaagtt | gctattgcat | tgattttaat | atttgtacat | aaacactgat | 180 |
| tttttgagc | attattttgt | atttgttgta | ctttaatacc | | | 220 |

<210> SEQ ID NO 189
<211> LENGTH: 417
<212> TYPE: DNA
<213> ORGANISM: Homo sapiens
<220> FEATURE:
<221> NAME/KEY: misc_feature
<222> LOCATION: (1)...(417)
<223> OTHER INFORMATION: n=A,T,C or G

<400> SEQUENCE: 189

| | | | | | |
|---|---|---|---|---|---|
| accatcttga | cagaggatac | atgctcccaa | aacgtttgtt | accacactta | aaaatcactg | 60 |
| ccatcattaa | gcatcnnttt | caaaattata | gccattcatg | atttactttt | tccagatgac | 120 |
| tatcattatt | ctagtccttt | gaatttgtaa | ggggaaaaaa | aacaaaaaca | aaaacttacg | 180 |
| atgcactttt | ctccagcaca | tcagatttca | aattgaaaat | taaagacatg | ctatggtaat | 240 |
| gcacttgcta | gtactacaca | ctttgtacaa | caaaaaacag | aggcaagaaa | caacggaaag | 300 |
| agaaaagcct | tcctttgttg | gcccttaaac | tgagtcaaga | tctgaaatgt | agagatgatc | 360 |
| tctgacgata | cctgtatgtt | cttattgtgt | aaataaaatt | gctggtatga | aatgaca | 417 |

<210> SEQ ID NO 190
<211> LENGTH: 497
<212> TYPE: DNA
<213> ORGANISM: Homo sapiens

<400> SEQUENCE: 190

| | | | | | |
|---|---|---|---|---|---|
| gcactgcggc | gctctcccgt | cccgcggtgg | ttgctgctgc | tgccgctgct | gctgggcctg | 60 |
| aacgcaggag | ctgtcattga | ctggcccaca | gaggagggca | aggaagtatg | ggattatgtg | 120 |
| acggtccgca | aggatgccta | catgttctgg | tggctctatt | atgccaccaa | ctcctgcaag | 180 |
| aacttctcag | aactgccccT | ggtcatgtgg | cttcagggcg | gtccaggcgg | ttctagcact | 240 |
| ggatttggaa | actttgagga | aattgggccc | cttgacagtg | atctcaaacc | acggaaaacc | 300 |
| acctggctcc | aggctgccag | tctcctattt | gtggataatc | ccgtgggcac | tgggttcagt | 360 |
| tatgtgaatg | gtagtggtgc | ctatgccaag | gacctggcta | tggtggcttc | agacatgatg | 420 |
| gttctcctga | agaccttctt | cagttgccac | aaagaattcc | agacagttcc | attctacatt | 480 |
| ttctcagagt | cctatgg | | | | | 497 |

<210> SEQ ID NO 191
<211> LENGTH: 175
<212> TYPE: DNA
<213> ORGANISM: Homo sapiens

<400> SEQUENCE: 191

| | | | | | |
|---|---|---|---|---|---|
| atgttgaata | ttttgcttat | taactttgtt | tattgtcttc | tccctcgatt | agaatattag | 60 |

```
ctacttgagt acaaggattt gagcctgtta cattcactgc tgaattttag gctcctggaa    120
gatacccagc attcaataga gaccacacaa taaatatatg tcaaataaaa aaaaa        175
```

<210> SEQ ID NO 192
<211> LENGTH: 526
<212> TYPE: DNA
<213> ORGANISM: Homo sapiens

<400> SEQUENCE: 192

```
agtaaacatt attatttttt ttatatttgc aaaggaaaca tatctaatcc ttcctataga    60
aagaacagta ttgctgtaat tccttttctt ttcttcctca tttcctctgc cccttaaaag   120
attgaagaaa gagaaacttg tcaactcata tccacgttat ctagcaaagt acataagaat   180
ctatcactaa gtaatgtatc cttcagaatg tgttggttta ccagtgacac cccatattca   240
tcacaaaatt aaagcaagaa gtccatagta atttatttgc taatagtgga ttttttaatgc  300
tcagagtttc tgaggtcaaa ttttatcttt tcacttacaa gctctatgat cttaaataat   360
ttacttaatg tattttggtg tattttcctc aaattaatat tggtgttcaa gactatatct   420
aattcctctg atcactttga gaaacaaact tttattaaat gtaaggcact tttctatgaa   480
ttttaaatat aaaaataaat attgttctga ttattactga aaaaaa                  526
```

<210> SEQ ID NO 193
<211> LENGTH: 553
<212> TYPE: DNA
<213> ORGANISM: Homo sapiens
<220> FEATURE:
<221> NAME/KEY: misc_feature
<222> LOCATION: (1)...(553)
<223> OTHER INFORMATION: n=A,T,C or G

<400> SEQUENCE: 193

```
tccattgtgg tggaattcgc tctctggtaa aggcgtgcag gtgttggccg cggcctctga    60
gctgggatga gccgtgctcc cggtggaagc aagggagccc agccggagcc atggccagta   120
cagtggtagc agttggactg accattgctg ctgcaggatt tgcaggccgt tacgttttgc   180
aagccatgaa gcatatggag cctcaagtaa acaagttttt caaagcctta ccaaaatctg   240
ccttcagtgg tggctattat agaggtgggt ttgaacccaa aatgacaaan cgggaagcan   300
cattaatact aggtgtaagc cctactgcca ataagggaa aataagagat gctcatcgac    360
gaattatgct tttaaatcat cctgacaaag gaggatctcc ttatatagca nccaaaatca   420
atgaagctaa agatttacta naaggtcaag ctaaaaaatg aagtaaatgt atgatgaatt   480
ttaagttcgt attagtttat gtatatgagt actaagtttt tataataaaa tgcctcagag   540
ctacaatttt aaa                                                      553
```

<210> SEQ ID NO 194
<211> LENGTH: 320
<212> TYPE: DNA
<213> ORGANISM: Homo sapiens

<400> SEQUENCE: 194

```
cccttcccaa tccatcagta aagacccat ctgccttgtc catgccgttt cccaacaggg     60
atgtcacttg atatgagaat ctcaaatctc aatgccttat aagcattcct tcctgtgtcc   120
attaagactc tgataattgt ctcccctcca taggaatttc tcccaggaaa gaaatatatc   180
cccatctccg tttcatatca gaactaccgt ccccgatatt cccttcagag agattaaaga   240
ccagaaaaaa gtgagcctct tcatctgcac ctgtaatagt ttcagttcct attttcttcc   300
```

```
attgacccat atttatacct                                              320
```

<210> SEQ ID NO 195
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n=A,T,C or G

<400> SEQUENCE: 195

```
aagcatgacc tggggaaatg gtcagacctt gtattgtgtt tttggccttg aaagtagcaa    60
gtgaccagaa tctgccatgg caacaggctt taaaaaagac ccttaaaaag acactgtctc   120
aactgtggtg ttagcaccag ccagctctct gtacatttgc tagcttgtag ttttctaaga   180
ctgagtaaac ttcttatttt tanaaagggg aggctggntt gtaactttcc ttgtacttaa   240
ttgggtaaaa gtcttttcca caaaccacca tctatttgt gaactttgtt agtcatcttt    300
tatttggtaa attatgaact                                              320
```

<210> SEQ ID NO 196
<211> LENGTH: 357
<212> TYPE: DNA
<213> ORGANISM: Homo sapiens
<220> FEATURE:
<221> NAME/KEY: misc_feature
<222> LOCATION: (1)...(357)
<223> OTHER INFORMATION: n=A,T,C or G

<400> SEQUENCE: 196

```
atataaaata atacgaaact ttaaaaagca ttggantgtc agtatgttga atcagtagtt    60
tcactttaac tgtaaacaat ttcttaggac accatttggg ctagtttctg tgtaagtgta   120
aatactacaa aaacttattt atactgttct tatgtcattt gttatattca tagatttata   180
tgatgatatg acatctggct aaaaagaaat tattgcaaaa ctaaccacta tgtacttttt   240
tataaatact gtatggacaa aaaatggcat tttttatatt aaattgttta gctctggcaa   300
aaaaaaaaaa ttttaagagc tggtactaat aaaggattat tatgactgtt aaaaaaa     357
```

<210> SEQ ID NO 197
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n=A,T,C or G

<400> SEQUENCE: 197

```
tcagctgagt accatcagga tatttanccc tttaagtgct gttttgggag tagaaaacta    60
aagcaacaat acttcctctt gacagctttg attggaatgg ggttattaga tcattcacct   120
tggtcctaca cttttagga tgcttggtga acataacacc acttataatg aacatccctg    180
gttcctatat ttgggctat gtgggtagga attgttactt gttactgcag cagcagccct    240
agaaagtaag cccagggctt cagatctaag ttagtccaaa agctaaatga tttaaagtca   300
agttgtaatg ctaggcataa gcactctata atacattaaa ttataggccg agcaattagg   360
gaatgtttct gaaacattaa acttgtattt atgtcactaa aattctaaca caaacttaaa   420
aaatgtgtct catacatatg ctgtactagg cttcatcatg catttctaaa tttgtgtatg   480
```

| | |
|---|---|
| atttgaatat atgaaagaat ttatacaaga gtgttattta aaattattaa aaataaatgt | 540 |
| atataatttg tacctattgt aaaaa | 565 |

<210> SEQ ID NO 198
<211> LENGTH: 484
<212> TYPE: DNA
<213> ORGANISM: Homo sapiens

<400> SEQUENCE: 198

| | |
|---|---|
| tatgtaagta ttggtgtctg ctttaaaaaa ggagacccag acttcacctg tccttttaa | 60 |
| acatttgaga acagtgttac tctgagcagt tgggccacct tcaccttatc cgacagctga | 120 |
| ctgttggatg tgtccattgt cgccagtttg gctgttgccc ggacaggaca ggacctccat | 180 |
| tgggcgcagc agcaggtggc agggtgtgg cttgaggtgg gtggcagcgt ctggtcctcc | 240 |
| tctctggtgc tttctgagag ggtctctaaa gcagagtgtg gttggcctgg gggaaggcag | 300 |
| agcacgtatt tctcccctct agtacctctg catttgtgag tgttccctct ggctttctga | 360 |
| agggcagcag actcttgagt atactgcaga ggacatgctt tatcagtagg tcctgagggc | 420 |
| tccagggct caactgacca agtaacacag aagttggggt atgtggccta tttgggtcgg | 480 |
| aaac | 484 |

<210> SEQ ID NO 199
<211> LENGTH: 429
<212> TYPE: DNA
<213> ORGANISM: Homo sapiens
<220> FEATURE:
<221> NAME/KEY: misc_feature
<222> LOCATION: (1)...(429)
<223> OTHER INFORMATION: n=A,T,C or G

<400> SEQUENCE: 199

| | |
|---|---|
| gcttatgttt tttgttttaa cttttgtttt ttaacattta gaatattaca ttttgtatta | 60 |
| tacagtacct ttctcanaca ttttgtanaa ttcatttcgg cagctcacta ggattttgct | 120 |
| gaacattaaa aagngtgata gcgatattag ngccaatcaa atggaaaaaa ggtagtctta | 180 |
| ataaacaana cacaacgttt ttatacaaca tactttaaaa tattaanaaa actccttaat | 240 |
| attgtttcct attaagtatt attctttggg caanattttc tgatgctttt gattttctct | 300 |
| caatttagca tttgctttng gttttttttct ctatttagca ttctgttaag gcacaaaaac | 360 |
| tatgtactgt atgggaaatg ttgtaaatat tacctttttcc acattttaaa cagacaactt | 420 |
| tgaatccaa | 429 |

<210> SEQ ID NO 200
<211> LENGTH: 279
<212> TYPE: DNA
<213> ORGANISM: Homo sapiens

<400> SEQUENCE: 200

| | |
|---|---|
| gcttttttga ggaattacag ggaagctcct ggaattgtac atggatatct ttatccctag | 60 |
| ggggaaatca aggagctggg caccectaat tctttatgga agtgtttaaa actattttaa | 120 |
| ttttattaca agtattacta gagtagtggt tctactctaa gatttcaaaa gtgcatttaa | 180 |
| aatcatacat gttcccgcct gcaaatatat tgttattttg gtggagaaaa aaatagtata | 240 |
| ttctacataa aaaattaaag atattaacta agaaaaaaa | 279 |

<210> SEQ ID NO 201
<211> LENGTH: 569

<212> TYPE: DNA
<213> ORGANISM: Homo sapiens

<400> SEQUENCE: 201

```
taggtcagta ttttagaaa ctcttaatag ctcatactct tgataccaaa agcagccctg    60
attgttaaag cacacacctg cacaagaagc agtgatggtt gcatttacat ttcctgggtg   120
cacaaaaaaa aattctcaaa aagcaaggac ttacgctttt tgcaaagcct ttgagaagtt   180
actggatcat aggaagctta taacaagaat ggaagattct taaataactc actttctttg   240
gtatccagta acagtagatg ttcaaaatat gtagctgatt aataccagca ttgtgaacgc   300
tgtacaacct tgtggttatt actaagcaag ttactactag cttctgaaaa gtagcttcat   360
aattaatgtt atttatacac tgccttccat gacttttact ttgccctaag ctaatctcca   420
aaatctgaaa tgctactcca atatcagaaa aaaggggga ggtggaatta tatttcctgt   480
gatttttaaga gtacagagaa tcatgcacat ctctgattag ttcatatatg tctagtgtgt   540
aataaaagtc aaagatgaac tctcaaaaa                                    569
```

<210> SEQ ID NO 202
<211> LENGTH: 501
<212> TYPE: DNA
<213> ORGANISM: Homo sapiens

<400> SEQUENCE: 202

```
attaataggc ttaataattg ttggcaagga tccttttgct ttctttggca tgcaagctcc    60
tagcatctgg cagtggggcc aagaaaataa ggtttatgca tgtatgatgg ttttcttctt   120
gagcaacatg attgagaacc agtgtatgtc aacaggtgca tttgagataa ctttaaatga   180
tgtacctgtg tggtctaagc tggaatctgg tcaccttcca tccatgcaac aacttgttca   240
aattcttgac aatgaaatga agctcaatgt gcatatggat tcaatcccac accatcgatc   300
atagcaccac ctatcagcac tgaaaactct tttgcattaa gggatcattg caagagcagc   360
gtgactgaca ttatgaaggc ctgtactgaa gacagcaagc tgttagtaca gaccagatgc   420
tttcttggca ggctcgttgt acctcttgga aaacctcaat gcaagatagt gtttcagtgc   480
tggcatattt tggaattctg c                                            501
```

<210> SEQ ID NO 203
<211> LENGTH: 261
<212> TYPE: DNA
<213> ORGANISM: Homo sapiens
<220> FEATURE:
<221> NAME/KEY: misc_feature
<222> LOCATION: (1)...(261)
<223> OTHER INFORMATION: n=A,T,C or G

<400> SEQUENCE: 203

```
gacaagctcc tggtcttgag atgtcttctc gttaangaga tgggcctttt ggaggtaaag    60
gataaaatga atgagttctg tcatgattca ctattntata acttgcatga cctttactgt   120
gttagctctt tgaatgttct tgaaatttta gactttcttt gtaaacaaat gatatgtcct   180
tatcattgta taaagctgt tatgtgcaac agtgtggaga ttccttgtct gatttaataa   240
aatacttaaa cactgaaaaa a                                            261
```

<210> SEQ ID NO 204
<211> LENGTH: 421
<212> TYPE: DNA
<213> ORGANISM: Homo sapiens

```
<400> SEQUENCE: 204
agcatctttt ctacaacgtt aaaattgcag aagtagctta tcattaaaaa acaacaacaa      60
caacaataac aataaatcct aagtgtaaat cagttattct accccctacc aaggatatca     120
gcctgttttt tccctttttt ctcctgggaa taattgtggg cttcttccca aatttctaca     180
gcctctttcc tcttctcatg cttgagcttc cctgtttgca cgcatgcgtg tgcaggactg     240
gcttgtgtgc ttggactcgg ctccaggtgg aagcatgctt tcccttgtta ctgttggaga     300
aactcaaacc ttcaagccct aggtgtagcc attttgtcaa gtcatcaact gtattttgt     360 actggcatta acaaaaaaag aagataaaat attgtaccat taaactttaa taaaacttta     420
a                                                                    421

<210> SEQ ID NO 205
<211> LENGTH: 460
<212> TYPE: DNA
<213> ORGANISM: Homo sapiens

<400> SEQUENCE: 205
tactctcaca atgaaggacc tggaatgaaa aatctgtgtc taaacaagtc ctctttagat      60
tttagtgcaa atccagagcc agcgtcggtt gcctcgagta attctttcat gggtaccttt     120
ggaaaagctc tcaggagacc tcacctagat gcctattcaa gctttggaca gccatcagat     180
tgtcagccaa gagcctttta tttgaaagct cattcttccc cagacttgga ctctgggtca     240
gaggaagatg ggaagaaag acagattttt caggaagaaa atcacatttg tacctttaaa     300
cagactttag aaaactacag gactccaaat tttcagtctt atgacttgga cacatagact     360
gaatgagacc aaaggaaaag cttaacatac tacctcaagg tgaaccttta tttaaaagag     420
agagaatctt atgttttta aatggagtta tgaattttaa                           460

<210> SEQ ID NO 206
<211> LENGTH: 481
<212> TYPE: DNA
<213> ORGANISM: Homo sapiens

<400> SEQUENCE: 206
tgtggtggaa ttcgggacgc ccccagaccc tgacttttc ctgcgtgggc cgtctcctcc      60
tgcggaagca gtgacctctg acccctggtg accttcgctt tgagtgcctt ttgaacgctg     120
gtcccgcggg acttggtttt ctcaagctct gtctgtccaa agacgctccg gtcgaggtcc     180
cgcctgccct gggtggatac ttgaacccca gacgcccctc tgtgctgctg tgtccggagg     240
cggccttccc atctgcctgc ccacccgag ctctttccgc cggcgcaggg tcccaagccc     300
acctcccgcc ctcagtcctg cggtgtgcgt ctgggcacgt cctgcacaca caatgcaagt     360
cctggcctcc gcgcccgccc gcccacgcga gccgtacccg ccgccaactc tgttattat     420 ggtgtgaccc cctggaggtg ccctcggccc accggggcta tttattgttt aatttatttg     480
t                                                                    481

<210> SEQ ID NO 207
<211> LENGTH: 605
<212> TYPE: DNA
<213> ORGANISM: Homo sapiens

<400> SEQUENCE: 207 acccttttg gattcagggc tcctcacaat taaaatgagt gtaatgaaac aaggtgaaaa       60
tatagaagca tccctttgta tactgttttg ctacttacag tgtacttggc attgctttat     120
```

```
ctcactggat tctcacggta ggatttctga gatcttaatc taagctccaa agttgtctac      180 tttttttgatc ctagggtgct ccttttgttt tacagagcag ggtcacttga tttgctagct    240
ggtggcagaa ttggcaccat tacccaggtc tgactgacca ccagtcagag gcactttatt     300
tgtatcatga aatgatttga aatcattgta aagcagcgaa gtctgataat gaatgccagc     360
tttccttgtg ctttgataac aaagactcca atattctgg agaacctgga taaaagtttg      420
aagggctaga ttgggatttg aagacaaaat tgtaggaaat cttacatttt tgcaataaca     480
aacattaatg aaagcaaaac attataaaag taattttaat tcaccacata cttatcaatt     540
tcttgatgct tccaaatgac atctaccaga tatggttttg tggacatctt tttctgttta    600
cataa                                                                 605

<210> SEQ ID NO 208
<211> LENGTH: 655
<212> TYPE: DNA
<213> ORGANISM: Homo sapiens

<400> SEQUENCE: 208
ggcgttgttc tggattcccg tcgtaactta aagggaaact ttcacaatgt ccggagccct      60
tgatgtcctg caaatgaagg aggaggatgt ccttaagttc cttgcagcag gaacccactt     120
aggtggcacc aatcttgact tccagatgga acagtacatc tataaaagga aaagtgatgg     180
catctatatc ataaatctca agaggacctg ggagaagctt ctgctggcag ctcgtgcaat     240
tgttgccatt gaaaaccctg ctgatgtcag tgttatatcc tccaggaata ctggccagag     300
ggctgtgctg aagtttgctg ctgccactgg agccactcca attgctggcc gcttcactcc     360
tggaaccttc actaaccaga tccaggcagc cttccgggag ccacggcttc ttgtggttac     420 tgacccccagg gctgaccacc agcctctcac ggaggcatct tatgttaacc tacctaccat    480
tgcgctgtgt aacacagatt ctcctctgcg ctatgtggac attgccatcc catgcaacaa    540
caagggagct cactcagtgg gtttgatgtg gtggatgctg gctcgggaag ttctgcgcat    600
gcgtggcacc atttcccgtg aacacccatg ggaggtcatg cctgatctgt acttc         655

<210> SEQ ID NO 209
<211> LENGTH: 621
<212> TYPE: DNA
<213> ORGANISM: Homo sapiens

<400> SEQUENCE: 209
catttagaac atggttatca tccaagacta ctctaccctg caacattgaa ctcccaagag      60
caaatccaca ttcctcttga gttctgcagc ttctgtgtaa ataggggcagc tgtcgtctat   120 gccgtagaat cacatgatct gaggaccatt catggaagct gctaaatagc ctagtctggg    180
gagtcttcca taaagttttg catggagcaa acaaacagga ttaaactagg tttggttcct    240
tcagccctct aaaagcatag ggcttagcct gcaggcttcc ttgggctttc tctgtgtgtg    300
tagttttgta aacactatag catctgttaa gatccagtgt ccatggaaac cttcccacat    360
gccgtgactc tggactatat cagttttttgg aaagcagggt tcctctgcct gctaacaagc   420
ccacgtggac cagtctgaat gtctttcctt tacacctatg ttttttaaata gtcaaacttc   480 aagaaacaat ctaaacaagt ttctgttgca tatgtgtttg tgaacttgta tttgtattta    540
gtaggcttct atattgcatt taacttgttt ttgtaactcc tgattcttcc ttttcggata   600
ctattgatga ataaagaaat t                                              621
```

<210> SEQ ID NO 210
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 210

| | | | |
|---|---|---|---|
| cgccttgggg agccggcggn ngagtccggg acgtggagac ccggggtccc ggcagccggg | | | 60 |
| nggcccgcgg gcccagggtg gggatgcacc gccgcgggt gggagctggc gccatcgcca | | | 120 |
| agaagaaact tgcagaggcc aagtataagg agcgagggac ggtcttggct gaggaccagc | | | 180 |
| tagcccagat gtcaaagcag ttggacatgt tcaagaccaa cctggaggaa tttgccagca | | | 240 |
| aacacaagca ggagatccgg aagaatcctg agttccgtgt gcagttccag gacatgtgtg | | | 300 |
| caaccattgg cgtggatccg ctggcctctg gaaaaggatt ttggtctgag atgctgggcg | | | 360 |
| tgggggactt ctattacgaa ctaggtgtcc aaattatcga agtgtgcctg cgctgaagc | | | 420 |
| atcggaatgg aggtctgata actttggagg aactacatca acaggtgttg aagggaaggg | | | 480 |
| gcaagttcgc ccaggatgtc agtcaagatg acctgatcag agccatcaag aaa | | | 533 |

<210> SEQ ID NO 211
<211> LENGTH: 451
<212> TYPE: DNA
<213> ORGANISM: Homo sapiens

<400> SEQUENCE: 211

| | | | |
|---|---|---|---|
| ttagcttgag ccgagaacga ggcgagaaag ctggagaccg aggagaccgc ctagagcgga | | | 60 |
| gtgaacgggg aggggaccgt ggggaccggc ttgatcgtgc gcggacacct gctaccaagc | | | 120 |
| ggagcttcag caaggaagtg gaggagcgga gtagagaacg gccctcccag cctgaggggc | | | 180 |
| tgcgcaaggc agctagcctc acggaggatc gggaccgtgg gcgggatgcc gtgaagcgag | | | 240 |
| aagctgccct accccagtg agccccctga aggcggctct ctctgaggag gagttagaga | | | 300 |
| agaaatccaa ggctatcatt gaggaatatc tccatctcaa tgacatgaaa gaggcagtcc | | | 360 |
| agtgcgtgca ggagctggcc tcaccctcct tgctcttcat ctttgtacgg catggtgtcg | | | 420 |
| agtctacgct ggagcgcagt gccattgctc g | | | 451 |

<210> SEQ ID NO 212
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 212

| | | | |
|---|---|---|---|
| gtgattattc ttgatcaggg agaagatcat ttagatttgt tttgcattcc ttanaatgga | | | 60 |
| gggcaacatt ccacagctgc cctggctgtg atgagtgtcc ttgcaggggc cggagtagga | | | 120 |
| gcactgggt gggggcggaa ttggggttac tcgatgtaag ggattccttg ttgttgtgtt | | | 180 |
| gagatccagt gcagttgtga tttctgtgga tcccagcttg gttccaggaa ttttgtgtga | | | 240 |
| ttggcttaaa tccagttttc aatcttcgac agctgggctg gaacgtgaac tcagtagctg | | | 300 |
| aacctgtctg acccggtcac gttcttggat cctcagaact ctttgctctt gtcggggtgg | | | 360 |
| gggtgggaac tcacgtgggg agcggtggct gagaaaatgt aaggattctg gaatacatat | | | 420 |

```
tccatgggac tttccttccc tctcctgctt cctctttttcc tgctccctaa c            471
```

<210> SEQ ID NO 213
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n=A,T,C or G

<400> SEQUENCE: 213

```
ctaattagaa acttgctgta ctttttnttt tcttttaggg gtcaaggacc ctctttatag     60
ctnccatttg cctacaataa attattgcag cagtttgcaa tactaaaata ttttttatag   120
actttatatt tttccttttg ataaagggat gctgcatagt agagttggtg taattaaact   180
atctcagccg tttccctgct ttccttctg ctccatatgc ctcattgtcc ttcagggag    240 ctcttttaat cttaaagttc tacatttcat gctcttagtc aaattctgtt acctttttaa   300
taactcttcc cactgcatat ttccatcttg aattggnggt tctaaattct gaactgtag   360 ttgagataca gctatttaat atttctggga gatgtgcatc cctcttctttt gtggttgccc   420 aaggttgttt tgcgtaactg anactccttg atatgcttca gagaatttag gcaaacactg   480
gccatggccg tgggagtact gggagtaaaa t                                   511
```

<210> SEQ ID NO 214
<211> LENGTH: 521
<212> TYPE: DNA
<213> ORGANISM: Homo sapiens

<400> SEQUENCE: 214

```
agcattgcca aataatccct aattttccac taaaaatata atgaaatgat gttaagcttt     60
ttgaaaagtt taggttaaac ctactgttgt tagattaatg tatttgttgc ttcccttat    120 ctggaatgtg gcattagctt ttttatttta accctcttta attcttattc aattccatga   180
cttaaggttg gagagctaaa cactgggatt tttggataac agactgacag ttttgcataa   240
ttataatcgg cattgtacat agaaaggata tggctaccct ttgttaaatc tgcactttct   300
aaatatcaaa aaagggaaat gaagtataaa tcaattttg tataatctgt ttgaaacatg   360
agttttattt gcttaatatt agggctttgc ccctttctg taagtctctt gggatcctgt   420
gtagaagctg ttctcattaa acaccaaaca gttaagtcca ttctctggta ctagctacaa   480
attcggtttc atattctact taacaattta ataaactga a                        521
```

<210> SEQ ID NO 215
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 215

```
gagcggagag cggaccngtn agagccctga gcagccccac cgccgccgcc ggcctagttn     60
ncatcacacc ccgggaggag ccgcagctgc cgcagccggc cccagtcacc atcaccgcaa   120
ccatgagcag cgaggccgag acccagcagc cgccgccgcc ccccccgcc gccccgcc    180 tcagcgccgc cgacaccaag cccggcacta cgggcagcgg cgcagggagc ggtggcccgg   240
```

```
gcggcctcac atcggcggcg cctgccggcg gggacaagaa ggtcatcgca acgaaggttt      300
tgggaacagt aaaatggttc aatgtaagga acggatatgg tttcatcaac aggaatgaca      360
ccaangaaga tgtatttgta c                                                381
```

<210> SEQ ID NO 216
<211> LENGTH: 425
<212> TYPE: DNA
<213> ORGANISM: Homo sapiens

<400> SEQUENCE: 216

```
ttactaacta ggtcattcaa ggaagtcaag ttaacttaaa catgtcacct aaatgcactt       60
gatggtgttg aaatgtccac cttcttaaat ttttaagatg aacttagttc taaagaagat      120
aacaggccaa tcctgaaggt actccctgtt tgctgcagaa tgtcagatat tttggatgtt      180
gcataagagt cctatttgcc ccagttaatt caacttttgt ctgcctgttt tgtggactgg      240
ctggctctgt tagaactctg tccaaaaagt gcatggaata taacttgtaa agcttcccac      300
aattgacaat atatatgcat gtgtttaaac caaatccaga aagcttaaac aatagagctg      360
cataatagta tttattaaag aatcacaact gtaaacatga gaataactta aggattctag      420
tttag                                                                  425
```

<210> SEQ ID NO 217
<211> LENGTH: 181
<212> TYPE: DNA
<213> ORGANISM: Homo sapiens

<400> SEQUENCE: 217

```
gagaaaccaa atgataggtt gtagagcctg atgactccaa acaaagccat cacccgcatt       60
cttcctcctt cttctggtgc tacagctcca agggcccttc accttcatgt ctgaaatgga      120
actttggctt tttcagtgga agaatatgtt gaaggtttca ttttgttcta gaaaaaaaaa      180
a                                                                      181
```

<210> SEQ ID NO 218
<211> LENGTH: 405
<212> TYPE: DNA
<213> ORGANISM: Homo sapiens

<400> SEQUENCE: 218

```
caggccttcc agttcactga caaacatggg gaagtgtgcc cagctggctg gaaacctggc       60
agtgatacca tcaagcctga tgtccaaaag agcaaagaat atttctccaa gcagaagtga      120
gcgctgggct gttttagtgc caggctgcgg tgggcagcca tgagaacaaa acctcttctg      180 tattttttt ttccattagt aaaacacaag acttcagatt cagccgaatt gtggtgtctt       240
acaaggcagg cctttcctac aggggtgga gagaccagcc tttcttcctt tggtaggaat       300
ggcctgagtt ggcgttgtgg gcaggctact ggtttgtatg atgtattagt agagcaaccc      360
attaatcttt tgtagtttgt attaaacttg aactgagaaa aaaaa                       405
```

<210> SEQ ID NO 219
<211> LENGTH: 216
<212> TYPE: DNA
<213> ORGANISM: Homo sapiens
<220> FEATURE:
<221> NAME/KEY: misc_feature
<222> LOCATION: (1)...(216)
<223> OTHER INFORMATION: n=A,T,C or G

<400> SEQUENCE: 219

```
actccaagag ttagggcagc agagtggagc gatttagaaa gaacatttta aaacaatcag    60
ttaatttacc atgtaaaatt gctgtaaatg ataatgtgta cagattttct gttcaaatat   120
tcaattgtaa acttcttgtt aagactgtta cgtttctatt gcttttgtat gggatattgc   180
aaaaataaaa aggaaagaac cctcttnaan aaaaaa                             216
```

<210> SEQ ID NO 220
<211> LENGTH: 380
<212> TYPE: DNA
<213> ORGANISM: Homo sapiens

<400> SEQUENCE: 220

```
cttacaaatt gccccccatgt gtagggaca cagaaccctt tgagaaaact tagattttg     60 tctgtacaaa gtctttgcct ttttccttct tcattttttt ccagtacatt aaatttgtca   120
atttcatctt tgagggaaac tgattagatg ggttgtgttt gtgttctgat ggagaaaaca   180
gcaccccaag gactcagaag atgatttta cagttcagaa cagatgtgtg caatattggt   240
gcatgtaata atgttgagtg gcagtcaaaa gtcatgattt ttatcttagt tcttcattac   300
tgcattgaaa aggaaaacct gtctgagaaa atgcctgaca gtttaattta aaactatggt   360
gtaagtcttt gacaaaaaaa                                               380
```

<210> SEQ ID NO 221
<211> LENGTH: 398
<212> TYPE: DNA
<213> ORGANISM: Homo sapiens

<400> SEQUENCE: 221

```
ggttagtaag ctgtcgactt tgtaaaaaag ttaaaaatga aaaaaaaagg aaaaatgaat    60
tgtatattta atgaatgaac atgtacaatt tgccactggg aggaggttcc ttttttgttgg  120 gtgagtctgc aagtgaattt cactgatgtt gatattcatt gtgtgtagtt ttatttcggt   180
cccagccccg tttcctttta ttttggagct aatgccagct gcgtgtctag ttttgagtgc   240
agtaaaatag aatcagcaaa tcactcttat tttcatcct tttccggtat tttttgggtt    300
gtttctgtgg gagcagtgta caccaactct tcctgtatat tgccttttg ctggaaaatg    360 ttgtatgttg aataaaattt tctataaaaa ttaaaaaa                           398
```

<210> SEQ ID NO 222
<211> LENGTH: 301
<212> TYPE: DNA
<213> ORGANISM: Homo sapiens
<220> FEATURE:
<221> NAME/KEY: misc_feature
<222> LOCATION: (1)...(301)
<223> OTHER INFORMATION: n=A,T,C or G

<400> SEQUENCE: 222

```
ttcgataatt gatctcatgg gctttccctg gaggaaaggt ttttttttgnt gtttattttt    60 taanaacttg aaacttgtaa actgagatgt ctgtagcttt tttgcccatc tgtagtgtat   120
gtgaagattt caaaacctga gagcactttt tctttgttta gaattatgag aaaggcacta   180
gatgacttta ggatttgcat ttttcccttt attgcctcat ttcttgtgac gccttgttgg   240
ggagggaaat ctgtttattt tttcctacaa ataaaaagct aagattctat atcgcaaaaa   300
a                                                                   301
```

<210> SEQ ID NO 223

```
<211> LENGTH: 200
<212> TYPE: DNA
<213> ORGANISM: Homo sapiens

<400> SEQUENCE: 223
gtaagtgctt aggaagaaac tttgcaaaca tttaatgagg atacactgtt cattttaaa      60
attccttcac actgtaattt aatgtgtttt atattctttt gtagtaaaac aacataactc    120
agatttctac aggagacagt ggttttattt ggattgtctt ctgtaatagg tttcaataaa    180
gctggatgaa cttaaaaaaa                                                 200

<210> SEQ ID NO 224
<211> LENGTH: 385
<212> TYPE: DNA
<213> ORGANISM: Homo sapiens

<400> SEQUENCE: 224
gaaaggtttg atccggactc aaagaaagca aaggagtgtg agccgccatc tgctggagca     60
gctgtaactg caagacctgg acaagagatt cgtcagcgaa ctgcagctca aagaaacctt    120
tctccaacac cagcaagccc taaccagggc cctcctccac aagttccagt atctcctgga    180
ccaccaaagg acagttctgc ccctggtgga ccccagaaa ggactgttac tccagcccta    240
tcatcaaatg tgttaccaag acatcttgga tcccctgcta cttcagtgcc tggaatgggt    300
aaacagagca cttaatgtta tttacagttt atattgtttt ctctggttac caataaaacg    360
ggccattttc aggtggtaaa aaaaa                                           385

<210> SEQ ID NO 225
<211> LENGTH: 560
<212> TYPE: PRT
<213> ORGANISM: Homo sapien

<400> SEQUENCE: 225

Met Glu Cys Leu Tyr Tyr Phe Leu Gly Phe Leu Leu Ala Ala Arg
 1               5                  10                  15

Leu Pro Leu Asp Ala Ala Lys Arg Phe His Asp Val Leu Gly Asn Glu
                20                  25                  30

Arg Pro Ser Ala Tyr Met Arg Glu His Asn Gln Leu Asn Gly Trp Ser
            35                  40                  45

Ser Asp Glu Asn Asp Trp Asn Glu Lys Leu Tyr Pro Val Trp Lys Arg
        50                  55                  60

Gly Asp Met Arg Trp Lys Asn Ser Trp Lys Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
                100                 105                 110

Asn Ile Val Tyr Glu Lys Asn Cys Arg Asn Glu Ala Gly Leu Ser Ala
            115                 120                 125

Asp Pro Tyr Val Tyr Asn Trp Thr Ala Trp Ser Glu Ser Asp Gly
        130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
                180                 185                 190
```

```
Arg Val Ser Val Asn Thr Ala Asn Val Thr Leu Gly Pro Gln Leu Met
            195                 200                 205
Glu Val Thr Val Tyr Arg Arg His Gly Arg Ala Tyr Val Pro Ile Ala
            210                 215                 220
Gln Val Lys Asp Val Tyr Val Thr Asp Gln Ile Pro Val Phe Val
225                 230                 235                 240
Thr Met Phe Gln Lys Asn Asp Arg Asn Ser Ser Asp Glu Thr Phe Leu
                245                 250                 255
Lys Asp Leu Pro Ile Met Phe Asp Val Leu Ile His Asp Pro Ser His
                260                 265                 270
Phe Leu Asn Tyr Ser Thr Ile Asn Tyr Lys Trp Ser Phe Gly Asp Asn
                275                 280                 285
Thr Gly Leu Phe Val Ser Thr Asn His Thr Val Asn His Thr Tyr Val
            290                 295                 300
Leu Asn Gly Thr Phe Ser Leu Asn Leu Thr Val Lys Ala Ala Ala Pro
305                 310                 315                 320
Gly Pro Cys Pro Pro Pro Pro Pro Pro Arg Pro Ser Lys Pro Thr
                325                 330                 335
Pro Ser Leu Gly Pro Ala Gly Asp Asn Pro Leu Glu Leu Ser Arg Ile
                340                 345                 350
Pro Asp Glu Asn Cys Gln Ile Asn Arg Tyr Gly His Phe Gln Ala Thr
            355                 360                 365
Ile Thr Ile Val Glu Gly Ile Leu Glu Val Asn Ile Ile Gln Met Thr
            370                 375                 380
Asp Val Leu Met Pro Val Pro Trp Pro Glu Ser Ser Leu Ile Asp Phe
385                 390                 395                 400
Val Val Thr Cys Gln Gly Ser Ile Pro Thr Glu Val Cys Thr Ile Ile
                405                 410                 415
Ser Asp Pro Thr Cys Glu Ile Thr Gln Asn Thr Val Cys Ser Pro Val
                420                 425                 430
Asp Val Asp Glu Met Cys Leu Leu Thr Val Arg Arg Thr Phe Asn Gly
            435                 440                 445
Ser Gly Thr Tyr Cys Val Asn Leu Thr Leu Gly Asp Asp Thr Ser Leu
            450                 455                 460
Ala Leu Thr Ser Thr Leu Ile Ser Val Pro Asp Arg Asp Pro Ala Ser
465                 470                 475                 480
Pro Leu Arg Met Ala Asn Ser Ala Leu Ile Ser Val Gly Cys Leu Ala
                485                 490                 495
Ile Phe Val Thr Val Ile Ser Leu Leu Val Tyr Lys Lys His Lys Glu
            500                 505                 510
Tyr Asn Pro Ile Glu Asn Ser Pro Gly Asn Val Val Arg Ser Lys Gly
            515                 520                 525
Leu Ser Val Phe Leu Asn Arg Ala Lys Ala Val Phe Phe Pro Gly Asn
            530                 535                 540
Gln Glu Lys Asp Pro Leu Leu Lys Asn Gln Glu Phe Lys Gly Val Ser
545                 550                 555                 560

<210> SEQ ID NO 226
<211> LENGTH: 9
<212> TYPE: PRT
<213> ORGANISM: Homo sapien

<400> SEQUENCE: 226

Ile Leu Ile Pro Ala Thr Trp Lys Ala
```

1          5

<210> SEQ ID NO 227
<211> LENGTH: 9
<212> TYPE: PRT
<213> ORGANISM: Homo sapien

<400> SEQUENCE: 227

Phe Leu Leu Asn Asp Asn Leu Thr Ala
1               5

<210> SEQ ID NO 228
<211> LENGTH: 9
<212> TYPE: PRT
<213> ORGANISM: Homo sapien

<400> SEQUENCE: 228

Leu Leu Gly Asn Cys Leu Pro Thr Val
1               5

<210> SEQ ID NO 229
<211> LENGTH: 10
<212> TYPE: PRT
<213> ORGANISM: Homo sapien

<400> SEQUENCE: 229

Lys Leu Leu Gly Asn Cys Leu Pro Thr Val
1               5                   10

<210> SEQ ID NO 230
<211> LENGTH: 10
<212> TYPE: PRT
<213> ORGANISM: Homo sapien

<400> SEQUENCE: 230

Arg Leu Thr Gly Gly Leu Lys Phe Phe Val
1               5                   10

<210> SEQ ID NO 231
<211> LENGTH: 9
<212> TYPE: PRT
<213> ORGANISM: Homo sapien

<400> SEQUENCE: 231

Ser Leu Gln Ala Leu Lys Val Thr Val
1               5

<210> SEQ ID NO 232
<211> LENGTH: 20
<212> TYPE: PRT
<213> ORGANISM: Homo sapiens

<400> SEQUENCE: 232

Ala Gly Ala Asp Val Ile Lys Asn Asp Gly Ile Tyr Ser Arg Tyr Phe
                5                   10                  15
Phe Ser Phe Ala
            20

<210> SEQ ID NO 233
<211> LENGTH: 21
<212> TYPE: PRT
<213> ORGANISM: Homo sapiens

<400> SEQUENCE: 233

```
Phe Phe Ser Phe Ala Ala Asn Gly Arg Tyr Ser Leu Lys Val His Val
                 5                  10                  15
Asn His Ser Pro Ser
             20

<210> SEQ ID NO 234
<211> LENGTH: 20
<212> TYPE: PRT
<213> ORGANISM: Homo sapiens

<400> SEQUENCE: 234

Phe Leu Val Thr Trp Gln Ala Ser Gly Pro Pro Glu Ile Ile Leu Phe
                 5                  10                  15
Asp Pro Asp Gly
             20

<210> SEQ ID NO 235
<211> LENGTH: 20
<212> TYPE: PRT
<213> ORGANISM: Homo sapiens

<400> SEQUENCE: 235

Leu Gln Ser Ala Val Ser Asn Ile Ala Gln Ala Pro Leu Phe Ile Pro
                 5                  10                  15
Pro Asn Ser Asp
             20

<210> SEQ ID NO 236
<211> LENGTH: 20
<212> TYPE: PRT
<213> ORGANISM: Homo sapiens

<400> SEQUENCE: 236

Ile Gln Asp Asp Phe Asn Asn Ala Ile Leu Val Asn Thr Ser Lys Arg
                 5                  10                  15
Asn Pro Gln Gln
             20

<210> SEQ ID NO 237
<211> LENGTH: 21
<212> TYPE: PRT
<213> ORGANISM: Homo sapiens

<400> SEQUENCE: 237

Arg Asn Ser Leu Gln Ser Ala Val Ser Asn Ile Ala Gln Ala Pro Leu
                 5                  10                  15
Phe Ile Pro Pro Asn
             20

<210> SEQ ID NO 238
<211> LENGTH: 20
<212> TYPE: PRT
<213> ORGANISM: Homo sapiens

<400> SEQUENCE: 238

Thr His Glu Ser His Arg Ile Tyr Val Ala Ile Arg Ala Met Asp Arg
                 5                  10                  15
Asn Ser Leu Gln
             20

<210> SEQ ID NO 239
<211> LENGTH: 20
```

```
<212> TYPE: PRT
<213> ORGANISM: Homo sapiens

<400> SEQUENCE: 239

Arg Asn Pro Gln Gln Ala Gly Ile Arg Glu Ile Phe Thr Phe Ser Pro
                 5                  10                  15

Gln Ile Ser Thr
            20

<210> SEQ ID NO 240
<211> LENGTH: 21
<212> TYPE: PRT
<213> ORGANISM: Homo sapiens

<400> SEQUENCE: 240

Gly Gln Ala Thr Ser Tyr Glu Ile Arg Met Ser Lys Ser Leu Gln Asn
                 5                  10                  15

Ile Gln Asp Asp Phe
            20

<210> SEQ ID NO 241
<211> LENGTH: 20
<212> TYPE: PRT
<213> ORGANISM: Homo sapiens

<400> SEQUENCE: 241

Glu Arg Lys Trp Gly Phe Ser Arg Val Ser Ser Gly Gly Ser Phe Ser
                 5                  10                  15

Val Leu Gly Val
            20

<210> SEQ ID NO 242
<211> LENGTH: 20
<212> TYPE: PRT
<213> ORGANISM: Homo sapiens

<400> SEQUENCE: 242

Gly Ser His Ala Met Tyr Val Pro Gly Tyr Thr Ala Asn Gly Asn Ile
                 5                  10                  15

Gln Met Asn Ala
            20

<210> SEQ ID NO 243
<211> LENGTH: 20
<212> TYPE: PRT
<213> ORGANISM: Homo sapiens

<400> SEQUENCE: 243

Val Asn His Ser Pro Ser Ile Ser Thr Pro Ala His Ser Ile Pro Gly
                 5                  10                  15

Ser His Ala Met
            20

<210> SEQ ID NO 244
<211> LENGTH: 20
<212> TYPE: PRT
<213> ORGANISM: Homo sapiens

<400> SEQUENCE: 244

Ala Val Pro Pro Ala Thr Val Glu Ala Phe Val Glu Arg Asp Ser Leu
                 5                  10                  15

His Phe Pro His
```

-continued

<210> SEQ ID NO 245
<211> LENGTH: 20
<212> TYPE: PRT
<213> ORGANISM: Homo sapiens

<400> SEQUENCE: 245

Lys Pro Gly His Trp Thr Tyr Thr Leu Asn Asn Thr His His Ser Leu
                 5                  10                  15

Gln Ala Leu Lys
            20

<210> SEQ ID NO 246
<211> LENGTH: 20
<212> TYPE: PRT
<213> ORGANISM: Homo sapiens

<400> SEQUENCE: 246

Asn Leu Thr Phe Arg Thr Ala Ser Leu Trp Ile Pro Gly Thr Ala Lys
                 5                  10                  15

Pro Gly His Trp
            20

<210> SEQ ID NO 247
<211> LENGTH: 20
<212> TYPE: PRT
<213> ORGANISM: Homo sapiens

<400> SEQUENCE: 247

Leu His Phe Pro His Pro Val Met Ile Tyr Ala Asn Val Lys Gln Gly
                 5                  10                  15

Phe Tyr Pro Ile
            20

<210> SEQ ID NO 248
<211> LENGTH: 20
<212> TYPE: PRT
<213> ORGANISM: Homo sapiens

<400> SEQUENCE: 248

Pro Glu Thr Gly Asp Pro Val Thr Leu Arg Leu Leu Asp Asp Gly Ala
                 5                  10                  15

Gly Ala Asp Val
            20

<210> SEQ ID NO 249
<211> LENGTH: 20
<212> TYPE: PRT
<213> ORGANISM: Homo sapiens

<400> SEQUENCE: 249

Gly Phe Tyr Pro Ile Leu Asn Ala Thr Val Thr Ala Thr Val Glu Pro
                 5                  10                  15

Glu Thr Gly Asp
            20

<210> SEQ ID NO 250
<211> LENGTH: 20
<212> TYPE: PRT
<213> ORGANISM: Homo sapiens

<400> SEQUENCE: 250

Phe Asp Pro Asp Gly Arg Lys Tyr Tyr Thr Asn Asn Phe Ile Thr Asn
                5                  10                  15

Leu Thr Phe Arg
            20

<210> SEQ ID NO 251
<211> LENGTH: 20
<212> TYPE: PRT
<213> ORGANISM: Homo sapiens

<400> SEQUENCE: 251

Leu Gln Ala Leu Lys Val Thr Val Thr Ser Arg Ala Ser Asn Ser Ala
                5                  10                  15

Val Pro Pro Ala
            20

<210> SEQ ID NO 252
<211> LENGTH: 153
<212> TYPE: PRT
<213> ORGANISM: Homo sapien

<400> SEQUENCE: 252

Met Ala Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
                35                  40                  45

Ala Ala Val Ser Ser Ile Phe Asn Ser Pro Glu Glu Phe Leu Gly Lys
50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
                100                 105                 110

Asn Met Cys Arg Phe Tyr Glu Met Lys Pro Arg Asp Val Asn Leu
            115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150

<210> SEQ ID NO 253
<211> LENGTH: 462
<212> TYPE: DNA
<213> ORGANISM: Homo sapien

<400> SEQUENCE: 253
atggccagtg tccgcgtggc ggcctacttt gaaaactttc tcgcggcgtg gcggcccgtg      60
aaagcctctg atggagatta ctacaccttg gctgtaccga tgggagatgt accaatggat     120
ggtatctctg ttgctgatat tggagcagcc gtctctagca tttttaattc tccagaggaa     180 ttttaggca aggccgtggg gctcagtgca gaagcactaa caatacagca aatatgctgat    240 gttttgtcca aggctttggg gaagaagtc cgagatgcaa agattacccc ggaagctttc      300
gagaagctgg gattccctgc agcaaaggaa atagccaata tgtgtcgttt ctatgaaatg     360

| | |
|---|---|
| aagccagacc gagatgtcaa tctcacccac caactaaatc ccaaagtcaa aagcttcagc | 420 |
| cagtttatct cagagaacca gggagccttc aagggcatgt ag | 462 |

<210> SEQ ID NO 254
<211> LENGTH: 8031
<212> TYPE: DNA
<213> ORGANISM: Homo sapien

<400> SEQUENCE: 254

| | |
|---|---|
| ggcgaatgg gacgcgccct gtagcggcgc attaagcgcg gcgggtgtgg tggttacgcg | 60 |
| agcgtgacc gctacacttg ccagcgccct agcgcccgct cctttcgctt tcttcccttc | 120 |
| tttctcgcc acgttcgccg gctttccccg tcaagctcta atcggggggc tccctttagg | 180 |
| ttccgattt agtgctttac ggcacctcga ccccaaaaaa cttgattagg gtgatggttc | 240 |
| cgtagtggg ccatcgccct gatagacggt ttttcgccct ttgacgttgg agtccacgtt | 300 |
| tttaatagt ggactcttgt tccaaactgg aacaacactc aaccctatct cggtctattc | 360 |
| tttgattta aagggatttt tgccgatttc ggcctattgg ttaaaaaatg agctgattta | 420 |
| caaaaattt aacgcgaatt ttaacaaaat attaacgttt acaatttcag gtggcacttt | 480 |
| cggggaaat gtgcgcggaa cccctatttg tttattttc taaatacatt caaatatgta | 540 |
| ccgctcatg aattaattct tagaaaaact catcgagcat caaatgaaac tgcaatttat | 600 |
| catatcagg attatcaata ccatattttt gaaaaagccg tttctgtaat gaaggagaaa | 660 |
| ctcaccgag gcagttccat aggatggcaa gatcctggta tcggtctgcg attccgactc | 720 |
| tccaacatc aatacaacct attaatttcc cctcgtcaaa aataaggtta tcaagtgaga | 780 |
| atcaccatg agtgacgact gaatccggtg agaatggcaa aagtttatgc atttctttcc | 840 |
| gacttgttc aacaggccag ccattacgct cgtcatcaaa atcactcgca tcaaccaaac | 900 |
| gttattcat cgtgattgc gcctgagcga gacgaaatac gcgatcgctg ttaaaaggac | 960 |
| attacaaac aggaatcgaa tgcaaccggc gcaggaacac tgccagcgca tcaacaatat | 1020 |
| ttcacctga atcaggatat tcttctaata cctggaatgc tgttttcccg gggatcgcag | 1080 |
| ggtgagtaa ccatgcatca tcaggagtac ggataaaatg cttgatggtc ggaagaggca | 1140 |
| aaattccgt cagccagttt agtctgacca tctcatctgt aacatcattg gcaacgctac | 1200 |
| tttgccatg tttcagaaac aactctggcg catcgggctt cccatacaat cgatagattg | 1260 |
| cgcacctga ttgcccgaca ttatcgcgag cccatttata cccatataaa tcagcatcca | 1320 |
| gttggaatt taatcgcggc ctagagcaag acgtttcccg ttgaatatgg ctcataacac | 1380 |
| ccttgtatt actgtttatg taagcagaca gttttattgt tcatgaccaa atcccttaa | 1440 |
| gtgagtttt cgttccactg agcgtcagac cccgtagaaa agatcaaagg atcttcttga | 1500 |
| atccttttt ttctgcgcgt aatctgctgc ttgcaaacaa aaaaaccacc gctaccagcg | 1560 |
| tggtttgtt tgccggatca agagctacca actcttttc cgaaggtaac tggcttcagc | 1620 |
| gagcgcaga taccaaatac tgtccttcta gtgtagccgt agttaggcca ccacttcaag | 1680 |
| actctgtag caccgcctac atacctcgct ctgctaatcc tgttaccagt ggctgctgcc | 1740 |
| gtggcgata agtcgtgtct taccgggttg gactcaagac gatagttacc ggataaggcg | 1800 |
| agcggtcgg gctgaacggg gggttcgtgc acacagccca gcttggagcg aacgacctac | 1860 |
| ccgaactga gatacctaca gcgtgagcta tgagaaagcg ccacgcttcc cgaagggaga | 1920 |
| aggcggaca ggtatccggt aagcggcagg gtcggaacag gagagcgcac gagggagctt | 1980 |
| caggggggaa acgcctggta tctttatagt cctgtcgggt ttcgccacct ctgacttgag | 2040 |

```
gtcgatttt tgtgatgctc gtcaggggg cggagcctat ggaaaaacgc cagcaacgcg    2100 ccttttac ggttcctggc cttttgctg ccttttgctc acatgttctt tcctgcgtta    2160 cccctgatt ctgtggataa ccgtattacc gcctttgagt gagctgatac cgctcgccgc    2220 gccgaacga ccgagcgcag cgagtcagtg agcgaggaag cggaagagcg cctgatgcgg    2280 attttctcc ttacgcatct gtgcggtatt tcacaccgca tatatggtgc actctcagta    2340 aatctgctc tgatgccgca tagttaagcc agtatacact ccgctatcgc tacgtgactg    2400 gtcatggct gcgccccgac acccgccaac acccgctgac gcgccctgac gggcttgtct    2460 ctcccggca tccgcttaca gacaagctgt gaccgtctcc gggagctgca tgtgtcagag    2520 ttttcaccg tcatcaccga aacgcgcgag gcagctgcgg taaagctcat cagcgtggtc    2580 tgaagcgat tcacagatgt ctgcctgttc atccgcgtcc agctcgttga gtttctccag    2640 agcgttaat gtctggcttc tgataaagcg ggccatgtta agggcggttt ttcctgtttt    2700 gtcactgat gcctccgtgt aagggggatt tctgttcatg ggggtaatga taccgatgaa    2760 cgagagagg atgctcacga tacgggttac tgatgatgaa catgcccggt tactggaacg    2820 tgtgagggt aaacaactgg cggtatggat gcggcgggac cagagaaaaa tcactcaggg    2880 caatgccag cgcttcgtta atacagatgt aggtgttcca cagggtagcc agcagcatcc    2940 gcgatgcag atccggaaca taatggtgca gggcgctgac ttccgcgttt ccagactttta    3000 gaaacacgg aaaccgaaga ccattcatgt tgttgctcag gtcgcagacg ttttgcagca    3060 cagtcgctt cacgttcgct cgcgtatcgg tgattcattc tgctaaccag taaggcaacc    3120 cgccagcct agccgggtcc tcaacgacag gagcacgatc atgcgcaccc gtggggccgc    3180 atgccggcg ataatggcct gcttctcgcc gaaacgtttg gtggcgggac cagtgacgaa    3240 gcttgagcg agggcgtgca agattccgaa taccgcaagc gacaggccga tcatcgtcgc    3300 ctccagcga aagcggtcct cgccgaaaat gacccagagc gctgccggca cctgtcctac    3360 agttgcatg ataaagaaga cagtcataag tgcggcgacg atagtcatgc cccgcgccca    3420 cggaaggag ctgactgggt tgaaggctct caagggcatc ggtcgagatc ccggtgccta    3480 tgagtgagc taacttacat taattgcgtt gcgctcactg cccgctttcc agtcgggaaa    3540 ctgtcgtgc cagctgcatt aatgaatcgg ccaacgcgcg gggagaggcg gtttgcgtat    3600 gggcgccag ggtggttttt cttttcacca gtgagacggg caacagctga ttgcccttca    3660 cgcctggcc ctgagagagt tgcagcaagc ggtccacgct ggtttgcccc agcaggcgaa    3720 atcctgttt gatggtggtt aacggcggga tataacatga gctgtcttcg gtatcgtcgt    3780 tcccactac cgagatatcc gcaccaacgc gcagcccgga ctcggtaatg gcgcgcattg    3840 gcccagcgc atctgatcg ttggcaacca gcatcgcagt gggaacgatg ccctcattca    3900 catttgcat ggtttgttga aaaccggaca tggcactcca gtcgccttcc cgttccgcta    3960 cggctgaat tgattgcga gtgagatatt tatgccagcc agccagacgc agacgcgccg    4020 gacagaact taatgggccc gctaacagcg cgatttgctg gtgacccaat gcgaccagat    4080 ctccacgcc cagtcgcgta ccgtcttcat gggagaaaat aatactgttg atgggtgtct    4140 gtcagagac atcaagaaat aacgccggaa cattagtgca ggcagcttcc acagcaatgg    4200 atcctggtc atccagcgga tagttaatga tcagcccact gacgcgttgc gcgagaagat    4260 gtgcaccgc cgctttacag gcttcgacgc cgcttcgttc taccatcgac accaccacgc    4320 ggcacccag ttgatcggcg cgagatttaa tcgccgcgac aatttgcgac ggcgcgtgca    4380
```

```
ggccagact ggaggtggca acgccaatca gcaacgactg tttgcccgcc agttgttgtg    4440 cacgcggtt gggaatgtaa ttcagctccg ccatcgccgc ttccactttt tcccgcgttt    4500 cgcagaaac gtggctggcc tggttcacca cgcgggaaac ggtctgataa agacaccgg    4560 atactctgc gacatcgtat aacgttactg gtttcacatt caccaccctg aattgactct    4620 ttccgggcg ctatcatgcc ataccgcgaa aggttttgcg ccattcgatg gtgtccggga    4680 ctcgacgct ctcccttatg cgactcctgc attaggaagc agcccagtag taggttgagg    4740 cgttgagca ccgccgccgc aaggaatggt gcatgcaagg agatggcgcc caacagtccc    4800 cggccacgg ggcctgccac catacccacg ccgaaacaag cgctcatgag cccgaagtgg    4860 gagcccgat cttccccatc ggtgatgtcg gcgatatagg cgccagcaac cgcacctgtg    4920 cgccggtga tgccggccac gatgcgtccg gcgtagagga tcgagatctc gatcccgcga    4980 attaatacg actcactata ggggaattgt gagcggataa caattcccct ctagaaataa    5040 tttgtttaa ctttaagaag gagatataca tatgcagcat caccaccatc accacggagt    5100 cagcttcaa gacaatgggt ataatggatt gctcattgca attaatcctc aggtacctga    5160 aatcagaac ctcatctcaa acattaagga aatgataact gaagcttcat tttacctatt    5220 aatgctacc aagagaagag tatttttcag aaatataaag attttaatac ctgccacatg    5280 aaagctaat aataacagca aaataaaaca agaatcatat gaaaaggcaa atgtcatagt    5340 actgactgg tatgggcac atgagagatga tccatacacc ctacaataca gagggtgtgg    5400 aaagaggga aaatacattc atttcacacc taatttccta ctgaatgata acttaacagc    5460 ggctacgga tcacgaggcc gagtgtttgt ccatgaatgg gcccacctcc gttggggtgt    5520 ttcgatgag tataacaatg acaaaccttt ctacataaat gggcaaaatc aaattaaagt    5580 acaaggtgt tcatctgaca tcacaggcat ttttgtgtgt gaaaaaggtc cttgccccca    5640 gaaaactgt attattagta agctttttaa agaaggatgc acctttatct acaatagcac    5700 caaaatgca actgcatcaa taatgttcat gcaaagttta tcttctgtgg ttgaattttg    5760 aatgcaagt acccacaacc aagaagcacc aaacctacag aaccagatgt gcagcctcag    5820 agtgcatgg gatgtaatca cagactctgc tgactttcac cacagctttc ccatgaacgg    5880 actgagctt ccacctcctc ccacattctc gcttgtagag gctggtgaca aagtggtctg    5940 ttagtgctg gatgtgtcca gcaagatggc agaggctgac agactccttc aactacaaca    6000 gccgcagaa ttttattttga tgcagattgt tgaaattcat accttcgtgg gcattgccag    6060 ttcgacagc aaaggagaga tcagagccca gctacaccaa attaacagca atgatgatcg    6120 aagttgctg gtttcatatc tgcccaccac tgtatcagct aaaacagaca tcagcatttg    6180 tcagggctt aagaaaggat ttgaggtggt tgaaaaactg aatggaaaag cttatggctc    6240 gtgatgata ttagtgacca gcggagatga taagcttctt ggcaattgct tacccactgt    6300 ctcagcagt ggttcaacaa ttcactccat tgccctgggt tcatctgcag ccccaaatct    6360 gaggaatta tcacgtctta caggaggttt aaagttcttt gttccagata tatcaaactc    6420 aatagcatg attgatgctt tcagtagaat ttcctctgga actggagaca ttttccagca    6480 catattcag cttgaaagta caggtgaaaa tgtcaaacct caccatcaat tgaaaaacac    6540 gtgactgtg ataatactg tgggcaacga cactatgttt ctagttacgt ggcaggccag    6600 ggtcctcct gagattatat tatttgatcc tgatggacga aaatactaca caaataattt    6660 atcaccaat ctaactttc ggacagctag tctttggatt ccaggaacag ctaagcctgg    6720 cactggact tacacccctga acaataccca tcattctctg caagccctga agtgacagt    6780
```

```
acctctcgc gcctccaact cagctgtgcc cccagccact gtggaagcct ttgtggaaag    6840 gacagcctc cattttcctc atcctgtgat gatttatgcc aatgtgaaac agggatttta    6900 cccattctt aatgccactg tcactgccac agttgagcca gagactggag atcctgttac    6960 ctgagactc cttgatgatg gagcaggtgc tgatgttata aaaaatgatg gaatttactc    7020 aggtatttt ttctcctttg ctgcaaatgg tagatatagc ttgaaagtgc atgtcaatca    7080 tctcccagc ataagcaccc cagcccactc tattccaggg agtcatgcta tgtatgtacc    7140 ggttacaca gcaaacggta atattcagat gaatgctcca aggaaatcag taggcagaaa    7200 gaggaggag cgaaagtggg gctttagccg agtcagctca ggaggctcct tttcagtgct    7260 ggagttcca gctggccccc accctgatgt gtttccacca tgcaaaatta ttgacctgga    7320 gctgtaaaa gtagaagagg aattgaccct atcttggaca gcacctggag aagactttga    7380 cagggccag gctacaagct atgaaataag aatgagtaaa agtctacaga atatccaaga    7440 gactttaac aatgctattt tagtaaatac atcaaagcga aatcctcagc aagctggcat    7500 agggagata tttacgttct caccccaaat ttccacgaat ggacctgaac atcagccaaa    7560 ggagaaaca catgaaagcc acagaattta tgttgcaata cgagcaatgg ataggaactc    7620 ttacagtct gctgtatcta acattgccca ggcgcctctg tttattcccc ccaattctga    7680 cctgtacct gccagagatt atcttatatt gaaaggagtt ttaacagcaa tgggtttgat    7740 ggaatcatt tgccttatta tagttgtgac acatcatact ttaagcagga aaagagagc    7800 gacaagaaa gagaatggaa caaaattatt ataatgaatt ctgcagatat ccatcacact    7860 gcggccgct cgagcaccac caccaccacc actgagatcc ggctgctaac aaagcccgaa    7920 ggaagctga gttggctgct gccaccgctg agcataact agcataaccc cttggggcct    7980 taaacgggt cttgagggt ttttgctga aaggaggaac tatatccgga t              8031
```

<210> SEQ ID NO 255
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 255

```
gtggccagng actagaaggc gaggcgccgc gggaccatgg cggcggcggc ggacgagcgg     60
agtccanagg acggagaaga cgaggaagag gaggagcagt tggttctggt ggaattatca    120
ggaattattg attcagactt cctctcaaaa tgtgaaaata aatgcaaggt tttgggcatt    180
gacactgaga ggcccattct gcaagtggac agctgtgtct ttgctgggga gtatgaagac    240
actctangga cctgtgttat atttgaagaa atgntnaac atgctgatac agaaggcaat    300
aataaaacag tgctaaaata taaatgccat acaatgaaga agctcagcat gacaagaact    360
ctcctgacag agaagaagga aggagaagaa aacatangtg g                        401
```

<210> SEQ ID NO 256
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

```
<400> SEQUENCE: 256
tggtggncct gggatgggga accgcggtgg cttccgngga ggtttcggca ntggcatccg      60 gggccgggt cgcggccgng gacggggccg gggccnangc cgnnganctc gcggangcaa     120
ggccgaggat aaggagtgga tgcccgtcac caacttgggc cgcttgncca aggacatgaa    180
nancaagccc ctgnaggaga tctatntctt cttccctgcc ccattaagga atcaagagat    240
catttgattt cttcctgggg gcctctctca aggatnaggt ttttgaagat tatgccagtg    300
canaaannan accccgttgc ccngtccatc tncacccaac ncttccaagg gcnattttg     360 tttaggcctc attncngggg ggaaccttaa cccaatttgg g                       401

<210> SEQ ID NO 257
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 257
atgtatgtaa aacacttcat aaaatgtaaa gggctataac aaatatgtta taaagtgatt    60
ctctcagccc tgaggtatac agaatcattt gcctcagact gctgttggat tttaaaattt   120
ttaaaatatc tgctaagtaa tttgctatgt cttctcccac actatcaata tgcctgcttc   180
taacaggctc cccactttct tttaatgtgc tgttatgagc tttggacatg agataaccgt   240
gcctgttcag agtgtctaca gtaagagctg acaaactct ggagggacac agtctttgag    300
acagctcttt tggttgcttt ccacttttct gaaaggttca cagtaacctt ctagataata   360
gaaactccca gttaaagcct angctancaa ttttttttag t                       401

<210> SEQ ID NO 258
<211> LENGTH: 401
<212> TYPE: DNA
<213> ORGANISM: Homo sapien

<400> SEQUENCE: 258
ggagcgctag gtcggtgtac gaccgagatt agggtgcgtg ccagctccgg gaggccgcgg    60 tgagggccg ggcccaagct gccgacccga gccgatcgtc agggtcgcca gcgcctcagc   120
tctgtggagg agcagcagta gtcggagggt gcaggatatt agaaatggct actccccagt   180
caattttcat cttttgcaatc tgcattttaa tgataacaga attaattctg gcctcaaaaa   240
gctactatga tatcttaggt gtgccaaaat cggcatcaga gcgccaaatc aagaaggcct   300
ttcacaagtt ggccatgaag taccaccctg acaaaaataa gacccagatg ctgaagcaaa   360
attcagagag attgcagaag catatgaaac actctcagat g                       401

<210> SEQ ID NO 259
<211> LENGTH: 401
<212> TYPE: DNA
<213> ORGANISM: Homo sapien

<400> SEQUENCE: 259
attgggtttg gagggaggat gatgacagag gaatgcccctt tggccatcac ggttttgatt   60
ctccagaata ttgtgggttt gatcatcaat gcagtcatgt taggctgcat tttcatgaaa   120
acagctcagg ctcacagaag ggcagaaact ttgattttca gccgccatgc tgtgattgcc   180
gtccgaaatg gcaagctgtg cttcatgttc cgagtgggtg acctgaggaa aagcatgatc   240
```

```
attagtgcct ctgtgcgcat ccaggtggtc aagaaaacaa ctacacctga aggggaggtg      300
gttcctattc accaactgga cattcctgtt gataacccaa tcgagagcaa taacattttt      360
ctggtggccc ctttgatcat ctgccacgtg attgacaagc g                          401
```

<210> SEQ ID NO 260
<211> LENGTH: 363
<212> TYPE: DNA
<213> ORGANISM: Homo sapien
<220> FEATURE:
<221> NAME/KEY: misc_feature
<222> LOCATION: (1)...(363)
<223> OTHER INFORMATION: n = A,T,C or G

<400> SEQUENCE: 260

```
aggaganang gaggggana tgaataggga tggagaggga natagtggat gagcagggca        60
canggagagg aancagaaag gagaggcaag acagggagac acacancaca nangangana      120 caggtgggg ctgggtggg gcatggagag cctttnangt cncccaggcc accctgctct        180
cgctggnctg ttgaaaccca ctccatggct tcctgccact gcagttgggc ccagggctgg      240
cttattnctg gaatgcaagt ggctgtggct tggagcctcc cctctggnnn anggaaannn      300
attgctccct tatctgcttg gaatatctga gttttccan cccggaaata aaacacacac       360
aca                                                                    363
```

<210> SEQ ID NO 261
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 261

```
cggctctccg ccgctctccc ggggtttcgg ggcacttggg tcccacagtc tggtcctgct       60
tcaccttccc ctgacctgag tagtcgccat ggcacaggtt ctcagaggca ctgngactga      120
cttccctgga tttgatgagc gggctgatgc anaaactctt cggaaggcta tgaaaggctt      180
gggcacagat gaggagagca tcctgactct gttgacatcc cgaagtaatg ctcagcgcca      240
ggaaatctct gcagctttta agactctgtt tggcagggat cttctggatg acctgaaatc      300
agaactaact ggaaaatttg aaaaattaat tgtggctctg atgaaaccct ctcggcttta      360
tgatgcttat gaactgaaac atgccttgaa gggagctgga a                          401
```

<210> SEQ ID NO 262
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 262

```
agtctanaac atttctaata ttttgngctt tcatatatca aaggagatta tgtgaaacta       60
tttttaaata ctgtaaagtg acatatagtt ataagatata tttctgtaca gtagagaaag      120
agtttataac atgaagaata ttgtaccatt atacattttc attctcgatc tcataagaaa      180
ttcaaaagaa taatgataga ggtgaaaata tgtttacttt ctctaaatca agcctagttg      240
```

```
tcaactcaaa aattatgntg catagtttta ttttgaattt aggttttggg actacttttt      300
tccancttca atgagaaaat aaaatctaca actcaggagt tactacagaa gttctaanta      360 ttttttgct aannagcnaa aaatataaac atatgaaaat g                          401
```

<210> SEQ ID NO 263
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 263

```
ctgtccgacc aagagaggcc ggccgagccc gaggcttggg cttttgcttt ctggcggagg      60
gatctgcggc ggtttaggag gcggcgctga tcctgggagg aagaggcagc tacgcggcg      120 gcggcggtgg cggctagggc ggcggcgaat aaagggggccg ccgccgggtg atgcggtgac    180
cactgcggca ggcccaggag ctgagtgggc cccggccctc agcccgtccc gncggacccg     240 cttttcctcaa ctctccatct tctcctgccg accgagatcg ccgaggcggn ctcaggctcc   300
ctancccctt ccccgtccct tccccncccc cgtccccgcc ccggggccg ccgccacccg     360 cctcccacca tggctctgaa ganaatccac aaggaattga a                         401
```

<210> SEQ ID NO 264
<211> LENGTH: 401
<212> TYPE: DNA
<213> ORGANISM: Homo sapien

<400> SEQUENCE: 264

```
aacaccagcc actccaggac ccctgaaggc ctctaccagg tcaccagtgt tctgcgccta      60
aagccacccc ctggcagaaa cttcagctgt gtgttctgga atactcacgt gagggaactt     120
actttggcca gcattgacct tcaaagtcag atggaaccca ggaccatcc aacttggctg     180 cttcacattt tcatcccctc ctgcatcatt gctttcattt tcatagccac agtgatagcc    240
ctaagaaaac aactctgtca aaagctgtat tcttcaaaag acacaacaaa agacctgtc     300 accacaacaa agagggaagt gaacagtgct gtgaatctga acctgtggtc ttgggagcca   360
gggtgacctg atatgacatc taaagaagct tctggactct g                         401
```

<210> SEQ ID NO 265
<211> LENGTH: 271
<212> TYPE: DNA
<213> ORGANISM: Homo sapien
<220> FEATURE:
<221> NAME/KEY: misc_feature
<222> LOCATION: (1)...(271)
<223> OTHER INFORMATION: n = A,T,C or G

<400> SEQUENCE: 265

```
gccacttcct gtggacatgg gcagagcgct gctgccagtt cctggtagcc ttgaccacna      60
cgctgggggg tctttgtgat ggtcatgggt ctcatttgca cttgggggtg tgggattcaa    120
gttagaagtt tctagatctg gccggcgcaa gtggctcaca cctgtaatcc cagcacttta    180
ggaggctgag gcaggcggat catgaggtca ggagatcgag accgtcctgg ctaacacagt    240 gaaacccccgt ctctactaaa aatacaaaaa a                                    271
```

<210> SEQ ID NO 266
<211> LENGTH: 401

```
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 266
attcataaat ttagctgaaa gatactgatt caatttgtat acagngaata taaatgagac      60
gacagcaaaa ttttcatgaa atgtaaaata tttttatagt ttgttcatac tatatgaggt     120
tctattttaa atgactttct ggattttaaa aaatttcttt aaatacaatc attttttgtaa    180 tatttatttt atgcttatga tctagataat tgcagaatat cattttatct gactctgtct     240
tcataagaga gctgtggccg aattttgaac atctgttata gggagtgatc aaattagaag     300
gcaatgtgga aaacaattc tgggaaagat ttctttatat gaagtccctg ccactagcca      360
gccatcctaa ttgatgaaag ttatctgttc acaggcctgc a                         401

<210> SEQ ID NO 267
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 267
gaagaggcat cacctgatcc cggagacctt tggagttaag aggcggcgga agcgagggcc     60
tgtggagtcg gatcctcttc ggggtgagcc agggtcggcg cgcgcggctg tctcanaact    120
catgcagctg ttcccgcgag gcctgtttga ggacgcgctg ccgcccatcg tgctgaggag   180
ccaggtgtac agccttgtgc ctgacaggac cgtggccgac cggcagctga aggagcttca   240
agagcanggg gagacaaaat cgtccagctg ggcttcnact tggatgccca tggaanttat   300
tctttcnctt ganggactta cnngggaccc aagaanccct tncaagggc ccttngtgga    360 tgggncccga aaccccnnta tttgcccttg gggggncca a                         401

<210> SEQ ID NO 268
<211> LENGTH: 223
<212> TYPE: DNA
<213> ORGANISM: Homo sapien

<400> SEQUENCE: 268
tcgccatgtt ggccaggctg gtcttgaact cctgactta agtgatccac ccgcctcaac      60
ctcccaaagt gctgggatta caggtgtgag ccaccgcgcc tggcctgata catactttta    120
gaatcaagta gtcacgcact ttttctgttc attttttctaa aaagtaaata tacaaatgtt   180
ttgttttttg tttttttgt ttgtttgttt ctgttttttt ttt                       223

<210> SEQ ID NO 269
<211> LENGTH: 401
<212> TYPE: DNA
<213> ORGANISM: Homo sapien

<400> SEQUENCE: 269
actatgtaaa ccacattgta cttttttta ctttggcaac aaatatttat acatacaaga      60
tgctagttca tttgaatatt ctcccaact tatccaagga tctccagctc taacaaaatg     120
gtttattttt atttaaatgt caatagttgt tttttaaaat ccaaatcaga ggtgcaggcc   180
```

```
accagttaaa tgccgtctat caggttttgt gccttaagag actacagagt caaagctcat    240 tttaaagga gtaggacaaa gttgtcacag gttttgttg ttgtttttat tgccccaaa       300 attacatgtt aatttccatt tatatcaggg attctattta cttgaagact gtgaagttgc    360
cattttgtct cattgttttc tttgacataa ctaggatcca t                         401
```

<210> SEQ ID NO 270
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 270

```
tggctgttga ttcacctcag cactgcttgg tatctgcacc ctacctctct ttagaggctg     60
ccttgtcaac tgaaaaatgc acctgacttc gagcaagact ctttccttag gttctggatc    120
tgtttgagcc ccatggcact gagctggaat ctgaggtct tgttccaagg atgtgatgat     180
gtgggagaat gttctttgaa agagcagaaa tccagtctgc atggaaacag cctgtagagn    240
agaagtttcc agtgataagt gttcactgtt ctaaggaggt acaccacagc tacctgaatt    300
ttcccaaaat gagtgcttct gtgcgttaca actggccttt gtacttgact gtgatgactt    360
tgttttttct tttcaattct anatgaacat gggaaaaaat g                         401
```

<210> SEQ ID NO 271
<211> LENGTH: 329
<212> TYPE: DNA
<213> ORGANISM: Homo sapien

<400> SEQUENCE: 271

```
ccacagcctc caagtcaggt ggggtggagt cccagagctg cacagggttt ggcccaagtt     60
tctaagggag gcacttcctc ccctcgccca tcagtgccag ccctgctgg ctggtgcctg     120 agccctcag acagcccct gccccgcagg cctgccttct cagggacttc tgcgggggct     180
gaggcaagcc atggagtgag acccaggagc cggacacttc tcaggaaatg cttttccca    240 accccagcc ccacccggt ggttcttcct gttctgtgac tgtgtatagt gccaccacag      300
cttatggcat ctcattgagg acaaaaaaa                                       329
```

<210> SEQ ID NO 272
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 272

```
nggctgntaa cntcggaggt nacttcctgg actatcctgg agacccctc cgcttccacg      60 nncatnatat cnctcatngc tgggcccntn angacacnat cccactccaa cacctgngng    120
atgctggncn cctnggaacc ancntcagaa ngaccctgnt cntntgtnnt ccgcaanctg    180
aagnnaangc gggntacacc tncntgcant ggnccacnct gcnggaact ntacacacct     240 acgggatgtg gctgcgccan gagccaagag cntttctgga tgattcccca gcctcttgnn    300
agggantcta caacattgct nnntacccttt ntccnncngc nnntnntgga ntacaggngn   360
tnntaacact acatcttttt tactgcnccn tncttggtgg g                         401
```

<210> SEQ ID NO 273
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 273

```
cagcaccatg aagatcaaga tcatcgcacc cccagagcgc aagtactcgg tgtggatcgg      60
tggctccatc ctggcctcac tgtccacctt ccagcagatg tggattagca agcaggagta     120
cgacgagtcg ggcccctcca tcgtccaccg caaatgcttc taaacggact cagcagatgc     180
gtagcatttg ctgcatgggt taattgagaa tagaaatttg ccctggcaa atgcacacac      240
ctcatgctag cctcacgaaa ctggaataag ccttcgaaaa gaaattgtcc ttgaagcttg     300
tatctgatat cagcactgga ttgtagaact tgttgctgat tttgaccttg tattgaagtt     360
aactgttccc cttggtatta acgtgtcagg gctgagtgnt c                        401
```

<210> SEQ ID NO 274
<211> LENGTH: 401
<212> TYPE: DNA
<213> ORGANISM: Homo sapien

<400> SEQUENCE: 274

```
ccacccacac ccaccgcgcc ctcgttcgcc tcttctccgg gagccagtcc gcgccaccgc      60
cgccgcccag gccatcgcca ccctccgcag ccatgtccac caggtccgtg tcctcgtcct     120
cctaccgcag gatgttcggc ggcccgggca ccgcgagccg gccgagctcc agccggagct     180
acgtgactac gtccacccgc acctacagcc tgggcagcgc gctgcgcccc agcaccagcc     240
gcagcctcta cgcctcgtcc ccgggcggcg tgtatgccac gcgctcctct gccgtgcgcc     300
tgcggagcag cgtgcccggg gtgcggctcc tgcaggactc ggtggacttc tcgctggccg     360
acgccatcaa caccgagttc aagaacaccc gcaccaacga g                        401
```

<210> SEQ ID NO 275
<211> LENGTH: 401
<212> TYPE: DNA
<213> ORGANISM: Homo sapien

<400> SEQUENCE: 275

```
ccacttccac cactttgtgg agcagtgcct tcagcgcaac ccggatgcca ggtatccctg      60
ctggcctggg cctgggcttc gggagagcag agggtgctca ggagggtaag gccagggtgt     120
gaagggactt acctcccaaa ggttctgcag gggaatctgg agctacacac aggagggatc     180
agctcctggg tgtgtcagag gccagcctgg ggagctctgg ccactgcttc ccatgagctg     240
agggagaggg agagggacc cgaggctgag gcataagtgg caggatttcg ggaagctggg     300
gacacggcag tgatgctgcg gtctctcctc ccctttccct ccaggccag tgccagcacc      360
ctcctgaacc actctttctt caagcagatc aagcgacgtg c                        401
```

<210> SEQ ID NO 276
<211> LENGTH: 401
<212> TYPE: DNA
<213> ORGANISM: Homo sapien
<220> FEATURE:
<221> NAME/KEY: misc_feature
<222> LOCATION: (1)...(401)

<223> OTHER INFORMATION: n = A,T,C or G

<400> SEQUENCE: 276

| tctgatattg | ntaccnttga | gccacctaag | ttagaagaaa | ttggaaatca | agaagttgtc | 60 |
| attgttgaag | aagcacagag | ttcagaagac | tttaacatgg | gctcttcctc | tagcagccag | 120 |
| tatactttct | gtcagccaga | aactgtattt | tcatctcagc | ctagtgatga | tgaatcaagt | 180 |
| agtgatgaaa | ccagtaatca | gcccagtcct | gcctttagac | gacgccgtgc | taggaagaag | 240 |
| accgtttctg | cttcagaatc | tgaagaccgg | ctagttggtg | aacaagaaac | tgaaccttct | 300 |
| aaggagttga | gtaaacgtca | gttcagtagt | ggtctcaata | agtgtgttat | acttgctttg | 360 |
| gtgattgcaa | tcagcatggg | atttggccat | ttctatggca | c | | 401 |

<210> SEQ ID NO 277
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 277

| aactttggca | acatatctca | gcaaaaacta | cagctatgtt | attcatgcca | aaataaaagc | 60 |
| tgtgcagagg | agtggctgca | atgaggtcac | aacggtggtg | gatgtaaaag | agatcttcaa | 120 |
| gtcctcatca | cccatccctc | gaactcaagt | cccgctcatt | acaaattctt | cttgccagtg | 180 |
| tccacacatc | ctgccccatc | aagatgttct | catcatgtgt | tacgagnggc | gctcaaggat | 240 |
| gatgcttctt | gaaaattgct | tagttgaaaa | atggagagat | cagcttagta | aaagatccat | 300 |
| acagtgggaa | gagaggctgc | aggaacagcg | ganaacagtt | caggacaaga | agaaaacagc | 360 |
| cgggcgcacc | agtcgtagta | atccccccaa | accaagggga | a | | 401 |

<210> SEQ ID NO 278
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 278

| aatgagtgtg | agaccacaaa | tgaatgccgg | gaggatgaaa | tgtgttggaa | ttatcatggc | 60 |
| ggcttccgtt | gttatccacg | aaatccttgt | caagatccct | acattctaac | accagagaac | 120 |
| cgatgtgttt | gcccagtctc | aaatgccatg | tgccgagaac | tgccccagtc | aatagtctac | 180 |
| aaatacatga | gcatccgatc | tgataggtct | gtgccatcag | acatcttcca | gatacaggcc | 240 |
| acaactattt | atgccaacac | catcaatact | tttcggatta | aatctggaaa | tgaaaatgga | 300 |
| gagtctacct | acgacaacaa | anccctgtaa | gtgcaatgct | tgtgctcgtg | aagncattat | 360 |
| caggaccaag | agaacatatc | gtggacctgg | agatgctgac | a | | 401 |

<210> SEQ ID NO 279
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 279

| | | | | | |
|---|---|---|---|---|---|
| aaattattgc | ctctgataca | tacctaagtn | aacanaacat | taatacctaa | gtaaacataa | 60 |
| cattacttgg | agggttgcag | nttctaantg | aaactgtatt | tgaaactttt | aagtatactt | 120 |
| taggaaacaa | gcatgaacgg | cagtctagaa | taccagaaac | atctacttgg | gtagcttggn | 180 |
| gccattatcc | tgtggaatct | gatatgtctg | gnagcatgtc | attgatggga | catgaagaca | 240 |
| tctttggaaa | tgatgagatt | atttcctgtg | ttaaaaaaaa | aaaaaatctt | aaattcctac | 300 |
| aatgtgaaac | tgaaactaat | aattttgatc | ctgatgtatg | gacagcgta | tctgtaccag | 360 |
| gctctaaata | caaaagnta | gggngacaag | nacatgttcc | t | | 401 |

<210> SEQ ID NO 280
<211> LENGTH: 326
<212> TYPE: DNA
<213> ORGANISM: Homo sapien

<400> SEQUENCE: 280

| | | | | | |
|---|---|---|---|---|---|
| gaagtggaat | tgtataattc | aattcgataa | ttgatctcat | gggctttccc | tggaggaaag | 60 |
| gtttttttg | ttgttttttt | tttaagaact | tgaaacttgt | aaactgagat | gtctgtagct | 120 |
| tttttgccca | tctgtagtgt | atgtgaagat | ttcaaaacct | gagagcactt | tttctttgtt | 180 |
| tagaattatg | agaaaggcac | tagatgactt | taggatttgc | attttcccct | ttattgcctc | 240 |
| atttcttgtg | acgccttgtt | ggggagggaa | atctgtttat | ttttttcctac | aaataaaaag | 300 |
| ctaagattct | atatcgcaaa | aaaaaa | | | | 326 |

<210> SEQ ID NO 281
<211> LENGTH: 374
<212> TYPE: DNA
<213> ORGANISM: Homo sapien

<400> SEQUENCE: 281

| | | | | | |
|---|---|---|---|---|---|
| caacgcgttt | gcaaatattc | ccctggtagc | ctacttcctt | accccgaat | attggtaaga | 60 |
| tcgagcaatg | gcttcaggac | atgggttctc | ttctcctgtg | atcattcaag | tgctcactgc | 120 |
| atgaagactg | gcttgtctca | gtgtttcaac | ctcaccaggg | ctgtctcttg | gtccacacct | 180 |
| cgctccctgt | tagtgccgta | tgacagcccc | catcaaatga | ccttggccaa | gtcacggttt | 240 |
| ctctgtggtc | aaggttggtt | ggctgattgg | tggaaagtag | ggtggaccaa | aggaggccac | 300 |
| gtgagcagtc | agcaccagtt | ctgcaccagc | agcgcctccg | tcctagtggg | tgttcctgtt | 360 |
| tctcctggcc | ctgg | | | | | 374 |

<210> SEQ ID NO 282
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 282

| | | | | | |
|---|---|---|---|---|---|
| agtgtggtgg | aattcccgca | tcctanncgc | cgactcacac | aaggcagagt | ngccatggag | 60 |
| aaaattccag | tgtcagcatt | cttgctcctt | gtggccctct | cctacactct | ggccagagat | 120 |
| accacagtca | aacctgnagc | caaaaaggac | acaaaggact | ctcgacccaa | actgccccan | 180 |
| accctctcca | gaggttgggg | tgaccaactc | atctggactc | anacatatga | agaagctcta | 240 |

```
tataaatcca agacaagcaa caaaccttg atgattattc atcacttgga tgagtgccca      300
cacagtcaag ctttaaagaa agtgtttgct gaaaataaag aaatccagaa attggcagag      360
cagtttgtcc tcctcaatct ggtttatgaa acaactgaca aaca                       404
```

<210> SEQ ID NO 283
<211> LENGTH: 184
<212> TYPE: DNA
<213> ORGANISM: Homo sapien
<220> FEATURE:
<221> NAME/KEY: misc_feature
<222> LOCATION: (1)...(184)
<223> OTHER INFORMATION: n = A,T,C or G

<400> SEQUENCE: 283

```
agtgtggtgg aattcacttg cttaanttgt gggcaaaaga gaaaagaag gattgatcag       60 agcattgtgc aatacagttt cattaactcc ttccctcgct ccccaaaaa tttgaatttt      120 tttttcaaca ctcttacacc tgttatggaa aatgtcaacc tttgtaagaa aaccaaaata    180
aaaa                                                                  184
```

<210> SEQ ID NO 284
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 284

```
ctattaatcc tgccacaata tttttaatta cgtacaaaga tctgacatgt cacccaggga      60
cccatttcac ccactgctct gtttggccgc cagtcttttg tctctctctt cagcaatggt    120
gaggcggata ccctttcctc ggggaanana aatccatggt ttgttgccct tgccaataac    180
aaaaatgttg gaaagtcgag tggcaaagct gttgccattg gcatctttca cgtgaaccac    240
gtcaaaagat ccagggtgcc tctctctgtt ggtgatcaca ccaattcttc ctaggttagc    300
acctccagtc accatacaca ggttaccagt gtcgaacttg atgaaatcag taatcttgcc    360
agtctctaaa tcaatctgaa tggtatcatt caccttgatg aggggatcgg ggtagcggat    420
g                                                                    421
```

<210> SEQ ID NO 285
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 285

```
ctgggtggta actctttatt tcattgtccg gaanaaagat gggagtggga acagggtgga      60
cactgtgcag gcttcagctt ccactccggg caggattcag gctatctggg accgcaggga    120
ctgccaggtg cacagccctg gctcccgagg caggcaggca aggtgacggg actgaagcc    180 cttttcanag ccttggagga gctggtccgt ccacaagcaa tgagtgccac tctgcagttt    240 gcagggatg gataaacagg gaaacactgt gcattcctca cagccaacag tgtaggtctt    300
ggtgaagccc cggcgctgag ctaagctcag gctgttccag ggagccacga aactgcaggt    360
a                                                                    361
```

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286

| | | | | | |
|---|---|---|---|---|---|
| tttgagtggc | agcgccttta | tttgtggggg | ccttcaaggn | agggtcgtgg | ggggcagcgg | 60 |
| ggaggaanag | ccganaaact | gtgtgaccgg | ggcctcaggt | ggtgggcatt | gggggctcct | 120 |
| cttgcanatg | cccattggca | tcaccggtgc | agccattggt | ggcagcgggt | accggtcctt | 180 |
| tcttgttcaa | catagggtag | gtggcagcca | cgggtccaac | tcgcttgagg | ctgggccctg | 240 |
| ggcgctccat | tttgtgttcc | angagcatgt | ggttctgtgg | cgggagcccc | acgcaggccc | 300 |
| tgaggatgtt | ctcgatgcag | ctgcgctggc | ggaaaa | | | 336 |

<210> SEQ ID NO 287
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 287

| | | | | | |
|---|---|---|---|---|---|
| tgggtaccaa | atttntttat | ttgaaggaat | ggnacaaatc | aaanaactta | agnggatgtt | 60 |
| ttggtacaac | ttatanaaaa | ggnaaaggaa | accccaacat | gcatgcnctg | ccttggngac | 120 |
| cagggaagtc | accccacggc | tatggggaaa | ttancccgag | gcttancttt | cattatcact | 180 |
| gtctcccagg | gngngcttgt | caaaaanata | ttccnccaag | ccaaattcgg | gcgctcccat | 240 |
| nttgcncaag | ttggtcacgt | ggtcacccaa | ttctttgatg | gctttcacct | gctcattcag | 300 |
| g | | | | | | 301 |

<210> SEQ ID NO 288
<211> LENGTH: 358
<212> TYPE: DNA
<213> ORGANISM: Homo sapien
<220> FEATURE:
<221> NAME/KEY: misc_feature
<222> LOCATION: (1)...(358)
<223> OTHER INFORMATION: n = A,T,C or G

<400> SEQUENCE: 288

| | | | | | |
|---|---|---|---|---|---|
| aagttttttaa | acttttttatt | tgcatattaa | aaaaattgng | cattccaata | attaaaatca | 60 |
| tttgaacaaa | aaaaaaaatg | gcactctgat | taaactgcat | tacagcctgc | aggacaccct | 120 |
| gggccagctt | ggttttactc | tanatttcac | tgtcgtccca | ccccacttct | tccaccccac | 180 |
| ttcttccttc | accaacatgc | aagttctttc | cttccctgcc | agccanatag | atagacagat | 240 |
| gggaaaggca | ggcgcggcct | tcgttgtcag | tagttctttg | atgtgaaagg | ggcagcacag | 300 |
| tcatttaaac | ttgatccaac | ctctttgcat | cttacaaagt | taaacagcta | aagaagt | 358 |

<210> SEQ ID NO 289
<211> LENGTH: 462
<212> TYPE: DNA
<213> ORGANISM: Homo sapien
<220> FEATURE:

<221> NAME/KEY: misc_feature
<222> LOCATION: (1)...(462)
<223> OTHER INFORMATION: n = A,T,C or G

<400> SEQUENCE: 289

```
ggcatcagaa atgctgttta tttctctgct gctcccaagc tggctggcct ttgcagagga      60
gcagacaaca gatgcatagt tgggganaaa gggaggacag gttccaggat agagggtgca     120
ggctgaggga ggaagggtaa naggaaggaa ggccatcctg gatccccaca tttcagtctc     180
anatgaggac aaagggactc ccaagccccc aaatcatcan aaaacaccaa ggagcaggag     240
gagcttgagc aggccccagg gagcctcana gccataccag ccactgtcta cttcccatcc     300
tcctctccca ttccctgtct gcttcanacc acctcccagc taagcccag ctccattccc      360
ccaatcctgg cccttgccag cttgacagtc acagtgcctg gaattccacc actgaggctt     420
ctcccagttg gattaggacg tcgccctgtt agcatgctgc cc                        462
```

<210> SEQ ID NO 290
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 290

```
tactttccta aactttatta agaaaaaag caataagcaa tggnggtaaa tctctanaac      60
atacccaatt ttctgggctt cctcccccga gaatgtgaca ttttgatttc caaacatgcc    120
anaagtgtat ggttcccaac tgtactaaag taggtganaa gctgaagtcc tcaagtgttc    180
atcttccaac ttttcccagt ctgtggtctg tctttggatc agcaataatt gcctgaacag    240
ctactatggc ttcgttgatt tttgtctgta gctctctgag ctcctctatg tgcagcaatc    300
gcanaatttg agcagcttca ttaanaactg catctcctgt gtcaaaacca anaatatgtt    360
tgtctaaagc aacaggtaag ccctcttttg tttgatttgc cttancaact gcatcctgtg    420
tcaggcgctc ctgaaccaaa atccgaattg ccttaagcat taccaggtaa tcatcatgac    480
g                                                                    481
```

<210> SEQ ID NO 291
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 291

```
tcatagtaat gtaaaaccat ttgtttaatt ctaaatcaaa tcactttcac aacagtgaaa     60
attagtgact ggttaaggng tgccactgta catatcatca ttttctgact ggggtcagga    120
cctggtccta gtccacaagg gtggcaggag gagggtggag gctaanaaca cagaaaacac    180
acaaaanaaa ggaaagctgc cttggcanaa ggatgaggng gtgagcttgc cgaaggatgg    240
tgggaagggg gctccctgtt ggggccgagc caggagtccc aagtcagctc tcctgcctta    300
cttagctcct ggcanagggt gagtggggac ctacgaggtt caaaatcaaa tggcatttgg    360
ccagcctggc tttactaaca g                                              381
```

<210> SEQ ID NO 292
<211> LENGTH: 371
<212> TYPE: DNA
<213> ORGANISM: Homo sapien
<220> FEATURE:
<221> NAME/KEY: misc_feature
<222> LOCATION: (1)...(371)
<223> OTHER INFORMATION: n = A,T,C or G

<400> SEQUENCE: 292

| | | | | | |
|---|---|---|---|---|---|
| gaaaaaataa | tccgtttaat | tgaaaaacct | gnaggatact | attccactcc | cccanatgag | 60 |
| gaggctgagg | anaccaaacc | cctacatcac | ctcgtagcca | cttctgatac | tcttcacgag | 120 |
| gcagcaggca | aagacaattc | ccaaaacctc | nacaaaagca | attccaaggg | ctgctgcagc | 180 |
| taccaccanc | acattttcc | tcagccagcc | cccaatcttc | tccacacagc | cctccttatg | 240 |
| gatcgccttc | tcgttgaaat | taatcccaca | gcccacagta | acattaatgc | ancaggagtc | 300 |
| ggggactcgg | ttcttcgaca | tggaagggat | tttctcccaa | tctgtgtagt | tagcagcccc | 360 |
| acagcactta | a | | | | | 371 |

<210> SEQ ID NO 293
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 293

| | | | | | |
|---|---|---|---|---|---|
| gatttaaaag | aaaacacttt | attgttcagc | aattaaaagt | tagccaaata | tgtatttttc | 60 |
| tccataattt | attgngatgt | tatcaacatc | aagtaaaatg | ctcattttca | tcatttgctt | 120 |
| ctgttcatgt | tttcttgaac | acgtcttcaa | ttttccttcc | aaaatgctgc | atgccacact | 180 |
| tgaggtaacg | aagcanaagt | attttaaac | atgacagcta | anaacattca | tctacagcaa | 240 |
| cctatatgct | caatacatgc | cgcgtgatcc | tagtagttt | ttcacaacct | tctacaagtt | 300 |
| tttggaaaac | atctgttatg | atgactttca | tacaccttca | cctcaaaggc | tttcttgcac | 360 |
| c | | | | | | 361 |

<210> SEQ ID NO 294
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 294

| | | | | | |
|---|---|---|---|---|---|
| tattttaaag | tttaattatg | attcanaaaa | aatcgagcga | ataactttct | ctgaaaaaat | 60 |
| atattgactc | tgtatanacc | acagttattg | gggganaagg | gctggtaggt | taaattatcc | 120 |
| tatttttat | tctgaaaatg | atattaatan | aagtcccgt | ttccagtctg | attataaga | 180 |
| tacatatgcc | caaaatggct | ganaataaat | acaacaggaa | atgcaaaagc | tgtaaagcta | 240 |
| agggcatgca | ananaaaatc | tcanaatacc | caaagnggca | acaaggaacg | tttggctgga | 300 |
| atttgaagtt | atttcagtca | tctttgtctt | tggctccatg | tttcaggatg | cgtgtgaact | 360 |
| cgatgtaatt | gaaattcccc | ttttatcaa | t | | | 391 |

<210> SEQ ID NO 295

<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 295

```
ttcttttgtt ttattgataa cagaaactgt gcataattac agatttgatg aggaatctgc      60
aaataataaa gaatgtgtct actgccagca aaatacaatt attccatgcc ctctcaacat     120
acaaatatag agttcttcac accanatggc tctggtgtaa caaagccatt ttanatgttt     180
aattgtgctt ctacaaaacc ttcanagcat gaggtagttt cttttaccta cnatattttc     240
cacatttcca ttattacact tttagtgagc taaaatcctt ttaacatagc ctgcggatga     300
tctttcacaa aagccaagcc tcatttacaa agggtttatt tct                       343
```

<210> SEQ ID NO 296
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 296

```
ttcttggata ttggttgttt ttgtgaaaaa gttttttgttt ttcttctcag tcaactgaat     60
tatttctcta ctttgccctc ctgatgccca catgananaa cttaanataa tttctaacag    120
cttccacttt ggaaaaaaaa aaaacctgtt ttcctcatgg aacccagga gttgaaagtg     180
gatanatcgc tctcaaaatc taaggctctg ttcagcttta cattatgtta cctgacgttt    240
t                                                                    241
```

<210> SEQ ID NO 297
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 297

```
gttgtggctg anaatgctgg agatgctcag ttctctccct cacaaggtag gccacaaatt      60
cttggtggtg ccctcacatc tggggtcttc aggcaccagc catgcctgcc gaggagtgct    120
gtcaggacan accatgtccg tgctaggccc aggcacagcc caaccactcc tcatccaagt    180
ctctcccagg tttctggtcc cgatgggcaa ggatgacccc tccagtggct ggtaccccac    240
catcccacta cccctcacat gctctcactc tccatcaggt ccccaatcct ggcttccctc    300
ttcacgaact ctcaaagaaa aggaaggata aaacctaaat aaaccagaca gaagcagctc    360
tggaaaagta caaaaagaca gccagaggtg t                                   391
```

<210> SEQ ID NO 298
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 298

| caagccaaac tgtntccagc tttattaaan atactttcca taaacaatca tggtatttca | 60 |
| ggcaggacat gggcanacaa tcgttaacag tatacaacaa ctttcaaact cccttnttca | 120 |
| atggactacc aaaaatcaaa aagccactat aaaacccaat gaagtcttca tctgatgctc | 180 |
| tgaacaggga aagtttaaag ngagggttga catttcacat ttagcatgtt gtttaacaac | 240 |
| ttttcacaag ccgaccctga ctttcaggaa gtgaaatgaa aatggcanaa tttatctgaa | 300 |
| natccacaat ctaaaaatgg a | 321 |

<210> SEQ ID NO 299
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 299

| tatcataaag agtgttgaag tttatttatt atagcaccat tgagacattt tgaaattgga | 60 |
| attggtaaaa aaataaaaca aaaagcattt gaattgtatt tggnggaaca gcaaaaaaag | 120 |
| agaagtatca ttttctttg tcaaattata ctgtttccaa acattttgga aataaataac | 180 |
| tggaattttg tcggtcactt gcactggttg acaagattag aacaagagga acacatatgg | 240 |
| agttaaattt ttttgttgg gatttcanat agagtttggt ttataaaaag caaacagggc | 300 |
| caacgtccac accaaattct tgatcaggac caccaatgtc atagggngca atatctacaa | 360 |
| taggtagtct cacagccttg cgtgttcgat attcaaagac t | 401 |

<210> SEQ ID NO 300
<211> LENGTH: 188
<212> TYPE: DNA
<213> ORGANISM: Homo sapien
<220> FEATURE:
<221> NAME/KEY: misc_feature
<222> LOCATION: (1)...(188)
<223> OTHER INFORMATION: n = A,T,C or G

<400> SEQUENCE: 300

| tgaatgcttt gtcatattaa gaaagttaaa gtgcaataat gtttgaaanac aataagtggt | 60 |
| ggtgtatctt gtttctaata agataaactt ttttgtcttt gctttatctt attagggagt | 120 |
| tgtatgtcag tgtataaaac atactgtgtg gtataacagg cttaataaat tctttaaaag | 180 |
| gaaaaaaa | 188 |

<210> SEQ ID NO 301
<211> LENGTH: 291
<212> TYPE: DNA
<213> ORGANISM: Homo sapien

<400> SEQUENCE: 301

| aagattttgt tttatttat tatggctaga aagacactgt tatagccaaa atcggcaatg | 60 |
| acactaaaga aatcctctgt gcttttcaat atgcaaatat atttcttcca agagttgccc | 120 |
| tggtgtgact tcaagagttc atgttaactt cttttctgga aacttccttt tcttagttgt | 180 |
| tgtattcttg aagagcctgg gccatgaaga gcttgcctaa gttttgggca gtgaactcct | 240 |
| tgatgttctg gcagtaagtg tttatctggc ctgcaatgag cagcgagtcc a | 291 |

<210> SEQ ID NO 302
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 302

| | | | | | |
|---|---|---|---|---|---|
| tgatttttca | taattttatt | aaatnatcac | tgggaaaact | aatggttcgc | gtatcacaca | 60 |
| attacactac | aatctgatag | gagtggtaaa | accagccaat | ggaatccagg | taaagtacaa | 120 |
| aaacgccacc | ttttattgtc | ctgtcttatt | tctcgggaag | gagggttcta | ctttacacat | 180 |
| ttcatgagcc | agcagtggac | ttgagttaca | atgtgtaggt | tccttgtggt | tatagctgca | 240 |
| gaagaagcca | tcaaattctt | gaggacttga | catctctcgg | aaagaagcaa | actagtggat | 300 |
| cccccgggct | gcaggaattc | gatatcaagc | ttatcgatac | c | | 341 |

<210> SEQ ID NO 303
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 303

| | | | | | |
|---|---|---|---|---|---|
| tgcagacagt | aaatnaattt | tatttgngtt | cacagaacat | actaggcgat | ctcgacagtc | 60 |
| gctccgtgac | agcccaccaa | cccccaaccc | tntacctcgc | agccacccta | aaggcgactt | 120 |
| caanaanatg | gaaggatctc | acggatctca | ttcctaatgg | tccgccgaag | tctcacacag | 180 |
| tanacagacg | gagttganat | gctggaggat | gcagtcacct | cctaaactta | cgacccacca | 240 |
| ccanacttca | tcccagccgg | gacgtcctcc | cccacccgag | tcctccccat | ttcttctcct | 300 |
| actttgccgc | agttccaggn | gtcctgcttc | caccagtccc | acaaagctca | ataaatacca | 360 |
| a | | | | | | 361 |

<210> SEQ ID NO 304
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 304

| | | | | | |
|---|---|---|---|---|---|
| ctctttacaa | cagcctttat | ttncggccct | tgatcctgct | cggatgctgg | tggaggccct | 60 |
| tagctccgcc | cgccaggctc | tgtgccgcct | ccccgcaggc | gcanattcat | gaacacggtg | 120 |
| ctcaggggct | tgaggccgta | ctcccccagc | gggagctggt | cctccagggg | cttcccctcg | 180 |
| aaggtcagcc | anaacaggtc | gtcctgcaca | ccctccagcc | cgctcacttg | ctgcttcagg | 240 |
| tgggccacgg | tctgcgtcag | ccgcacctcg | taggtgctgc | tgcggcccct | gttattcctc | 300 |
| a | | | | | | 301 |

<210> SEQ ID NO 305
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 305

| | | | | | |
|---|---|---|---|---|---|
| ganaggctag | taacatcagt | tttattgggt | tggggnggca | accatagcct | ggctgggggn | 60 |
| ggggctggcc | ctcacaggtt | gttgagttcc | agcagggtct | ggtccaaggt | ctggtgaatc | 120 |
| tcgacgttct | cctccttggc | actggccaag | gtctcttcta | ggtcatcgat | ggttttctcc | 180 |
| aactttgcca | canacctctc | ggcaaactct | gctcgggtct | canccctcctt | cagcttctcc | 240 |
| tccaacagtt | tgatctcctc | ttcatattta | tcttctttgg | gggaatactc | ctcctctgag | 300 |
| gccatcaggg | acttgagggc | ctggtccatg | g | | | 331 |

<210> SEQ ID NO 306
<211> LENGTH: 457
<212> TYPE: DNA
<213> ORGANISM: Homo sapien

<400> SEQUENCE: 306

| | | | | | |
|---|---|---|---|---|---|
| aatatgtaaa | ggtaataact | tttattatat | taaagacaat | gcaaacgaaa | acagaattg | 60 |
| agcagtgcaa | aatttaaagg | actgttttgt | tctcaaagtt | gcaagtttca | aagccaaaag | 120 |
| aattatatgt | atcaaatata | taagtaaaaa | aaagttagac | tttcaagcct | gtaatcccag | 180 |
| cactttggga | ggctgaggca | ggtggatcac | taacattaaa | aagacaacat | tagattttgt | 240 |
| cgatttatag | caattttata | aatatataac | tttgtcactt | ggatcctgaa | gcaaaataat | 300 |
| aaagtgaatt | tgggattttt | gtacttggta | aaaagtttaa | caccctaaat | tcacaactag | 360 |
| tggatccccc | gggctgcagg | aattcgatat | caagcttatc | gataccgtcg | acctcgaggg | 420 |
| ggggcccggt | acccaattcg | ccctatagtg | agtcgta | | | 457 |

<210> SEQ ID NO 307
<211> LENGTH: 491
<212> TYPE: DNA
<213> ORGANISM: Homo sapien

<400> SEQUENCE: 307

| | | | | | |
|---|---|---|---|---|---|
| gtgcttggac | ggaacccggc | gctcgttccc | caccccggcc | ggccgcccat | agccagccct | 60 |
| ccgtcacctc | ttcaccgcac | cctcggactg | ccccaaggcc | cccgccgccg | ctccagcgcc | 120 |
| gcgcagccac | cgccgccgcc | gccgcctctc | cttagtcgcg | gccatgacga | ccgcgtccac | 180 |
| ctcgcaggtg | cgccagaact | accaccagga | ctcagaggcc | gccatcaacc | gccagatcaa | 240 |
| cctggagctc | tacgcctcct | acgtttacct | gtccatgtct | tactactttg | accgcgatga | 300 |
| tgtggctttg | aagaactttg | ccaaatactt | tcttcaccaa | tctcatgagg | agagggaaca | 360 |
| tgctgagaaa | ctgatgaagc | tgcagaacca | acgaggtggc | cgaatcttcc | ttcaggatat | 420 |
| caagaaacca | gactgtgatg | actgggagag | cgggctgaat | gcaatggagt | gtgcattaca | 480 |
| tttggaaaaa | a | | | | | 491 |

<210> SEQ ID NO 308
<211> LENGTH: 421
<212> TYPE: DNA
<213> ORGANISM: Homo sapien

<400> SEQUENCE: 308

| | | | | | |
|---|---|---|---|---|---|
| ctcagcgctt | cttctttctt | ggtttgatcc | tgactgctgt | catggcgtgc | cctctggaga | 60 |

| | |
|---|---|
| aggccctgga tgtgatggtg tccaccttcc acaagtactc gggcaaagag ggtgacaagt | 120 |
| tcaagctcaa caagtcagaa ctaaaggagc tgctgacccg ggagctgccc agcttcttgg | 180 |
| ggaaaaggac agatgaagct gctttccaga agctgatgag caacttggac agcaacaggg | 240 |
| acaacgaggt ggacttccaa gagtactgtg tcttcctgtc ctgcatcgcc atgatgtgta | 300 |
| acgaattctt tgaaggcttc ccagataagc agcccaggaa gaaatgaaaa ctcctctgat | 360 |
| gtggttgggg ggtctgccag ctggggccct ccctgtcgcc agtgggcact tttttttttc | 420 |
| c | 421 |

<210> SEQ ID NO 309
<211> LENGTH: 321
<212> TYPE: DNA
<213> ORGANISM: Homo sapien

<400> SEQUENCE: 309

| | |
|---|---|
| accaaatggc ggatgacgcc ggtgcagcgg gggggcccgg gggccctggt ggccctggga | 60 |
| tggggaaccg cggtggcttc cgcggaggtt tcggcagtgg catccggggc cggggtcgcg | 120 |
| gccgtggacg gggccggggc cgaggccgcg gagctcgcgg aggcaaggcc gaggataagg | 180 |
| agtggatgcc cgtcaccaag ttgggccgct tggtcaagga catgaagatc aagtccctgg | 240 |
| aggagatcta tctcttctcc ctgcccatta aggaatcaga gatcattgat ttcttcctgg | 300 |
| gggcctctct caaggatgag g | 321 |

<210> SEQ ID NO 310
<211> LENGTH: 381
<212> TYPE: DNA
<213> ORGANISM: Homo sapien

<400> SEQUENCE: 310

| | |
|---|---|
| ttaaccagcc atattggctc aataaatagc ttcggtaagg agttaatttc cttctagaaa | 60 |
| tcagtgccta ttttcctgg aaactcaatt ttaaatagtc caattccatc tgaagccaag | 120 |
| ctgttgtcat tttcattcgg tgacattctc tcccatgaca cccagaaggg gcagaagaac | 180 |
| cacatttttc atttatagat gtttgcatcc tttgtattaa aattattttg aagggttgc | 240 |
| ctcattggat ggctttttt ttttttcctcc agggagaagg ggagaaatgt acttggaaat | 300 |
| taatgtatgt ttacatctct ttgcaaattc ctgtacatag agatatattt tttaagtgtg | 360 |
| aatgtaacaa catactgtga a | 381 |

<210> SEQ ID NO 311
<211> LENGTH: 538
<212> TYPE: DNA
<213> ORGANISM: Homo sapien

<400> SEQUENCE: 311

| | |
|---|---|
| tttgaattta caccaagaac ttctcaataa agaaaatca tgaatgctcc acaatttcaa | 60 |
| cataccacaa gagaagttaa tttcttaaca ttgtgttcta tgattatttg taagaccttc | 120 |
| accaagttct gatatctttt aaagacatag ttcaaaattg cttttgaaaa tctgtattct | 180 |
| tgaaaatatc cttgttgtgt attaggtttt taaataccag ctaaaggatt acctcactga | 240 |
| gtcatcagta ccctcctatt cagctcccca agatgatgtg ttttttgctta ccctaagaga | 300 |
| ggttttcttc ttatttttag ataattcaag tgcttagata aattatgttt tctttaagtg | 360 |
| tttatggtaa actcttttaa agaaaattta atatgttata gctgaatctt tttggtaact | 420 |
| ttaaatctttt atcatagact ctgtacatat gttcaaatta gctgcttgcc tgatgtgtgt | 480 |

```
atcatcggtg ggatgacaga acaaacatat ttatgatcat gaataatgtg ctttgtaa      538
```

<210> SEQ ID NO 312
<211> LENGTH: 176
<212> TYPE: DNA
<213> ORGANISM: Homo sapien

<400> SEQUENCE: 312

```
ggaggagcag ctgagagata gggtcagtga atgcggttca gcctgctacc tctcctgtct   60
tcatagaacc attgccttag aattattgta tgacacgttt tttgttggtt aagctgtaag  120
gttttgttct ttgtgaacat gggtattttg aggggagggt ggaggagta gggaag       176
```

<210> SEQ ID NO 313
<211> LENGTH: 396
<212> TYPE: DNA
<213> ORGANISM: Homo sapien

<400> SEQUENCE: 313

```
ccagcacccc caggccctgg gggacctggg ttctcagact gccaaagaag ccttgccatc   60
tggcgctccc atggctcttg caacatctcc ccttcgtttt tgagggggtc atgccggggg  120
agccaccagc ccctcactgg gttcggagga gagtcaggaa gggccaagca cgacaaagca  180
gaaacatcgg atttggggaa cgcgtgtcaa tcccttgtgc cgcagggctg ggcgggagag  240
actgttctgt tccttgtgta actgtgttgc tgaaagacta cctcgttctt gtcttgatgt  300
gtcaccgggg caactgcctg ggggcgggga tgggggcagg gtggaagcgg ctccccattt  360
tataccaaag gtgctacatc tatgtgatgg gtgggg                            396
```

<210> SEQ ID NO 314
<211> LENGTH: 311
<212> TYPE: DNA
<213> ORGANISM: Homo sapien

<400> SEQUENCE: 314

```
cctcaacatc ctcagagagg actggaagcc agtccttacg ataaactcca taatttatgg   60
cctgcagtat ctcttcttgg agcccaaccc cgaggaccca ctgaacaagg aggccgcaga  120
ggtcctgcag aacaaccggc ggctgtttga gcagaacgtg cagcgctcca tgcggggtgg  180
ctacatcggc tccacctact ttgagcgctg cctgaaatag ggttggcgca tacccacccc  240
cgccacggcc acaagccctg gcatcccctg caaatattta ttggggccca tgggtagggg  300
tttgggggc g                                                        311
```

<210> SEQ ID NO 315
<211> LENGTH: 336
<212> TYPE: DNA
<213> ORGANISM: Homo sapien

<400> SEQUENCE: 315

```
tttagaacat ggttatcatc caagactact ctaccctgca acattgaact cccaagagca   60
aatccacatt cctcttgagt tctgcagctt ctgtgtaaat agggcagctg tcgtctatgc  120
cgtagaatca catgatctga ggaccattca tggaagctgc taaatagcct agtctgggga  180
gtcttccata aagttttgca tggagcaaac aaacaggatt aaactaggtt tggttccttc  240
agccctctaa aagcataggg cttagcctgc aggcttcctt gggctttctc tgtgtgtgta  300
gttttgtaaa cactatagca tctgttaaga tccagt                            336
```

<210> SEQ ID NO 316
<211> LENGTH: 436
<212> TYPE: DNA
<213> ORGANISM: Homo sapien

<400> SEQUENCE: 316

| | | | | | |
|---|---|---|---|---|---|
| aacatggtct | gcgtgcctta | agagagacgc | ttcctgcaga | acaggacctg | actacaaaga | 60 |
| atgtttccat | tggaattgtt | ggtaaagact | tggagtttac | aatctatgat | gatgatgatg | 120 |
| tgtctccatt | cctggaaggt | cttgaagaaa | gaccacagag | aaaggcacag | cctgctcaac | 180 |
| ctgctgatga | acctgcagaa | aaggctgatg | aaccaatgga | acattaagtg | ataagccagt | 240 |
| ctatatatgt | attatcaaat | atgtaagaat | acaggcacca | catactgatg | acaataatct | 300 |
| atactttgaa | ccaaaagttg | cagagtggtg | gaatgctatg | ttttaggaat | cagtccagat | 360 |
| gtgagttttt | tccaagcaac | ctcactgaaa | cctatataat | ggaatacatt | tttctttgaa | 420 |
| agggtctgta | taatca | | | | | 436 |

<210> SEQ ID NO 317
<211> LENGTH: 196
<212> TYPE: DNA
<213> ORGANISM: Homo sapien

<400> SEQUENCE: 317

| | | | | | |
|---|---|---|---|---|---|
| tattccttgt | gaagatgata | tactattttt | gttaagcgtg | tctgtattta | tgtgtgagga | 60 |
| gctgctggct | tgcagtgcgc | gtgcacgtgg | agagctggtg | cccggagatt | ggacggcctg | 120 |
| atgctccctc | ccctgccctg | gtccagggaa | gctggccgag | ggtcctggct | cctgaggggc | 180 |
| atctgcccct | cccccca | | | | | 196 |

<210> SEQ ID NO 318
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 318

| | | | | | |
|---|---|---|---|---|---|
| gacgcttnng | ccgtaacgat | gatcggagac | atcctgctgt | tcgggacgtt | gctgatgaat | 60 |
| gccgggcgg | tgctgaactt | taagctgaaa | aagaaggaca | cncagggctt | tggggaggag | 120 |
| tncagggagc | ccaacacagg | tgacaacatc | cgggaattct | tgctgancct | cagatacttt | 180 |
| cnaatcttca | tcnccctgtg | gaacatcttc | atgatgttct | gcatgattgt | gctgntcggc | 240 |
| tcttgaatcc | cancgatgaa | accannaact | cactttcccg | ggatgccgan | tctccattcc | 300 |
| tccattcctg | atgacttcaa | naatgttttt | gaccaaaaaa | ccgacaacct | tcccagaaag | 360 |
| tccaagctcg | tggtgggngg | a | | | | 381 |

<210> SEQ ID NO 319
<211> LENGTH: 506
<212> TYPE: DNA
<213> ORGANISM: Homo sapien

<400> SEQUENCE: 319

| | | | | | |
|---|---|---|---|---|---|
| ctaagcttta | cgaatggggt | gacaacttat | gataaaaact | agagctagtg | aattagccta | 60 |
| tttgtaaata | cctttgttat | aattgatagg | atacatcttg | gacatggaat | tgttaagcca | 120 |
| cctctgagca | gtgtatgtca | ggacttgttc | attaggttgg | cagcagaggg | gcagaaggaa | 180 |

```
ttatacaggt agagatgtat gcagatgtgt ccatatatgt ccatatttac attttgatag      240
ccattgatgt atgcatctct tggctgtact ataagaacac attaattcaa tggaaataca      300
ctttgctaat attttaatgg tatagatctg ctaatgaatt ctcttaaaaa catactgtat      360
tctgttgctg tgtgtttcat tttaaattga gcattaaggg aatgcagcat ttaaatcaga      420
actctgccaa tgcttttatc tagaggcgtg ttgccatttt tgtcttatat gaaatttctg      480
tcccaagaaa ggcaggatta catctt                                           506
```

<210> SEQ ID NO 320
<211> LENGTH: 351
<212> TYPE: DNA
<213> ORGANISM: Homo sapien

<400> SEQUENCE: 320

```
ctgacctgca ggacgaaacc atgaagagcc tgatccttct tgccatcctg gccgccttag       60
cggtagtaac tttgtgttat gaatcacatg aaagcatgga atcttatgaa cttaatccct      120
tcattaacag gagaaatgca ataccttca tatcccctca gcagagatgg agagctaaag      180
tccaagagag gatccgagaa cgctctaagc ctgtccacga gctcaatagg gaagcctgtg      240
atgactacag actttgcgaa cgctacgcca tggtttatgg atacaatgct gcctataatc      300
gctacttcag gaagcgccga gggaccaaat gagactgagg gaagaaaaaa a              351
```

<210> SEQ ID NO 321
<211> LENGTH: 421
<212> TYPE: DNA
<213> ORGANISM: Homo sapien

<400> SEQUENCE: 321

```
ctcggaggcg ttcagctgct tcaagatgaa gctgaacatc tccttcccag ccactggctg       60
ccagaaactc attgaagtgg acgatgaacg caaacttcgt actttctatg agaagcgtat      120
ggccacagaa gttgctgctg acgctctggg tgaagaatgg aagggttatg tggtccgaat      180
cagtggtggg aacgacaaac aaggtttccc catgaagcag ggtgtcttga cccatggccg      240
tgtccgcctg ctactgagta agggcattc ctgttacaga ccaaggagaa ctggagaaag      300
aaagagaaaa tcagttcgtg gttgcattgt ggatgcaaat ctgagcgttc tcaacttggt      360
tattgtaaaa aaggagaga aggatattcc tggactgact gatactacag tgcctcgccg      420
c                                                                      421
```

<210> SEQ ID NO 322
<211> LENGTH: 521
<212> TYPE: DNA
<213> ORGANISM: Homo sapien

<400> SEQUENCE: 322

```
agcagctctc ctgccacagc tcctcacccc ctgaaaatgt tcgcctgctc caagtttgtc       60
tccactccct ccttggtcaa gagcacctca cagctgctga ccgtccgct atctgcagtg      120 gtgctgaaac gaccggagat actgacagat gagagcctca gcagcttggc agtctcatgt      180 cccttacct cacttgtctc tagccgcagc ttccaaacca cgccatttc aagggacatc      240 gacacagcag ccaagttcat ggagctgggg ctgccacag ttggggtggc tggttctggg      300
gctgggattg gaactgtgtt tgggagcctc atcattggtt atgccaggaa cccttctctg      360
aagcaacagc tcttctccta cgccattctg ggctttgccc tctcggaggc catggggctc      420
```

| | |
|---|---|
| ttttgtctga tggtagcctt tctcatcctc tttgccatgt gaaggagccg tctccacctc | 480 |
| ccatagttct cccgcgtctg gttggccccg tgtgttcctt t | 521 |

<210> SEQ ID NO 323
<211> LENGTH: 435
<212> TYPE: DNA
<213> ORGANISM: Homo sapien

<400> SEQUENCE: 323

| | |
|---|---|
| ccgaggtcgc acgcgtgaga cttctccgcc gcagacgccg ccgcgatgcg ctacgtcgcc | 60 |
| tcctacctgc tggctgccct aggggggcaac tcctccccca gcgccaagga catcaagaag | 120 |
| atcttggaca gcgtgggtat cgaggcggac gacgaccggc tcaacaaggt tatcagtgag | 180 |
| ctgaatggaa aaacattga agacgtcatt gcccagggta ttggcaagct tgccagtgta | 240 |
| cctgctggtg gggctgtagc cgtctctgct gccccaggct ctgcagcccc tgctgctggt | 300 |
| tctgcccctg ctgcagcaga ggagaagaaa gatgagaaga aggaggagtc tgaagagtca | 360 |
| gatgatgaca tgggatttgg cctttttgat taaattcctg ctcccctgca aataaagcct | 420 |
| ttttacacat ctcaa | 435 |

<210> SEQ ID NO 324
<211> LENGTH: 521
<212> TYPE: DNA
<213> ORGANISM: Homo sapien

<400> SEQUENCE: 324

| | |
|---|---|
| aggagatcga ctttcggtgc ccgcaagacc agggctggaa cgccgagatc acgctgcaga | 60 |
| tggtgcagta caagaatcgt caggccatcc tggcggtcaa atccacgcgg cagaagcagc | 120 |
| agcacctggt ccagcagcag ccccctcgc agccgcagcc gcagccgcag ctccagcccc | 180 |
| aaccccagcc tcagcctcag ccgcaacccc agccccaatc acaacccag cctcagcccc | 240 |
| aacccaagcc tcagcccag cagctccacc cgtatccgca tccacatcca catccacact | 300 |
| ctcatcctca ctcgcaccca cccctcacc cgcaccgca tccgccacaa ataccgcacc | 360 |
| cacacccaca gccgcactcg cagccgcacg ggcaccggct tctccgcagc acctccaact | 420 |
| ctgcctgaaa ggggcagctc ccgggcaaga caaggttttg aggacttgag gaagtgggac | 480 |
| gagcacattt ctattgtctt cacttggatc aaaagcaaaa c | 521 |

<210> SEQ ID NO 325
<211> LENGTH: 451
<212> TYPE: DNA
<213> ORGANISM: Homo sapien

<400> SEQUENCE: 325

| | |
|---|---|
| attttcattt ccattaacct ggaagctttc atgaatattc tcttctttta aaacatttta | 60 |
| acattattta aacagaaaaa gatgggctct ttctggttag ttgttacatg atagcagaga | 120 |
| tattttact tagattactt tgggaatgag agattgttgt cttgaactct ggcactgtac | 180 |
| agtgaatgtg tctgtagttg tgttagtttg cattaagcat gtataacatt caagtatgtc | 240 |
| atccaaataa gaggcatata cattgaattg tttttaatcc tctgacaagt tgactcttcg | 300 |
| acccccaccc ccacccaaga catttttaata gtaaatagag agagagagaa gagttaatga | 360 |
| acatgaggta gtgttccact ggcaggatga cttttcaata gctcaaatca atttcagtgc | 420 |
| ctttatcact tgaattatta acttaatttg a | 451 |

<210> SEQ ID NO 326
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 326

| | | | | | |
|---|---|---|---|---|---|
| cgcggtcgta | agggctgagg | attttttggtc | cgcacgctcc | tgctcctgac | tcaccgctgt | 60 |
| tcgctctcgc | cgaggaacaa | gtcggtcagg | aagcccgcgc | gcaacagcca | tggcttttaa | 120 |
| ggataccgga | aaacacccg | tggagccgga | ggtggcaatt | caccgaattc | gaatcaccct | 180 |
| aacaagccgc | aacgtaaaat | ccttggaaaa | ggtgtgtgct | gacttgataa | gaggcgcaaa | 240 |
| agaaaagaat | ctcaaagtga | aaggaccagt | tcgaatgcct | accaagactt | tgagantcac | 300 |
| tacaagaaaa | actccttgtg | gtgaaggttc | taagacgtgg | gatcgtttcc | agatgagaat | 360 |
| tcacaagcga | ctcattgact | tgcacagtcc | ttctgagatt | gttaagcaga | ttacttccat | 420 |
| c | | | | | | 421 |

<210> SEQ ID NO 327
<211> LENGTH: 456
<212> TYPE: DNA
<213> ORGANISM: Homo sapien

<400> SEQUENCE: 327

| | | | | | |
|---|---|---|---|---|---|
| atcttgacga | ggctgcggtg | tctgctgcta | ttctccgagc | ttcgcaatgc | cgcctaagga | 60 |
| cgacaagaag | aagaaggacg | ctggaaagtc | ggccaagaaa | gacaaagacc | cagtgaacaa | 120 |
| atccgggggc | aaggccaaaa | agaagaagtg | gtccaaaggc | aaagttcggg | acaagctcaa | 180 |
| taacttagtc | ttgtttgaca | aagctaccta | tgataaactc | tgtaaggaag | ttcccaacta | 240 |
| taaacttata | accccagctg | tggtctctga | gagactgaag | attcgaggct | ccctggccag | 300 |
| ggcagcccctt | caggagctcc | ttagtaaagg | acttatcaaa | ctggtttcaa | agcacagagc | 360 |
| tcaagtaatt | taccagagaa | ataccaaggg | tggagatgct | ccagctgctg | gtgaagatgc | 420 |
| atgaataggt | ccaaccagct | gtacatttgg | aaaaat | | | 456 |

<210> SEQ ID NO 328
<211> LENGTH: 471
<212> TYPE: DNA
<213> ORGANISM: Homo sapien

<400> SEQUENCE: 328

| | | | | | |
|---|---|---|---|---|---|
| gtggaagtga | catcgtcttt | aaaccctgcg | tggcaatccc | tgacgcaccg | ccgtgatgcc | 60 |
| cagggaagac | agggcgacct | ggaagtccaa | ctacttcctt | aagatcatcc | aactattgga | 120 |
| tgattatccg | aaatgtttca | ttgtgggagc | agacaatgtg | ggctccaagc | agatgcagca | 180 |
| gatccgcatg | tcccttcgcg | ggaaggctgt | ggtgctgatg | ggcaagaaca | ccatgatgcg | 240 |
| caaggccatc | cgagggcacc | tggaaaacaa | cccagctctg | gagaaactgc | tgcctcatat | 300 |
| ccgggggaat | gtgggctttg | tgttcaccaa | ggaggacctc | actgagatca | gggacatgtt | 360 |
| gctggccaat | aaggtgccag | ctgctgcccg | tgctggtgcc | attgccccat | gtgaagtcac | 420 |
| tgtgccagcc | cagaacactg | gtctcgggcc | cgagaagacc | tccttttttcc | a | 471 |

<210> SEQ ID NO 329
<211> LENGTH: 278
<212> TYPE: DNA

-continued

```
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 329
gtttaaactt aagcttggta ccgagctcgg atccactagt ccagtgtggt ggaattctag      60
aaattgagat gccccccag gccagcaaat gttccttttt gttcaaagtc tatttttatt     120
ccttgatatt tttctttttt tttttttttt ttgnggatgg ggacttgtga attttctaa     180 aggtgctatt taacatggga gganagcgtg tgcggctcca gcccagcccg ctgctcactt    240
tccaccctct ctccacctgc ctctggcttc tcaggcct                            278

<210> SEQ ID NO 330
<211> LENGTH: 338
<212> TYPE: DNA
<213> ORGANISM: Homo sapien

<400> SEQUENCE: 330
ctcaggcttc aacatcgaat acgccgcagg ccccttcgcc ctattcttca tagccgaata     60
cacaaacatt attataataa acaccctcac cactacaatc ttcctaggaa caacatatga    120
cgcactctcc cctgaactct acacaacata ttttgtcacc aagaccctac ttctaacctc    180
cctgttctta tgaattcgaa cagcataccc ccgattccgc tacgaccaac tcatacacct    240
cctatgaaaa aacttcctac cactcaccct agcattactt atatgatatg tctccatacc    300
cattacaatc tccagcattc cccctcaaac ctaaaaaa                            338
```

COMPOUNDS AND METHODS FOR THERAPY AND DIAGNOSIS OF LUNG CANCER

REFERENCE TO RELATED APPLICATIONS

This application is a continuation-in-part of U.S. patent application Ser. No. 09/476,496, filed Dec. 30, 1999, which is a continuation-in-part of U.S. patent application Ser. No. 09/466,396, filed Dec. 17, 1999, which is a continuation-in-part of U.S. patent application Ser. No. 09/285,479, filed Apr. 2, 1999, which is a 371 of PCT Application No. PCT/US99/05798, filed Mar. 17, 1999, which claims priority from U.S. patent application Ser. No. 09/221,107, filed Dec. 22, 1998, which is a continuation-in-part of U.S. patent application Ser. No. 09/123,912, filed Jul. 27, 1998, now U.S. Pat. No. 6,312,695, which is a continuation-in-part of U.S. patent application Ser. No. 09/040,802, filed Mar. 18, 1998.

TECHNICAL FIELD

The present invention relates generally to therapy and diagnosis of cancer, such as lung cancer. The invention is more specifically related to polypeptides comprising at least a portion of a lung tumor protein, and to polynucleotides encoding such polypeptides. Such polypeptides and polynucleotides may be used in vaccines and pharmaceutical compositions for prevention and treatment of lung cancer, and for the diagnosis and monitoring of such cancers.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compositions and methods for the diagnosis and therapy of cancer, such as lung cancer. In one aspect, the present invention provides polypeptides comprising at least a portion of a lung tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253 and 254–330; (b) variants of a sequence recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253 and 254–330; and (c) complements of a sequence of (a) or (b). In specific embodiments, the polypeptides of the present invention comprise at least a portion of a tumor protein that includes an amino acid sequence selected from the group consisting of sequences recited in any one of SEQ ID NO: 152, 155, 156, 165, 166, 169, 170, 172, 174, 176 and 226–252 and variants thereof.

The present invention further provides polynucleotides that encode a polypeptide as described above, or a portion thereof (such as a portion encoding at least 15 amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above, and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Determined T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells determined from a patient with one or more of: (i) a polypeptide comprising at least an immunogenic portion of a lung tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided. These and other aspects of the present invention will become apparent upon reference to the following detailed description and attached drawings. All references disclosed herein are hereby incorporated by reference in their entirety as if each was incorporated individually.

SEQUENCE IDENTIFIERS

SEQ ID NO: 1 is the determined cDNA sequence for LST-S1-2
SEQ ID NO: 2 is the determined cDNA sequence for LST-S1-28
SEQ ID NO: 3 is the determined cDNA sequence for LST-S1-90
SEQ ID NO: 4 is the determined cDNA sequence for LST-S1-144
SEQ ID NO: 5 is the determined cDNA sequence for LST-S1-133
SEQ ID NO: 6 is the determined cDNA sequence for LST-S1-169
SEQ ID NO: 7 is the determined cDNA sequence for LST-S2-6
SEQ ID NO: 8 is the determined cDNA sequence for LST-S2-11
SEQ ID NO: 9 is the determined cDNA sequence for LST-S2-17
SEQ ID NO: 10 is the determined cDNA sequence for LST-S2-25
SEQ ID NO: 11 is the determined cDNA sequence for LST-S2-39
SEQ ID NO: 12 is a first determined cDNA sequence for LST-S2-43
SEQ ID NO: 13 is a second determined cDNA sequence for LST-S2-43
SEQ ID NO: 14 is the determined cDNA sequence for LST-S2-65
SEQ ID NO: 15 is the determined cDNA sequence for LST-S2-68
SEQ ID NO: 16 is the determined cDNA sequence for LST-S2-72
SEQ ID NO: 17 is the determined cDNA sequence for LST-S2-74

SEQ ID NO: 18 is the determined cDNA sequence for LST-S2-103
SEQ ID NO: 19 is the determined cDNA sequence for LST-S2-N1-1F
SEQ ID NO: 20 is the determined cDNA sequence for LST-S2-N1-2A
SEQ ID NO: 21 is the determined cDNA sequence for LST-S2-N1-4H
SEQ ID NO: 22 is the determined cDNA sequence for LST-S2-N1-5A
SEQ ID NO: 23 is the determined cDNA sequence for LST-S2-N1-6B
SEQ ID NO: 24 is the determined cDNA sequence for LST-S2-N1-7B
SEQ ID NO: 25 is the determined cDNA sequence for LST-S2-N1-7H
SEQ ID NO: 26 is the determined cDNA sequence for LST-S2-N1-8A
SEQ ID NO: 27 is the determined cDNA sequence for LST-S2-N1-8D
SEQ ID NO: 28 is the determined cDNA sequence for LST-S2-N1-9A
SEQ ID NO: 29 is the determined cDNA sequence for LST-S2-N1-9E
SEQ ID NO: 30 is the determined cDNA sequence for LST-S2-N1-10A
SEQ ID NO: 31 is the determined cDNA sequence for LST-S2-N1-10G
SEQ ID NO: 32 is the determined cDNA sequence for LST-S2-N1-11A
SEQ ID NO: 33 is the determined cDNA sequence for LST-S2-N1-12C
SEQ ID NO: 34 is the determined cDNA sequence for LST-S2-N1-12E
SEQ ID NO: 35 is the determined cDNA sequence for LST-S2-B1-3D
SEQ ID NO: 36 is the determined cDNA sequence for LST-S2-B1-6C
SEQ ID NO: 37 is the determined cDNA sequence for LST-S2-N1-5D
SEQ ID NO: 38 is the determined cDNA sequence for LST-S2-B1-5F
SEQ ID NO: 39 is the determined cDNA sequence for LST-S2-B1-6G
SEQ ID NO: 40 is the determined cDNA sequence for LST-S2-B1-8A
SEQ ID NO: 41 is the determined cDNA sequence for LST-S2-B1-8D
SEQ ID NO: 42 is the determined cDNA sequence for LST-S2-B1-10A
SEQ ID NO: 43 is the determined cDNA sequence for LST-S2-B1-9B
SEQ ID NO: 44 is the determined cDNA sequence for LST-S2-B1-9F
SEQ ID NO: 45 is the determined cDNA sequence for LST-S2-B1-12D
SEQ ID NO: 46 is the determined cDNA sequence for LST-S2-I2-2B
SEQ ID NO: 47 is the determined cDNA sequence for LST-S2-I2-5F
SEQ ID NO: 48 is the determined cDNA sequence for LST-S2-I2-6B
SEQ ID NO: 49 is the determined cDNA sequence for LST-S2-I2-7F
SEQ ID NO: 50 is the determined cDNA sequence for LST-S2-I2-8G
SEQ ID NO: 51 is the determined cDNA sequence for LST-S2-I2-9E
SEQ ID NO: 52 is the determined cDNA sequence for LST-S2-I2-12B
SEQ ID NO: 53 is the determined cDNA sequence for LST-S2-H2-2C
SEQ ID NO: 54 is the determined cDNA sequence for LST-S2-H2-1G
SEQ ID NO: 55 is the determined cDNA sequence for LST-S2-H2-4G
SEQ ID NO: 56 is the determined cDNA sequence for LST-S2-H2-3H
SEQ ID NO: 57 is the determined cDNA sequence for LST-S2-H2-5G
SEQ ID NO: 58 is the determined cDNA sequence for LST-S2-H2-9B
SEQ ID NO: 59 is the determined cDNA sequence for LST-S2-H2-10H
SEQ ID NO: 60 is the determined cDNA sequence for LST-S2-H2-12D
SEQ ID NO: 61 is the determined cDNA sequence for LST-S3-2
SEQ ID NO: 62 is the determined cDNA sequence for LST-S3-4
SEQ ID NO: 63 is the determined cDNA sequence for LST-S3-7
SEQ ID NO: 64 is the determined cDNA sequence for LST-S3-8
SEQ ID NO: 65 is the determined cDNA sequence for LST-S3-12
SEQ ID NO: 66 is the determined cDNA sequence for LST-S3-13
SEQ ID NO: 67 is the determined cDNA sequence for LST-S3-14
SEQ ID NO: 68 is the determined cDNA sequence for LST-S3-16
SEQ ID NO: 69 is the determined cDNA sequence for LST-S3-21
SEQ ID NO: 70 is the determined cDNA sequence for LST-S3-22
SEQ ID NO: 71 is the determined cDNA sequence for LST-S1-7
SEQ ID NO: 72 is the determined cDNA sequence for LST-S1-A-1E
SEQ ID NO: 73 is the determined cDNA sequence for LST-S1-A-1G
SEQ ID NO: 74 is the determined cDNA sequence for LST-S1-A-3E
SEQ ID NO: 75 is the determined cDNA sequence for LST-S1-A-4E
SEQ ID NO: 76 is the determined cDNA sequence for LST-S1-A-6D
SEQ ID NO: 77 is the determined cDNA sequence for LST-S1-A-8D
SEQ ID NO: 78 is the determined cDNA sequence for LST-S1-A-10A
SEQ ID NO: 79 is the determined cDNA sequence for LST-S1-A-10C
SEQ ID NO: 80 is the determined cDNA sequence for LST-S1-A-9D
SEQ ID NO: 81 is the determined cDNA sequence for LST-S1-A-10D
SEQ ID NO: 82 is the determined cDNA sequence for LST-S1-A-9H
SEQ ID NO: 83 is the determined cDNA sequence for LST-S1-A-11D
SEQ ID NO: 84 is the determined cDNA sequence for LST-S1-A-12D
SEQ ID NO: 85 is the determined cDNA sequence for LST-S1-A-11E SEQ ID NO: 86 is the determined cDNA sequence for LST-S1-A-12E
SEQ ID NO: 87 is the determined cDNA sequence for L513S (T3).
SEQ ID NO: 88 is the determined cDNA sequence for L513S contig 1.
SEQ ID NO: 89 is a first determined cDNA sequence for L514S.
SEQ ID NO: 90 is a second determined cDNA sequence for L514S.
SEQ ID NO: 91 is a first determined cDNA sequence for L516S.
SEQ ID NO: 92 is a second determined cDNA sequence for L516S.
SEQ ID NO: 93 is the determined cDNA sequence for L517S.
SEQ ID NO: 94 is the extended cDNA sequence for LST-S1-169 (also known as L519S).
SEQ ID NO: 95 is a first determined cDNA sequence for L520S.
SEQ ID NO: 96 is a second determined cDNA sequence for L520S.
SEQ ID NO: 97 is a first determined cDNA sequence for L521S.
SEQ ID NO: 98 is a second determined cDNA sequence for L521S.
SEQ ID NO: 99 is the determined cDNA sequence for L522S.
SEQ ID NO: 100 is the determined cDNA sequence for L523S.
SEQ ID NO: 101 is the determined cDNA sequence for L524S.
SEQ ID NO: 102 is the determined cDNA sequence for L525S.
SEQ ID NO: 103 is the determined cDNA sequence for L526S.
SEQ ID NO: 104 is the determined cDNA sequence for L527S.
SEQ ID NO: 105 is the determined cDNA sequence for L528S.
SEQ ID NO: 106 is the determined cDNA sequence for L529S.
SEQ ID NO: 107 is a first determined cDNA sequence for L530S.
SEQ ID NO: 108 is a second determined cDNA sequence for L530S.
SEQ ID NO: 109 is the determined full-length cDNA sequence for L531S short form
SEQ ID NO: 110 is the predicted amino acid sequence encoded by SEQ ID NO: 109.
SEQ ID NO: 111 is the determined full-length cDNA sequence for L531S long form
SEQ ID NO: 112 is the predicted amino acid sequence encoded by SEQ ID NO: 111.
SEQ ID NO: 113 is the determined full-length cDNA sequence for L520S.
SEQ ID NO: 114 is the predicted amino acid sequence encoded by SEQ ID NO: 113.
SEQ ID NO: 115 is the determined cDNA sequence for contig 1.
SEQ ID NO: 116 is the determined cDNA sequence for contig 3.
SEQ ID NO: 117 is the determined cDNA sequence for contig 4.
SEQ ID NO: 118 is the determined cDNA sequence for contig 5.
SEQ ID NO: 119 is the determined cDNA sequence for contig 7.
SEQ ID NO: 120 is the determined cDNA sequence for contig 8.
SEQ ID NO: 121 is the determined cDNA sequence for contig 9.
SEQ ID NO: 122 is the determined cDNA sequence for contig 10.
SEQ ID NO: 123 is the determined cDNA sequence for contig 12.
SEQ ID NO: 124 is the determined cDNA sequence for contig 11.
SEQ ID NO: 125 is the determined cDNA sequence for contig 13.
SEQ ID NO: 126 is the determined cDNA sequence for contig 15.
SEQ ID NO: 127 is the determined cDNA sequence for contig 16.
SEQ ID NO: 128 is the determined cDNA sequence for contig 17.
SEQ ID NO: 129 is the determined cDNA sequence for contig 19.
SEQ ID NO: 130 is the determined cDNA sequence for contig 20.
SEQ ID NO: 131 is the determined cDNA sequence for contig 22.
SEQ ID NO: 132 is the determined cDNA sequence for contig 24.
SEQ ID NO: 133 is the determined cDNA sequence for contig 29.
SEQ ID NO: 134 is the determined cDNA sequence for contig 31.
SEQ ID NO: 135 is the determined cDNA sequence for contig 33.
SEQ ID NO: 136 is the determined cDNA sequence for contig 38.
SEQ ID NO: 137 is the determined cDNA sequence for contig 39.
SEQ ID NO: 138 is the determined cDNA sequence for contig 41.
SEQ ID NO: 139 is the determined cDNA sequence for contig 43.
SEQ ID NO: 140 is the determined cDNA sequence for contig 44.
SEQ ID NO: 140 is the determined cDNA sequence for contig 45.
SEQ ID NO: 142 is the determined cDNA sequence for contig 47.
SEQ ID NO: 142 is the determined cDNA sequence for contig 48.
SEQ ID NO: 144 is the determined cDNA sequence for contig 49.
SEQ ID NO: 145 is the determined cDNA sequence for contig 50.
SEQ ID NO: 146 is the determined cDNA sequence for contig 53.
SEQ ID NO: 147 is the determined cDNA sequence for contig 54.
SEQ ID NO: 148 is the determined cDNA sequence for contig 56.
SEQ ID NO: 149 is the determined cDNA sequence for contig 57.
SEQ ID NO: 150 is the determined cDNA sequence for contig 58.
SEQ ID NO: 151 is the full-length cDNA sequence for L530S.
SEQ ID NO: 152 is the amino acid sequence encoded by SEQ ID NO: 151
SEQ ID NO: 153 is the full-length cDNA sequence of a first variant of L514S SEQ ID NO: 154 is the full-length cDNA sequence of a second variant of L514S
SEQ ID NO: 155 is the amino acid sequence encoded by SEQ ID NO: 153.
SEQ ID NO: 156 is the amino acid sequence encoded by SEQ ID NO: 154.
SEQ ID NO: 157 is the determined cDNA sequence for contig 59.
SEQ ID NO: 158 is the full-length cDNA sequence for L763P (also referred to as contig 22).
SEQ ID NO: 159 is the amino acid sequence encoded by SEQ ID NO: 158.
SEQ ID NO: 160 is the full-length cDNA sequence for L762P (also referred to as contig 17).
SEQ ID NO: 161 is the amino acid sequence encoded by SEQ ID NO: 160.
SEQ ID NO: 162 is the determined cDNA sequence for L515S.
SEQ ED NO: 163 is the full-length cDNA sequence of a first variant of L524S.
SEQ ID NO: 164 is the full-length cDNA sequence of a second variant of L524S.
SEQ ID NO: 165 is the amino acid sequence encoded by SEQ ID NO: 163.
SEQ ID NO: 166 is the amino acid sequence encoded by SEQ ID NO: 164.
SEQ ID NO: 167 is the full-length cDNA sequence of a first variant of L762P.
SEQ ID NO: 168 is the full-length cDNA sequence of a second variant of L762P.
SEQ ID NO: 169 is the amino acid sequence encoded by SEQ ID NO: 167.
SEQ ID NO: 170 is the amino acid sequence encoded by SEQ ID NO: 168.
SEQ ID NO: 171 is the full-length cDNA sequence for L773P (also referred to as contig 56).
SEQ ID NO: 172 is the amino acid sequence encoded by SEQ ID NO: 171.
SEQ ID NO: 173 is an extended cDNA sequence for L519S.
SEQ ID NO: 174 is the predicted amino acid sequence encoded by SEQ ID NO: 174.
SEQ ID NO: 175 is the full-length cDNA sequence for L523S.
SEQ ID NO: 176 is the predicted amino acid sequence encoded by SEQ ID NO: 175.
SEQ ID NO: 177 is the determined cDNA sequence for LST-sub5-7A.
SEQ ID NO: 178 is the determined cDNA sequence for LST-sub5-8G.
SEQ ID NO: 179 is the determined cDNA sequence for LST-sub5-8H.
SEQ ID NO: 180 is the determined cDNA sequence for LST-sub5-10B.
SEQ ID NO: 181 is the determined cDNA sequence for LST-sub5-10H.
SEQ ID NO: 182 is the determined cDNA sequence for LST-sub5-12B.
SEQ ID NO: 183 is the determined cDNA sequence for LST-sub5-11C.
SEQ ID NO: 184 is the determined cDNA sequence for LST-sub6-1c.
SEQ ID NO: 185 is the determined cDNA sequence for LST-sub6-2f.
SEQ ID NO: 186 is the determined cDNA sequence for LST-sub6-2G.
SEQ ID NO: 187 is the determined cDNA sequence for LST-sub6-4d.
SEQ ID NO: 188 is the determined cDNA sequence for LST-sub6-4e.
SEQ ID NO: 189 is the determined cDNA sequence for LST-sub6-4f.
SEQ ID NO: 190 is the determined cDNA sequence for LST-sub6-3h.
SEQ ID NO: 191 is the determined cDNA sequence for LST-sub6-5d.
SEQ ID NO: 192 is the determined cDNA sequence for LST-sub6-5h.
SEQ ID NO: 193 is the determined cDNA sequence for LST-sub6-6h.
SEQ ID NO: 194 is the determined cDNA sequence for LST-sub6-7a.
SEQ ID NO: 195 is the determined cDNA sequence for LST-sub6-8a.
SEQ ID NO: 196 is the determined cDNA sequence for LST-sub6-7d.
SEQ ID NO: 197 is the determined cDNA sequence for LST-sub6-7e.
SEQ ID NO: 198 is the determined cDNA sequence for LST-sub6-8e.
SEQ ID NO: 199 is the determined cDNA sequence for LST-sub6-7g.
SEQ ID NO: 200 is the determined cDNA sequence for LST-sub6-9f.
SEQ ID NO: 201 is the determined cDNA sequence for LST-sub6-9h.
SEQ ID NO: 202 is the determined cDNA sequence for LST-sub6-11b.
SEQ ID NO: 203 is the determined cDNA sequence for LST-sub6-11c.
SEQ ID NO: 204 is the determined cDNA sequence for LST-sub6-12c.
SEQ ID NO: 205 is the determined cDNA sequence for LST-sub6-12e.
SEQ ID NO: 206 is the determined cDNA sequence for LST-sub6-12f.
SEQ ID NO: 207 is the determined cDNA sequence for LST-sub6-11g.
SEQ ID NO: 208 is the determined cDNA sequence for LST-sub6-12g.
SEQ ID NO: 209 is the determined cDNA sequence for LST-sub6-12h.
SEQ ID NO: 210 is the determined cDNA sequence for LST-sub6-II-1a.
SEQ ID NO: 211 is the determined cDNA sequence for LST-sub6-II-2b.
SEQ ID NO: 212 is the determined cDNA sequence for LST-sub6-II-2g.
SEQ ID NO: 213 is the determined cDNA sequence for LST-sub6-II-1h.
SEQ ID NO: 214 is the determined cDNA sequence for LST-sub6-II-4a.
SEQ ID NO: 215 is the determined cDNA sequence for LST-sub6-II-4b.
SEQ ID NO: 216 is the determined cDNA sequence for LST-sub6-II-3e.
SEQ ID NO: 217 is the determined cDNA sequence for LST-sub6-II-4f.
SEQ ID NO: 218 is the determined cDNA sequence for LST-sub6-II-4g.
SEQ ID NO: 219 is the determined cDNA sequence for LST-sub6-II-4h.
SEQ ID NO: 220 is the determined cDNA sequence for LST-sub6-II-5c.
SEQ ID NO: 221 is the determined cDNA sequence for LST-sub6-II-5e.

SEQ ID NO: 222 is the determined cDNA sequence for LST-sub6-II-6f.
SEQ ID NO: 223 is the determined cDNA sequence for LST-sub6-II-5g.
SEQ ID NO: 224 is the determined cDNA sequence for LST-sub6-II-6g.
SEQ ID NO: 225 is the amino acid sequence for L528S.
SEQ ID NO: 226–251 are synthetic peptides derived from L762P.
SEQ ID NO: 252 is the expressed amino acid sequence of L514S.
SEQ ID NO: 253 is the DNA sequence corresponding to SEQ ID NO: 252.
SEQ ID NO: 254 is the DNA sequence of a L762P expression construct.
SEQ ID NO: 255 is the determined cDNA sequence for clone 23785.
SEQ ID NO: 256 is the determined cDNA sequence for clone 23786.
SEQ ID NO: 257 is the determined cDNA sequence for clone 23788.
SEQ ID NO: 258 is the determined cDNA sequence for clone 23790.
SEQ ID NO: 259 is the determined cDNA sequence for clone 23793.
SEQ ID NO: 260 is the determined cDNA sequence for clone 23794.
SEQ ID NO: 261 is the determined cDNA sequence for clone 23795.
SEQ ID NO: 262 is the determined cDNA sequence for clone 23796.
SEQ ID NO: 263 is the determined cDNA sequence for clone 23797.
SEQ ID NO: 264 is the determined cDNA sequence for clone 23798.
SEQ ID NO: 265 is the determined cDNA sequence for clone 23799.
SEQ ID NO: 266 is the determined cDNA sequence for clone 23800.
SEQ ID NO: 267 is the determined cDNA sequence for clone 23802.
SEQ ID NO: 268 is the determined cDNA sequence for clone 23803.
SEQ ID NO: 269 is the determined cDNA sequence for clone 23804.
SEQ ID NO: 270 is the determined cDNA sequence for clone 23805.
SEQ ID NO: 271 is the determined cDNA sequence for clone 23806.
SEQ ID NO: 272 is the determined cDNA sequence for clone 23807.
SEQ ID NO: 273 is the determined cDNA sequence for clone 23808.
SEQ ID NO: 274 is the determined cDNA sequence for clone 23809.
SEQ ID NO: 275 is the determined cDNA sequence for clone 23810.
SEQ ID NO: 276 is the determined cDNA sequence for clone 23811.
SEQ ID NO: 277 is the determined cDNA sequence for clone 23812.
SEQ ID NO: 278 is the determined cDNA sequence for clone 23813.
SEQ ID NO: 279 is the determined cDNA sequence for clone 23815.
SEQ ID NO: 280 is the determined cDNA sequence for clone 25298.
SEQ ID NO: 281 is the determined cDNA sequence for clone 25299.
SEQ ID NO: 282 is the determined cDNA sequence for clone 25300.
SEQ ID NO: 283 is the determined cDNA sequence for clone 25301
SEQ ID NO: 284 is the determined cDNA sequence for clone 25304
SEQ ID NO: 285 is the determined cDNA sequence for clone 25309.
SEQ ID NO: 286 is the determined cDNA sequence for clone 25312.
SEQ ID NO: 287 is the determined cDNA sequence for clone 25317.
SEQ ID NO: 288 is the determined cDNA sequence for clone 25321.
SEQ ID NO: 289 is the determined cDNA sequence for clone 25323.
SEQ ID NO: 290 is the determined cDNA sequence for clone 25327.
SEQ ID NO: 291 is the determined cDNA sequence for clone 25328.
SEQ ID NO: 292 is the determined cDNA sequence for clone 25332.
SEQ ID NO: 293 is the determined cDNA sequence for clone 25333.
SEQ ID NO: 294 is the determined cDNA sequence for clone 25336.
SEQ ID NO: 295 is the determined cDNA sequence for clone 25340.
SEQ ID NO: 296 is the determined cDNA sequence for clone 25342.
SEQ ID NO: 297 is the determined cDNA sequence for clone 25356.
SEQ ID NO: 298 is the determined cDNA sequence for clone 25357.
SEQ ID NO: 299 is the determined cDNA sequence for clone 25361.
SEQ ID NO: 300 is the determined cDNA sequence for clone 25363.
SEQ ID NO: 301 is the determined cDNA sequence for clone 25397.
SEQ ID NO: 302 is the determined cDNA sequence for clone 25402.
SEQ ID NO: 303 is the determined cDNA sequence for clone 25403.
SEQ ID NO: 304 is the determined cDNA sequence for clone 25405.
SEQ ID NO: 305 is the determined cDNA sequence for clone 25407.
SEQ ID NO: 306 is the determined cDNA sequence for clone 25409.
SEQ ID NO: 307 is the determined cDNA sequence for clone 25396.
SEQ ID NO: 308 is the determined cDNA sequence for clone 25414.
SEQ ID NO: 309 is the determined cDNA sequence for clone 25410.
SEQ ID NO: 310 is the determined cDNA sequence for clone 25406.
SEQ ID NO: 311 is the determined cDNA sequence for clone 25306.
SEQ ID NO: 312 is the determined cDNA sequence for clone 25362.
SEQ ID NO: 313 is the determined cDNA sequence for clone 25360.
SEQ ID NO: 314 is the determined cDNA sequence for clone 25398.

SEQ ID NO: 315 is the determined cDNA sequence for clone 25355.
SEQ ID NO: 316 is the determined cDNA sequence for clone 25351.
SEQ ID NO: 317 is the determined cDNA sequence for clone 25331.
SEQ ID NO: 318 is the determined cDNA sequence for clone 25338.
SEQ ID NO: 319 is the determined cDNA sequence for clone 25335.
SEQ ID NO: 320 is the determined cDNA sequence for clone 25329.
SEQ ID NO: 321 is the determined cDNA sequence for clone 25324.
SEQ ID NO: 322 is the determined cDNA sequence for clone 25322.
SEQ ID NO: 323 is the determined cDNA sequence for clone 25319.
SEQ ID NO: 324 is the determined cDNA sequence for clone 25316.
SEQ ID NO: 325 is the determined cDNA sequence for clone 25311.
SEQ ID NO: 326 is the determined cDNA sequence for clone 25310.
SEQ ID NO: 327 is the determined cDNA sequence for clone 25302.
SEQ ID NO: 328 is the determined cDNA sequence for clone 25315.
SEQ ID NO: 329 is the determined cDNA sequence for clone 25308.
SEQ ID NO: 330 is the determined cDNA sequence for clone 25303.

DETAILED DESCRIPTION OF THE INVENTION

As noted above, the present invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a lung tumor protein or a variant thereof. A "lung tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human lung tumor proteins. Sequences of polynucleotides encoding specific tumor proteins are provided in SEQ ID NO: 1–109, 111, 113, 115–151, 153, 154, 157, 158, 160, 162–164, 167, 168, 171, 173, 175, 177–224 and 255–330.

Lung Tumor Protein Polynucleotides

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native lung tumor protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor.* 11:105; Santou, N. Nes, M. (1987) *Mol Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native lung tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a lung tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a lung tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a fill length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Certain nucleic acid sequences of cDNA molecules encoding portions of lung tumor proteins are provided in SEQ ID NO: 1–109, 111, 113, 115–151, 153, 154,157, 158, 160, 162–164, 167, 168, 171, 173, 175, 177–224 and 255–330.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a lung tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a lung tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus).). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Lung Tumor Polypeptides

Within the context of the present invention, polypeptides may comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have nonessential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum urine and/or tumor biopsies ) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria;

however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. Irvine, Calif. (see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed under conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lung tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 µg/ml, preferably 200 ng/ml–25 µg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be $CD4^+$ and/or $CD8^+$. Lung tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a lung tumor polypeptide, polynucleotide or APC can be expanded in number either in vitro or in vivo. Proliferation of such T cells in vitro may be accomplished in a variety of ways. For example, the T cells can be re-exposed to a lung tumor polypeptide, or a short peptide corresponding to an immunogenic portion of such a polypeptide, with or without the addition of T cell growth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259: 1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436, 727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the lung tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner. (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tumor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/or $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 μg/ml). It may be desirable to incubate another aliquot of a T cell sample in the absence of lung tumor polypeptide to serve as a control. For $CD4^-$ T cells, activation is preferably detected by evaluating proliferation of the T cells. For $CD8^-$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a lung tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–109, 111, 113, 115–151, 153, 154,157, 158, 160, 162–164, 167, 168, 171, 173, 175, 177–224 and 255–330. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostics Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLE 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual,* Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA cDNA library subtraction was performed using the above lung squamous cell carcinoma and normal lung cDNA libraries, as described by Hara et al. (*Blood,* 84:189–199, 1994) with some modifications. Specifically, a lung squamous cell carcinoma-specific subtracted cDNA library was generated as follows. Normal tissue cDNA library (80 µg) was digested with BamHI and XhoI, followed by a filling-in reaction with DNA polymerase Klenow fragment. After phenol-chloroform extraction and ethanol precipitation, the DNA was dissolved in 133 µl of $H_2O$, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl $H_2O$ to form the driver DNA.

To form the tracer DNA, 10 µg lung squamous cell carcinoma cDNA library was digested with NotI and SpeI, phenol chloroform extracted and passed through Chroma spin-400 columns (Clontech, Palo Alto, Calif.). Typically, 5 µg of cDNA was recovered after the sizing column. Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained $1.76 \times 10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third or the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192, 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences from a Lung Adenocarcinoma Library

A human lung adenocarcinoma cDNA expression library was constructed as described above. The library contained $3.2 \times 10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

In further studies, a cDNA library (referred to as mets3616A) was constructed from a metastatic lung adenocarcinoma. The determined cDNA sequences of 25 clones sequenced at random from this library are provided in SEQ ID NO: 255–279. The mets3616A cDNA library was subtracted against a cDNA library prepared from a pool of normal lung, liver, pancreas, skin, kidney, brain and resting PBMC. To increase the specificity of the subtraction, the driver was spiked with genes that were determined to be most abundant in the mets3616A cDNA library, such as EF1-alpha, integrin-beta and anticoagulant protein PP4, as well as with cDNAs that were previously found to be differentially expressed in subtracted lung adenocarcinoma cDNA libraries. The determined cDNA sequences of 51 clones isolated from the subtracted library (referred to as mets3616A-S1) are provided in SEQ ID NO: 280–330.

Comparison of the sequences of SEQ ID NO: 255–330 with those in the public databases revealed no significant homologies to the sequences of SEQ ID NO: 255–258, 260, 262–264, 270, 272, 275, 276, 279, 281, 287, 291, 296, 300 and 310. The sequences of SEQ ID NO: 259, 261, 265–269, 271, 273, 274, 277, 278, 282–285, 288–290, 292, 294, 297–299, 301, 303–309, 313, 314, 316, 320–324 and 326–330 showed some homology to previously identified gene sequences, while the sequences of SEQ ID NO: 280, 286, 293, 302, 310, 312, 315, 317–319 and 325 showed some homology to previously isolated expressed sequence tags (ESTs).

EXAMPLE 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 $\mu$g of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 $\mu$l of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-12-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99: that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequence for L503S is provided in SEQ ID NO: 151, with the corresponding predicted amino acid sequence being provided in SEQ ID NO: 152. Due to polymorphisms, the clone L531S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence being provided in SEQ ID NO: 155. The second variant form of L514S full-length cDNA is provided in SEQ ID NO: 154. with its corresponding amino acid sequence being provided in SEQ ID NO: 156.

Full length cloning for L524S (SEQ ID NO: 101) yielded two variants (SEQ ID NO: 163 and 164) with the corresponding predicted amino acid sequences of SEQ ID NO: 165 and 166, respectively. Both variants have been shown to encode parathyroid hormone-related peptide.

Attempts to isolate the full-length cDNA for L519S. resulted in the isolation of the extended cDNA sequence provided in SEQ ID NO: 173, which contains a potential open reading frame. The predicted amino acid sequence encoded by the sequence of SEQ ID NO: 173 is provided in SEQ ID NO: 174. Additionally, the full-length cDNA sequence for L523S, a known gene, is provided in SEQ ID NO: 175, with the corresponding predicted amino acid sequence provided in SEQ ID NO: 176.

Comparison of the sequences of L514S and L531S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Further analysis has demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related genes have been extensively documented as potential markers for lung cancer including CYFRA2.1 (Pastor, A., et al, *Eur. Respir. J.,* 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521S is over-expressed in normal skin. Both belong to a family of small proline rich proteins and represent markers for fully differentiated squamous cells. L521S has been described as a specific marker for lung squamous tumor (Hu, R., et al, i Lung Cancer, 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metatasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J. Pathol.* 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel17, which is reported to be preferentially expressed in low-metastatic potential melanoma cell lines. This suggests that L528S may be a shared antigen in both melanoma and lung squamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was also examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using standard techniques. In a first study, L523S was found to be expressed in a number of lung adenocarcinomas and squamous cell carcinomas, as well as normal tonsil. No expression was observed in normal lung. In a second study using a normal tissue blot (HB-12) from Clontech. no expression was observed in brain, skeletal muscle, colon, thymus, spleen, kidney, liver, small intestine, lung or PBMC, although there was strong expression in placenta.

EXAMPLE 3
Isolation and Characterization of Lung Tumor Polypeptides by PCR-Based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7-Adv vector (Clontech, Palo Alto, Calif.) and transformed into DH5α *E. Coli* (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the the EMBL and GenBank databases, as described above, revealed no significant homologies to 13 of these clones, hereinafter referred to as Contigs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue-type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17); with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

The full-length cDNA sequence for Contig 22, also referred to as L763P, is provided in SEQ ID NO: 158, with the corresponding predicted amino acid sequence being provided in SEQ ID NO: 159. Real-time RT-PCR analysis of L763P revealed that it is highly expressed in 3/4 lung squamous tumors as well as 4/4 head and neck squamous tumors, with low level expression being observed in normal brain, skin, soft pallet and trachea.

The full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1 (SEQ ID NO: 167, with the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

The full-length cDNA sequence for contig 56 (SEQ ID NO: 148), also referred to as L773P, is provided in SEQ ID NO: 171, with the predicted amino acid sequence in SEQ ID NO: 172. L773P was found to be identical to dihydroxyl dehydrogenase at the 3' portion of the gene, with divergent 5' sequence. As a result, the 69 N-terminal amino acids are unique. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

EXAMPLE 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 5

Preparation of Antibodies Against Lung Cancer Antigens

Polyclonal antibodies against the lung cancer antigens L514S, L528S and L531S (SEQ ID NO: 155, 225 and 112, respectively) were prepared as follows.

Rabbits were immunized with recombinant protein expressed in and purified from $E.\ coli$ as described above. For the initial immunization, 400 $\mu$g of antigen combined with muramyl dipeptide (MDP) was injected subcutaneously (S.C.). Animals were boosted S.C. 4 weeks later with 200 $\mu$g of antigen mixed with incomplete Freund's Adjuvant (IFA). Subsequent boosts of 100 $\mu$g of antigen mixed with IFA were injected S.C. as necessary to induce high antibody titer responses. Serum bleeds from immunized rabbits were tested for antigen-specific reactivity using ELISA assays with purified protein. Polyclonal antibodies against L514S, L528S and L531S were affinity purified from high titer polyclonal sera using purified protein attached to a solid support.

Immunohistochemical analysis using polyclonal antibodies against L514S was performed on a panel of 5 lung tumor samples, 5 normal lung tissue samples and normal colon, kidney, liver, brain and bone marrow. Specifically, tissue samples were fixed in formalin solution for 24 hours and embedded in paraffin before being sliced into 10 micron sections. Tissue sections were permeabilized and incubated with antibody for 1 hr. HRP-labeled anti-mouse followed by incubation with DAB chromogen was used to visualize L5 14S immunoreactivity. L514S was found to be highly expressed in lung tumor tissue with little or no expression being observed in normal lung, brain or bone marrow. Light staining was observed in colon and kidney. Staining was seen in normal liver but no mRNA has been detected in this tissue making this result suspect.

EXAMPLE 6

Peptide Priming of Mice and Propagation of CTL Lines

Immunogenic peptides from the lung cancer antigen L762P (SEQ ID NO: 161) for HLA-A2/$K^b$-restricted CD8+ T cells were identified as follows.

The location of HLA-A2 binding peptides within the lung cancer antigen L762P (SEQ ID NO: 161) was predicted using a computer program which prodicts peptides sequences likely to being to HLA-A*0201 by fitting to the known peptide binding motif for HLA-A*0201 (Rupert et al. (1993) Cell 74:929; Rammensee et al. (1995) Immunogenetics 41:178–228). A series of 19 synthetic peptides corresponding to a selected subset of the predicted HLA-A*0201 binding peptides was prepared as described above.

Mice expressing the transgene for human HLA A2/$K^b$ (provided by Dr L. Sherman, The Scripps Research Institute, La Jolla, Calif.) were immunized with the synthetic peptides, as described by Theobald et al., Proc. Natl. Acad. Sci. USA 92:11993–11997, 1995 with the following modifications. Mice were immunized with 50 $\mu$g of L726P peptide and 120 $\mu$g of an I-$A^b$ binding peptide derived from hepatitis B Virus protein emulsified in incomplete Freund's adjuvant. Three weeks later these mice were sacrificed and single cell suspensions prepared. Cells were then resuspended at 7×10$^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×10$^{-5}$ M 2-mercaptoethanol, 50 U/ml penicillin and streptomycin, and cultured in the presence of irradiated (3000 rads) L762P peptide—(5 $\mu$g/ml) and 10 mg/ml B$_2$-microglobulin—(3 $\mu$g/ml) LPS blasts (A2 transgenic spleens cells cultured in the presence of 7 $\mu$g/ml dextran sulfate and 25 $\mu$g/ml LPS for 3 days). After six days, cells (5×10$^5$/ml) were restimulated with 2.5×10$^6$/ml peptide pulsed irradiated (20,000 rads) EL4A2Kb cells (Sherman et al, Science 258:815–818, 1992) and 5×10$^6$/ml irradiated (3000 rads) A2/$K^b$-transgenic spleen feeder cells. Cells were cultured in the presence of 10 U/ml IL-2. Cells were restimulated on a weekly basis as described, in preparation for cloning the line.

Peptide-specific cell lines were cloned by limiting dilution analysis with irradiated (20,000 rads) L762P peptide-pulsed EL4 A2Kb tumor cells (1×10$^4$ cells/well) as stimulators and irradiated (3000 rads) A2/$K^b$-transgenic spleen cells as feeders (5×10$^5$ cells/well) grown in the presence of 10 U/ml IL-2. On day 7, cells were restimulated as before. On day 14, clones that were growing were isolated and maintained in culture.

Cell lines specific for L762P-87 (SEQ ID NO: 226; corresponding to amino acids 87–95 of SEQ ID NO: 161), L,726P-145 (SEQ ID NO: 227; corresponding to amino acids 145–153 of SEQ ID NO: 161), L726P-585 (SEQ ID NO: 228; corresponding to amino acids 585–593 of SEQ ID NO: 161), L762P-425 (SEQ ID NO: 229; corresponding to amino acids 425–433 of SEQ ID NO: 161), L762P(10)-424 (SEQ ID NO: 230; corresponding to amino acids 424–433 of SEQ ID NO: 161) and L762P(10)-458 (SEQ ID NO: 231; corresponding to amino acids 458–467 of SEQ ID NO: 161) demonstrated significantly higher reactivity (as measured by percent specific lysis) against L762P peptide-pulsed EL4-A2/K$^b$ tumor target cells than control peptide-pulsed EL4-A2/K$^b$ tumor target cells.

EXAMPLE 7

Identification of CD4 Immunogenic T Cell Epitopes Derived from the Lung Cancer Antigen L762P CD4 T cell lines specific for the antigen L762P (SEQ ID NO: 161) were generated as follows.

A series of 28 overlapping peptides were synthesized that spanned approximately 50% of the L762P sequence. For priming, peptides were combined into pools of 4–5 peptides, pulsed at 20 micrograms/ml into dendritic cells for 24 hours. The dendritic cells were then washed and mixed with positively selected CD4+ T cells in 96 well U-bottomed plates. Forty cultures were generated for each peptide pool. Cultures were restimulated weekly with fresh dendritic cells loaded with peptide pools. Following a total of 3 stimulation cycles, cells were rested for an additional week and tested for specificity to antigen presenting cells (APC) pulsed with peptide pools using interferon-gamma ELISA and proliferation assays. For these assays, adherent monocytes loaded with either the relevant peptide pool or an irrelevant peptide were used as APC. T cell lines that appeared to specifically recognize L762P peptide pools both by cytokine release and proliferation were identified for each pool. Emphasis was placed on identifying T cells with proliferative responses. T cell lines that demonstrated either both L762P-specific cytokine secretion and proliferation, or strong proliferation alone were further expanded to be tested for recognition of individual peptides from the pools, as well as for recognition of recombinant L762P. The source of recombinant L762P was E. coli, and the material was partially purified and endotoxin positive. For these peptides, 10 micrograms of individual peptides, 10 or 2 micrograms of an irrelevant peptide, and 2 or 0.5 micrograms of either L762P protein or an irrelevant, equally impure, E. coli generated recombinant protein. Significant interferon-gamma production and CD4 T cell proliferation was induced by a number of L762P-derived peptides in each pool. The amino acid sequences for these peptides are provided in SEQ ID NO: 232–251. These peptides correspond to amino acids 661–680, 676–696, 526–545, 874–893, 811–830, 871–891, 856–875, 826–845, 795–815, 736–755, 706–725, 706–725, 691–710, 601–620, 571–590, 556–575, 616–635, 646–665, 631–650, 541–560 and 586–605, respectively, of SEQ ID NO: 161.

EXAMPLE 8

Protein Expression of Lung Tumor-Specific Antigens a) Expression of L514S in E. coli The lung tumor antigen L514S (SEQ ID NO: 89) was subcloned into the expression vector pE32b at NcoI and NotI sites, and transformed into E. coli using standard techniques. The protein was expressed from residues 3–153 of SEQ ID NO: 89. The expressed amino acid sequence and the corresponding DNA sequence are provided in SEQ ID NO: 252 and 253, respectively.

b) Expression of L762P

Amino acids 32–944 of the lung tumor antigen L762P (SEQ ID NO: 161), with a 6× His Tag, were subcloned into a modified pET28 expression vector, using kanamycin resistance, and transformed into BL21 CodonPlus using standard techniques. Low to moderate levels of expression were observed. The determined DNA sequence of the L762P expression construct is provided in SEQ ID NO: 254.

From the foregoing it will be appreciated that, although specific embodiments of the invention have been described herein for purposes of illustration, various modifications may be made without deviating from the spirit and scope of the invention Accordingly, the invention is not limited except as by the appended claims.

What is claimed is:

1. A method for determining the presence of lung cancer in a patient, comprising:
   (a) obtaining a biological sample from the patient;
   (b) contacting the biological sample with a binding agent that binds to a polypeptide having the amino acid sequence provided in SEQ ID NO:176;
   (c) detecting in the sample an amount of the polypeptide that binds to the binding agent; and
   (d) comparing the amount of the polypeptide to a predetermined cut-off valve, and
   wherein higher amount of said polypeptide than the predetermined cut-off value indicates the presence of lung cancer in the patient.

2. A method according to claim 1, wherein the binding agent is an antibody.

3. A method according to claim 2, wherein the antibody is a monoclonal antibody.

4. A method for monitoring the progression of lung cancer in a patient, comprising:
   (a) obtaining a biological sample from the patient;
   (b) contacting the biological sample with a binding agent that binds to a polypeptide having the amino acid sequence provided in SEQ ID NO:176;
   (c) detecting in the sample an amount of the polypeptide that binds to the binding agent;
   (d) repeating steps (b) and (c) using a biological sample obtained from the patient at a subsequent point in time; and
   (e) comparing the amount of the polypeptide detected in step (c) to the amount detected in step (d), and
   therefrom monitoring the progression of lung cancer in the patient.

5. A method according to claim 4, wherein the binding agent is an antibody.

6. A method according to claim 5, wherein the antibody is a monoclonal antibody.

* * * * *